(12) United States Patent
Schnute

(10) Patent No.: US 9,920,054 B2
(45) Date of Patent: Mar. 20, 2018

(54) METHYL- AND TRIFLUOROMETHYL-SUBSTITUTED PYRROLOPYRIDINE MODULATORS OF RORC2 AND METHODS OF USE THEREOF

(71) Applicant: Pfizer Inc., New York, NY (US)

(72) Inventor: Mark Edward Schnute, Acton, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/581,310

(22) Filed: Apr. 28, 2017

(65) Prior Publication Data

US 2017/0233390 A1 Aug. 17, 2017

Related U.S. Application Data

(63) Continuation of application No. 14/864,840, filed on Sep. 24, 2015, now Pat. No. 9,670,201.

(60) Provisional application No. 62/055,811, filed on Sep. 26, 2014, provisional application No. 62/110,048, filed on Jan. 30, 2015, provisional application No. 62/209,124, filed on Aug. 24, 2015.

(51) Int. Cl.
*C07D 401/14* (2006.01)
*C07D 401/04* (2006.01)
*A61K 31/437* (2006.01)
*C07D 471/04* (2006.01)

(52) U.S. Cl.
CPC ......... *C07D 471/04* (2013.01); *C07D 401/14* (2013.01)

(58) Field of Classification Search
CPC .. C07D 401/02; C07D 401/10; C07D 401/14; A61K 31/437; A61K 31/4353
USPC ............... 546/119, 121; 514/300, 303
See application file for complete search history.

(56) References Cited

U.S. PATENT DOCUMENTS

| 5,708,008 A | 1/1998 | Audia et al. |
| 5,817,671 A | 10/1998 | Filla et al. |
| 5,998,412 A | 12/1999 | Broka et al. |
| 7,989,447 B2 | 8/2011 | Maddaford et al. |
| 2002/0040019 A1 | 4/2002 | Cai et al. |
| 2003/0191124 A1 | 10/2003 | Merce-Vidal et al. |
| 2005/0176751 A1 | 8/2005 | Pou et al. |
| 2005/0245540 A1 | 11/2005 | Takeshita et al. |
| 2006/0258721 A1 | 11/2006 | Maddaford et al. |
| 2009/0197881 A1 | 8/2009 | Kugimiya et al. |
| 2010/0004243 A1 | 1/2010 | Congreve et al. |
| 2011/0172265 A1 | 7/2011 | Valeur et al. |
| 2012/0083475 A1 | 4/2012 | Griffioen et al. |
| 2012/0101080 A1 | 4/2012 | Schoenmakers et al. |
| 2016/0046597 A1* | 2/2016 | Schnute ............ C07D 401/14 514/210.18 |

FOREIGN PATENT DOCUMENTS

| EP | 0842934 | 5/1996 |
| EP | 0832650 | 4/1998 |
| WO | 2012139775 | 10/2012 |
| WO | 2013064231 | 5/2013 |
| WO | 2013171729 | 11/2013 |
| WO | 2013178362 | 12/2013 |
| WO | 2014026328 | 2/2014 |
| WO | 2014086894 | 6/2014 |
| WO | 2015015378 | 2/2015 |
| WO | 2015083130 | 6/2015 |

OTHER PUBLICATIONS

Filia, Sandra, et al., "Novel Potent 5-HT1F Receptor Agonists: Structure-Activity Studies of a Series of Substituted N [3-(1-Methyl-4-piperidinyl)-1H pyrrolo[3,2,b]pyridin-5-yl]amides," Journal of Medicinal Chemistry, American Chemical Society, 46, 3060-3071 (2003).

Forbes, I.T., et al., "CCR2B Receptor Antagonists: Conversation of a Weak HTS Hit to Potent Lead Compound," Bioorganic & Medicinal Chemistry Letters, 10, 1803-1806 (2000).

Hutton, Jennie, et al., "Structure-Based Design of Potent and Selective Leishmania N-Myristoyltransferase Inhibitors," Journal of Medicinal Chemistry, 57, 8664-8670 (2014).

Zhang D. et al., "Design, Synthesis and Evaluation of Bicyclic Benzamides as Novel 5-HT1F Receptor Agonists," Bioorganic & Medicinal Chemistry Letters, 14, 6011-6016 (2004).

* cited by examiner

*Primary Examiner* — Niloofar Rahmani
(74) *Attorney, Agent, or Firm* — James T. Wasicak

(57) ABSTRACT

The present invention provides methyl- and trifluoromethyl-substituted pyrrolopyridines, pharmaceutical compositions thereof, methods of modulating RORγ activity and/or reducing the amount of IL-17 in a subject, and methods of treating various medical disorders using such pyrrolopyridines and pharmaceutical compositions thereof.

5 Claims, 2 Drawing Sheets

METHYL- AND TRIFLUOROMETHYL-SUBSTITUTED PYRROLOPYRIDINE MODULATORS OF RORC2 AND METHODS OF USE THEREOF

BACKGROUND OF THE INVENTION

Retinoid-related orphan receptors (ROR) are reported to have an important role in numerous biological processes. Scientific investigations relating to each of retinoid-related orphan receptors RORα, RORβ, and RORγ have been described in the literature. Continuing research in this field is spurred by the promise of developing new therapeutic agents to treat medical disorders associated with retinoid-related orphan receptor activity.

RORγ has been reported to be expressed in high concentration in various tissues, such as thymus, kidney, liver, muscle, and certain fat tissue. Two isoforms of RORγ have been identified and are referred to as γ1 and γ2 (also referred to as RORγt). Expression of the γ2 isoform has been reported to appear in, for example, double-positive thymocytes. Compounds capable of modulating RORγt activity are contemplated to provide a therapeutic benefit in the treatment of multiple medical disorders, including immune and inflammatory disorders.

Numerous immune and inflammatory disorders continue to afflict millions of patients worldwide. Significant advances have been made in treating these disorders. However, current therapies do not provide satisfactory results for all patients due to, for example, detrimental side effects or insufficient efficacy. Treatments for immune and inflammatory disorders vary depending on the particular medical disorder, and often involve use of immunosuppressive drugs. Surgery (e.g., splenectomy), plasmapheresis, or radiation can be used in certain instances.

One exemplary immune disorder in need of better therapy is psoriasis. Psoriasis is a T cell-mediated inflammatory disease that affects approximately 2% to 3% of adults and has a substantial adverse impact on the quality of life for patients suffering from this disorder. Plaques resulting from psoriasis can be painful and are visually unappealing. Various therapeutics have been developed in an attempt to treat psoriasis. However, the traditional therapies for psoriasis often have toxic adverse effects. Accordingly, a need exists for improved treatments for psoriasis as well as other immune and inflammatory disorders.

SUMMARY

The present invention provides compounds, pharmaceutical compositions, methods of inhibiting RORγ activity and/or reducing the amount of IL-17 in a subject, and methods of treating various medical disorders using such compounds. In particular, one aspect of the invention relates to compounds represented by Formula I:

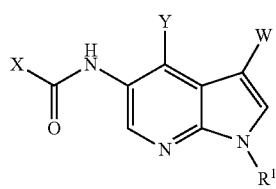

and pharmaceutically acceptable salts, pharmaceutically active metabolites, pharmaceutically acceptable prodrugs, and pharmaceutically acceptable solvates thereof; wherein $R^1$, X, Y and W are as defined in the Detailed Description.

Another aspect of the invention provides a method of treating a subject suffering from a medical disorder. The method comprises administering to the subject a therapeutically effective amount of a compound of Formula I or a pharmaceutically acceptable salt or solvate thereof, as described in the Detailed Description. A large number of disorders may be treated using the compounds described herein. For example, the compounds described herein may be used to treat an immune disorder or inflammatory disorder, such as rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, epidermal hyperplasia, and other medical disorders described herein.

DETAILED DESCRIPTION

Figure 1:
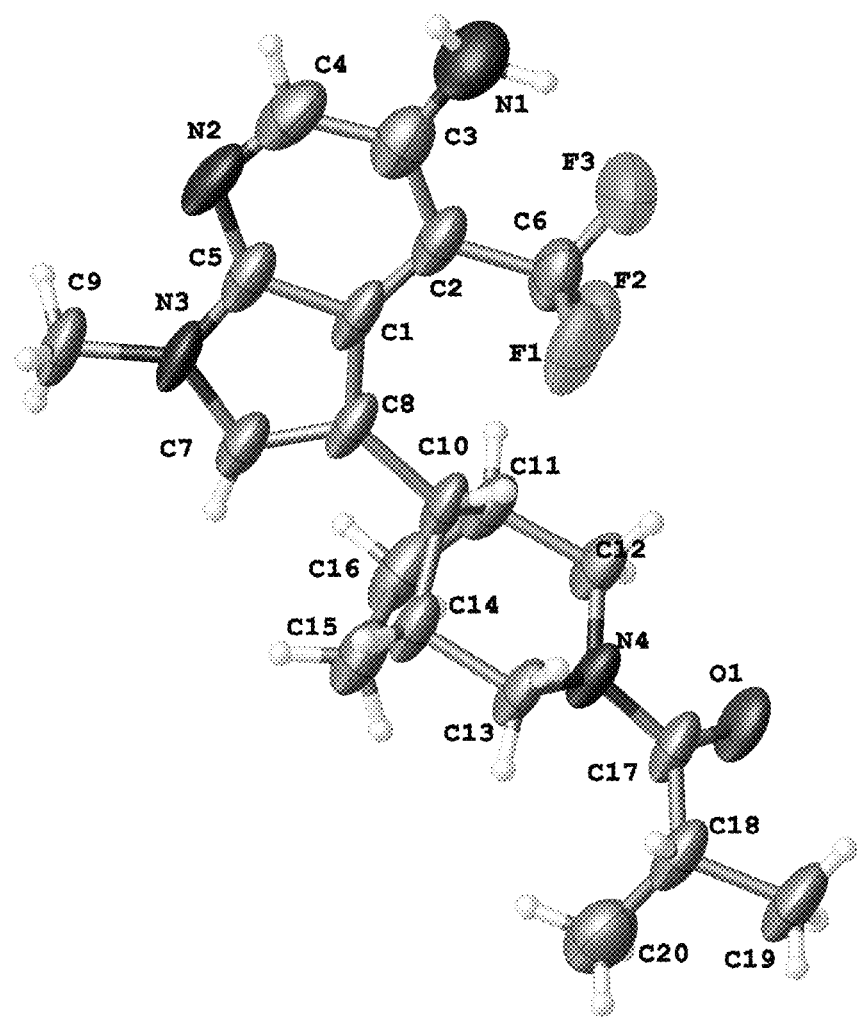
FIG. 1 is an X-ray crystal structure (ORTEP drawing) of 1-{(8-anti)-[5-amino-1-methyl-4-(trifluoromethyl)-1H-pyrrolo[2,3-b]pyridin-3-yl]-3-azabicyclo[3.2.1]oct-3-yl}-2-methylpropan-1-one.

The invention provides compounds, pharmaceutical compositions, methods of modulating RORγ activity and/or reducing the amount of IL-17 in a subject, and therapeutic uses of said compounds and pharmaceutical compositions. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein.

Chemical names, common names, and chemical structures may be used interchangeably to describe the same structure. If a chemical compound is referred to using both a chemical structure and a chemical name, and an ambiguity exists between the structure and the name, the structure predominates.

Definitions

"ROR" stands for Retinoic acid receptor-related Orphan Receptor. There are three forms of ROR, ROR-α, -β, and -γ and each is encoded by a separate gene (RORA, RORB, and RORC respectively). There are two subtypes of RORC: 1 and 2. Subtype 2 is also called "t". The human RORC gene is also called TOR; RORG; RZRG; NRIF3; and RZR-GAMMA. The human protein RORC is also called nuclear receptor ROR-gamma; nuclear receptor RZR-gamma; retinoic acid-binding receptor gamma; retinoid-related orphan receptor gamma; RAR-related orphan receptor C, isoform a; RAR-related orphan nuclear receptor variant 2; nuclear receptor subfamily 1 group F member 3. As used herein, "RORγ" and "RORC2" are used interchangeably to refer to a protein from a RORC subtype 2 gene.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "alkyl" refers to a substituent obtained by removing a hydrogen from a saturated, straight (i.e. unbranched) or branched carbon chain (or carbon), or combination thereof, which has the number of carbon atoms designated (i.e. $C_1$-$C_6$ means one to six carbons). Examples of alkyl substituents include methyl, ethyl, propyl (including n-propyl and isopropyl), butyl (including n-butyl, isobutyl, sec-butyl and tert-butyl), pentyl, isoamyl, hexyl and the like.

The term "haloalkyl" is an alkyl in which at least one hydrogen on the alkyl is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "cycloalkyl" refers to a substituent obtained by removing a hydrogen atom from a saturated carbocycle having the number of carbon atoms designated (i.e. $C_3$-$C_8$ means three to eight carbons). Cycloalkyl refers to both a radical of a single ring saturated carbocycle, such as cyclopropyl, cyclobutyl, cyclopentyl and cyclohexyl. as well as a radical of a two or three ring bridged, fused or spiro saturated carbocycle, such as bicyclo[4.2.0]octane and decalinyl.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described such that it "may be substituted" or as being "optionally substituted" with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent. To illustrate further, if an amino nitrogen is described as being optionally substituted with up to 2 non-hydrogen substituents, then the nitrogen will be optionally substituted with up to 2 non-hydrogen substituents if the amino nitrogen is a primary nitrogen, whereas the amino nitrogen will be optionally substituted with up to only 1 non-hydrogen substituent if the amino nitrogen is a secondary nitrogen.

As used herein compounds of Formula I may be referred to as a "compound(s) of the invention." Such terms are also defined to include all forms of the Formula I including hydrates, solvates, isomers, crystalline and non-crystalline forms, isomorphs, polymorphs, and metabolites thereof. For example, the compounds of Formula I and pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

In some embodiments, compounds described herein could be prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Saulnier et al., (1994), Bioorganic and Medicinal Chemistry Letters, Vol. 4, p. 1985).

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., Am. J. Physiol., 269:G210-218 (1995); McLoed et al., Gastroenterol, 106:405-413 (1994); Hochhaus et al., Biomed. Chrom., 6:283-286 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987, all incorporated herein in their entirety.

The compounds of the invention may have asymmetric carbon atoms. The carbon-carbon bonds of the compounds of the invention may be depicted herein using a solid line, a solid wedge or a dotted wedge. The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Stereoisomers of compounds of the invention include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The present invention also includes isotopically-labeled compounds, which are identical to those recited in Formula I herein, but for the fact that one or more atoms are replaced by an atom having an atomic mass or mass number different from the atomic mass or mass number usually found in nature. Examples of isotopes that may be incorporated into compounds of the invention include isotopes of hydrogen, carbon, nitrogen, oxygen, phosphorus, fluorine and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$. Certain isotopically-labeled compounds of Formula I, for example those into which radioactive isotopes such as $^{3}H$ and $^{14}O$ are incorporated, are useful in drug and/or substrate tissue distribution assays.

Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labeled compounds the invention may generally be prepared by carrying out the procedures disclosed in the Schemes and/or in the Exemplification below, by substituting an isotopically-labeled reagent for a non-isotopically-labeled reagent.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-benzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (i.e., decyl, lauryl, myristyl, and stearyl chlorides, bromides, and iodides), arylalkyl halides (i.e., benzyl and phenethyl bromides), and others.

In one embodiment, hemisalts of acids and bases may also be formed, for example, hemisulphate and hemicalcium salts.

Compounds

In the following description of compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

In certain embodiments, the compounds of the invention described herein are selective for RORγ over RORα and/or RORβ.

Generally, an inhibitor compound of RORγ used in the methods described herein is identified or characterized in an in vitro assay, e.g., an acellular biochemical assay or a cellular functional assay. Such assays are useful to determine an in vitro $IC_{50}$ for said compounds. In some embodiments, the RORγ inhibitor compound used for the methods described herein inhibits RORγ activity with an in vitro $IC_{50}$ of less than 25 µM (e.g., less than 20 µM, less than 10 µM, less than 1 µM, less than 0.5 µM, less than 0.4 µM, less than 0.3 µM, less than 0.1, less than 0.08 µM, less than 0.06 µM, less than 0.05 µM, less than 0.04 µM, less than 0.03 µM, less than less than 0.02 µM, less than 0.01, less than 0.008 µM, less than 0.006 µM, less than 0.005 µM, less than 0.004 µM, less than 0.003 µM, less than less than 0.002 µM, less than 0.001, less than 0.00099 µM, less than 0.00098 µM, less than 0.00097 µM, less than 0.00096 µM, less than 0.00095 µM, less than 0.00094 µM, less than 0.00093 µM, less than 0.00092, or less than 0.00090 µM). In some embodiments, the RORγ inhibitor compound is a compound described in the Exemplification.

Described herein are compounds of Formula I. Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom can be converted to an N-oxide by methods well known in the art. In certain embodiments, isomers and chemically protected forms of compounds having a structure represented by Formula I are also provided.

One aspect of the invention relates to a compound of Formula I:

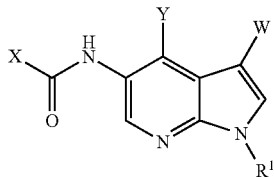

I or a pharmaceutically acceptable salt, pharmaceutically active metabolite, pharmaceutically acceptable prodrug, or pharmaceutically acceptable solvate thereof, wherein, Y is —CH$_3$ or —CF$_3$;

X is phenyl optionally substituted with one, two, three, four or five substituents independently selected from the group consisting of —CH$_3$, —CH$_2$CH$_3$, —CH$_2$OH, —OH, —OCH$_3$, —SCH$_3$, —OCH$_2$CH$_3$, —OCH$_2$CH$_2$OH, —OCH$_2$CH$_2$OCH$_3$, —F, —Cl, —Br and —CN;

R$^1$ is —CH$_3$ or —CH$_2$CH$_3$;

W is

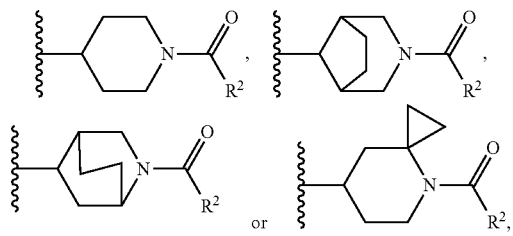

each optionally substituted with one, two, three, four or five —CH$_3$; and

R$^2$ is (C$_1$-C$_6$)alkyl, (C$_3$-C$_{10}$)cycloalkyl, phenyl, tetrahydrothiophenyl, thietanyl or indanyl, optionally substituted with one, two, three, four or five substitutents independently selected for each occurrence from the group consisting of —F, —Cl, —Br, —OH, (C$_1$-C$_3$)alkyl, (C$_1$-C$_3$)haloalkyl and (C$_3$-C$_8$)cycloalkyl.

In certain embodiments, the present invention relates to any of the aforementioned compounds, provided that when Y is —CH$_3$, X is

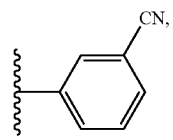

R$^1$ is —CH$_3$ and W is

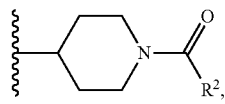

then R$^2$ is not

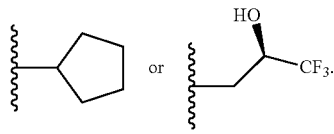 [SMILES: *C1CCCC1 ; "or" ; *C[C@@H](O)C(F)(F)F]

In certain embodiments, the present invention relates to any of the aforementioned compounds, wherein Y is —CH$_3$.

In certain embodiments, the present invention relates to any of the aforementioned compounds, wherein Y is —CF$_3$.

In certain embodiments, the present invention relates to any of the aforementioned compounds, wherein R$^1$ is —CH$_3$.

In certain embodiments, the present invention relates to any of the aforementioned compounds, wherein R$^1$ is —CH$_2$CH$_3$.

In certain embodiments, the present invention relates to any of the aforementioned compounds, wherein W is

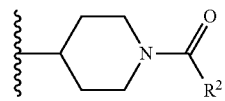

optionally substituted with one, two, three, four or five —CH$_3$.

In certain embodiments, the present invention relates to any of the aforementioned compounds, wherein W is

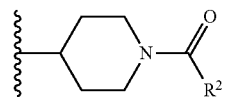

optionally substituted with one, two, three, four or five —CH$_3$; and R$^1$ is —CH$_3$.

In certain embodiments, the present invention relates to any of the aforementioned compounds, wherein W is

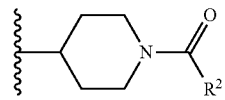

optionally substituted with one, two, three, four or five —CH₃; R¹ is —CH₃; and Y is —CH₃.

In certain embodiments, the present invention relates to any of the aforementioned compounds, wherein W is

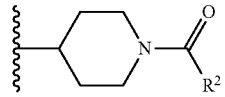

optionally substituted with one, two, three, four or five —CH₃; R¹ is —CH₃; and Y is —CF₃.

In certain embodiments, the present invention relates to any of the aforementioned compounds, wherein W is

optionally substituted with one, two, three, four or five —CH₃.

In certain embodiments, the present invention relates to any of the aforementioned compounds, wherein W is

optionally substituted with one, two, three, four or five —CH₃; and R¹ is —CH₃.

In certain embodiments, the present invention relates to any of the aforementioned compounds, wherein W is

optionally substituted with one, two, three, four or five —CH₃; R¹ is —CH₃; and Y is —CH₃.

In certain embodiments, the present invention relates to any of the aforementioned compounds, wherein W is

optionally substituted with one, two, three, four or five —CH₃; R¹ is —CH₃; and Y is —CF₃.

In certain embodiments, the present invention relates to any of the aforementioned compounds, wherein W is

optionally substituted with one, two, three, four or five —CH₃.

In certain embodiments, the present invention relates to any of the aforementioned compounds, wherein W is

optionally substituted with one, two, three, four or five —CH₃; and R¹ is —CH₃.

In certain embodiments, the present invention relates to any of the aforementioned compounds, wherein W is

optionally substituted with one, two, three, four or five —CH₃; R¹ is —CH₃; and Y is —CH₃.

In certain embodiments, the present invention relates to any of the aforementioned compounds, wherein W is

optionally substituted with one, two, three, four or five —CH₃; R¹ is —CH₃; and Y is —CF₃.

In certain embodiments, the present invention relates to any of the aforementioned compounds, wherein W is

optionally substituted with one, two, three, four or five —CH₃.

In certain embodiments, the present invention relates to any of the aforementioned compounds, wherein W is

optionally substituted with one, two, three, four or five —CH₃; and R¹ is —CH₃.

In certain embodiments, the present invention relates to any of the aforementioned compounds, wherein W is

optionally substituted with one, two, three, four or five —CH₃; R¹ is —CH₃; and Y is —CH₃.

In certain embodiments, the present invention relates to any of the aforementioned compounds, wherein W is

optionally substituted with one, two, three, four or five —CH₃; R¹ is —CH₃; and Y is —CF₃.

In certain embodiments, the present invention relates to any of the aforementioned compounds, wherein W is

optionally substituted with one, two, three, four or five —CH₃.

In certain embodiments, the present invention relates to any of the aforementioned compounds, wherein W is

optionally substituted with one, two, three, four or five —CH₃; and R¹ is —CH₃.

In certain embodiments, the present invention relates to any of the aforementioned compounds, wherein W is

optionally substituted with one, two, three, four or five —CH₃; R¹ is —CH₃; and Y is —CH₃.

In certain embodiments, the present invention relates to any of the aforementioned compounds, wherein W is

optionally substituted with one, two, three, four or five —CH₃; R¹ is —CH₃; and Y is —CF₃.

In certain embodiments, the present invention relates to any of the aforementioned compounds, wherein W is

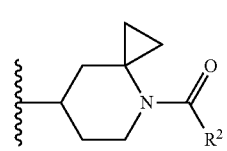

optionally substituted with one, two, three, four or five —CH₃.

In certain embodiments, the present invention relates to any of the aforementioned compounds, wherein W is

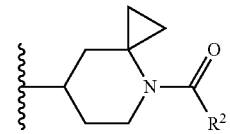

optionally substituted with one, two, three, four or five —CH₃; and R¹ is —CH₃.

In certain embodiments, the present invention relates to any of the aforementioned compounds, wherein W is

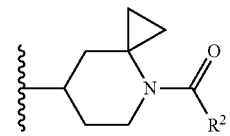

optionally substituted with one, two, three, four or five —CH₃; R¹ is —CH₃; and Y is —CH₃.

In certain embodiments, the present invention relates to any of the aforementioned compounds, wherein W is

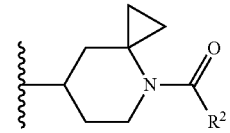

optionally substituted with one, two, three, four or five —CH₃; R¹ is —CH₃; and Y is —CF₃.

In certain embodiments, the present invention relates to any of the aforementioned compounds, wherein W is

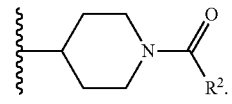

In certain embodiments, the present invention relates to any of the aforementioned compounds, wherein W is

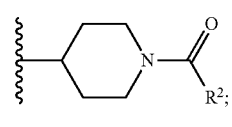

and R¹ is —CH₃.

In certain embodiments, the present invention relates to any of the aforementioned compounds, wherein W is

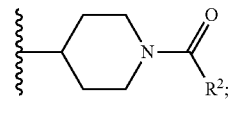

R¹ is —CH₃; and Y is —CH₃.

In certain embodiments, the present invention relates to any of the aforementioned compounds, wherein W is

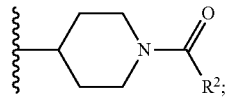

$R^1$ is —CH$_3$; and Y is —CF$_3$.

In certain embodiments, the present invention relates to any of the aforementioned compounds, wherein W is

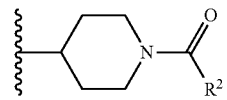

substituted with one —CH$_3$.

In certain embodiments, the present invention relates to any of the aforementioned compounds, wherein W is

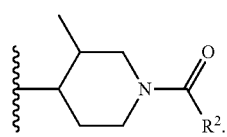

In certain embodiments, the present invention relates to any of the aforementioned compounds, wherein W is

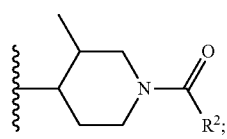

and $R^1$ is —CH$_3$.

In certain embodiments, the present invention relates to any of the aforementioned compounds, wherein W is

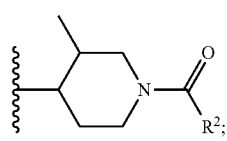

$R^1$ is —CH$_3$; and Y is —CH$_3$.

In certain embodiments, the present invention relates to any of the aforementioned compounds, wherein W is

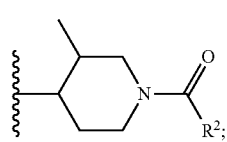

$R^1$ is —CH$_3$; and Y is —CF$_3$.

In certain embodiments, the present invention relates to any of the aforementioned compounds, wherein W is

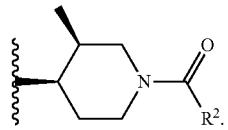

In certain embodiments, the present invention relates to any of the aforementioned compounds, wherein W is

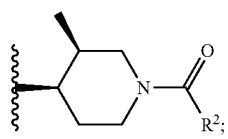

and $R^1$ is —CH$_3$.

In certain embodiments, the present invention relates to any of the aforementioned compounds, wherein W is

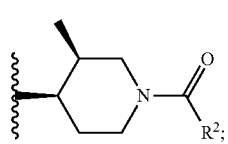

$R^1$ is —CH$_3$; and Y is —CH$_3$.

In certain embodiments, the present invention relates to any of the aforementioned compounds, wherein W is

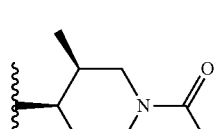

$R^1$ is —CH$_3$; and Y is —CF$_3$.

In certain embodiments, the present invention relates to any of the aforementioned compounds, wherein W is

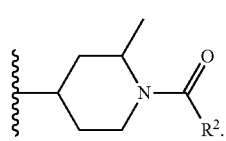

In certain embodiments, the present invention relates to any of the aforementioned compounds, wherein W is

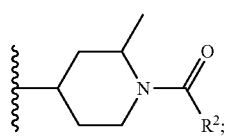

and $R^1$ is —CH$_3$.

In certain embodiments, the present invention relates to any of the aforementioned compounds, wherein W is

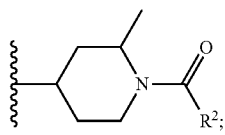

R¹ is —CH₃; and Y is —CH₃.

In certain embodiments, the present invention relates to any of the aforementioned compounds, wherein W is

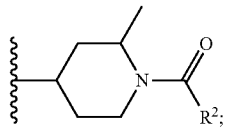

R¹ is —CH₃; and Y is —CF₃.

In certain embodiments, the present invention relates to any of the aforementioned compounds, wherein W is

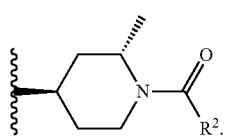

In certain embodiments, the present invention relates to any of the aforementioned compounds, wherein W is

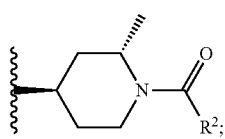

and R¹ is —CH₃.

In certain embodiments, the present invention relates to any of the aforementioned compounds, wherein W is

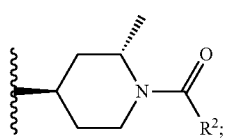

R¹ is —CH₃; and Y is —CH₃.

In certain embodiments, the present invention relates to any of the aforementioned compounds, wherein W is

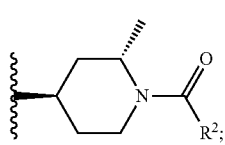

R¹ is —CH₃; and Y is —CF₃.

In certain embodiments, the present invention relates to any of the aforementioned compounds, wherein W is

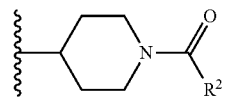

substituted with two —CH₃.

In certain embodiments, the present invention relates to any of the aforementioned compounds, wherein W is

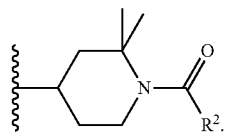

In certain embodiments, the present invention relates to any of the aforementioned compounds, wherein W is

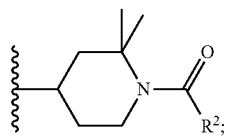

and R¹ is —CH₃.

In certain embodiments, the present invention relates to any of the aforementioned compounds, wherein W is

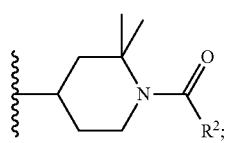

R¹ is —CH₃; and Y is —CH₃.

In certain embodiments, the present invention relates to any of the aforementioned compounds, wherein W is

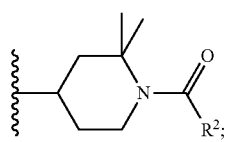

R¹ is —CH₃; and Y is —CF₃.

In certain embodiments, the present invention relates to any of the aforementioned compounds, wherein W is

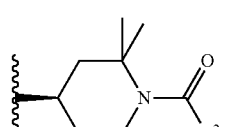

In certain embodiments, the present invention relates to any of the aforementioned compounds, wherein W is

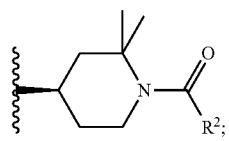

and R¹ is —CH₃.

In certain embodiments, the present invention relates to any of the aforementioned compounds, wherein W is

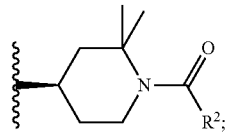

R¹ is —CH₃; and Y is —CH₃.

In certain embodiments, the present invention relates to any of the aforementioned compounds, wherein W is

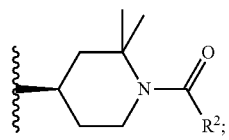

R¹ is —CH₃; and Y is —CF₃.

In certain embodiments, the present invention relates to any of the aforementioned compounds, wherein X is unsubstituted phenyl.

In certain embodiments, the present invention relates to any of the aforementioned compounds, wherein X is phenyl substituted with one, two, three, four or five substituents independently selected from the group consisting of —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is phenyl substituted with one substituent selected from the group consisting of with —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is phenyl substituted with two substituents independently selected from the group consisting of —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is phenyl substituted with three substituents independently selected from the group consisting of —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is phenyl substituted with four substituents independently selected from the group consisting of —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is phenyl substituted with five substituents independently selected from the group consisting of —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is phenyl substituted with —CN and optionally substituted with one or two substituents independently selected from the group consisting of —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is phenyl substituted with —Cl and optionally substituted with one or two substituents independently selected from the group consisting of —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is

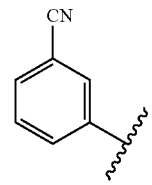 [SMILES: *c1cccc(C#N)c1]

optionally substituted with one additional substituent selected from the group consisting of —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is

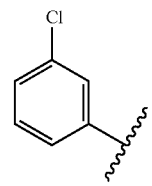

substituted with one additional substituent selected from the group consisting of —CH₃, —CH₂CH₃, —CH₂OH, —OH, —OCH₃, —SCH₃, —OCH₂CH₃, —OCH₂CH₂OH, —OCH₂CH₂OCH₃, —F, —Cl, —Br and —CN.

In certain embodiments, the present invention relates to any of the aforementioned compounds, wherein X is

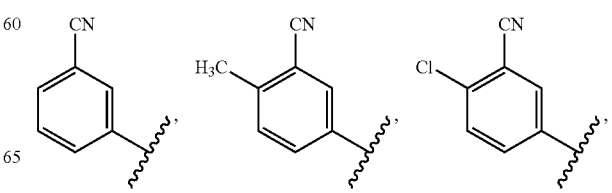

-continued

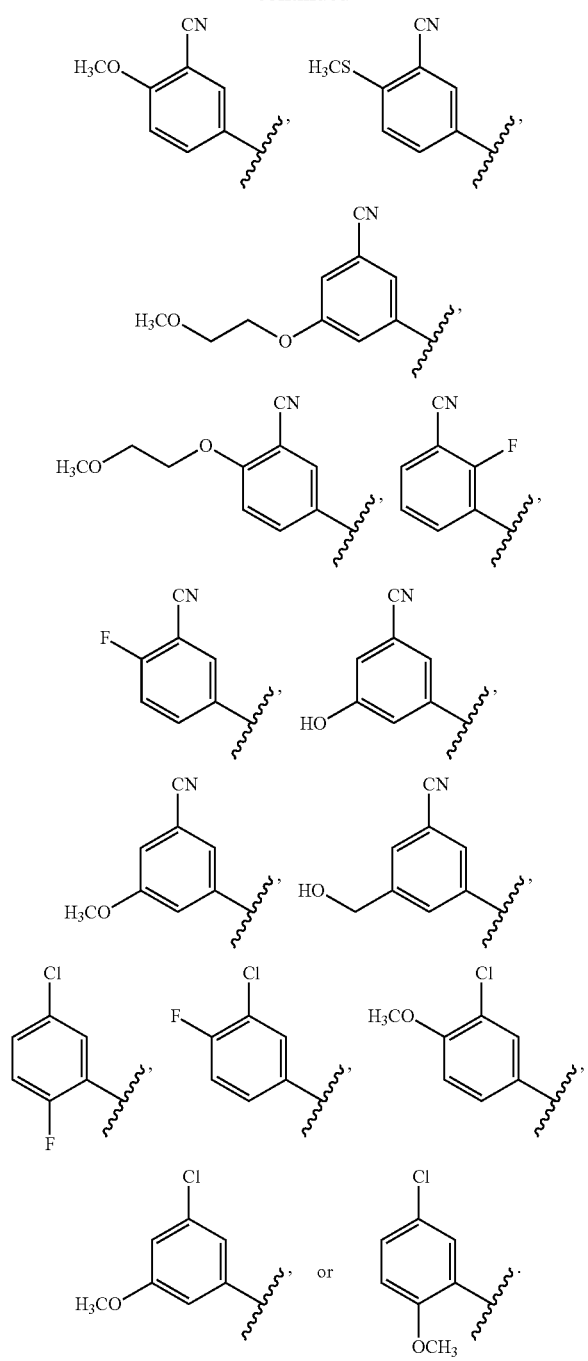

In certain embodiments, the present invention relates to any of the aforementioned compounds, wherein X is

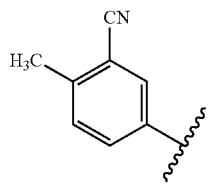

In certain embodiments, the present invention relates to any of the aforementioned compounds, wherein X is

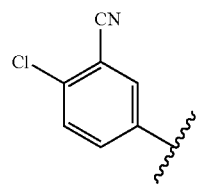

In certain embodiments, the present invention relates to any of the aforementioned compounds, wherein X is

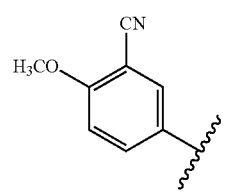

In certain embodiments, the present invention relates to any of the aforementioned compounds, wherein X is

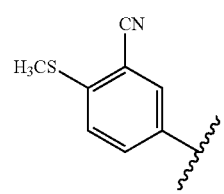

In certain embodiments, the present invention relates to any of the aforementioned compounds, wherein X is

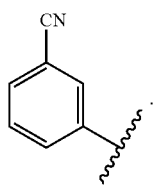

In certain embodiments, the present invention relates to any of the aforementioned compounds, wherein X is

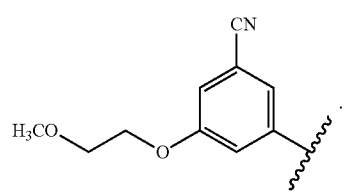 [SMILES: *c1cc(C#N)cc(OCCOC)c1]

In certain embodiments, the present invention relates to any of the aforementioned compounds, wherein X is

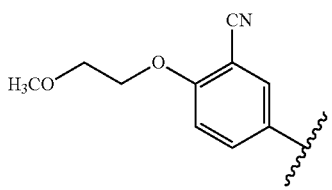

In certain embodiments, the present invention relates to any of the aforementioned compounds, wherein X is

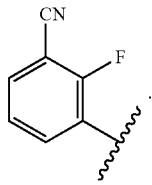 [SMILES: *c1cccc(C#N)c1F]

In certain embodiments, the present invention relates to any of the aforementioned compounds, wherein X is

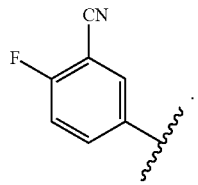

In certain embodiments, the present invention relates to any of the aforementioned compounds, wherein X is

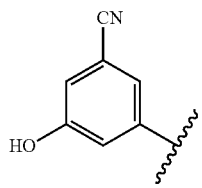

In certain embodiments, the present invention relates to any of the aforementioned compounds, wherein X is

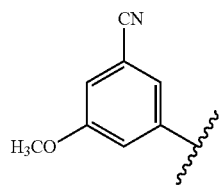

In certain embodiments, the present invention relates to any of the aforementioned compounds, wherein X is

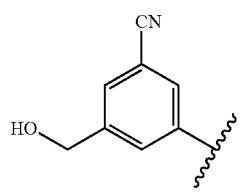

In certain embodiments, the present invention relates to any of the aforementioned compounds, wherein X is

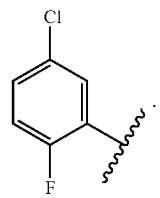 [SMILES: *c1cc(Cl)ccc1F]

In certain embodiments, the present invention relates to any of the aforementioned compounds, wherein X is

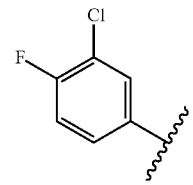

In certain embodiments, the present invention relates to any of the aforementioned compounds, wherein X is

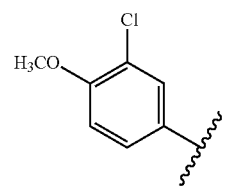

In certain embodiments, the present invention relates to any of the aforementioned compounds, wherein X is

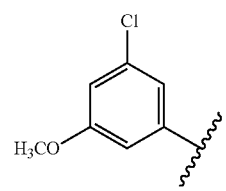

In certain embodiments, the present invention relates to any of the aforementioned compounds, wherein X is

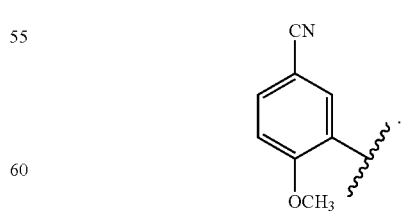

In certain embodiments, the present invention relates to any of the aforementioned compounds, wherein $R^2$ is $(C_1$-$C_6)$alkyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is unsubstituted $(C_1\text{-}C_6)$alkyl. In certain embodiments, the present invention relates to any of the aforementioned compounds, wherein $R^2$ is unsubstituted branched $(C_1\text{-}C_6)$alkyl.

In certain embodiments, the present invention relates to any of the aforementioned compounds, wherein $R^2$ is $(C_1\text{-}C_3)$alkyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is methyl optionally substituted with one, two or three substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is ethyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is n-propyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is i-propyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is methyl substituted with $(C_3\text{-}C_6)$cycloalkyl.

In certain embodiments, the present invention relates to any of the aforementioned compounds, wherein $R^2$ is ethyl substituted with —$CF_3$.

In certain embodiments, the present invention relates to any of the aforementioned compounds, wherein $R^2$ is ethyl substituted with —OH and —$CF_3$.

In certain embodiments, the present invention relates to any of the aforementioned compounds, wherein $R^2$ is ethyl substituted with cycloalkyl.

In certain embodiments, the present invention relates to any of the aforementioned compounds, wherein $R^2$ is $(C_3\text{-}C_{10})$cycloalkyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is unsubstituted $(C_3\text{-}C_{10})$cycloalkyl.

In certain embodiments, the present invention relates to any of the aforementioned compounds, wherein $R^2$ is cyclopropyl optionally substituted with one, two, three or four substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is cyclobutyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is cyclopentyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is cyclohexyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is cycloheptyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is cyclooctyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is phenyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is phenyl optionally substituted with one, two, three, four or five substitutents independently selected for each occurrence from the group consisting of —F, —Cl, —Br, —OH and —$CH_3$.

In certain embodiments, the present invention relates to any of the aforementioned compounds, wherein $R^2$ is indanyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is unsubstituted indanyl.

In certain embodiments, the present invention relates to any of the aforementioned compounds, wherein $R^2$ is tetrahydrothiophenyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein $R^2$ is unsubstituted tetrahydrothiophenyl.

In certain embodiments, the present invention relates to any of the aforementioned compounds, wherein $R^2$ is thietanyl optionally substituted with one, two, three, four or five substitutents independently selected for each occurrence from the group consisting of —F, —Cl, —Br, —OH, $(C_1\text{-}C_3)$alkyl, $(C_1\text{-}C_3)$haloalkyl and $(C_3\text{-}C_{10})$cycloalkyl.

In certain embodiments, the present invention relates to any of the aforementioned compounds, wherein R² is unsubstituted thietanyl.

In certain embodiments, the present invention relates to any of the aforementioned compounds, wherein R² is

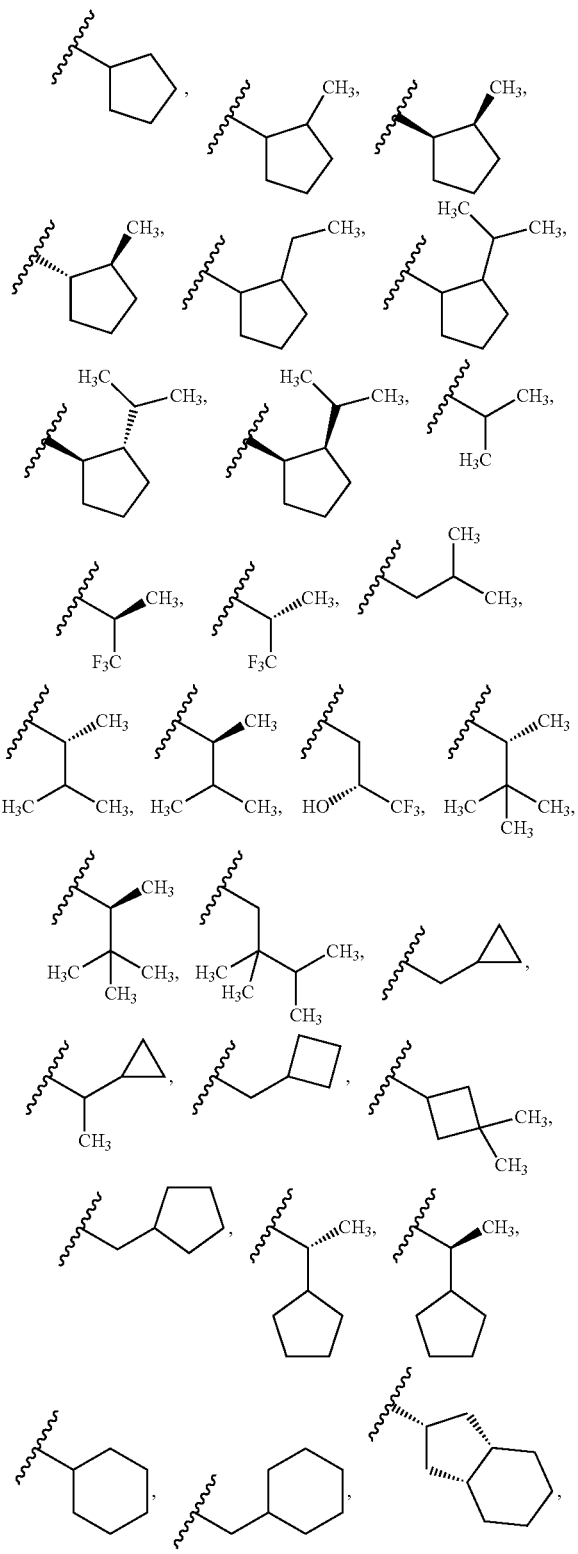

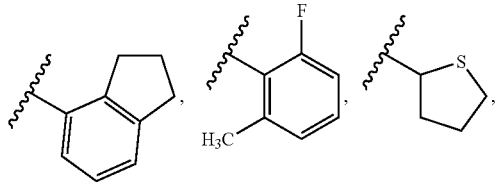

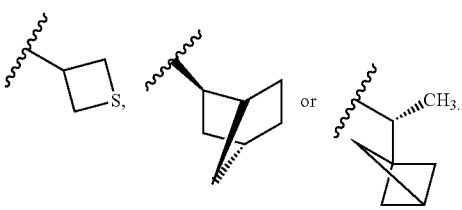

In certain embodiments, the present invention relates to any of the aforementioned compounds, wherein R² is

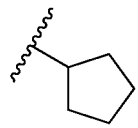

In certain embodiments, the present invention relates to any of the aforementioned compounds, wherein R² is

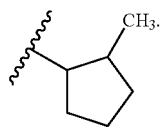 [SMILES: *C1CCCC1C]

In certain embodiments, the present invention relates to any of the aforementioned compounds, wherein R² is

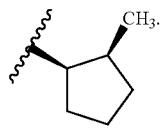 [SMILES: *[C@@H]1CCC[C@@H]1C]

In certain embodiments, the present invention relates to any of the aforementioned compounds, wherein R² is

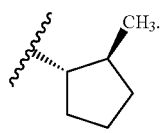 [SMILES: *[C@H]1CCC[C@@H]1C]

In certain embodiments, the present invention relates to any of the aforementioned compounds, wherein R² is

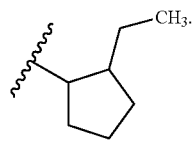 [SMILES: *C1CCCC1CC]

In certain embodiments, the present invention relates to any of the aforementioned compounds, wherein $R^2$ is

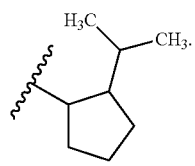 [SMILES: *C1CCCC1C(C)C]

In certain embodiments, the present invention relates to any of the aforementioned compounds, wherein $R^2$ is

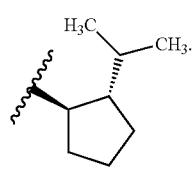 [SMILES: *[C@@H]1CCC[C@H]1C(C)C]

In certain embodiments, the present invention relates to any of the aforementioned compounds, wherein $R^2$ is

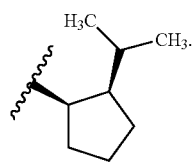 [SMILES: *[C@@H]1CCC[C@@H]1C(C)C]

In certain embodiments, the present invention relates to any of the aforementioned compounds, wherein $R^2$ is

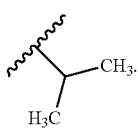

In certain embodiments, the present invention relates to any of the aforementioned compounds, wherein $R^2$ is

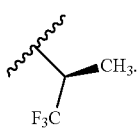

In certain embodiments, the present invention relates to any of the aforementioned compounds, wherein $R^2$ is

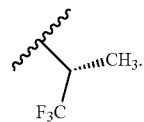

In certain embodiments, the present invention relates to any of the aforementioned compounds, wherein $R^2$ is

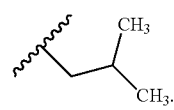

In certain embodiments, the present invention relates to any of the aforementioned compounds, wherein $R^2$ is

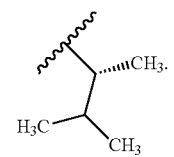

In certain embodiments, the present invention relates to any of the aforementioned compounds, wherein $R^2$ is

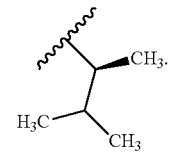 [SMILES: *[C@@H](C)C(C)C]

In certain embodiments, the present invention relates to any of the aforementioned compounds, wherein $R^2$ is

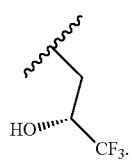

In certain embodiments, the present invention relates to any of the aforementioned compounds, wherein $R^2$ is

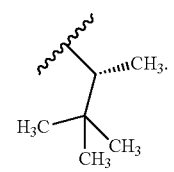

In certain embodiments, the present invention relates to any of the aforementioned compounds, wherein $R^2$ is

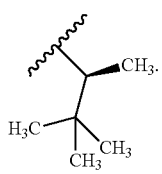

In certain embodiments, the present invention relates to any of the aforementioned compounds, wherein R² is

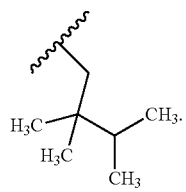

In certain embodiments, the present invention relates to any of the aforementioned compounds, wherein R² is

In certain embodiments, the present invention relates to any of the aforementioned compounds, wherein R² is

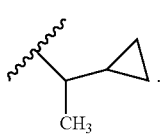

In certain embodiments, the present invention relates to any of the aforementioned compounds, wherein R² is

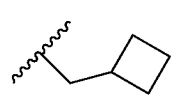

In certain embodiments, the present invention relates to any of the aforementioned compounds, wherein R² is

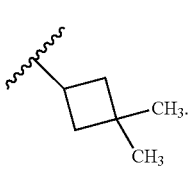

In certain embodiments, the present invention relates to any of the aforementioned compounds, wherein R² is

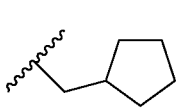

In certain embodiments, the present invention relates to any of the aforementioned compounds, wherein R² is

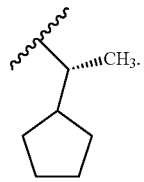 [SMILES: *[C@H](C)C1CCCC1]

In certain embodiments, the present invention relates to any of the aforementioned compounds, wherein R² is

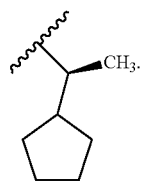 [SMILES: *[C@@H](C)C1CCCC1]

In certain embodiments, the present invention relates to any of the aforementioned compounds, wherein R² is

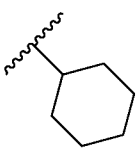

In certain embodiments, the present invention relates to any of the aforementioned compounds, wherein R² is

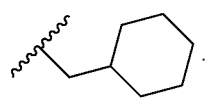 [SMILES: *CC1CCCCC1]

In certain embodiments, the present invention relates to any of the aforementioned compounds, wherein R² is

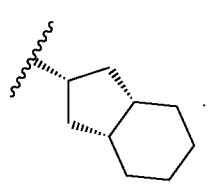 [SMILES: *[C@H]1C[C@H]2CCCC[C@H]2C1]

In certain embodiments, the present invention relates to any of the aforementioned compounds, wherein R² is

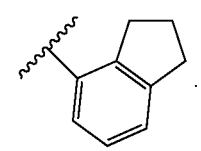 [SMILES: *c1cccc2c1CCC2]

In certain embodiments, the present invention relates to any of the aforementioned compounds, wherein R² is

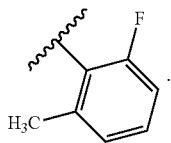

In certain embodiments, the present invention relates to any of the aforementioned compounds, wherein R² is

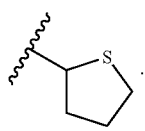

In certain embodiments, the present invention relates to any of the aforementioned compounds, wherein R² is

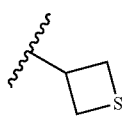

In certain embodiments, the present invention relates to any of the aforementioned compounds, wherein R² is

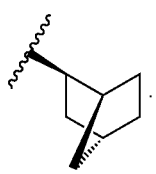 [SMILES: *[C@@H]1C[C@@H]2CC[C@H]1C2]

In certain embodiments, the present invention relates to any of the aforementioned compounds, wherein R² is

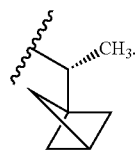 [SMILES: *[C@H](C)C12CC(C1)C2]

Another embodiment of the invention is a compound selected from the group consisting of the compounds of Examples 1-100, 109-113 and pharmaceutically acceptable salts thereof.

Therapeutic Applications

It is contemplated that the compounds of Formula I provide therapeutic benefits to subjects suffering from an immune disorder or inflammatory disorder. Accordingly, one aspect of the invention provides a method of treating a disorder selected from the group consisting of an immune disorder or inflammatory disorder. The method comprises administering a therapeutically effective amount of a compound of Formula I to a subject in need thereof to ameliorate a symptom of the disorder, wherein Formula I are as described above. In certain embodiments, the particular compound of Formula I is a compound defined by one of the embodiments described above.

In certain embodiments, the disorder is an immune disorder. In certain other embodiments, the disorder is an inflammatory disorder. In certain other embodiments, the disorder is an autoimmune disorder. In certain other embodiments, the disorder is rheumatoid arthritis, psoriasis, chronic graft-versus-host disease, acute graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, or epidermal hyperplasia.

In certain other embodiments, the disorder is cartilage inflammation, bone degradation, arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, dermatomyositis, psoriatic arthritis, vasculitis, myositis, polymyositis, osteoarthritis, polyarteritis nodosa, Wegener's granulomatosis, arteritis, polymyalgia rheumatica, sarcoidosis, sclerosis, primary biliary sclerosis, sclerosing cholangitis, dermatitis, atopic dermatitis, atherosclerosis, Still's disease, chronic obstructive pulmonary disease, Guillain-Barre disease, Type I diabetes mellitus, Graves' disease, Addison's disease, Raynaud's phenomenon, autoimmune hepatitis, psoriatic epidermal hyperplasia, plaque psoriasis, guttate psoriasis, inverse psoriasis, pustular psoriasis, erythrodermic psoriasis, giant cell arteritis, nonalcoholic hepatic steatosis, or an immune disorder associated with or arising from activity of pathogenic lymphocytes.

In certain embodiments, the psoriasis is plaque psoriasis, guttate psoriasis, inverse psoriasis, pustular psoriasis, or erythrodermic psoriasis.

In certain other embodiments, the disorder is noninfectious uveitis, Behcet's disease or Vogt-Koyanagi-Harada syndrome.

Another aspect of the invention provides for the use of a compound of Formula I in the manufacture of a medicament. In certain embodiments, the medicament is for treating a disorder described herein.

Another aspect of the invention provides for the use of a compound of Formula I for treating a medical disorder, such a medical disorder described herein.

Further, it is contemplated that compounds of Formula I can inhibit the activity of RORγ. Accordingly, another aspect of the invention provides a method of inhibiting the activity of RORγ. The method comprises exposing a RORγ to an effective amount of a compound of Formula I to inhibit said RORγ, wherein Formula I is as described above. In certain embodiments, the particular compounds of Formula I are the compound defined by one of the embodiments described herein.

Further, it is contemplated that compounds of Formula I can reduce the amount of interleukin-17 (IL-17) in a subject. IL-17 is a cytokine that affects numerous biological functions, including inducing and mediating pro-inflammatory responses. Accordingly, another aspect of the invention provides a method of reducing the amount of IL-17 in a subject. The method comprises administering to a subject an effective amount of a compound of I to reduce the amount of IL-17 in the subject, wherein Formula I is as described above. In certain embodiments, the particular compounds of Formula I are the compounds defined by one of the embodiments described herein.

In certain embodiments, the subject is a human. In certain embodiments, administering the compound reduces the amount of IL-17 produced by Th-17 cells in the subject. A change in the amount of IL-17 produced by, for example, Th-17 cells can be measured using procedures described in the literature, such as an ELISA assay or intracellular staining assay.

Further, it is contemplated that compounds of Formula I may inhibit the synthesis of IL-17 in a subject. Accordingly, another aspect of the invention provides a method of inhibiting the synthesis IL-17 in a subject. The method comprises administering to a subject an effective amount of a compound of Formula I to inhibit the synthesis IL-17 in the subject, wherein Formula I is as described above. In certain embodiments, the particular compounds of Formula I are the compounds defined by one of the embodiments described herein.

The description above describes multiple embodiments providing definitions for variables used herein. The application specifically contemplates all combinations of such variables.

Combination Therapy

Another aspect of the invention provides for combination therapy. For example, the compounds of Formula I or their pharmaceutically acceptable salts may be used in combination with additional therapeutic agents to treat medical disorders, such as medical disorders associated with inappropriate IL-17 pathway activity. Exemplary additional therapeutic agents include, for example, (1) a TNF-α inhibitor; (2) a non-selective COX-I/COX-2 inhibitor; (3) a selective COX-2 inhibitor, such as celecoxib and rofecoxib; (4) other agents for treating inflammatory disease and autoimmune disease including, for example, methotrexate, leflunomide, sulfasalazine, azathioprine, penicillamine, bucillamine, actarit, mizoribine, lobenzarit, hydroxychloroquine, d-penicillamine, aurothiomalate, auranofin, parenteral gold, oral gold, cyclophosphamide, Lymphostat-B, a BAFF/APRIL inhibitor, CTLA-4-Ig, or a mimetic of CTLA-4-Ig; (5) a leukotriene biosynthesis inhibitor, such as a 5-lipoxygenase (5-LO) inhibitor, or a 5-lipoxygenase activating protein (FLAP) antagonist; (6) a LTD4 receptor antagonist; (7) a phosphodiesterase type IV (PDE-IV) inhibitor, such as cilomilast (ariflo) or roflumilast; (8) an antihistamine HI receptor antagonist; (9) an od- and oc2-adrenoceptor agonist; (10) an anticholinergic agent; (11) a β-adrenoceptor agonist; (12) an insulin-like growth factor type I (IGF-1) mimetic; (13) a glucocorticosoid; (14) a kinase inhibitor such as an inhibitor of a Janus Kinase (e.g., JAK 1 and/or JAK2 and/or JAK 3 and/or TYK2), p38 MAPK, Syk or IKK2; (15) a B-cell target biologic such as rituximab; (16) a selective co-stimulation modulator such as abatacept; (17) an interleukin inhibitor or interleukin receptor inhibitor, such as the IL-1 inhibitor anakinra, IL-6 inhibitor tocilizumab, and IL12/IL-23 inhibitor ustekimumab; (18) an anti-IL17 antibody, anti-IL21 antibody, or anti-IL22 antibody (19) a S1P1 agonist, such as fingolimod; (20) an interferon, such as interferon beta 1; (21) an integrin inhibitor such as natalizumab; (22) a mTOR inhibitor such as rapamycin, cyclosporin and tacrolimus; (23) a non-steroidal antiinflammatory agent (NSAID), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and pyrazolones (apazone, bezpiperylon, feprazone, mofebutazone, oxyphenbutazone, phenylbutazone); (24) a NRF2 pathway activator, such as the fumaric acid derivative, BG-12; and (25) a chemokine or chemokine receptor inhibitor, such as a CCR9 antagonist.

In certain embodiments, the additional therapeutic agent is selected from the group consisting of corticosteroids, vitamin D3, anthralin and retinoids. In certain embodiments, the additional therapeutic agent is a corticosteroid. In certain embodiments, the additional therapeutic agent is vitamin D3. In certain embodiments, the additional therapeutic agent is anthralin. In certain embodiments, the additional therapeutic agent is a retinoid.

The amount of the compounds of Formula I and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a compound of Formula I may be administered during a time when the additional therapeutic agent(s) exerts its prophylactic or therapeutic effect, or vice versa.

The doses and dosage regimen of the active ingredients used in the combination therapy may be determined by an attending clinician. In certain embodiments, the compound of Formula I and the additional therapeutic agent(s) are administered in doses commonly employed when such agents are used as monotherapy for treating the disorder. In other embodiments, the compound of Formula I and the additional therapeutic agent(s) are administered in doses lower than the doses commonly employed when such agents are used as monotherapy for treating the disorder. In certain embodiments, a compound of Formula I and the additional therapeutic agent(s) are present in the same composition, which is suitable for oral administration.

In certain embodiments, the compound of Formula I and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of a compound of Formula I, a pharmaceutically acceptable carrier, vehicle or diluent, and optionally at least one additional therapeutic agent listed above.

Pharmaceutical Compositions and Dosing Considerations

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts. The term "therapeutically effective amount" as used herein refers to that amount of the compound being administered which will relieve to some extent one or more of the symptoms of the disorder being treated.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The invention also includes pharmaceutical compositions utilizing one or more of the present compounds along with one or more pharmaceutically acceptable carriers, excipients, vehicles, etc.

Topical formulations of the presently disclosed compounds may be administered topically, (intra)dermally, or transdermally to the skin or mucosa. Topical administration using such preparations encompasses all conventional methods of administration across the surface of the body and the inner linings of body passages including epithelial and mucosal tissues, including transdermal, epidermal, buccal, pulmonary, ophthalmic, intranasal, vaginal and rectal modes of administration. Typical formulations for this purpose include gels, hydrogels, lotions, solutions, creams, colloid, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Such topical formulations may be prepared in combination with additional pharmaceutically acceptable excipients.

In certain embodiments, a penetration enhancer may be used. Examples of penetration enhancers include, for example, saturated C10-C18 fatty alcohols (such as decyl alcohol, lauryl alcohol, myristyl alcohol, cetyl alcohol and stearyl alcohol), cis-unsaturated C10-C18 fatty alcohols (such as oleyl alcohol, linoleyl alcohol, γ-linolenyl alcohol and linolenyl alcohol), C10-C18 fatty acids (which when saturated may include capric acid, lauric acid, myristic acid, palmitic acid, stearic acid and arachidic acid), cis-unsaturated fatty acids (such as palmitoleic acid (cis-9-hexadecenoic acid), oleic acid (cis-9-octadecenoic acid), cis-vaccenic acid (cis-11-octadecenoic acid), linoleic acid (cis-9,12-octadecadienoic acid), γ-linolenic acid (cis-6,9,12-octadecatrienoic acid), linolenic acid (cis-9,12,15-octadecatrienoic acid) and arachidonic acid (cis-5,8,11,14-eicosatetraenoic acid)). In certain embodiments, the penetration enhancers may be used amounts ranging from about 0.1 to about 5% (w/v).

In certain embodiments, topical formulations which contain one or more compounds of the invention in therapeutically effective amounts that may be given in daily or twice daily doses to patients in need.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Other excipients which enhance the stability of the formulations include aldehyde scavengers, such as glycerine and propylene glycol, and antioxidants, such as butyl hydroxyanisole (BHA), butyl hydroxytoluene (BHT), propyl gallate, ascorbic acid (Vitamin C), polyphenols, tocopherols (Vitamin E), and their derivatives.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Formulations suitable for topical administration to the eye include, for example, eye drops wherein the compound of this invention is dissolved or suspended in a suitable carrier. A typical formulation suitable for ocular or aural administration may be in the form of drops of a micronised suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg.

When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. In certain embodiments, preferred dosing is one administration per day.

The invention further provides a unit dosage form (such as a tablet or capsule) comprising a compound of Formula I or a specific compound described herein, or pharmaceutically acceptable salts thereof, in a therapeutically effective amount for the treatment of an immune or inflammatory disorder, such as one of the particular immune disorders or inflammatory disorders described herein.

General Synthetic Schemes and Procedures

The compounds of Formula I may be prepared by the methods described below, together with synthetic methods known in the art of organic chemistry, or modifications and derivatizations that are familiar to those of ordinary skill in the art. The starting materials used herein are commercially available or may be prepared by routine methods known in the art (such as those methods disclosed in standard reference books such as the COMPENDIUM OF ORGANIC SYNTHETIC METHODS, Vol. I-VI (published by Wiley-Interscience)). Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference.

Compounds of Formula I or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Compounds of Formula I may be prepared as single enantiomer or as a mixture of individual enantiomers which includes racemic mixtures. Methods to obtain preferentially a single enantiomer from a mixture of individual enantiomers or a racemic mixture are well known to those ordinarily skilled in the art of organic chemistry. Such methods include but are not limited to preferential crystallization of diastereomeric salts (e.g. tartrate or camphor sulfonate), covalent derivatization by a chiral, non-racemic reagent followed by separation of the resulting diastereomers by common methods (e.g. crystallization, chromatographic separation, or distillation) and chemical reversion to scalemic compound, Simulated Moving Bed technology, or high/medium-pressure liquid chromatography or supercritical fluid chromatography employing a chiral stationary phase. These techniques may be performed on the final compounds of the invention or on any intermediates to compounds of the invention which bear a stereogenic center. Also, to facilitate separation by any of the methods described above, the compounds of the invention or any intermediates to the compounds of the invention which bear a stereogenic center may be transiently reacted with an achiral reagent, separated, and then reverted to scalemic compound by standard synthetic techniques.

Compounds of Formula (I) may be prepared as described in Scheme A. Cross-coupling of aryl halides A-1 (prepared as described in Schemes B-C) with vinyl boronates (prepared as described in Scheme D) or vinyl boronic acids affords compounds of the Formula A-2. Subsequent reduction of the nitro group and the olefin furnished compounds of Formula A-3. The resulting amine A-3 may be transformed to amides by the reaction with acid chlorides in the presence of base or carboxylic acids with appropriate coupling agents to afford compounds of Formula A-4.

SCHEME A

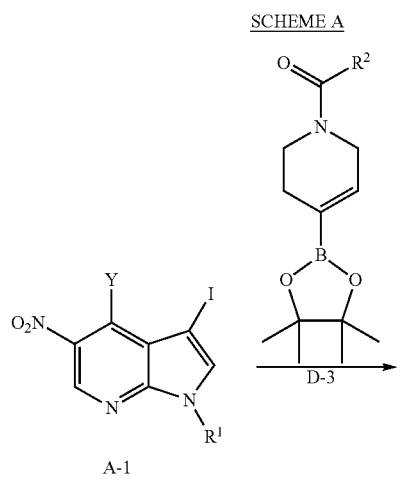

The intermediate of Formula A-1 employed in Scheme A where Y is trifluoromethyl is prepared as described in Scheme B. Transhalogenation of 4-chloro-1H-pyrrolo[2,3-b]pyridine (B-1) employing sodium iodide followed by sulfonylation of the resulting iodide B-2 with phenylsulfonyl chloride and base provides compound B-3. Nitration of B-3 with a tetraalkylammonium salt affords compound B-4 which is then subjected to copper-mediated trifluoromethylation to provide compound B-5. Alkylation of the indole nitrogen by iodomethane or iodoethane in the presence of an inorganic base provides compounds of the Formula A-1 (Y=trifluoromethyl).

SCHEME B

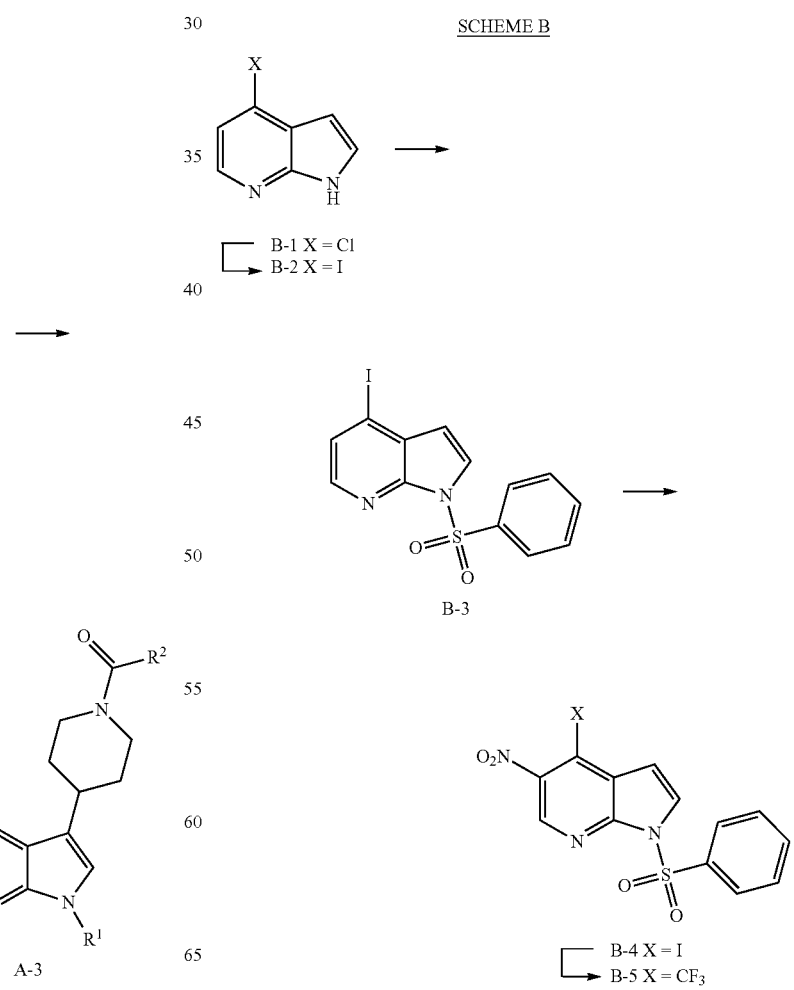

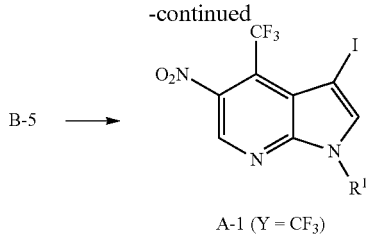

A-1 (Y = CF₃)

The intermediate of Formula A-1 employed in Scheme A where Y is methyl is prepared as described in Scheme C. Nitration of C-1 provides compound C-2 which is then converted to C-3 by the treatment with trimethylaluminum in the presence of a palladium catalyst. Deprotection of the indole nitrogen followed by iodination provided compound C-5. Alkylation of the indole nitrogen by iodomethane or iodoethane in the presence of an inorganic base provides compounds of the Formula A-1 (Y=methyl).

SCHEME C

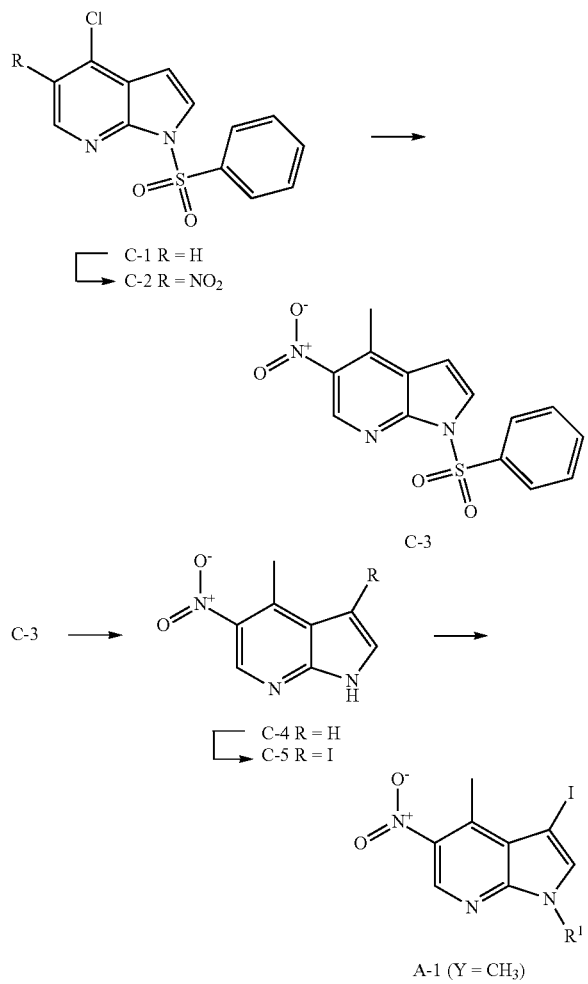

SCHEME D

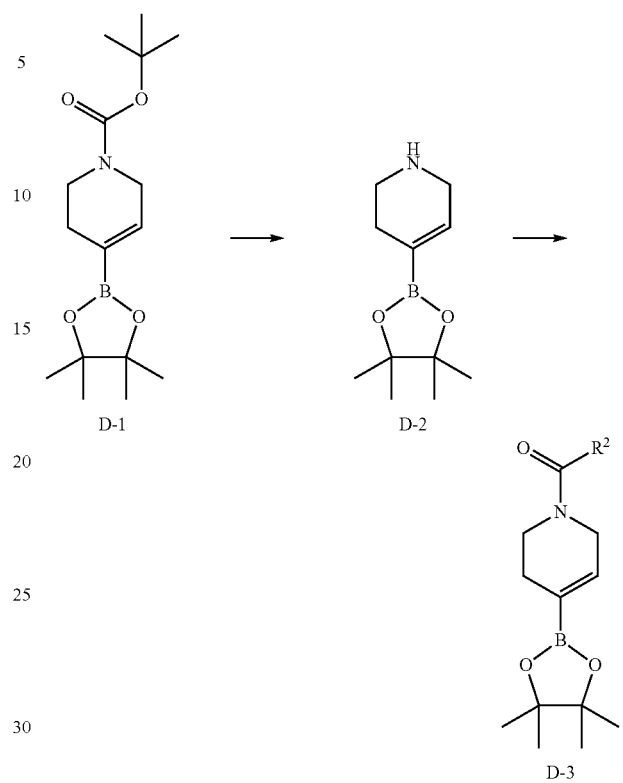

Alternatively, compounds of Formula (I) may be prepared as described in Scheme E. Cross-coupling of aryl halides A-1 (prepared as described in Schemes B-C) with vinyl boronate D-1 followed by reduction of the nitro group and the olefin furnished compounds of the Formula E-2. Subsequent benzoylation of the resulting amine followed by acid-mediated removal of the carbamate functionality provides compounds of the Formula E-4. Acylation of the resulting amine E-4 with acid chlorides (R²COCl) or carboxylic acids (R²CO₂H) provides compounds of the Formula E-5.

SCHEME E

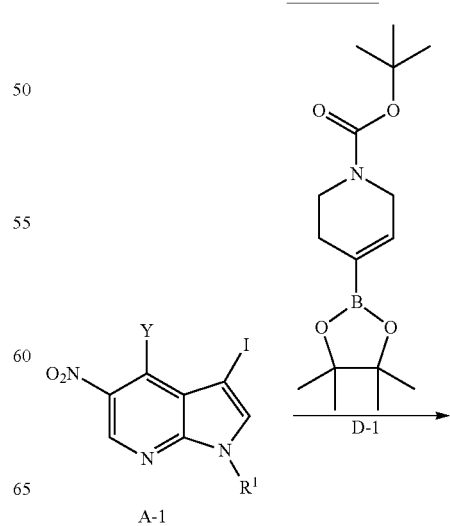

The intermediate of Formula D-3 employed in Scheme A is prepared as described in Scheme D. Acid-mediated removal of the carbamate functionality found in D-1 followed by acylation of the resulting amine with acid chlorides (R²COCl) or carboxylic acids (R²CO₂H) provides compounds of the Formula D-3.

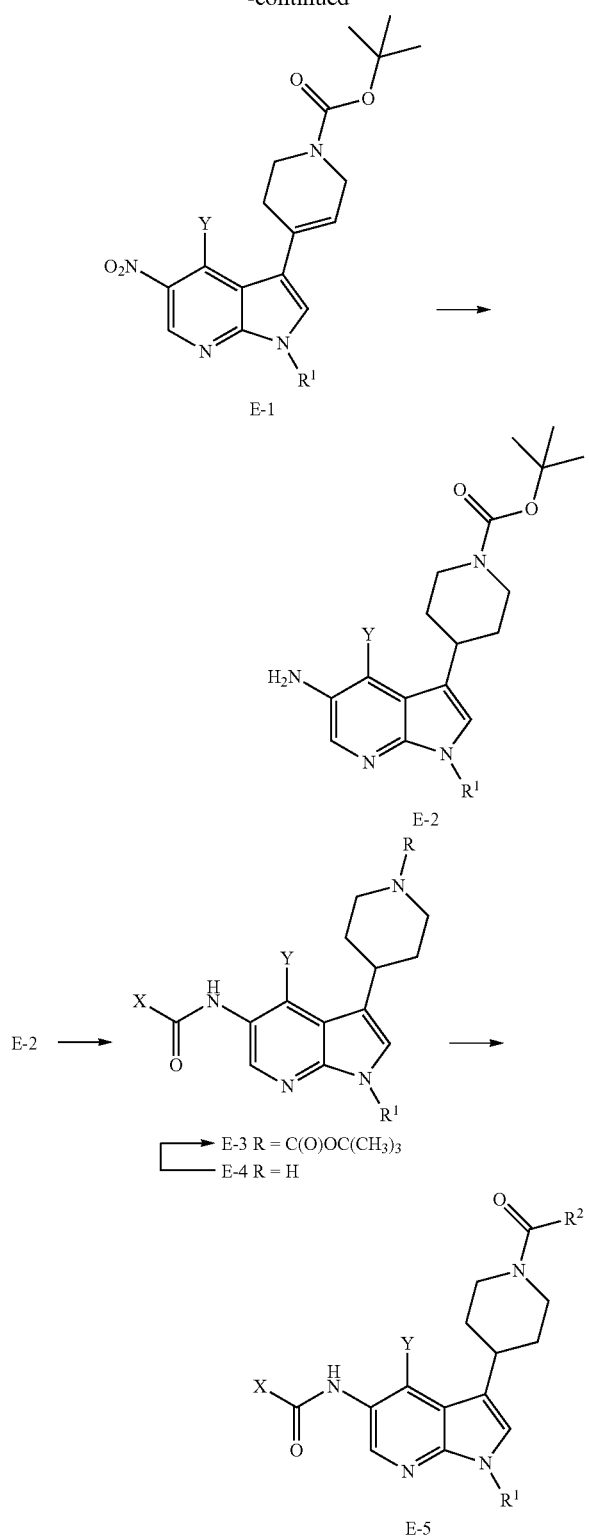

SCHEME F

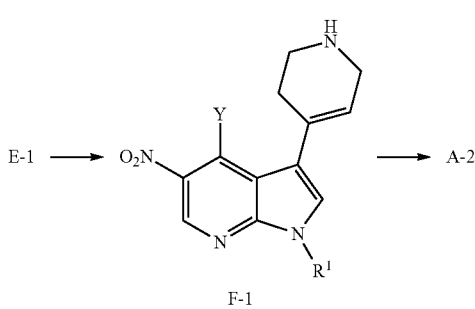

Carboxylic acids of the Formula R²CO₂H employed in Scheme D-E and subsequent Schemes may be commercially available, prepared by procedures described in the literature, or prepared as described in Scheme G. Examples of R²CO₂H prepared by literature procedures include the following: (3ar,7ac)-hexahydro-indan-2ξ-carboxylic acid (Granger, R., et al, Bull. Soc. Chim. Fr. 1968, 1445-50.); 3,3,4-trimethyl-pentanoic acid (Beckwith, A., et al, Australian J. Chem. 1977, 30, 2733-39.); and (1S,2R,4R)-bicyclo[2.2.1]heptane-2-carboxylic acid (Evans, D. A. et al, J. Am. Chem. Soc. 1988, 110, 1238.). (R)-2,3,3-Trimethylbutanoic acid and (S)-2,3,3-trimethylbutanoic acid may be prepared as described by Kido, M. et al Tetrahedron: Asym. 2007, 18, 1934-1947; and thietane acid (see WO2013/7582, which is hereby incorporated by reference for the preparation of thietane acid). The following acids were prepared using procedures which are described in this application: (R)-2-(bicyclo[1.1.1]pentan-1-yl)propanoic acid, (S)-2-(bicyclo[1.1.1]pentan-1-yl)propanoic acid, (R)-2-cyclopentylpropanoic acid, and (S)-2-cyclopentylpropanoic acid. Specific examples of R₂CO₂H according to the Formula G-4 can be prepared from acids G-1 where R may be alkyl, cycloalkyl or aryl which are reacted with an optically active chiral oxazolidinone (e.g. (R)-benzyl oxazolidinone, (R)-4-Isopropyl-2-oxazolidinone) to provide compounds of the Formula G-2. Base mediated alkylation and subsequent removal of the oxazolidinone auxiliary furnishes acids of the Formula G-4 in high optical purity. By employing a chiral oxazolidinone of a different absolute configuration (e.g. (S)-benzyl oxazolidinone, (S)-4-Isopropyl-2-oxazolidinone), chiral acids G-4 of both configurations can be obtained.

Alternatively, compounds of Formula (I) may be prepared as described in Scheme F. Compounds of the Formula E-1 (prepared as described in Scheme E) are treated with acid to afford the corresponding amines F-1. The resulting amine is then reacted with an acid chlorides (R²COCl) in the presence of a base or a carboxylic acids (R²CO₂H) in the

SCHEME G

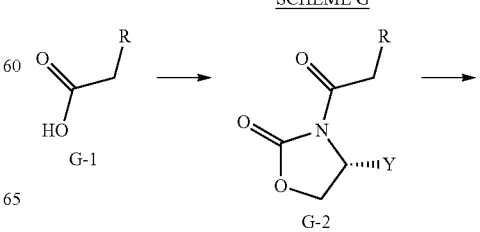

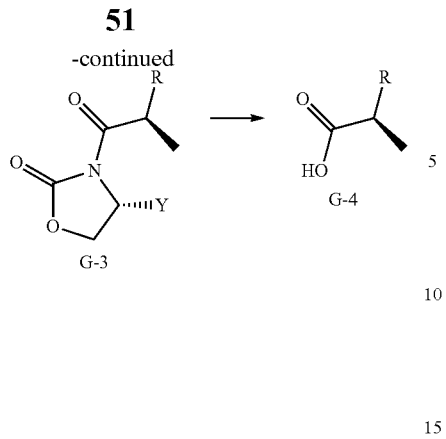

G-3

G-4

Alternatively, compounds of Formula (I) may be prepared as described in Scheme H where R may be one or more methyl substituents or a bridged ethynyl radical. Aryl halides of the Formula A-1 (prepared as described in Schemes B-C) are converted to the corresponding boronates through catalytic methods involving palladium. Cross-coupling of the resulting boronate H-1 with vinyl triflates (prepared as described in Schemes I-N,S) followed by reduction of the nitro group and the olefin affords compounds of the Formula H-4. Subsequent benzoylation of the resulting amine followed by acid-mediated removal of the carbamate functionality provides H-6. Acylation of the resulting amine H-6 with acid chlorides ($R^2COCl$) or carboxylic acids ($R^2CO_2H$) provides compounds of the Formula H-7.

SCHEME H

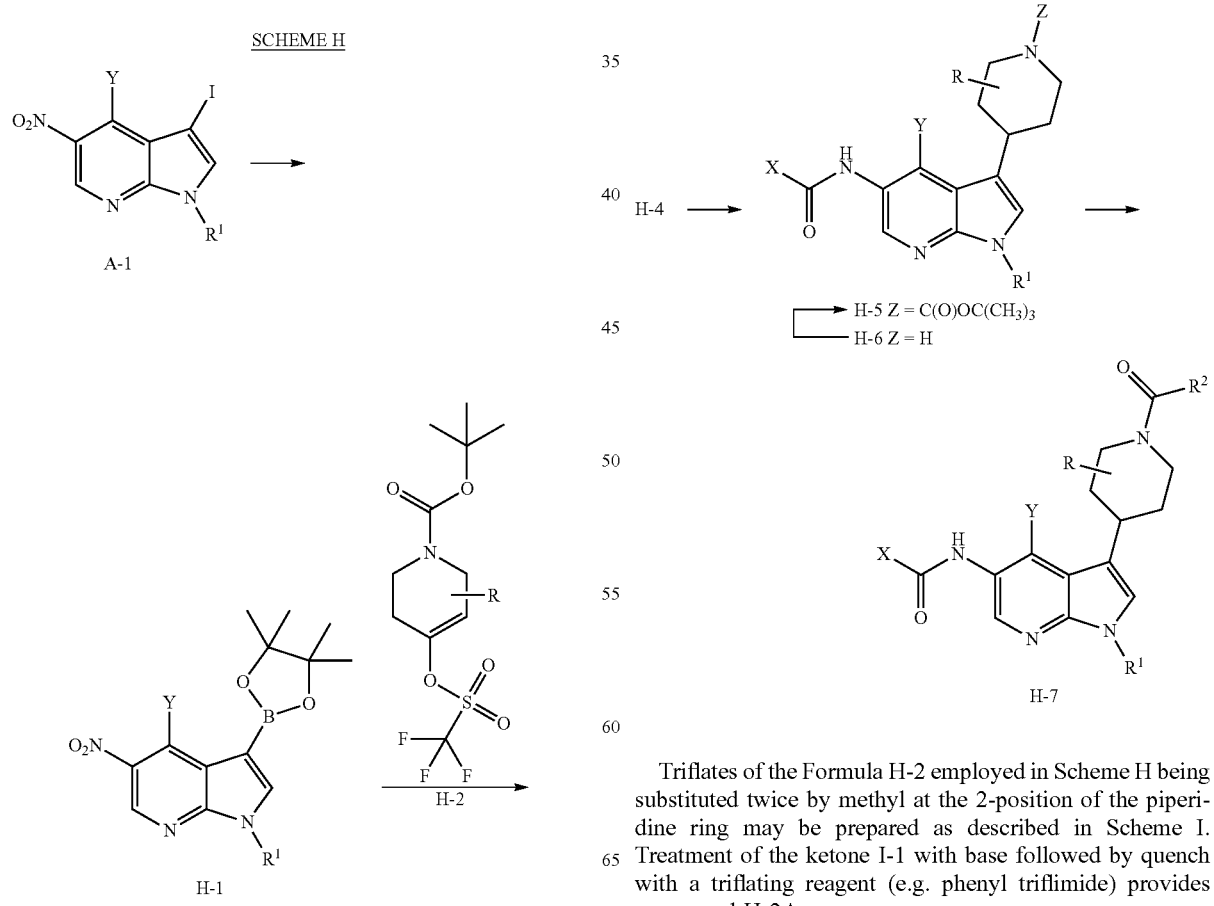

Triflates of the Formula H-2 employed in Scheme H being substituted twice by methyl at the 2-position of the piperidine ring may be prepared as described in Scheme I. Treatment of the ketone I-1 with base followed by quench with a triflating reagent (e.g. phenyl triflimide) provides compound H-2A.

SCHEME I

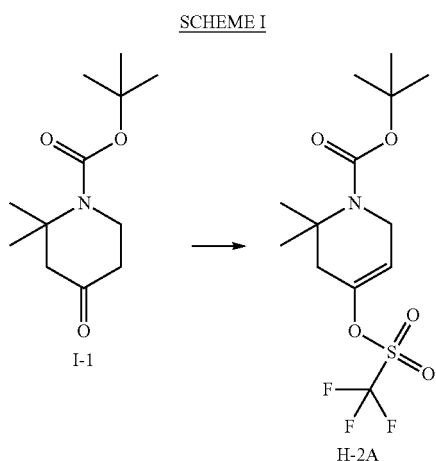

Triflates of the Formula H-2 employed in Scheme H being substituted by methyl at the 3-position of the piperidine ring may be prepared as described in Scheme J. Hydrogenolysis of J-1 affords the corresponding amine J-2 which is then treated with base and reagents capable of generating t-butyl carbamates (e.g. di-tert-butyl dicarbonate) to provide J-3. Treatment of the resulting ketone J-3 with base followed by quench with a triflating reagent (e.g. phenyl triflimide) provides compound H-2B.

SCHEME J

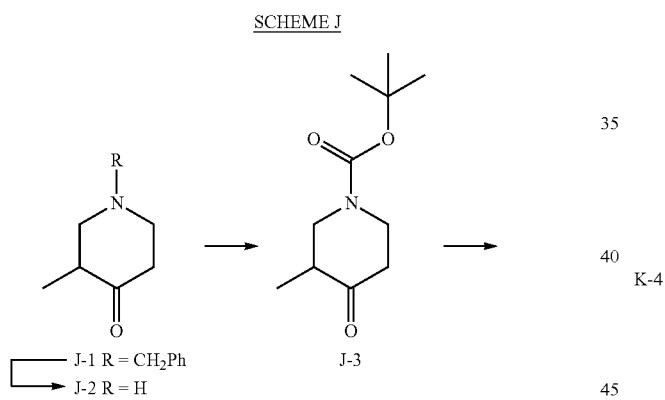

Triflates of the Formula H-2 employed in Scheme H being substituted by an ethynyl radical connecting both 2-positions of the piperidine ring may be prepared as described in Scheme K. Condensation of compounds K-1 and K-2 in the presence of base affords compound K-3. Diester K-3 undergoes cyclization in the presence of base (e.g. potassium tert-butoxide) to provide K-4 which upon heating results in compound K-5. Carbamoylation of the resulting amine K-5 provides compound K-6. Treatment of the resulting ketone K-6 with base followed by quench with a triflating reagent (e.g. phenyl triflimide) provides compound H-2C.

SCHEME K

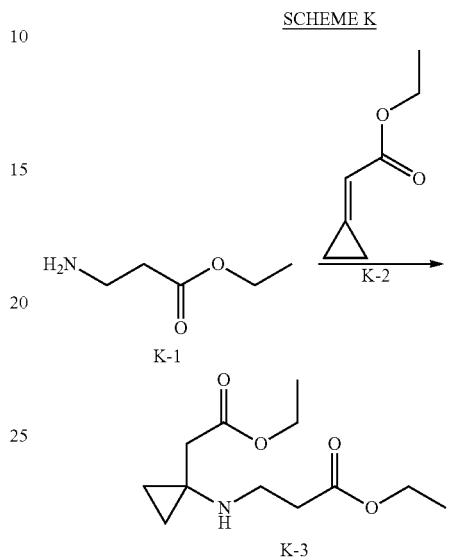

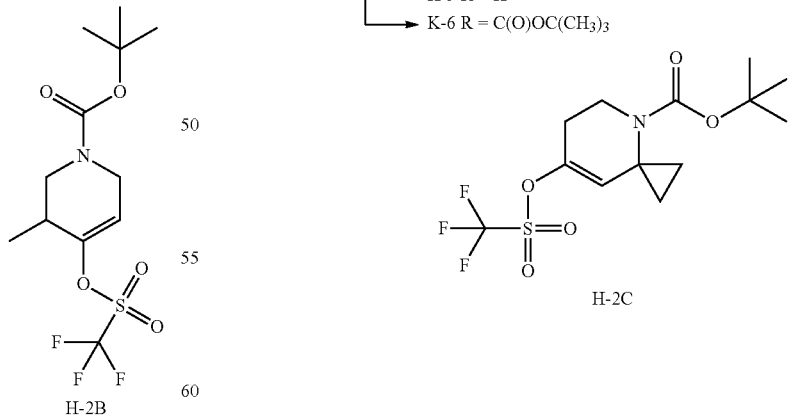

Triflates of the Formula H-2 employed in Scheme H being substituted by methyl at the 2-position and the 6-position of the piperidine ring may be prepared as described in Scheme L. Treatment of the ketone L-1 with base followed by quench with a triflating reagent (e.g. phenyl triflimide) provides compound H-2D.

SCHEME L

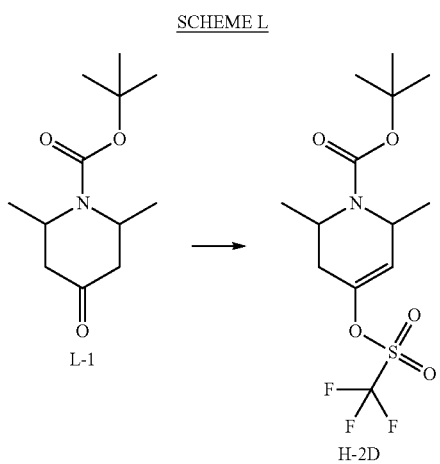

Triflates of the Formula H-2 employed in Scheme H being substituted by methyl at the 2-position and the 5-position of the piperidine ring may be prepared as described in Scheme M. Treatment of the ketone M-1 with base followed by quench with a triflating reagent (e.g. phenyl triflimide) provides compound H-2E.

SCHEME M

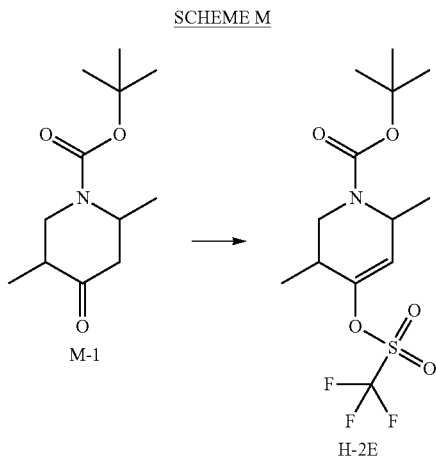

Triflates of the Formula H-2 employed in Scheme H being substituted by methyl at the 3-position and the 5-position of the piperidine ring may be prepared as described in Scheme N. Ketone N-1 is deprotonated with a strong base and then subsequently reacted with an alkyl halide (e.g. methyl iodide) to provide N-2. Hydrogenolysis of N-2 with hydrogen and a palladium catalyst in the presence of a carbomoylating reagent (e.g. di-tert-butyl dicarbonate) affords N-3. Treatment of the resulting ketone N-3 with base followed by quenching with a triflating reagent (e.g. phenyl triflimide) provides compound H-2F.

SCHEME N

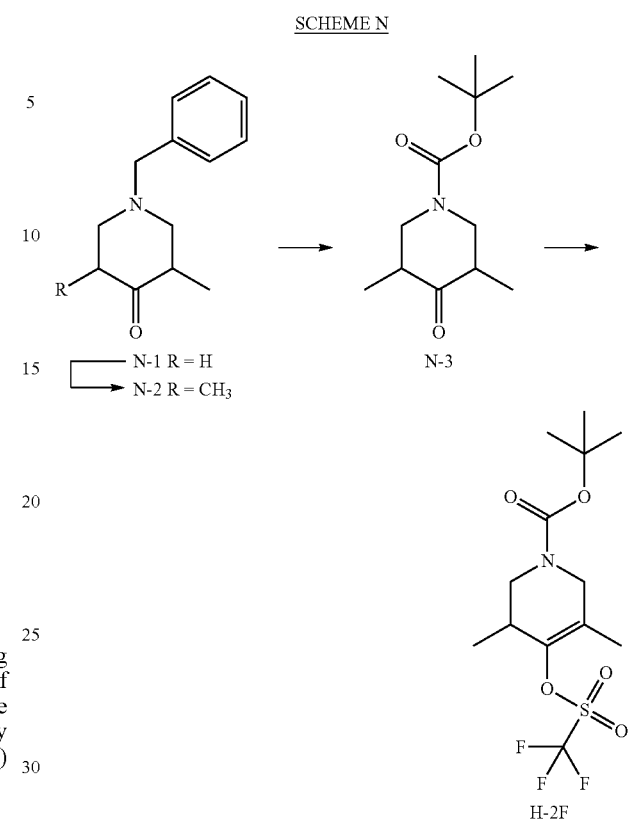

Alternatively, compounds of Formula (I) where the piperidine is substituted by methyl at the 2-position may be prepared as described in Scheme O. Hydrogenolysis of O-1 followed by acylation of the resulting amine O-2 with acid chlorides ($R_2COCl$) or carboxylic acids ($R_2CO_2H$) affords compounds of the Formula O-3. Treatment of the resulting ketone O-3 with base followed by quench with a triflating reagent (e.g. phenyl triflimide) provides compound O-4. Cross-coupling of O-4 with aryl boronates of the Formula H-1 provides compounds of the Formula O-5 which are converted to O-6 after reduction of the nitro group and olefin. Subsequent benzoylation provides compounds of the Formula O-8. This method of preparation may also be applied to the opposite enantiomer relative to what is exemplified.

SCHEME O

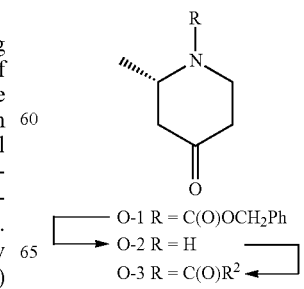

-continued

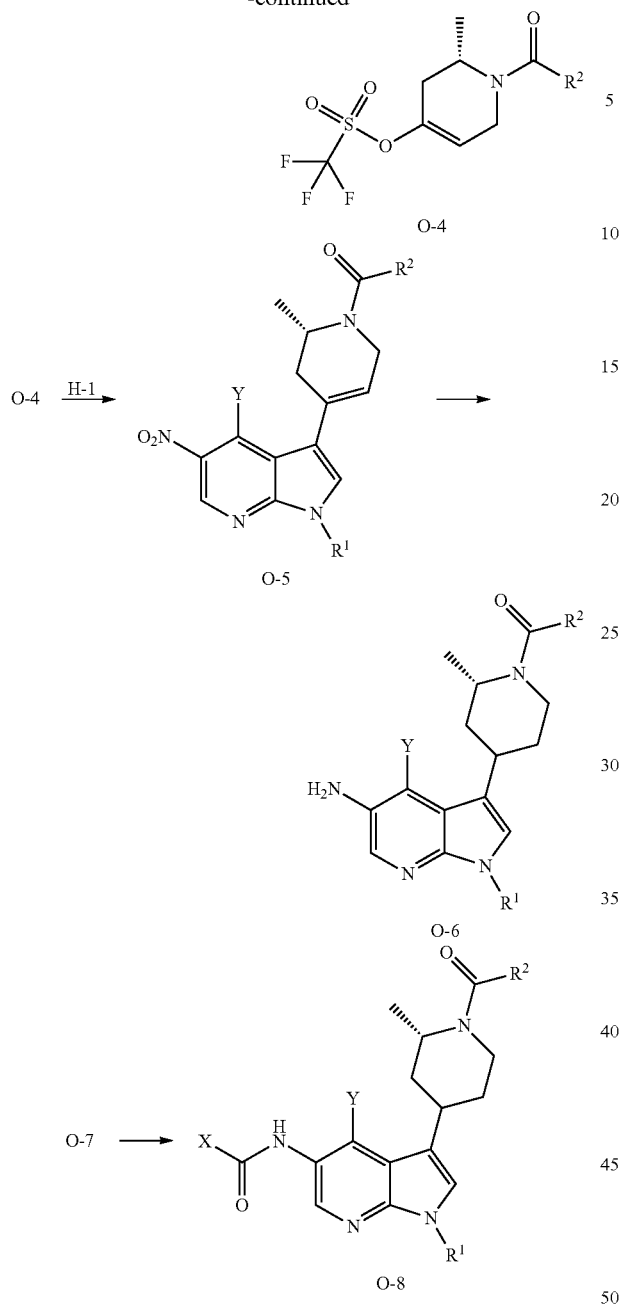

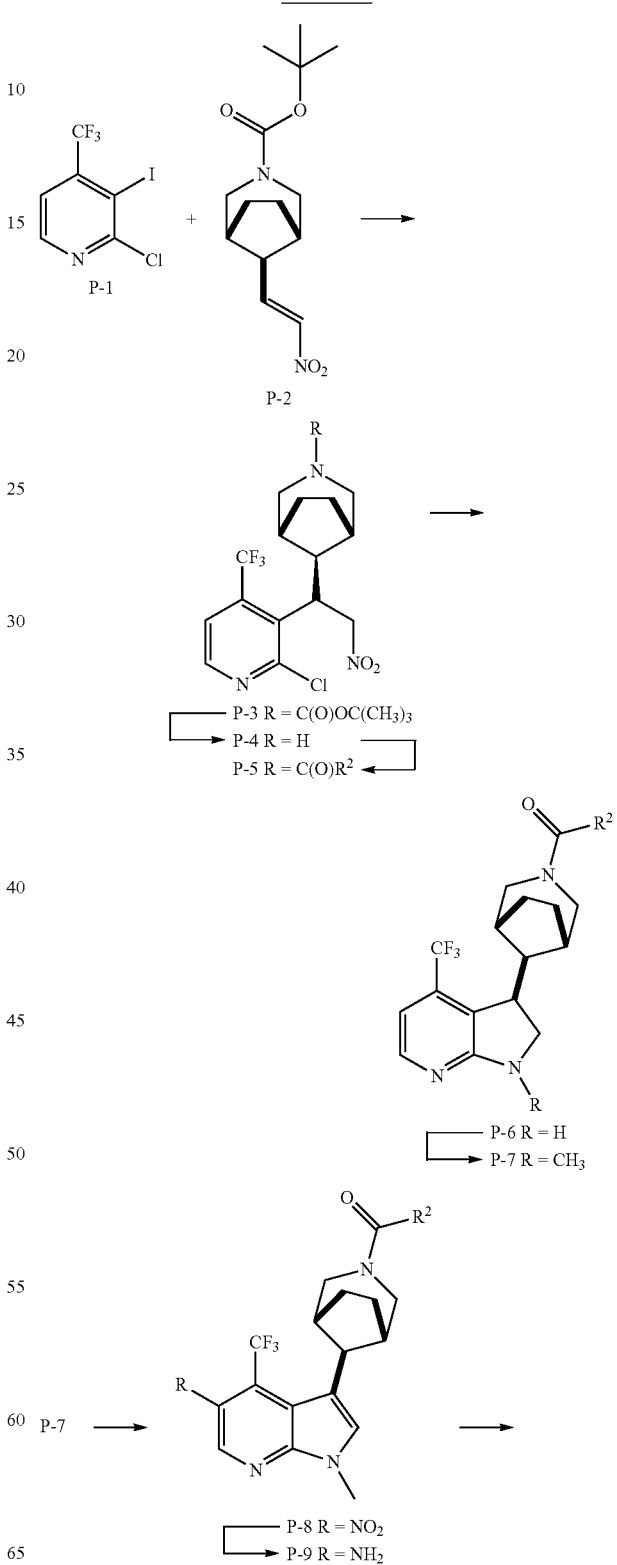

of the nitro group and subsequent benzoylation through amide bond formation conditions provides compounds of the Formula P-10.

SCHEME P

Compounds of Formula (I) may be prepared as described in Scheme P. Metallation of iodopyridine P-1 followed by conjugate addition of the resulting anion with the nitroalkene P-2 (prepared as described in Scheme Q) provides the substituted pyridine P-3. Removal of the carbamate group through treatment with acid followed by reaction of the resulting amine with carboxylic acids ($R^2CO_2H$) or carboxylic acid chlorides ($R^2COCl$) under amide bond-forming conditions provides compounds of the Formula P-5. Reduction of the nitro group followed by treatment with either acidic or basic conditions facilitates cyclization to form 2,3-dihydro-7-azaindoles P-6. Treatment of P-6 with methyl iodide and base affords compounds P-7. Treatment of P-7 with tetraalkylammonium salts results in nitration at the 5-position and aromatization of the ring system. Reduction -continued

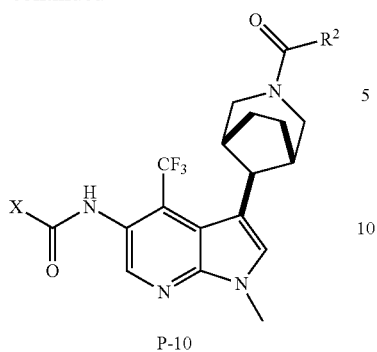

P-10

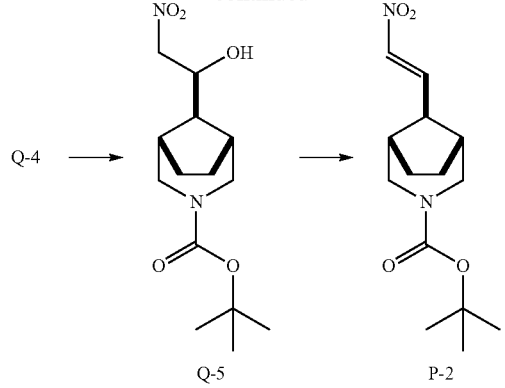

Q-5    P-2

Compounds P-2 employed in Scheme P may be prepared as described in Scheme Q. The commercially available bicyclic ketone was first converted to the carbamate-protected derivative Q-2 by reduction of the benzyl group in the presence of the appropriate carbamic anhydride. Next, homologation of the ketone through the use of phosphonium salts and base furnishes methyl vinyl ether Q-3 which upon treatment with acid provides the corresponding aldehyde Q-4. Treatment of Q-4 with nitromethane in the presence of base followed by elimination of water from the resulting nitroalcohol Q-5 provides nitroalkene P-2.

Compounds of Formula (I) may be prepared as exemplified by the synthetic route described in Scheme R. Lithiation of dihalopyridine R-1 followed by addition to nitroolefin P-2, prepared as described in Scheme P, results in the 1,4-addition product R-2. The amine protecting group is removed in the presence of acid (e.g. HCl) to afford compound R-3 as a corresponding salt form of the acid used. Condensation of R-3 with an appropriate acid chloride ($R^2COCl$) or activated carboxylic acid ($R^2CO_2H$) affords compounds of the Formula R-4. A zinc-mediated reductive cyclization reaction on R-4 provides dihydropyrrolopyridines of the Formula R-5. Methylation of R-5 using iodomethane and sodium hydride followed by nitration-oxidation using tetramethylammonium nitrate affords compounds of the Formula R-7. Zinc-mediated methylation of R-7 provides 4-methylpyrrolopyridines of the Formula R-8. Reduction of the nitro group, followed by acylation with an appropriate benzoyl chloride (XCOCl) or activated benzoic acid ($XCO_2H$) furnishes compounds of the Formula R-9.

SCHEME Q

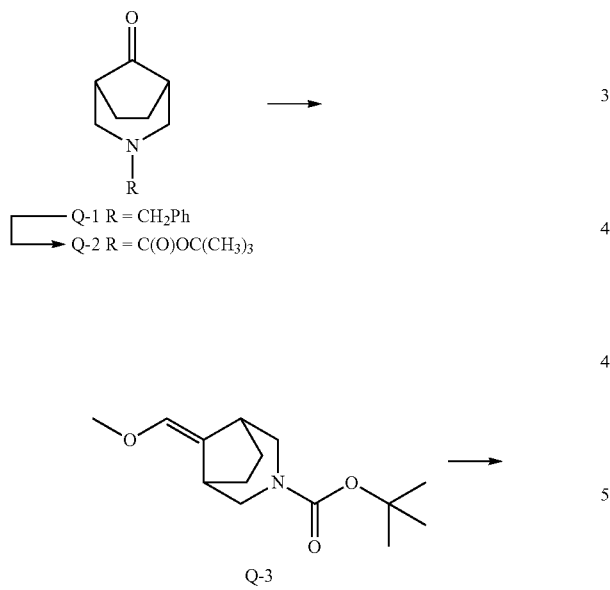

Q-1 R = $CH_2Ph$
Q-2 R = $C(O)OC(CH_3)_3$

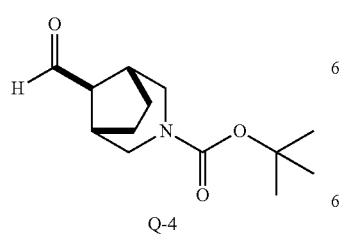

Q-4

SCHEME R

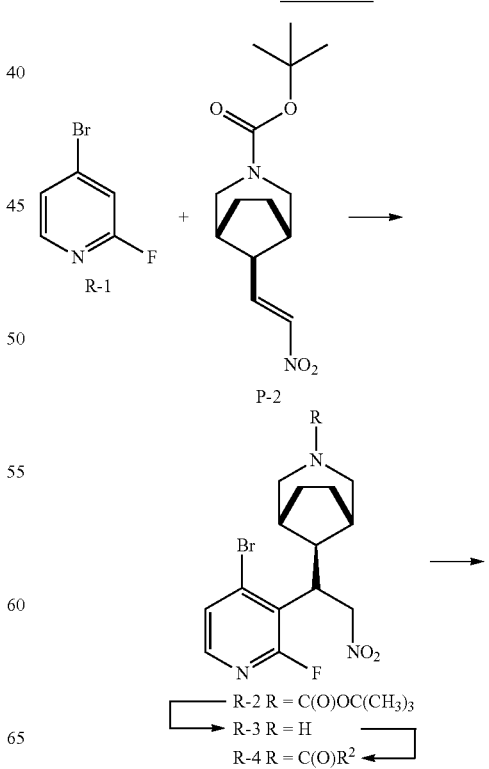

R-2 R = $C(O)OC(CH_3)_3$
R-3 R = H
R-4 R = $C(O)R^2$

-continued

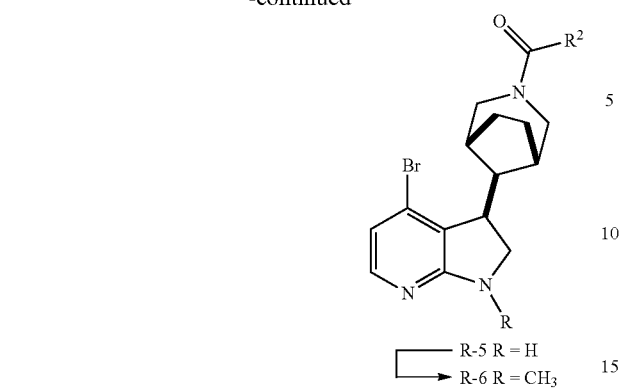

R-5 R = H
R-6 R = CH₃

SCHEME S

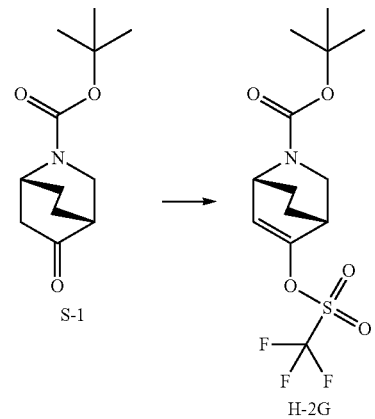

H-2G

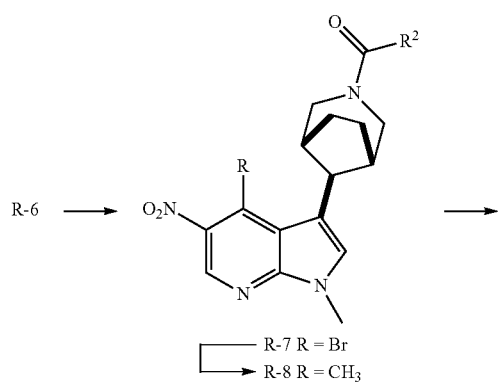

R-6 →

R-7 R = Br
R-8 R = CH₃

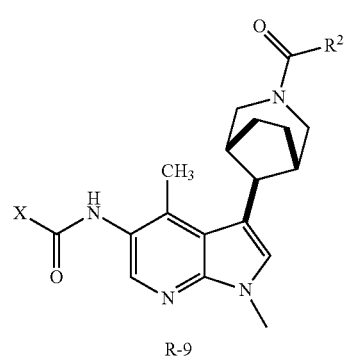

R-9

Triflates of the Formula H-2 employed in Scheme H being bridged by an ethylene (—CH₂CH₂—) group between the 2- and 6-positions of the piperidine ring may be prepared as described in Scheme S. Treatment of the ketone S-1 with base followed by quench with a triflating reagent (e.g. phenyl triflimide) provides compound H-2G.

EXEMPLIFICATION

The invention now being generally described, will be more readily understood by reference to the following examples, which are included merely for purposes of illustration of certain aspects and embodiments of the present invention, and are not intended to limit the invention. The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. Coupling constants (J values) are reported in Hertz.

Chiral purity of scalemic compounds was determined by chiral SFC (super-critical fluid chromatography) employing one of the following conditions: Method A: Chiralpak AD-3 150×4.6 mm ID, 3 μm, IPA/CO₂ (0.05% DEA), 5-40%, 2.5 mL/min, 10 min; Method B: Chiralpak AS-H 150×4.6 mm ID, 5 μm, MeOH/CO₂ (0.05% DEA), 5-40%, 3 mL/min, 10 min; Method C: ChiralCel OJ-H 250×4.6 mm ID, 5 μm, IPA/CO₂ (0.05% DEA), 5-40%, 2.35 mL/min, 10 min; Method D: Lux Cellulose-1 250 mm×4.6 mm ID, 5 μm, MeOH/CO₂ (0.2% NH₄⁺), 5-60%, 3 mL/min, 10 min; Method E: ChiralPak AD-3 50×4.6 mm ID, 3 μm, IPA/CO₂ (0.05% DEA), 5-40%, 2.5 mL/min, 10 min; Method F: ChiralCel OD-3 150×4.6 mm ID, 3 μm, IPA/CO₂ (0.05% DEA) 40%, 2.5 mL/min; Method G: ChiralCel OJ-H 100× 4.6 mm ID, 5 μm, Ethanol/CO₂ (0.05% DEA), 5-20%, 2.35 mL/min, 20 min; Method H: Chiralcel OJ-3 50×4.6 mm, 3 μm, MeOH/CO₂ (0.05% DEA), 5-40%, 4 mL/min, 3 min; Method I: Chiralpak AD-3 50×4.6 mm, 3 μm, EtOH/CO₂ (0.05% DEA), 5-40%, 4 mL/min, 3 min; Method J: Chiralcel OD-H 4.6×100 mm, 5 μm, EtOH/CO₂ (0.2% NH₄⁺), 40-60%, 1.5 mL/min, 5 min; Method K: Chiralcel OJ-3 50×4.6 mm, 3 μm, MeOH/CO$_2$ (0.05% DEA), 5-40%, 4 mL/min, 10 min; Method L: DIKMA Diamonsil(2) C18 200×20 mm, 5 μm, MeCN/H$_2$O, 35 ml/min, 10 min; Method M: Chiralpak AD-3 50×4.6 mm ID, 3 μm, EtOH/CO$_2$ (0.05% DEA), 5-40%, 4.0 mL/min, 2.5 min; Method N: Chiralpak AS-3 100×4.6 mm, 3 μm, MeOH/CO$_2$ (0.05% DEA), 5-40%, 2.8 mL/min, 8 min; Method 0: Chiralcel OJ-2 50×3.0 mm, 5 μm, EtOH/CO$_2$ (0.2% NH$_4^+$), 5-40%, 6 mL/min, 10 min; Method P: Ultimate XB-C18 50×3.0 mm, 3 μm, MeCN/H$_2$O, 35 mL/min, 5 min; Method Q: Chiralpak AD-H 250×4.6 mm ID, 5 μm, EtOH/CO$_2$ (0.05% DEA), 5-40%, 2.5 mL/min, 10 min; Method R: Chiralpak AD-3 50×4.6 mm ID, 3 μm, MeOH/CO$_2$ (0.05% DEA), 5-40%, 4.0 mL/min, 7.5 min; Method S: ChiralCel OJ-H 250×30 mm ID, 5 μm, EtOH/CO$_2$ (0.05% DEA), 20%, 60 mL/min, 10 min; Method T: Chiralpak AS-H 100×4.6 mm ID, 5 μm, MeCN/MeOH/CO$_2$ (0.05% DEA), 15/15/70, 1.5 mL/min, 10 min; Method U: Chiralpak AS-H 150×4.6 mm ID, 5 μm, MeOH/CO$_2$ (0.05% DEA), 5-40%, 3 mL/min, 8 min; Method V: Chiralpak AS-H 250×4.6 mm ID, 5 μm, EtOH/CO$_2$ (0.05% DEA), 5-40%, 2.35 mL/min, 10 min; Method W: Chiralcel OJ-3 50×4.6 mm ID, 3 μm, EtOH/CO$_2$ (0.05% DEA), 5-40%, 4 mL/min, 10 min; Method X: Chiralcel OJ-H, 250×4.6 mm, ID, 5 μm, MeOH/CO$_2$ (0.05% DEA), 5-40%, 2.35 mL/min, 10 min; Method Y: Chiralpak AD-3, 50×4.6 mm, ID, 3 μm, EtOH/CO$_2$ (0.05% DEA), 5-40%, 4 mL/min, 10 min; Method Z: Chiralpak AS-H, 100×4.6 mm, ID, 5 μm, ACN/MeOH (50/50)/CO$_2$, 1.5 mL/min, 10 min; Method AA: ChiralCel IA, 100×4.6 mm, 5 μm, CO$_2$/MeOH, 60/40, 1.5 mL/min, 10 min. Method AB: Ultimate XB-C18, 3 μm, 50×3 mm, MeCN/H$_2$O (0.1% TFA), 1-100%, 1.5 mL/min, 10 min; Method AC: Chiral Tech OD-H, 5 μm, 250×4.6 mm, CO$_2$/MeOH, 5-40%, 3.0 mL/min, 10 min.

For syntheses referencing procedures in other Examples, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluants/gradients were chosen to provide appropriate Rf's or retention times (RetT).

The chemical names for the compounds of the invention described below were generated using CambridgeSoft's ChemBioDraw Ultra version 13.0.2 (CambridgeSoft Corp., Cambridge Mass.).

The following abbreviations are used herein: DCM: dichloromethane; DEA: diethylamine; DIPEA: diisopropylethylamine; DME: 1,2-dimethoxyethane; DMF: dimethylformamide; EtOAc: ethyl acetate; EtOH: ethanol; HATU: 1-[bis(dimethylamino)-methylene]-1H-1,2,3-triazolo[4,5-b]pyridinium 3-oxid hexafluorophosphate; MeOH: methanol; MTBE: methyl t-butyl ether; PE: petroleum ether; TEA: triethylamine; and THF: tetrahydrofuran.

Example 1

Preparation of 3-cyano-N-(3-(1-(cyclopentanecarbonyl)piperidin-4-yl)-1-methyl-4-(trifluoromethyl)-1H-pyrrolo[2,3-b]pyridin-5-yl)-5-methoxybenzamide

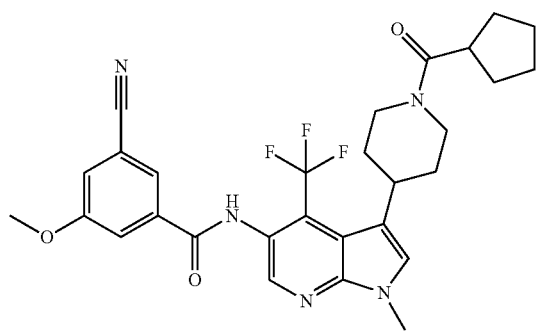 [SMILES: COc1cc(C#N)cc(C(=O)Nc2cnc3c(c(C4CCN(C(=O)C5CCCC5)CC4)cn3C)c2C(F)(F)F)c1]

Step 1: 4-iodo-1H-pyrrolo[2,3-b]pyridine. This reaction was carried out in three parallel batches. To a solution of 4-chloro-1H-pyrrolo[2,3-b]pyridine (500 g, 3.28 mol) in acetonitrile (20 L) was added NaI (2950 g, 19.66 mol) at room temperature. Then acetyl chloride (1030 g, 13.11 mol) was added dropwise to the reaction mixture at room temperature. The reaction mixture was stirred at 100° C. for 60 hr. The reaction mixture was cooled to room temperature and neutralized with aqueous NaHCO$_3$ to pH=7. The mixture was stirred for 30 min. The reaction mixtures from three batches were concentrated. NaHSO$_3$ (saturated, 1 L) was added to the reaction mixture. The mixture was stirred for 20 min and extracted with DCM (20 L×3). The combined organic layer was concentrated to give crude product. To a solution of the crude product in MeOH (20 L) was added NaOH (2 M, 10 L) at room temperature. The reaction mixture was stirred at room temperature for 3 hr. The reaction mixture was extracted with DCM (20 L×3). The combined organic layers were washed with brine (10 L), dried over Na$_2$SO$_4$, filtered and concentrated to give the title compound (1500 g, 93.7% combined yield) as a yellow solid. The material was used for the next step without further purification. $^1$H NMR (CDCl$_3$) δ 10.44 (br s, 1H), 7.96 (d, J=5.2 Hz, 1H), 7.53 (d, J=4.8 Hz, 1H), 7.42 (d, J=2.4 Hz, 1H), 6.43 (d, J=2.8 Hz, 1H).

Step 2: 4-Iodo-1-(phenylsulfonyl)-1H-pyrrolo[2,3-b]pyridine. This reaction was carried out in three parallel batches. To a solution of NaOH (344 g, 8.61 mol) in DCM (16 L) was added tetrabutylammonium sulphate (48.7 g, 143.4 mmol) at 0° C. Then 4-iodo-1H-pyrrolo[2,3-b]pyridine (700 g, 2.87 mol) was added to the reaction mixture at 0° C. The reaction mixture was stirred at 0° C. for 10 min. Phenyl sulphonyl chloride (760 g, 4.30 mol) was added dropwise to the reaction mixture at 0° C. After addition, the reaction mixture was stirred at room temperature overnight. The reaction mixtures from three batches were combined. DCM (15 L) and water (20 L) were added to the reaction mixture. The aqueous layer was extracted with DCM (10 L×2). The combined organic layers were washed with brine (10 L), dried over Na$_2$SO$_4$, filtered and concentrated to give crude product. The crude product was triturated with MeOH (3 L) and filtered to give the title compound (2950 g, 89.2% combined yield) as a yellow solid. The material was used for next step without further purification (6:1, PDT:SM). $^1$H NMR (CDCl$_3$) δ 8.19 (d, J=8.0 Hz, 1H), 8.05 (d, J=5.6 Hz, 1H), 7.81 (d, J=4.0 Hz, 1H), 7.65-7.55 (m, 2H), 7.55-7.45 (m, 2H), 6.53 (d, J=4.4 Hz, 1H).

Step 3: 4-Iodo-5-nitro-1-(phenylsulfonyl)-1H-pyrrolo[2,3-b]pyridine. This reaction was carried out in two parallel batches. To a stirred solution of tetramethylammonium nitrate (708.8 g, 5.21 mol) in DCM (8 L) was added dropwise trifluoroacetic anhydride (1090 g, 5.21 mol) at 20° C. Then the reaction suspension was stirred at 20° C. for 1.5 hr. The suspension was cooled in a dry ice/acetone bath. A solution of 4-iodo-1-(phenylsulfonyl)-1H-pyrrolo[2,3-b]pyridine (1000 g, 2.60 mol) in DCM (4 L) was added dropwise to the reaction mixture while keeping the reaction temperature at −65° C. under $N_2$. The reaction was allowed to stir at −65° C. for 2 hr. Then the reaction mixture was stirred for another 40 hr at room temperature under $N_2$. The reaction mixtures from two batches were combined. The stirred reaction was quenched with 5% aqueous $NaHCO_3$ to pH=8. The DCM layer was separated and washed with water (15 L×3). The combined water layers were extracted with DCM (25 L×4). The combined organic layers were dried over $Na_2SO_4$ and concentrated to give crude product. The crude product was slurried with EtOAc (20 L) overnight. The suspension was filtered and concentrated to give the title compound (1450 g, 64.9% combined yield) as a yellow solid. The crude product was used to next step. $^1$H NMR (DMSO-$d_6$) δ 8.88 (s, 1H), 8.27 (d, J=4.0 Hz, 1H), 8.16 (d, J=7.6 Hz, 2H), 7.81-7.77 (m, 1H), 7.69-7.66 (m, 2H), 6.89 (d, J=4.0 Hz, 1H).

Step 4. 5-Nitro-1-(phenylsulfonyl)-4-(trifluoromethyl)-1H-pyrrolo[2,3-b]pyridine. This reaction was carried out in four parallel batches. To a solution of 4-iodo-5-nitro-1-(phenylsulfonyl)-1H-pyrrolo[2,3-b]pyridine (300 g, 699 mmol) in DMF (1.8 L) was added methyl 2,2-difluoro-2-(fluorosulfonyl)acetate (268.57 g, 1398 mmol) and CuI (266.3 g, 1398 mmol) at room temperature. After addition, the reaction mixture was degassed and purged with $N_2$ three times. The mixture was heated to 110° C. and stirred for 1 hr at this temperature. The mixture was filtered through Celite® and the filter cake was washed with EtOAc (500 mL×3). The filtrate was concentrated and the residue was purified by silica gel column chromatography (DCM:PE, 10:90-100:0) to give the title compound (830 g, 80% combined yield) as a white solid. $^1$H NMR (CDCl$_3$) δ 8.88 (s, 1H), 8.23 (d, J=7.6 Hz, 2H), 8.10 (d, J=4.0 Hz, 1H), 7.70-7.66 (m, 1H), 7.59-7.55 (m, 2H), 6.96 (d, J=2.0 Hz, 1H).

Step 5. 3-iodo-1-methyl-5-nitro-4-(trifluoromethyl)-1H-pyrrolo[2,3-b]pyridine. This reaction was carried out in eight parallel batches. To a stirred solution of 5-nitro-1-(phenylsulfonyl)-4-(trifluoromethyl)-1H-pyrrolo[2,3-b]pyridine (66.5 g, 179.1 mmol) in 2-methyltetrahydrofuran:EtOH (2:1, 2520 mL) was added KOH (51.25 g, 913.4 mmol) at 0° C. After addition, the reaction mixture was allowed to warm to room temperature and stir for 30 min. $I_2$ (145.47 g, 573.14 mmol) was added and stirred for another 1 hr. $K_2CO_3$ (123.77 g, 8975.5 mmol) and $CH_3I$ (254.2 g, 1.791 mol) were added to the reaction mixture. Then the reaction mixture was allowed to stir at room temperature overnight. The reaction mixture was concentrated to give a residue. The residue was dissolved in DCM (4 L) and washed with 10% of aqueous $NaHSO_3$ (2.5 L×4), washed with brine, and dried over $Na_2SO_4$. The organic layer was concentrated to give crude product, which was triturated with MTBE (700 ml) and filtered to afford the title compound (333 g, 60% combined yield) as a yellow solid. $^1$H NMR (CDCl$_3$) δ 8.64 (s, 1H), 7.75 (s, 1H), 3.98 (s, 3H).

Step 6a: 4-(4,4,5,5-tetramethyl-1,3,2-dioxaborolan-2-yl)-1,2,3,6-tetrahydropyridine: To the solution of tert-butyl 4-(4,4,5,5-tetramethyl-1,3,2-dioxaborolan-2-yl)-5,6-dihydropyridine-1(2H)-carboxylate (2.50 g, 8.085 mmol) in EtOAc (25 mL) was added dropwise HCl-EtOAc (20 mL) at room temperature. The mixture was stirred at room temperature for 3 hr. The reaction mixture was concentrated to give the title compound (2.20 g, 130% crude yield) as a white solid. This material was used without further purification.

Step 6b: cyclopentyl(4-(4,4,5,5-tetramethyl-1,3,2-dioxaborolan-2-yl)-5,6-dihydropyridin-1(2H)-yl)methanone: To a solution of 4-(4,4,5,5-tetramethyl-1,3,2-dioxaborolan-2-yl)-1,2,3,6-tetrahydropyridine (500 mg, 2.39 mmol) and TEA (968 mg, 9.57 mmoL) in DCM (10 mL) was added dropwise cyclopentyl acid chloride (317 mg, 2.39 mmol) while cooling in an ice/water bath. The reaction turned into a slurry and was allowed to stir at room temperature for 16 h. The reaction mixture was washed with water, dried over $Na_2SO_4$, and concentrated to give the crude product which was purified by silica gel column chromatography (EtOAc/heptane, 0:100-20:80) to give the title compound (530 mg, 72.6%) as a colourless oil. LC/MS [M+H]=306.0. $^1$H NMR (CDCl$_3$) δ 6.53-6.45 (m, 1H), 4.14-4.09 (m, 2H), 3.64-3.54 (m, 2H), 2.95-2.80 (m, 1H), 2.55-2.20 (s, br, 2H), 1.87-1.67 (m, 6H), 1.65-1.50 (m, 2H), 1.27 (s, 12H).

Step 6c: cyclopentyl(4-(1-methyl-5-nitro-4-(trifluoromethyl)-1H-pyrrolo[2,3-b]pyridin-3-yl)-5,6-dihydropyridin-1(2H)-yl)methanone. A solution of cyclopentyl(4-(4,4,5,5-tetramethyl-1,3,2-dioxaborolan-2-yl)-5,6-dihydropyridin-1(2H)-yl)methanone (340 mg, 0.916 mmol), 3-iodo-1-methyl-5-nitro-4-(trifluoromethyl)-1H-pyrrolo[2,3-b]pyridine (308 mg, 1.01 mmol), Pd(PPh$_3$)$_4$ (106 mg, 0.0916 mmol) and K$_3$PO$_4$ (389 mg, 1.83 mmol) in dioxane/H$_2$O (8 mL/2 mL) was heated to 60° C. and stirred for 16 hr under $N_2$. The reaction mixture was diluted with water (25 mL) and extracted with EtOAc (2×25 mL). The EtOAc extracts were dried over Na$_2$SO$_4$, filtered, and concentrated to give the crude product. Two batches were combined, which was then purified by silica gel column chromatography (PE:EtOAc,100:0-100:30) to give the title compound (320 mg, yield: 41.3%) as a yellow solid. LC/MS [M+H]=423.1. $^1$H NMR (CDCl$_3$) δ 8.76 (s, 1H), 7.39 (s, 1H), 5.75-5.68 (m, 1H), 4.25 (m, 2H), 3.96 (s, 3H), 3.85 (t, J=6 Hz, 1H), 3.75 (t, J=6 Hz, 1H), 3.05-2.85 (m, 1H), 2.40 (s, br, 2H), 1.90-1.70 (m, 6H), 1.65-1.55 (m, 2H).

Step 7: (4-(5-amino-1-methyl-4-(trifluoromethyl)-1H-pyrrolo[2,3-b]pyridin-3-yl)piperidin-1-yl)(cyclopentyl)methanone. To a solution of cyclopentyl(4-(1-methyl-5-nitro-4-(trifluoromethyl)-1H-pyrrolo[2,3-b]pyridin-3-yl)-5,6-dihydropyridin-1(2H)-yl)methanone (320 mg, 0.758 mmol) in MeOH (30 mL) and DCM (10 mL) was added Pd(OH)$_2$/C (42.6 mg). The mixture was then purged with hydrogen three times and stirred under hydrogen gas (50 psi) at 50° C. for 4 hr. The reaction mixture was filtered to remove the catalyst and fresh catalyst (42.6 mg) was added to the filtrate. The mixture was stirred under hydrogen (50 psi) at 50° C. for 16 hr. The mixture was filtered through a pad of Celite® and concentrated to give the crude product (320 mg) which was purified by silica gel column chromatography (MeOH/DCM, 0:100-10:90) to give the title compound (70 mg, 23%) as an off-white solid. LC/MS [M+H]=395.0. $^1$H NMR (CD$_3$OD) δ 7.96 (s, 1H), 7.31 (s, 1H), 4.70 (d, J=12 Hz, 1H), 4.22 (d, J=12 Hz, 1H), 3.77 (s, 3H), 3.20-3.05 (m, 3H), 2.73-2.65 (m, 1H), 2.07-1.47 (m, 14H).

Step 8: 3-cyano-N-(3-(1-(cyclopentanecarbonyl)piperidin-4-yl)-1-methyl-4-(trifluoromethyl)-1H-pyrrolo[2,3-b]pyridin-5-yl)-5-methoxybenzamide: To an IKA vial was added (4-(5-amino-1-methyl-4-(trifluoromethyl)-1H-pyrrolo[2,3-b]pyridin-3-yl)piperidin-1-yl)(cyclopentyl)methanone (30 mg, 0.092 mmol), 3-cyano-5-methoxybenzoic acid (0.111 mmol, 1.2 eq), 2-chloromethylpyridinium iodide (23.6 mg, 0.092 mmol), DIPEA (47.7 mg, 0.369 mmol) and THF (3 mL). The mixture was stirred at 70° C. for 16 hr. The reaction mixture was purified by prep-HPLC. The fractions were lyophilized to give the title compound (20 mg, 40.0%) as a white solid. LC/MS [M+H]=554.0. $^1$H NMR (CDCl$_3$) δ 8.55 (s, 1H), 8.12 (s, 1H), 7.78 (s, 1H), 7.73 (s, 1H), 7.35 (s, 1H), 7.25 (s, 1H), 4.82 (d, J=12 Hz, 1H), 4.10 (d, J=12 Hz, 1H), 3.93 (s, 3H), 3.91 (s, 3H), 3.19-3.13 (m, 2H), 2.95 (quint, J=8 Hz, 1H), 2.72-2.60 (m, 1H), 2.01 (dd, J=28, 12 Hz, 2H), 1.85-1.45 (m, 10H).

Examples 2-4

The following Examples 2-4 were prepared analogous to Example 1 employing the appropriate carboxylic acid coupling reagent in Step 6b and the appropriate carboxylic acid coupling reagent in Step 8.

| Ex. | Structure | Name/Characterization |
|---|---|---|
| 2 | 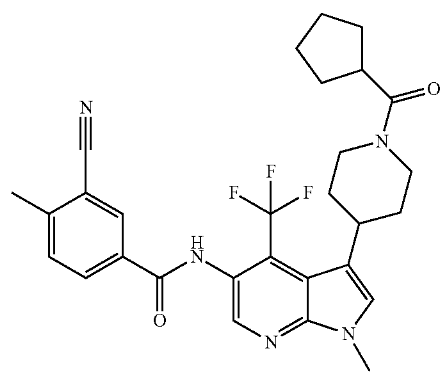 [SMILES: Cc1ccc(C(=O)Nc2cnc3c(c(C4CCN(C(=O)C5CCCC5)CC4)cn3C)c2C(F)(F)F)cc1C#N] | 3-cyano-N-(3-(1-(cyclopentanecarbonyl)piperidin-4-yl)-1-methyl-4-(trifluoromethyl)-1H-pyrrolo[2,3-b]pyridin-5-yl)-4-methylbenzamide. LC/MS [M + H] = 538.0. $^1$H NMR (CDCl$_3$) δ 8.55 (s, 1H), 8.19 (s, 1H), 8.08-8.04 (m, 2 H), 7.49 (d, J = 8 Hz, 1H), 7.23 (s, 1H), 4.81 (d, J = 12 Hz, 1H), 4.10 (d, J = 12 Hz, 1H), 3.90 (s, 3H), 3.18-3.12 (m, 2H), 2.94 (quint, J = 8 Hz, 1H), 2.70-2.62 (m, 4H), 2.01 (dd, J = 24, 13 Hz, 2H), 1.95-1.50 (m, 10H) |
| 3 | 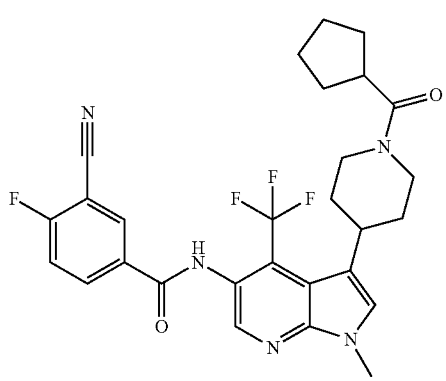 [SMILES: Cn1cc(C2CCN(C(=O)C3CCCC3)CC2)c2c(C(F)(F)F)c(NC(=O)c3ccc(F)c(C#N)c3)cnc21] | 3-cyano-N-(3-(1-(cyclopentanecarbonyl)piperidin-4-yl)-1-methyl-4-(trifluoromethyl)-1H-pyrrolo[2,3-b]pyridin-5-yl)-4-fluorobenzamide. LC/MS [M + H] = 542.0. $^1$H NMR (CDCl$_3$) δ 8.52 (s, 1H), 8.29-8.18 (m, 3H), 7.39 (t, J = 8.4 Hz, 1H), 7.25 (s, 1H), 4.80 (d, br, J = 10.8 Hz, 1H), 4.11 (d, br, J = 10.8 Hz, 1H), 3.91 (s, 3H), 3.16 (t, br, J = 11.6 Hz, 2H), 2.95 (quint, J = 8.0 Hz, 1H), 2.65 (m, 1H), 2.45-2.15 (m, 2H), 2.15-1.93 (m, 2H), 1.93-1.67 (m, 4H), 1.67-1.43 (m, 4H). |
| 4 | 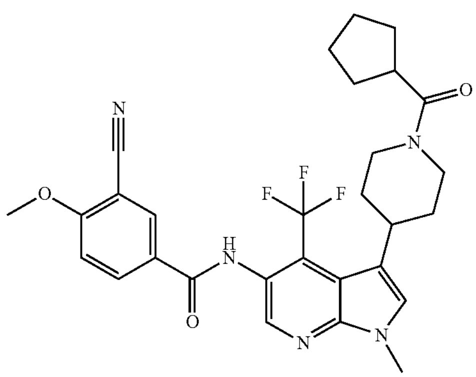 [SMILES: COc1ccc(C(=O)Nc2cnc3c(c(C4CCN(C(=O)C5CCCC5)CC4)cn3C)c2C(F)(F)F)cc1C#N] | 3-cyano-N-(3-(1-(cyclopentanecarbonyl)piperidin-4-yl)-1-methyl-4-(trifluoromethyl)-1H-pyrrolo[2,3-b]pyridin-5-yl)-4-methoxybenzamide. LC/MS [M + H] = 554.0; $^1$H NMR (500 MHz, CDCl$_3$) δ 8.55 (s, 1H), 8.19-8.14 (m, 2H), 7.99 (s, 1H), 7.23 (s, 1H), 7.10 (dd, J = 3.0, 6.3 Hz, 1H), 4.84-4.77 (m, 1H), 4.12-4.06 (m, 1H), 4.03 (s, 3H), 3.90 (s, 3H), 3.20-3.10 (m, 2H), 2.98-2.90 (m, 1H), 2.69-2.59 (m, 1H), 2.07-2.00 (m, 1H), 2.00-1.93 (m, 1H), 1.91-1.79 (m, 4H), 1.78-1.69 (m, 2H), 1.64-1.40 (m, 4H). |

Example 5

Preparation of 3-cyano-N-(3-(1-isobutyrylpiperidin-4-yl)-1-methyl-4-(trifluoromethyl)-1H-pyrrolo[2,3-b]pyridin-5-yl)benzamide

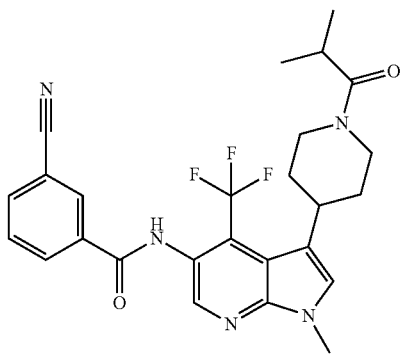 [SMILES: CC(C)C(=O)N1CCC(c2cn(C)c3ncc(NC(=O)c4cccc(C#N)c4)c(C(F)(F)F)c23)CC1]

Step 1: tert-butyl 4-(1-methyl-5-nitro-4-(trifluoromethyl)-1H-pyrrolo[2,3-b]pyridin-3-yl)-3,6-dihydropyridine-1(2H)-carboxylate. This reaction was carried out in six parallel batches. To a stirred solution of 3-iodo-1-methyl-5-nitro-4-(trifluoromethyl)-1H-pyrrolo[2,3-b]pyridine (prepared as described in Example 1, 52.5 g, 141.49 mmol) and tert-butyl 4-(4,4,5,5-tetramethyl-1,3,2-dioxaborolan-2-yl)-3,6-dihydropyridine-1(2H)-carboxylate (65.62 g, 212.2 mmol) in DME:EtOH (4:1, 1850 mL) was added Pd(PPh$_3$)$_4$ (8.17 g, 7.07 mmol). After addition, the mixture was degassed three times with N$_2$. A slurry of K$_2$CO$_3$ (78.22 g, 565.95 mmol) in H$_2$O (141 ml) was added slowly to the reaction. After addition, the reaction mixture was heated to 78° C. and stirred for 18 hr. The reaction mixture was then cooled to room temperature and poured into water. The mixture was then extracted with EtOAc (1 L×3), and the combined organic layers were washed with brine, dried over Na$_2$SO$_4$ and concentrated. The resulting residue was purified by silica gel column chromatography (EtOAc:PE, 20:80-80:20) to give the title compound (270 g, 75% combined yield) as a yellow solid. $^1$H-NMR (400 MHz, CDCl$_3$) δ 8.74 (s, 1H), 7.37 (s, 1H), 5.69-5.66 (m, 1H), 4.05-4.02 (m, 2H), 3.94 (s, 3H), 3.67-3.62 (m, 2H), 2.36-2.31 (m, 2H), 1.51 (s, 9H).

Step 2: 1-methyl-5-nitro-3-(1,2,3,6-tetrahydropyridin-4-yl)-4-(trifluoromethyl)-1H-pyrrolo[2,3-b]pyridine hydrochloride. This reaction was carried out in two batches. To a solution of tert-butyl 4-(1-methyl-5-nitro-4-(trifluoromethyl)-1H-pyrrolo[2,3-b]pyridin-3-yl)-3,6-dihydropyridine-1(2H)-carboxylate (140 g, 0.329 mol) in DCM:EtOAc (1:1, 1200 mL) was added dropwise a 4 M solution of HCl/Dioxane (1 L) at 0° C. After addition, the mixture was warmed to 20° C. and stirred for 3 hr. The reaction mixture was then filtered, and the solid was washed with MTBE (500 mL). The solid was then dried under vacuum to provide the hydrochloride salt of the title compound (182 g, 77% combined yield) as a white solid. $^1$H-NMR (400 MHz, DMSO-d$_6$) δ 9.38 (br. s., 2H), 8.99 (s, 1H), 8.04 (s, 1H), 5.67-5.74 (m, 1H), 3.93 (s, 3H), 3.76-3.64 (m, 2H), 3.32-3.21 (m, 2H)

Step 3: 2-methyl-1-(4-(1-methyl-5-nitro-4-(trifluoromethyl)-1H-pyrrolo[2,3-b]pyridin-3-yl)-3,6-dihydropyridin-1(2H)-yl)propan-1-one. This reaction was carried out in two batches. To a solution of 1-methyl-5-nitro-3-(1,2,3,6-tetrahydropyridin-4-yl)-4-(trifluoromethyl)-1H-pyrrolo[2,3-b] pyridine hydrochloride (91 g, 0.25 mol) in DCM (1 L) was added TEA (90 mL) and isobutyryl chloride (42 g, 0.39 mol) at 0° C. After addition, the mixture was stirred at 20° C. for 14 h. The mixture was then quenched with water (400 mL), and the organic layer was concentrated. The crude product was purified by silica gel column chromatography (DCM) to provide the title compound (182 g, 91% combined yield) as a yellow solid. $^1$H-NMR (400 MHz, CDCl$_3$) δ 8.75 (s, 1H), 7.38 (s, 1H), 5.74-5.65 (m, 1H), 4.06-4.02 (m, 2H), 3.95 (s, 3H), 3.64-3.62 (m, 1H), 2.361-2.32 (m, 2H), 1.60-1.40 (m, 9H).

Step 4a: 1-(4-(5-amino-1-methyl-4-(trifluoromethyl)-1H-pyrrolo[2,3-b]pyridin-3-yl)piperidin-1-yl)-2-methylpropan-1-one. This reaction was carried out in eighteen parallel batches. To a solution of 2-methyl-1-(4-(1-methyl-5-nitro-4-(trifluoromethyl)-1H-pyrrolo[2,3-b]pyridin-3-yl)-3,6-dihydropyridin-1(2H)-yl)propan-1-one (10 g, 25.25 mmol) in EtOH (400 mL) was added Pd(OH)$_2$/C (5 g, 35.71 mmol) at 20° C. The mixture was hydrogenated under 50 psi hydrogen gas at 50° C. for 24 hr. The mixture was filtered and the solid was washed with DCM (1 L). The combined filtrates were concentrated under reduced pressure to give the title compound (180 g, 107% combined crude yield) as a gray solid which was used in the next step directly without further purification. $^1$H-NMR (400 MHz, CDCl$_3$) δ 7.90 (s, 1H), 7.04 (s, 1H), 4.85-4.77 (m, 1H), 4.19 (br. s., 2H), 4.07-3.98 (m, 1H), 3.78 (s, 3H), 3.16-3.09 (m, 2H), 2.84-2.80 (m, 1H), 2.63-2.61 (m, 1H), 2.08-1.87 (m, 2H), 1.57-1.36 (m, 2H), 1.16-1.12 (m, 6H).

Step 4b: 1-(4-(5-amino-1-methyl-4-(trifluoromethyl)-1H-pyrrolo[2,3-b]pyridin-3-yl)piperidin-1-yl)-2-methylpropan-1-one hydrochloride. To a solution of 1-(4-(5-amino-1-methyl-4-(trifluoromethyl)-1H-pyrrolo[2,3-b]pyridin-3-yl)piperidin-1-yl)-2-methylpropan-1-one (180 g, 0.49 mol) in DCM/EtOAc (400 mL/400 mL) was added dropwise HCl/EtOAc (750 mL, 4M) at 0° C. After addition, the mixture was stirred at 20° C. for 3 h. The mixture was then filtered and the filter cake washed with DCM (500 mL). The solid was dried under vacuum to give the title compound (220 g, 110% crude yield) as a yellow solid. $^1$H NMR (partial, 400 MHz, DMSO-d$_6$) δ 8.50 (s, 1H), 7.84 (s, 1H), 3.80 (s, 3H), 3.14-2.95 (m, 2H), 2.91-2.89 (m, 1H), 1.96-1.74 (m, 2H), 1.56-1.39 (m, 2H), 1.10-1.01 (m, 6H). A large water peak obscured a portion of the spectrum.

Step 5: 3-cyano-N-(3-(1-isobutyrylpiperidin-4-yl)-1-methyl-4-(trifluoromethyl)-1H-pyrrolo[2,3-b]pyridin-5-yl)benzamide. This reaction was carried out in three parallel batches. To a solution of 1-(4-(5-amino-1-methyl-4-(trifluoromethyl)-1H-pyrrolo[2,3-b]pyridin-3-yl)piperidin-1-yl)-2-methylpropan-1-one (70 g, 0.17 mol) in DCM (700 mL) was added pyridine (40 mL) and 3-cyanobenzoyl chloride (31 g, 0.187 mol) at 0° C. The mixture was stirred at 0° C. for 3 hr. The reaction was monitored by TLC (MTBE) until it was determined that the starting material was consumed, at which time the mixture the mixture was poured into water (300 mL). The organic layers were then extracted and washed with water (1 L×2). The organic layers were combined and concentrated to give the crude residue which was then suspended in EtOH (180 mL) and heated to 90° C. for 1 hr. The mixture was then cooled and the resulting precipitate was filtered and rinsed with cold EtOH (300 mL). The filter cake was then dried under vacuum to give the title compound (156 g, 62% combined yield) as a white solid. LC/MS [M+H]=498.2; $^1$HNMR (400 MHz, CDCl$_3$) δ 8.50 (s, 2H), 8.29-8.27 (m, 1H), 8.21-8.19 (m, 1H), 7.86-7.83 (m, 1H), 7.23 (s, 1H), 4.78-4.75 (m, 1H), 4.10-4.02 (m, 1H), 3.90 (s, 3H), 3.18-3.12 (m, 2H), 2.86-2.81 (m, 1H), 2.63-

2.57 (m, 1H), 2.05-1.92 (m, 3H), 1.47-1.44 (m, 2H), 1.15-1.10 (m, 6H); $^{13}$CNMR (100 MHz, DMSO-d$_6$) δ 174.5, 165.5, 147.0, 143.9, 135.8, 135.2, 132.8, 131.9, 131.7, 130.5, 125.4, 124.6, 122.7 (q, J=278 Hz), 118.7, 117.5, 113.9, 112.2, 46.2, 42.6, 35.7, 34.5, 33.7, 29.5, 20.1, 19.8, 19.0; mp=222° C.

Examples 6-13

The following Examples 6-13 were prepared analogous to Example 5 employing the appropriate carboxylic acid or carboxylic acid chloride coupling reagents in Step 5.

| Ex. | Structure | Name/Characterization |
|---|---|---|
| 6 | 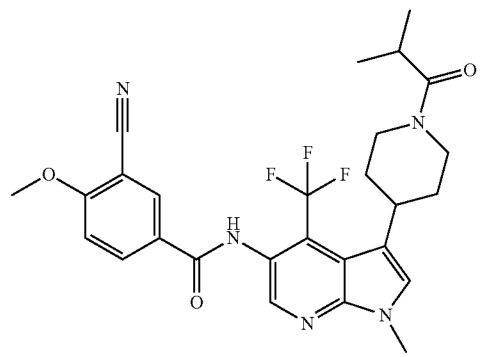 [SMILES: COc1ccc(C(=O)Nc2cnc3c(c(C4CCN(C(=O)C(C)C)CC4)cn3C)c2C(F)(F)F)cc1C#N] | 3-cyano-N-(3-(1-isobutyrylpiperidin-4-yl)-1-methyl-4-(trifluoromethyl)-1H-pyrrolo[2,3-b]pyridin-5-yl)-4-methoxybenzamide. LC/MS [M + H] = 528. $^1$H NMR (500 MHz, DMSO-d$_6$) δ 10.42 (s, NH), 8.37 (d, J = 2.2 Hz, 1H), 8.30 (dd, J = 2.2, 8.9 Hz, 1H), 8.29 (s, 1H), 7.85 (s, 1H), 7.44 (d, J = 8.9 Hz, 1H), 4.63-4.55 (m, 1H), 4.13-4.05 (m, 1H), 4.02 (s, 3H), 3.85 (s, 3H), 3.13-3.04 (m, 2H), 2.95-2.88 (m, 1H), 2.57-2.52 (m, 1H), 1.96-1.82 (m, 2H), 1.60-1.40 (m, 2H), 1.03 (dd, J = 6.4, 20.9 Hz, 6H). |
| 7 | 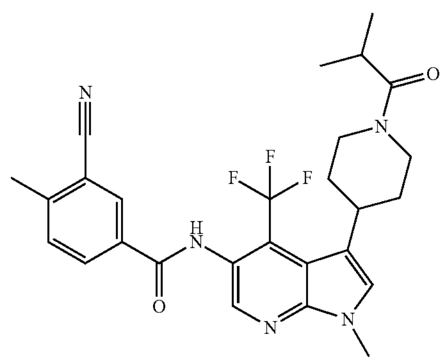 [SMILES: Cc1ccc(C(=O)Nc2cnc3c(c(C4CCN(C(=O)C(C)C)CC4)cn3C)c2C(F)(F)F)cc1C#N] | 3-cyano-N-(3-(1-isobutyrylpiperidin-4-yl)-1-methyl-4-(trifluoromethyl)-1H-pyrrolo[2,3-b]pyridin-5-yl)-4-methylbenzamide. LC/MS [M + H] = 512. $^1$H NMR (500 MHz, CD$_3$OD) δ 8.30 (s, 1H), 8.29 (d, J = 1.7 Hz, 1H), 8.16 (dd, J = 1.9, 7.9 Hz, 1H), 7.63 (s, 1H), 7.63 (d, J = 8.2 Hz, 1H), 4.76-4.70 (m, 1H), 4.24-4.18 (m, 1H), 3.91 (s, 3H), 3.44-3.38 (m, 1H), 3.26-3.20 (m, 1H), 3.05-2.98 (m, 1H), 2.74-2.66 (m, 1H), 2.65 (s, 3H), 2.11-2.05 (m, 1H), 2.04-1.98 (m, 1H), 1.68-1.54 (m, 2H), 1.13 (dd, J = 6.8, 19.7 Hz, 6H). |
| 8 | 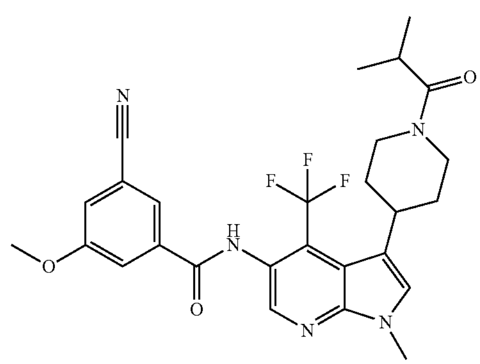 [SMILES: COc1cc(C#N)cc(C(=O)Nc2cnc3c(c(C4CCN(C(=O)C(C)C)CC4)cn3C)c2C(F)(F)F)c1] | 3-cyano-N-(3-(1-isobutyrylpiperidin-4-yl)-1-methyl-4-(trifluoromethyl)-1H-pyrrolo[2,3-b]pyridin-5-yl)-5-methoxybenzamide. LC/MS [M + H] = 528. $^1$H-NMR (500 MHz, CD$_3$OD) δ 8.30 (s, 1H), 7.90 (t, J = 1.4 Hz, 1H), 7.83-7.81 (m, 1H), 7.63 (s, 1H), 7.55-7.53 (m, 1H), 4.77-4.69 (m, 1H), 4.24-4.16 (m, 1H), 3.94 (s, 3H), 3.90 (s, 3H), 3.28-3.17 (m, 2H), 3.06-2.96 (m, 1H), 2.74-2.66 (m, 1H), 2.11-2.04 (m, 1H), 2.04-1.97 (m, 1H), 1.68-1.52 (m, 2H), 1.13 (dd, J = 7.1, 19.7 Hz, 6H) |
| 9 | 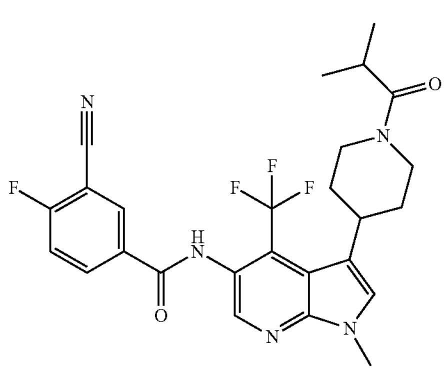 [SMILES: CC(C)C(=O)N1CCC(c2cn(C)c3ncc(NC(=O)c4ccc(F)c(C#N)c4)c(C(F)(F)F)c23)CC1] | 3-cyano-4-fluoro-N-(3-(1-isobutyrylpiperidin-4-yl)-1-methyl-4-(trifluoromethyl)-1H-pyrrolo[2,3-b]pyridin-5-yl)benzamide. LC/MS [M + H] = 516. $^1$H NMR (500 MHz, CD$_3$OD): δ 8.40 (dd, J = 2.3, 6.1 Hz, 1H), 8.37-8.32 (m, 1H), 8.31 (s, 1H), 7.64 (s, 1H), 7.58 (t, J = 8.9 Hz, 1H), 4.76-4.70 (m, 1H), 4.24-4.17 (m, 1H), 3.91 (s, 3H), 3.26-3.20 (m, 2H), 3.06-2.97 (m, 1H), 2.74-2.66 (m, 1H), 2.11-2.05 (m, 1H), 2.04-1.98 (m, 1H), 1.68-1.53 (m, 2H), 1.13 (dd, J = 6.8, 19.7 Hz, 6H). |

| Ex. | Structure | Name/Characterization |
|---|---|---|
| 10 | 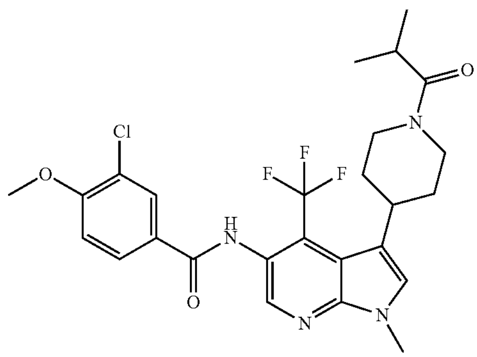 [SMILES: COc1ccc(C(=O)Nc2cnc3c(c(C4CCN(C(=O)C(C)C)CC4)cn3C)c2C(F)(F)F)cc1Cl] | 3-chloro-N-(3-(1-isobutyrylpiperidin-4-yl)-1-methyl-4-(trifluoromethyl)-1H-pyrrolo[2,3-b]pyridin-5-yl)-4-methoxybenzamide. LC/MS [M + H] = 537.45. ¹H NMR (400 MHz, CDCl₃) δ 8.61 (s, 1H), 7.99 (d, J = 1.8 Hz, 1H), 7.90-7.81 (m, 2H), 7.23 (s, 1H), 7.05 (d, J = 8.6 Hz, 1H), 4.84 (d, J = 13.1 Hz, 1H), 4.06 (d, J = 13.5 Hz, 1H), 4.00 (s, 3H), 3.91 (s, 3H), 3.17 (t, J = 12.2 Hz, 2H), 2.86 (dt, J = 13.5, 6.8 Hz, 1H), 2.65 (t, J = 12.4 Hz, 1H), 2.11-1.97 (m, 2H), 1.55-1.42 (m, 2H), 1.17 (dd, J = 9.5, 7.2 Hz, 6H). |
| 11 | 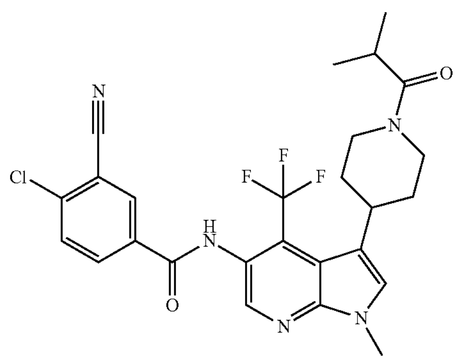 [SMILES: CC(C)C(=O)N1CCC(c2cn(C)c3ncc(NC(=O)c4ccc(Cl)c(C#N)c4)c(C(F)(F)F)c23)CC1] | 4-chloro-3-cyano-N-(3-(1-isobutyrylpiperidin-4-yl)-1-methyl-4-(trifluoromethyl)-1H-pyrrolo[2,3-b]pyridin-5-yl)benzamide. LC/MS [M + H] = 532. ¹H NMR (400 MHz, CDCl₃) δ 8.54 (s, 1H), 8.28 (br. s., 1H), 8.12 (d, J = 8.1 Hz, 1H), 8.07 (br. s., 1H), 7.69 (d, J = 8.5 Hz, 1H), 7.26 (br.s., 1H), 4.83 (d, J = 12.6 Hz, 1H), 4.42 (d, J = 7.2 Hz, 1H), 4.06 (d, J = 13.0 Hz, 1H), 3.92 (s, 3H), 3.17 (t, J = 12.6 Hz, 2H), 2.86 (dt, J = 13.2, 6.7 Hz, 1H), 2.64 (t, J = 12.4 Hz, 1H), 2.11-1.94 (m, 2H), 1.54-1.40 (m, 1H), 1.16 (dd, J = 9.7, 7.0 Hz, 6H). |
| 12 | 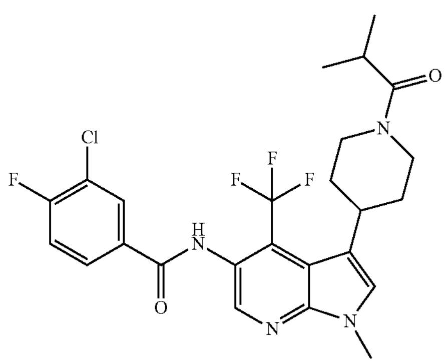 [SMILES: CC(C)C(=O)N1CCC(c2cn(C)c3ncc(NC(=O)c4ccc(F)c(Cl)c4)c(C(F)(F)F)c23)CC1] | 3-chloro-4-fluoro-N-(3-(1-isobutyrylpiperidin-4-yl)-1-methyl-4-(trifluoromethyl)-1H-pyrrolo[2,3-b]pyridin-5-yl)benzamide. LC/MS [M + H] = 525.15. ¹H NMR (400 MHz, CDCl₃) δ 8.62-8.53 (m, 1H), 8.07-7.70 (m, 3H), 7.56 (d, J = 8.6 Hz, 1H), 7.26-7.21 (m, 1H), 4.83 (d, J = 12.1 Hz, 1H), 4.06 (d, J = 13.0 Hz, 1H), 3.95-3.88 (m, 3H), 3.16 (t, J = 12.1 Hz, 2H), 2.97-2.81 (m, 2H), 2.64 (t, J = 12.4 Hz, 1H), 2.12-1.94 (m, 2H), 1.57-1.42 (m, 1H), 1.16 (dd, J = 9.9, 7.2 Hz, 6H). |
| 13 | 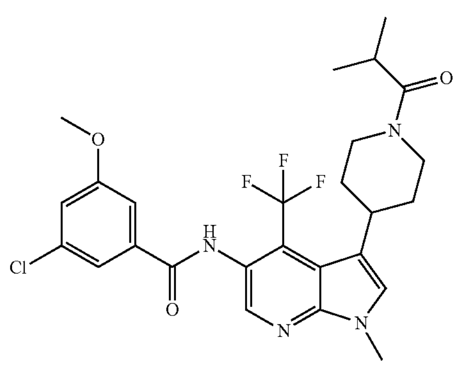 [SMILES: COc1cc(Cl)cc(C(=O)Nc2cnc3c(c(C4CCN(C(=O)C(C)C)CC4)cn3C)c2C(F)(F)F)c1] | 3-chloro-N-(3-(1-isobutyrylpiperidin-4-yl)-1-methyl-4-(trifluoromethyl)-1H-pyrrolo[2,3-b]pyridin-5-yl)-5-methoxybenzamide. LC/MS [M + H] = 537.45. ¹H NMR (400 MHz, DMSO-d₆) δ 10.46 (s, 1H), 8.29 (s, 1H), 7.85 (s, 1H), 7.62 (s, 1H), 7.51 (s, 1H), 7.31 (t, J = 2.0 Hz, 1H), 4.60 (d, J = 12.3 Hz, 1H), 4.09 (d, J = 12.8 Hz, 1H), 3.86 (s, 3H), 3.82 (s, 3H), 3.09 (d, J = 7.9 Hz, 2H), 2.97-2.86 (m, 1H), 2.60-2.50 (m, 1H), 1.97-1.81 (m, 2H), 1.59-1.39 (m, 2H), 0.90 (d, J = 6.6 Hz, 3H), 1.03 (d, J = 6.6 Hz, 3H). |

Example 14

Preparation of 3-cyano-N-(3-(1-(2-cyclopentylacetyl)piperidin-4-yl)-1-methyl-4-(trifluoromethyl)-1H-pyrrolo[2,3-b]pyridin-5-yl)benzamide

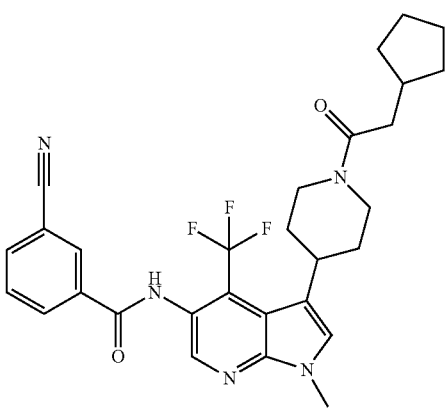 [SMILES: Cn1cc(C2CCN(C(=O)CC3CCCC3)CC2)c2c(C(F)(F)F)c(NC(=O)c3cccc(C#N)c3)cnc21]

Step 1: tert-butyl 4-(5-(3-cyanobenzamido)-1-methyl-4-(trifluoromethyl)-1H-pyrrolo[2,3-b]pyridin-3-yl)piperidine-1-carboxylate. A stirred mixture of tert-butyl 4-(1-methyl-5-nitro-4-(trifluoromethyl)-1H-pyrrolo[2,3-b]pyridin-3-yl)-3,6-dihydropyridine-1(2H)-carboxylate (prepared as described in Example 5, 1400 mg, 3.53 mmol) in EtOH (50 mL) and DCM (10 mL) was purged with $N_2$ and then $Pd(OH)_2/C$ (1000 mg, 7.121 mmol) was added at room temperature. The reaction mixture was stirred at 50° C. under hydrogen gas (50 psi). After 4 hr, the mixture was filtered and the filtrate was concentrated. The crude product was purified by silica gel column chromatography (PE: EtOAc, 70:30) to afford tert-butyl 4-(5-amino-1-methyl-4-(trifluoromethyl)-1H-pyrrolo[2,3-b]pyridin-3-yl)piperidine-1-carboxylate (1.02 g, 68.3%) as a white solid which was immediately brought up in THF (50 mL). 3-cyanobenzoyl chloride (650 mg, 4.42 mmol), 2-chloromethylpyridinium iodide (2050 mg, 8.03 mmol), and DIPEA (2080 mg, 16.1 mmol) were added at room temperature. The mixture was then stirred for 8 hr at ambient temperature. Upon consumption of the starting materials as demonstrated by TLC, water was added to the reaction the mixture, and the mixture was then extracted with DCM. The organic layer was separated, dried over $Na_2SO_4$, and concentrated. The crude product was purified by silica gel column chromatography (PE: EtOAc, 9:1-8:2) to afford the title compound (1.3 g, 61%) as a white solid. $^1$H-NMR (400 MHz, $CDCl_3$) δ 8.56 (s, 1H), 8.24-8.18 (m, 1H), 8.15-8.01 (m, 1H), 7.88-7.86 (m, 1H), 7.69-7.65 (m, 1H), 4.24 (br s, 1H), 3.91 (s, 3H), 3.08-3.02 (m, 1H), 2.85-2.80 (m, 2H), 1.95-1.91 (m, 2H), 1.48 (s, 9H).

Step 2: 3-cyano-N-(1-methyl-3-(piperidin-4-yl)-4-(trifluoromethyl)-1H-pyrrolo[2,3-b]pyridin-5-yl)benzamide. To the stirred solution of tert-butyl 4-(5-(3-cyanobenzamido)-1-methyl-4-(trifluoromethyl)-1H-pyrrolo[2,3-b]pyridin-3-yl)piperidine-1-carboxylate (500 mg, 0.948 mmol) in DCM (10 mL) was added 4M HCl in dioxane at room temperature, then stirred for 1 hr at ambient temperature. The product hydrochloride was precipitated out. The solvent was removed under reduced pressure to afford the hydrochloride salt of the title compound (80 mg). LC/MS [M+H]=427.9. $^1$H NMR (400 MHz, DMSO-$d_6$) δ 9.11 (br s, 2H), 8.46 (s, 1H), 8.35-8.32 (m, 2H), 8.14-8.11 (m, 1H), 7.82-7.79 (m, 2H), 3.90 (s, 3H), 3.40-3.36 (m, 2H), 3.13-3.00 (m, 3H), 2.09-1.84 (m, 4H), Step 3: 3-cyano-N-(3-(1-(2-cyclopentylacetyl)piperidin-4-yl)-1-methyl-4-(trifluoromethyl)-1H-pyrrolo[2,3-b]pyridin-5-yl)benzamide. 3-Cyano-N-(1-methyl-3-(piperidin-4-yl)-4-(trifluoromethyl)-1H-pyrrolo[2,3-b]pyridin-5-yl)benzamide hydrochloride (80 mg, 0.152 mmol) was treated with DCM (2 mL), TEA (0.5 mL, 3.59 mmol), HATU (90 mg, 0.24 mmol) and 2-cyclopentylacetic acid (0.374 mmol, 2 eq). The mixture was then stirred at room temperature for 1 hr or until the reaction mixture had shown to be complete by LCMS. The reaction mixture was concentrated. The residue was purified by silica gel column chromatography (PE:EtOAc, 70:30) to provide the title compound (25.9 mg, 35%) as a while solid. LC/MS [M+Na]=560.0. $^1$H NMR (400 MHz, $CDCl_3$) δ 8.59 (s, 1H), 8.30-8.11 (m, 2H), 8.01-7.82 (m, 2H), 7.68 (t, J=7.8 Hz, 1H), 7.27-7.20 (m, 2H), 4.83 (d, J=13.1 Hz, 1H), 4.01 (d, J=12.6 Hz, 1H), 3.92 (s, 3H), 3.16 (t, J=11.8 Hz, 2H), 2.72 (m, 1H), 2.39-1.81 (m, 7H), 1.64-1.41 (m, 5H), 1.29-1.03 (m, 2H).

Examples 15-27

The following Examples 15-27 were prepared analogous to Example 14 employing the appropriate carboxylic acid coupling reagent in Step 3.

| Ex. | Structure | Name/Characterization |
|---|---|---|
| 15 | 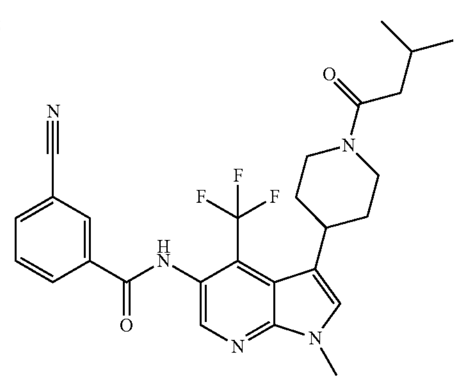 [SMILES: CC(C)CC(=O)N1CCC(c2cn(C)c3ncc(NC(=O)c4cccc(C#N)c4)c(C(F)(F)F)c23)CC1] | 3-cyano-N-(1-methyl-3-(1-(3-methylbutanoyl)piperidin-4-yl)-4-(trifluoromethyl)-1H-pyrrolo[2,3-b]pyridin-5-yl)benzamide. LC/MS [M + Na] = 534.1. $^1$H NMR (400 MHz, $CDCl_3$) δ 8.58 (s, 1H), 8.29-8.10 (m, 2H), 7.99 (s, 1H), 7.89 (d, J = 8.0 Hz, 1H), 7.68 (t, J = 7.8 Hz, 1H), 7.24 (s, 1H), 4.84 (d, J = 15.6 Hz, 1H), 4.00 (d, J = 12.6 Hz, 1H), 3.92 (s, 3H), 3.23-3.01 (m, 2H), 2.49-2.71 (m, 1H), 2.26 (d, J = 7.0 Hz, 2H), 1.86-2.20 (m, 3H), 1.36-1.61 (m, 2H), 1.00-0.88 (m, 6H). |

| Ex. | Structure | Name/Characterization |
|---|---|---|
| 16 | 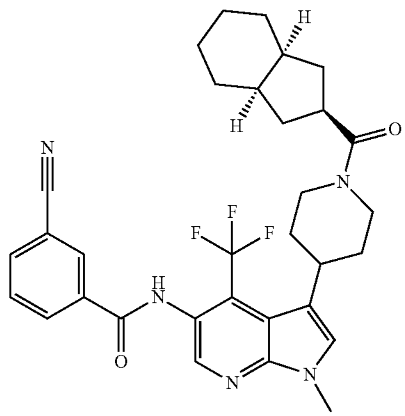 [SMILES: Cn1cc(C2CCN(C(=O)[C@H]3C[C@H]4CCCC[C@H]4C3)CC2)c2c(C(F)(F)F)c(NC(=O)c3cccc(C#N)c3)cnc21] | 5-cyano-N-(1-methyl-3-(1-((2r,3aR,7aS)-octahydro-1H-indene-2-carbonyl)piperidin-4-yl)-4-(trifluoromethyl)-1H-pyrrolo[2,3-b]pyridin-5-yl)benzamide. LC/MS [M + H] = 578.1. $^1$H NMR (400 MHz, CDCl$_3$) δ 8.58 (s, 1H), 8.27-8.12 (m, 2H), 7.98-7.85 (m, 2H), 7.68 (t, J = 7.8 Hz, 1H), 7.25 (s, 1H), 4.84 (d, J = 15.1 Hz, 1H), 4.06 (d, J = 13.6 Hz, 1H), 3.92 (s, 3H), 3.23-2.95 (m, 3H), 2.76-2.57 (m, 1H), 2.09-1.79 (m, 8H), 1.61-1.39 (m, 6H), 1.35-1.20 (m, 4H). |
| 17 | 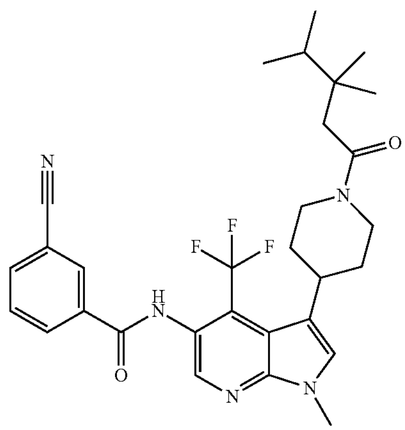 [SMILES: CC(C)C(C)(C)CC(=O)N1CCC(c2cn(C)c3ncc(NC(=O)c4cccc(C#N)c4)c(C(F)(F)F)c23)CC1] | 3-cyano-N-(1-methyl-4-(trifluoromethyl)-3-(1-(3,3,4-trimethylpentanoyl)piperidin-4-yl)-1H-pyrrolo[2,3-b]pyridin-5-yl)benzamide. LC/MS [M + Na] = 576.1. $^1$H NMR (400 MHz, CDCl$_3$) δ 8.58 (s, 1H), 8.12-8.31 (m, 2H), 8.00 (br. s., 1H), 7.89 (d, J = 7.5 Hz, 1H), 7.68 (t, J = 7.5 Hz, 1H), 7.24 (s, 1H), 4.88 (d, J = 14.6 Hz, 1H), 4.06 (d, J = 13.1 Hz, 1H), 3.92 (s, 3H), 3.16 (br. s., 2H), 2.62 (t, J = 12.8 Hz, 1H), 2.41-2.21 (m, 2H), 2.08-1.92 (m, 3H), 1.74-1.65 (m, 1H), 1.62-1.39 (m, 1H), 1.01-0.88 (m, 12H). |
| 18 | 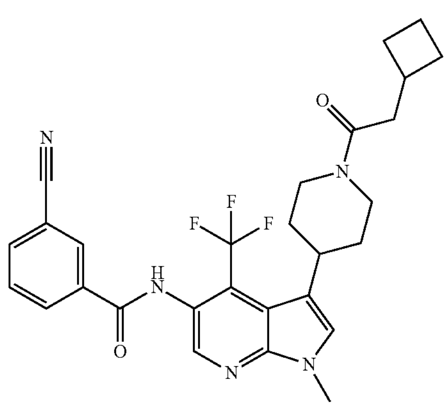 [SMILES: Cn1cc(C2CCN(C(=O)CC3CCC3)CC2)c2c(C(F)(F)F)c(NC(=O)c3cccc(C#N)c3)cnc21] | 3-cyano-N-(3-(1-(2-cyclobutylacetyl)piperidin-4-yl)-1-methyl-4-(trifluoromethyl)-1H-pyrrolo[2,3-b]pyridin-5-yl)benzamide. LC/MS [M + H] = 524.0. $^1$H NMR (400 MHz, CDCl$_3$) δ 8.57 (s, 1H), 8.25 (s, 1H), 8.18 (d, J = 8.0 Hz, 1H), 8.06 (s, 1H), 7.88 (d, J = 7.5 Hz, 1H), 7.67 (t, J = 7.8 Hz, 1H), 7.24 (s, 1H), 4.78 (d, J = 14.1 Hz, 1H), 3.97 (d, J = 14.1 Hz, 1H), 3.91 (s, 3H), 3.20-3.07 (m, 2H), 2.72 (dt, J = 15.6, 7.8 Hz, 1H), 2.67-2.57 (m, 1H), 2.50 (d, J = 7.5 Hz, 2H), 2.23-2.11 (m, 2H), 2.07-1.80 (m, 4H), 1.78-1.67 (m, 2H), 1.55-1.36 (m, 2H). |

| Ex. | Structure | Name/Characterization |
|---|---|---|
| 19 | 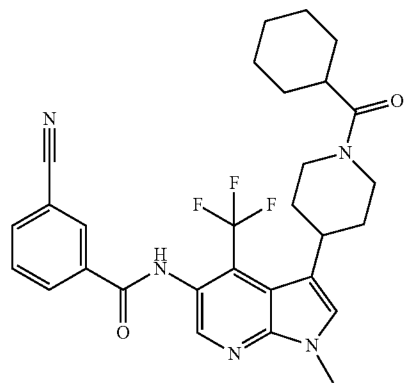 [SMILES: Cn1cc(C2CCN(C(=O)C3CCCCC3)CC2)c2c(C(F)(F)F)c(NC(=O)c3cccc(C#N)c3)cnc21] | 3-cyano-N-(3-(1-(cyclohexanecarbonyl)piperidin-4-yl)-1-methyl-4-(trifluoromethyl)-1H-pyrrolo[2,3-b]pyridin-5-yl)benzamide. LC/MS [M + H] = 538.1. $^1$H NMR (400 MHz, CDCl$_3$) δ 8.58 (s, 1H), 8.25 (s, 1H), 8.18 (d, J = 8.0 Hz, 1H), 8.00 (s, 1H), 7.89 (d, J = 7.5 Hz, 1H), 7.72-7.61 (m, 1H), 7.25 (s, 1H), 4.82 (d, J = 14.6 Hz, 1H), 4.04 (d, J = 13.1 Hz, 1H), 3.91 (s, 3H), 3.24-3.07 (m, 2H), 2.70-2.43 (m, 2H), 2.11-1.95 (m, 2H), 1.85-1.69 (m, 5H), 1.62-1.41 (m, 3H), 1.35-1.15 (m, 4H). |
| 20 | 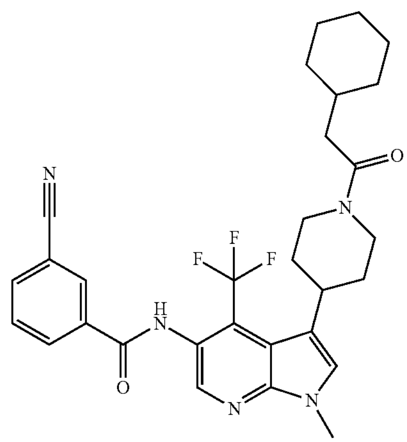 [SMILES: Cn1cc(C2CCN(C(=O)CC3CCCCC3)CC2)c2c(C(F)(F)F)c(NC(=O)c3cccc(C#N)c3)cnc21] | 3-cyano-N-(3-(1-(2-cyclohexylacetyl)piperidin-4-yl)-1-methyl-4-(trifluoromethyl)-1H-pyrrolo[2,3-b]pyridin-5-yl)benzamide. LC/MS [M + H] = 552.1; $^1$H NMR (400 MHz, CDCl$_3$) δ 8.58 (br. s., 1H), 8.28-8.13 (m, 2H), 7.98 (br. s., 1H), 7.89 (d, J = 7.0 Hz, 1H), 7.68 (t, J = 7.8 Hz, 1H), 7.25 (br. s., 1H), 4.84 (d, J = 11.5 Hz, 1H), 4.00 (d, J = 11.5 Hz, 1H), 3.92 (s, 3H), 3.16 (t, J = 11.5 Hz, 2H), 2.73-2.58 (m, 1H), 2.26 (d, J = 7.0 Hz, 2H), 2.10-1.94 (m, 2H), 1.86-1.63 (m, 6H), 1.61-1.39 (m, 2H), 1.35-1.09 (m, 3H), 1.05-0.87 (m, 2H). |
| 21 | 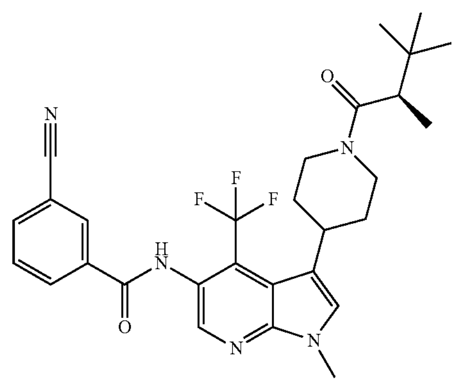 [SMILES: C[C@@H](C(=O)N1CCC(c2cn(C)c3ncc(NC(=O)c4cccc(C#N)c4)c(C(F)(F)F)c23)CC1)C(C)(C)C] | (R)-3-cyano-N-(1-methyl-4-(trifluoromethyl)-3-(1-(2,3,3-trimethylbutanoyl)piperidin-4-yl)-1H-pyrrolo[2,3-b]pyridin-5-yl)benzamide. LC/MS [M + Na] = 562.1; Chiral LC: Rt = 5.26 min (Method A); $^1$H NMR (400 MHz, CDCl$_3$) δ 8.56 (br. s., 1H), 8.04-8.29 (m, 3H), 7.88 (d, J = 8.0 Hz, 1H), 7.74-7.59 (m, 1H), 7.23 (s, 1H), 4.89 (br. s., 1H), 4.20 (d, J = 13.1 Hz, 1H), 3.91 (s, 3H), 3.16 (t, J = 12.6 Hz, 2H), 2.77-2.44 (m, 2H), 2.13-1.83 (m, 2H), 1.54-1.31 (m, 2H), 1.22-0.84 (m, 12H). |
| 22 | 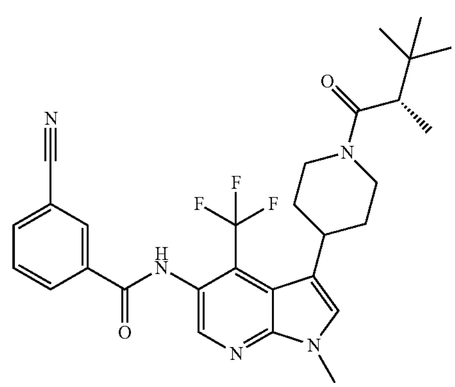 [SMILES: C[C@H](C(=O)N1CCC(c2cn(C)c3ncc(NC(=O)c4cccc(C#N)c4)c(C(F)(F)F)c23)CC1)C(C)(C)C] | (S)-3-cyano-N-(1-methyl-4-(trifluoromethyl)-3-(1-(2,3,3-trimethylbutanoyl)piperidin-4-yl)-1H-pyrrolo[2,3-b]pyridin-5-yl)benzamide. LC/MS [M + Na] = 562.1; Chiral LC: Rt = 4.91 min (Method A); $^1$H NMR (400 MHz, CDCl$_3$) δ 8.56 (br. s., 1H), 8.29-8.04 (m, 3H), 7.88 (d, J = 8.0 Hz, 1H), 7.74-7.59 (m, 1H), 7.23 (s, 1H), 4.89 (br. s., 1H), 4.20 (d, J = 13.1 Hz, 1H), 3.91 (s, 3H), 3.16 (t, J = 12.6 Hz, 2H), 2.77-2.44 (m, 2H), 2.13-1.83 (m, 2H), 1.54-1.31 (m, 2H), 1.22-0.84 (m, 12H). |

| Ex. | Structure | Name/Characterization |
|---|---|---|
| 23 | 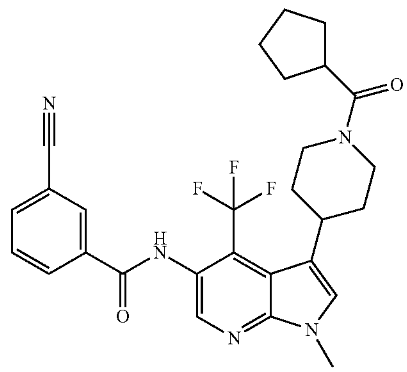 [SMILES: Cn1cc(C2CCN(C(=O)C3CCCC3)CC2)c2c(C(F)(F)F)c(NC(=O)c3cccc(C#N)c3)cnc21] | 3-cyano-N-(3-(1-(cyclopentanecarbonyl)piperidin-4-yl)-1-methyl-4-(trifluoromethyl)-1H-pyrrolo[2,3-b]pyridin-5-yl)benzamide. LC/MS [M + H] = 524.5. $^1$H NMR (400 MHz, DMSO-d$_6$) δ 10.59 (s, 1H), 8.42 (s, 1H), 8.33-8.22 (m, 1H), 8.11 (d, J = 7.4 Hz, 1H), 7.86 (s, 1H), 7.79 (t, J = 7.8 Hz, 1H), 4.59 (d, J = 14.4 Hz, 1H), 4.12 (d, J = 11.3 Hz, 1H), 3.93-3.74 (m, 2H), 3.17-2.95 (m, 2H), 2.74-2.52 (m, 2 H, 2.05-1.35 (m, 9H), 1.35-1.08 (m, 2H). |
| 24 | 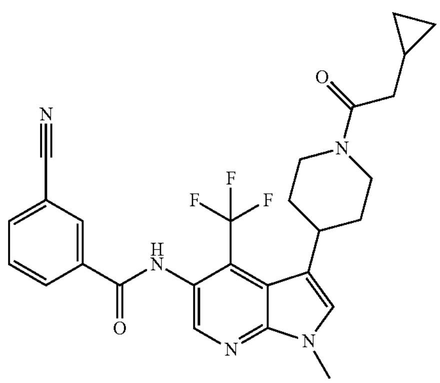 [SMILES: Cn1cc(C2CCN(C(=O)CC3CC3)CC2)c2c(C(F)(F)F)c(NC(=O)c3cccc(C#N)c3)cnc21] | 3-cyano-N-(3-(1-(2-cyclopropylacetyl)piperidin-4-yl)-1-methyl-4-(trifluoromethyl)-1H-pyrrolo[2,3-b]pyridin-5-yl)benzamide. LC/MS [M + Na] = 532.1; $^1$H NMR (400 MHz, CDCl$_3$): δ 8.54 (s, 1H), 8.30-8.18 (m, 3H), 7.89-7.86 (m, 1H), 7.68-7.64 (m, 1H), 7.27-7.24 (m, 1H), 4.82-4.79 (m, 1H), 3.96-3.91 (m, 4H), 3.16-3.13 (m, 2H), 2.67-2.61 (m, 1H), 2.32-2.31 (m, 2H), 2.05-1.96 (m,2H), 1.54-1.45 (m, 2H), 1.10-1.02 (m, 1H), 0.57-0.55 (m. 2H), 0.19-0.18 (m, 2H). |
| 25 | 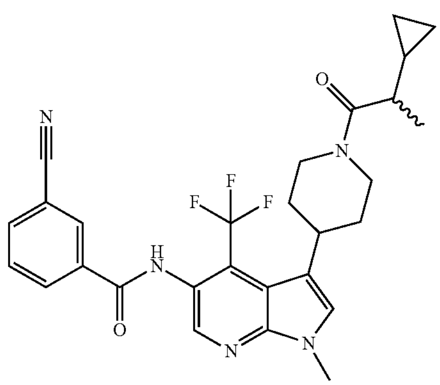 [SMILES: CC(C(=O)N1CCC(c2cn(C)c3ncc(NC(=O)c4cccc(C#N)c4)c(C(F)(F)F)c23)CC1)C1CC1] | Rac-3-cyano-N-(3-(1-(2-cyclopropylpropanoyl)piperidin-4-yl)-1-methyl-4-(tnfluoromethyl)-1H-pyrrolo[2,3-b]pyridin-5-yl)benzamide. LC/MS [M + H] = 524.1; $^1$H NMR (400 MHz, CDCl$_3$) δ 8.63 (s, 1H), 8.48 (s, 1H), 8.29-8.20 (m, 2H), 7.85-7.83 (m, 1H), 7.64-7.61 (m, 1H), 7.27-7.22 (m, 1H), 4.81-4.78 (m, 1H), 3.98-3.89 (m, 4H), 3.22-3.05 (m, 2H), 2.72-2.55 (m, 1H), 2.20-1.92 (m, 3H), 1.50-1.09 (m, 6H), 0.70-0.45 (m, 2H), 0.14 (br s, 2 H). |
| 26 | 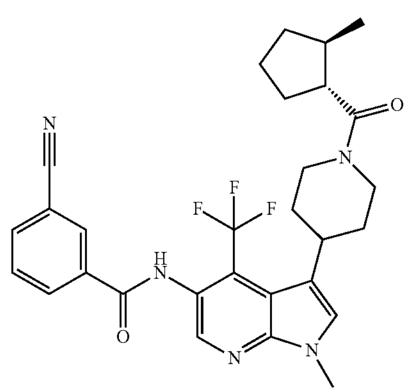 [SMILES: C[C@@H]1CCC[C@H]1C(=O)N1CCC(c2cn(C)c3ncc(NC(=O)c4cccc(C#N)c4)c(C(F)(F)F)c23)CC1] | Rac-3-cyano-N-(1-methyl-3-(1-((1S*,2S*)-2-methylcyclopentane-1-carbonyl)piperidin-4-yl)-4-(trifluoromethyl)-1H-pyrrolo[2,3-b]pyridin-5-yl)benzamide. LC/MS [M + H] = 538.1; Chiral LC: Rt = 5.51 min (Method A); $^1$H NMR (400 MHz, CDCl$_3$) δ 8.52 (s, 1H), 8.27-8.19 (m, 3H), 7.88-7.86 (m, 1H), 7.65 (m, 1H), 7.25-7.23 (m, 1H), 4.84-4.81 (m, 1H), 4.12-4.08 (m, 1H), 3.91(s, 3H), 3.20-3.10 (m, 2H), 2.65-2.58 (m, 1H), 2.50-2.48 (m, 1H), 2.46-2.30 (m, 1H), 2.18-1.75 (m, 4H), 1.71-1.63 (m, 3H), 1.48-1.35 (m, 2H), 1.26-1.21 (m, 1H), 1.04-0.99 (m, 3H). |

| Ex. | Structure | Name/Characterization |
|---|---|---|
| 27 | 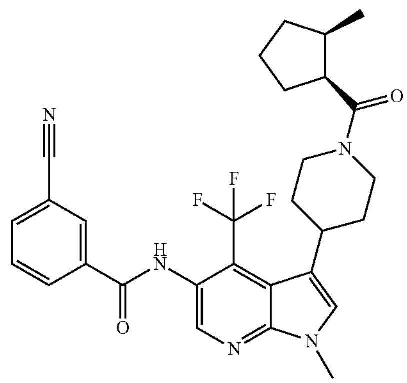 [SMILES: C[C@@H]1CCC[C@@H]1C(=O)N1CCC(c2cn(C)c3ncc(NC(=O)c4cccc(C#N)c4)c(C(F)(F)F)c23)CC1] | Rac-3-cyano-N-(1-methyl-3-(1-((1R*,2S*)-2-methylcyclopentane-1-carbonyl)piperidin-4-yl)-4-(trifluoromethyl)-1H-pyrrolo[2,3-b]pyridin-5-yl)benzamide. LC/MS [M + H] = 538.1; Chiral LC: Rt = 5.79 min (Method A); $^1$H NMR (400 MHz, CDCl$_3$) δ 8.55 (s, 1H), 8.27-8.19 (m, 3H), 7.89-7.87 (m, 1H), 7.69-7.65 (m, 1H), 7.24-7.23 (m, 1H), 4.88-4.82 (m, 1H), 4.12-4.10 (m, 1H), 3.92 (s, 3H), 3.19-3.11 (m, 2H), 3.09-2.95 (m, 1H), 2.95-2.60 (m, 1H), 2.40-2.28 (m, 1H), 2.27-2.15 (m, 1H), 2.13-1.91 (m, 2H), 1.90-1.32 (m, 6H), 0.95-0.82 (m, 3H). |

Examples 28-29

The following Examples 28-29 were prepared analogous to Example 14 employing tetrahydrothiophene-2-carboxylic acid in Step 3. The resulting racemic mixture was resolved by chiral SFC (Chiralcel OJ, 250×30 mm, 5 μm; 30% MeOH; 60 mL/min). Isolation of the first eluting isomer afforded Example 28 and isolation of the second eluting isomer afforded Example 29.

| Ex. | Structure | Name/Characterization |
|---|---|---|
| 28 | Absolute stereochemistry arbitrary | (R)-3-cyano-N-(1-methyl-3-(1-(tetrahydrothiophene-2-carbonyl)piperidin-4-yl)-4-(trifluoromethyl)-1H-pyrrolo[2,3-b]pyridin-5-yl)benzamide. LC/MS [M + H] = 542.1. Chiral SFC: Rt = 4.878 min (Method N). $^1$H NMR (400 MHz, CDCl$_3$) δ 8.55 (s, 1H), 8.25-8.17 (m, 3H), 7.89-7.85 (m, 1H), 7.66-7.64 (m, 1H), 7.27-7.24 (m, 1H), 4.78-4.74 (m, 1H), 4.07-4.00 (m, 2H), 3.91 (s, 3H), 3.20-3.14 (m, 2H), 2.99-2.89 (m, 2H), 2.76-2.62 (m, 1H), 2.60-2.47 (m, 1H), 2.35-2.20 (m, 1H), 2.12-1.85 (m, 4H), 1.78-1.45 (m, 2H). |
| 29 | Absolute stereochemistry arbitrary | (S)-3-cyano-N-(1-methyl-3-(1-(tetrahydrothiophene-2-carbonyl)piperidin-4-yl)-4-(trifluoromethyl)-1H-pyrrolo[2,3-b]pyridin-5-yl)benzamide. LC/MS [M + H] = 542.1. Chiral SFC: Rt = 5.214 min (Method N). $^1$H NMR (400 MHz, CDCl$_3$) δ 8.55 (s, 1H), 8.25-8.17 (m, 3H), 7.89-7.85 (m, 1H), 7.66-7.64 (m, 1H), 7.27-7.24 (m, 1H), 4.78-4.74 (m, 1H), 4.07-4.00 (m, 2H), 3.91 (s, 3H), 3.20-3.14 (m, 2H), 2.99-2.89 (m, 2H), 2.76-2.62 (m, 1H), 2.60-2.47 (m, 1H), 2.35-2.20 (m, 1H), 2.12-1.85 (m, 4H), 1.78-1.45 (m, 2H). |

Examples 30-31

The following Examples 30-31 were prepared analogous to Example 14 however employing 3-cyano-4-methoxybenzoic acid in Step 1.

7.86 mmol) in toluene (1200 mL) at room temperature under N₂. After addition, the reaction mixture was purged with N₂ for several times and then was heated at 80° C. for 3.5 hr. The reaction mixture was cooled to room temperature and poured into ice-water slowly. After standing overnight, the

| Ex. | Structure | Name/Characterization |
|---|---|---|
| 30 | 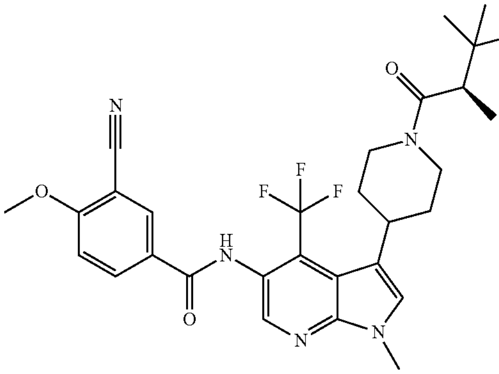 | (R)-3-cyano-4-methoxy-N-(1-methyl-4-(trifluoromethyl)-3-(1-(2,3,3-trimethylbutanoyl)piperidin-4-yl)-1H-pyrrolo[2,3-b]pyridin-5-yl)benzamide. LC/MS [M + H] = 570.2; Chiral LC: Rt = 7.01 min (Method A); $^1$H NMR (400 MHz, CDCl$_3$) δ 8.54 (br. s., 1H), 8.18 (br. s., 2H), 8.03 (br. s., 1H), 7.22 (s, 1H), 7.11 (d, J = 6.5 Hz, 1H), 4.90 (br. s., 1H), 4.20 (d, J = 13.1 Hz, 1H), 4.04 (s, 3H), 3.99 (s, 3H), 3.15 (t, J = 12.3 Hz, 2H), 2.80-2.46 (m, 2H), 2.12-1.89 (m, 2H), 1.75-1.32 (m, 2H), 1.24-0.72 (m, 12H). |
| 31 | 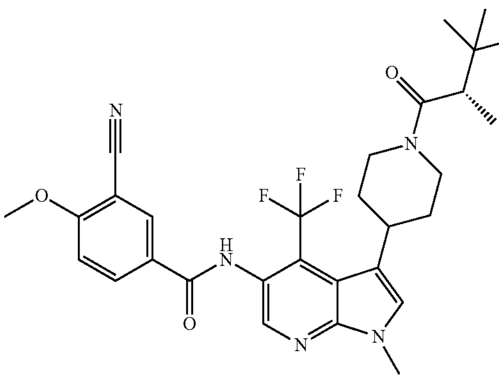 | (S)-3-cyano-4-methoxy-N-(1-methyl-4-(trifluoromethyl)-3-(1-(2,3,3-trimethylbutanoyl)piperidin-4-yl)-1H-pyrrolo[2,3-b]pyridin-5-yl)benzamide. LC/MS [M + H] = 570.2; Chiral LC: Rt = 6.43 min (Method A); $^1$H NMR (400 MHz, CDCl$_3$) δ 8.54 (br. s., 1H), 8.18 (br. s., 2H), 8.03 (br. s., 1H), 7.22 (s, 1H), 7.11 (d, J = 6.5 Hz, 1H), 4.90 (br. s., 1H), 4.20 (d, J = 13.1 Hz, 1H), 4.04 (s, 3H), 3.99 (s, 3H), 3.15 (t, J = 12.3 Hz, 2H), 2.80-2.46 (m, 2H), 2.12-1.89 (m, 2H), 1.75-1.32 (m, 2H), 1.24-0.72 (m, 12H). |

Example 32

Preparation of (R)-3-cyano-N-(1,4-dimethyl-3-(1-(2,3,3-trimethylbutanoyl)piperidin-4-yl)-1H-pyrrolo[2,3-b]pyridin-5-yl)benzamide

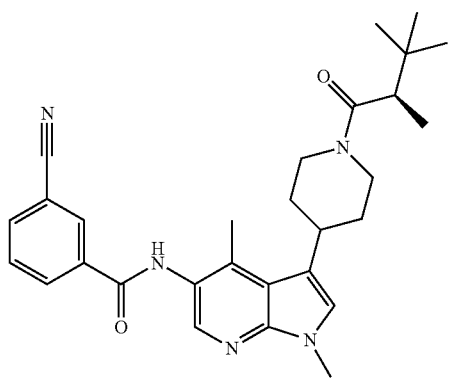 [SMILES: Cc1c(NC(=O)c2cccc(C#N)c2)cnc2c1c(C1CCN(C(=O)[C@H](C)C(C)(C)C)CC1)cn2C]

Step 1: 4-methyl-1H-pyrrolo[2,3-b]pyridine. A solution of MeMgBr (655 mL, 1.97 mol, 3 M in ether) was added dropwise to a stirred suspension of 4-chloro-1H-pyrrolo[2,3-b]pyridine (60 g, 393.2 mmol) and Pd(dppf)Cl₂ (5.75 g, mixture was filtered and further washed with EtOAc several times. The filtrate was extracted with EtOAc (2×5 L). The combined organic layers were washed with brine, dried over Na₂SO₄ and concentrated. The residue was triturated with PE to give the title compound (48.2 g, 93%) as a off-yellow solid. $^1$HNMR (400 MHz, CDCl₃) δ 11.27 (br. s., 1H), 8.25-8.23 (m, 1H), 7.37-7.35 (m, 1H), 6.93-6.91 (m, 1H), 6.55-6.53 (m, 1H), 2.60 (s, 3H).

Step 2: 4-methyl-1-(phenylsulfonyl)-1H-pyrrolo[2,3-b]pyridine. Bu₄NBr (9.14 g, 28.4 mmol), KOH (63.6 g, 1.134 mol, 33% in water) and PhSO₂Cl (160 g, 908 mmol) were added to a stirred solution of 4-methyl-1H-pyrrolo[2,3-b]pyridine (75 g, 567 mmol) in DCM (1600 mL) at room temperature. The reaction mixture was stirred at room temperature for 2.5 hr. The mixture was washed with brine, dried over Na₂SO₄ and concentrated. The residue was triturated with MTBE to afford the title compound (112 g, 72.7%) as a brown solid. $^1$HNMR (400 MHz, CDCl₃) δ 8.32-8.30 (m, 1H), 8.21-8.15 (m, 2H), 7.70-7.68 (m, 1H), 7.58-7.52 (m, 1H), 7.50-7.42 (m, 2H), 6.99-6.97 (m, 1H), 6.63-6.61 (m, 1H), 2.48 (s, 3H).

Step 3: 4-methyl-5-nitro-1-(phenylsulfonyl)-1H-pyrrolo[2,3-b]pyridine. A solution of tetrabutylammonium nitrate (201 g, 661 mmol) in DCM (400 mL) was added dropwise to a stirred solution of 4-methyl-1-(phenylsulfonyl)-1H-pyrrolo[2,3-b]pyridine (120 g, 441 mmol) in DCM (1600 mL) at −10° C. (CF₃CO)₂O (139 g, 661 mmol) was then added dropwise at −5° C. and the mixture was stirred at 0° C. for 20 min. The reaction mixture were washed with water (7 L), dried over Na$_2$SO$_4$ and concentrated. The residue was triturated with MTBE to afford the title compound (89.1 g, 63.7%) as a yellow solid. $^1$HNMR (400 MHz, CDCl$_3$) δ 9.05 (s, 1H), 8.22-8.20 (m, 2H), 7.88-7.87 (m, 1H), 7.71-7.59 (m, 1H), 7.58-7.46 (m, 2H), 6.79-6.78 (m, 1H), 2.78 (s, 3H).

Step 4: 4-methyl-5-nitro-1H-pyrrolo[2,3-b]pyridine. Potassium carbonate (43.8 g, 316 mmol) and morpholine (138 g, 1.58 mol) were added to a stirred suspension of 4-methyl-5-nitro-1-(phenylsulfonyl)-1H-pyrrolo[2,3-b]pyridine (50 g, 158 mmol) in MeOH (1.8 L) at room temperature. The mixture was heated at reflux for 10 min. The reaction mixture was then cooled to room temperature and most of the MeOH was removed under vacuum. To the residue was added DCM (1 L), sat. NH$_4$Cl (1 L) and water (0.5 L). The mixture was stirred at room temperature for 30 min and left standing overnight. The resulting solids were filtered, washed with water and DCM several times, and dried to afford the title compound (25 g, 89.7%) as an off-yellow solid. $^1$HNMR (400 MHz, DMSO-d$_6$) δ 12.35 (br. s., 1H), 8.90 (s, 1H), 7.69-7.67 (m, 1H), 6.86-6.84 (m, 1H), 2.81 (s, 3H).

Step 5: 1,4-dimethyl-5-nitro-1H-pyrrolo[2,3-b]pyridine. Potassium carbonate (80 g, 576 mmol) and iodomethane (123 g, 864 mmol) were added to a stirred suspension of 4-methyl-5-nitro-1H-pyrrolo[2,3-b]pyridine (34 g, 192 mmol) in DMF (600 mL) at room temperature. The mixture was stirred at room temperature for 3 hr. The reaction mixture was then poured into water (5 L), stirred at room temperature for 20 min and filtered. The filtrate was extracted with EtOAc (2×3 L). The combined organic layers were washed with brine, dried over Na$_2$SO$_4$ and concentrated. The solid from filtration and the residue from the filtrate were combined and purified by silica gel column chromatography (DCM) to provide the title compound (26.5 g, 71%) as a yellow solid. $^1$HNMR (400 MHz, CDCl$_3$) δ 9.06 (s, 1H), 7.30-7.28 (m, 1H), 6.67-6.65 (m, 1H), 3.93 (s, 3H), 2.86 (s, 3H).

Step 6: 3-iodo-1,4-dimethyl-5-nitro-1H-pyrrolo[2,3-b]pyridine. N-Iodosuccinimide (49.5 g, 220 mmol) was added to a stirred suspension of 1,4-dimethyl-5-nitro-1H-pyrrolo[2,3-b]pyridine (35 g, 183 mmol) in DMF (400 mL) at room temperature. The mixture was stirred at room temperature for 1 hr. The reaction mixture was then poured into water (3 L), stirred at room temperature for 20 min, and was then filtered. The resulting solid was washed with water and MTBE several times and then dried to afford the title compound (52.6 g, 90%) as a yellow solid. $^1$HNMR (400 MHz, DMSO-d$_6$) δ 8.84 (s, 1H), 7.96 (s, 1H), 3.81 (s, 3H), 2.96 (s, 3H).

Step 7: tert-butyl 4-(1,4-dimethyl-5-nitro-1H-pyrrolo[2,3-b]pyridin-3-yl)-3,6-dihydropyridine-1(2H)-carboxylate. To a stirred suspension of 3-iodo-1,4-dimethyl-5-nitro-1H-pyrrolo[2,3-b]pyridine (4.5 g, 14 mmol) and tert-butyl 4-(4,4,5,5-tetramethyl-1,3,2-dioxaborolan-2-yl)-3,6-dihydropyridine-1(2H)-carboxylate (7.85 g, 56.8 mmol) in 1,2-dimethoxyethane:ethanol (4:1, 150 mL) were added K$_2$CO$_3$ (7.85 g, 56.8 mmol) and Pd(PPh$_3$)$_4$ (0.82 g, 0.71 mmol) at room temperature under N$_2$. The mixture was degassed with N$_2$ several times and then was heated at refluxing for 2 hr. The reaction mixture was cooled to room temperature and poured into sat. NH$_4$Cl (500 mL). The mixture was extracted with EtOAc (2×500 mL). The combined organic layers was washed with brine, dried over Na$_2$SO$_4$ and concentrated. The residue was triturated with EtOAc and filtered. The filtrate was concentrated and the resulting residue was purified by silica gel column chromatography (EtOAc:DCM, 0:100-30:70) to afford the title compound (2.1 g, 40%) as a yellow solid. $^1$HNMR (400 MHz, CDCl$_3$) δ 8.97 (s, 1H), 7.09 (s, 1H), 5.74 (br. s., 1H), 4.07-4.06 (m, 2H), 3.88 (s, 3H), 3.66-3.65 (m, 2H), 2.80 (s, 3H), 2.40 (br. s., 2H), 1.51 (s, 9H).

Step 8: tert-butyl 4-(5-amino-1,4-dimethyl-1H-pyrrolo[2,3-b]pyridin-3-yl)piperidine-1-carboxylate. To a Parr vessel charged with tert-butyl 4-(1,4-dimethyl-5-nitro-1H-pyrrolo[2,3-b]pyridin-3-yl)-3,6-dihydropyridine-1(2H)-carboxylate (390 mg, 1.05 mmol) and TEA (0.22 µL, 1.58 mmol) in MeOH (4 mL) was added 10% Pd/C (112 mg, 0.11 mmol). The vessel was sealed, its atmosphere replaced with hydrogen gas (100 psi) and shaken for 6 hr. The reaction mixture was then filtered through a pad of Celite® and rinsed with MeOH (2 mL). The filtrate was then concentrated under reduced pressure to afford the title compound (361 mg, 100%) as a colorless oil which was not purified further. $^1$HNMR (400 MHz, CD$_3$OD) δ 7.80 (s, 1H), 6.97 (s, 1H), 4.16 (d, J=13.3 Hz, 2H), 3.66 (s, 3H), 3.27 (t, J=1.6 Hz, 2H), 3.14 (t, J=11.7 Hz, 1H), 2.89 (br. s., 2H), 2.47 (s, 3H), 1.97 (d, J=13.3 Hz, 2H), 1.55-1.45 (m, 2H), 1.44 (s, 9H).

Step 9: tert-butyl 4-(5-(3-cyanobenzamido)-1,4-dimethyl-1H-pyrrolo[2,3-b]pyridin-3-yl)piperidine-1-carboxylate. TEA (0.437 mL, 3.14 mmol) and 3-cyanobenzoyl chloride (208 mg, 1.26 mmol) were added successively to a solution of tert-butyl 4-(5-amino-1,4-dimethyl-1H-pyrrolo[2,3-b]pyridin-3-yl)piperidine-1-carboxylate (361 mg, 1.05 mmol) in DCM (10 mL) at 0° C. The mixture was stirred at 0° C. for 15 min, then the ice bath was removed, and the solution was stirred at room temperature. After complete consumption of the starting material as determined by TLC, the reaction was quenched with sat. NaHCO$_3$ and extracted with DCM three times. The combined organic layers were washed with brine, dried over Na$_2$SO$_4$, filtered, and concentrated under reduced pressure. The residue was purified by silica gel column chromatography (80:20 Heptane:EtOAc) to afford the title compound (472 mg, 95%) as a white solid. $^1$H NMR (400 MHz, CD$_3$OD) δ ppm 8.38 (s, 1H), 8.34-8.29 (m, 1H), 8.12 (s, 1H), 7.98 (d, J=7.8 Hz, 1H), 7.79-7.71 (m, 1H), 7.23 (s, 1H), 4.21 (d, J=11.7 Hz, 2H), 3.81 (s, 3H), 3.31-3.22 (m, 1H), 2.93 (s, 2H), 2.63 (s, 3H), 2.06 (d, J=11.7 Hz, 2H), 1.65-1.52 (m, 2H), 1.48 (s, 9H).

Step 10: 3-cyano-N-(1,4-dimethyl-3-(piperidin-4-yl)-1H-pyrrolo[2,3-b]pyridin-5-yl)benzamide. To a stirred solution of tert-butyl 4-(5-(3-cyanobenzamido)-1,4-dimethyl-1H-pyrrolo[2,3-b]pyridin-3-yl)piperidine-1-carboxylate (500 mg, 1.05 mmol) in DCM (10 mL) was added a solution of HCl/dioxane (4N, 10 mL) at room temperature. The mixture was stirred for 1 hr at ambient temperature. The solvent was removed from the resulting precipitate under reduced pressure to afford the hydrochloride salt of the title compound (430 mg, 99%). LC/MS [M+H+]=374.0; $^1$H NMR (400 MHz, DMSO-d$_6$) δ 10.52 (s, 1H), 9.21-9.19 (m, 1H), 9.07-9.05 (m, 1H), 8.51 (s, 1H), 8.37-8.35 (m, 1H), 8.21 (s, 1H), 8.10-8.08 (m, 1H), 7.80-7.75 (m, 1H), 7.42 (s, 1H), 3.56 (s, 3H), 3.36-3.32 (m, 2H), 2.56 (s, 3H), 2.09-2.06 (m, 2H), 1.88-1.79 (m, 2H).

Step 11: (R)-3-cyano-N-(1,4-dimethyl-3-(1-(2,3,3-trimethylbutanoyl)piperidin-4-yl)-1H-pyrrolo[2,3-b]pyridin-5-yl)benzamide. 3-Cyano-N-(1,4-dimethyl-3-(piperidin-4-yl)-1H-pyrrolo[2,3-b]pyridin-5-yl)benzamide hydrochloride (350 mg, 0.78 mmol) was treated with DMF (2.6 mL), DIPEA (1.38 mL, 7.84 mmol), HATU (392 mg, 1.02 mmol), and (−)-(R)-2,3,3-trimethylbutanoic acid (Kido, M.; Sugiyama, S.; Satoh, T. Tetrahedron: Assym 2007, 18, 1934-47.) (133 mg, 1.02 mmol). The reaction mixture was stirred at room temperature for 1 hr. The reaction mixture was concentrated and the residue was purified by silica gel column chromatography (40:60, Heptane:EtOAc) to afford the title compound (336 mg, 92%). LC/MS [M+H]=486.1; Chiral LC: Rt=3.50 min (Method B); $^1$H NMR (CDCl$_3$) δ 8.51 (br s, 1H), 8.29-8.21 (m, 3H), 7.89-7.86 (m, 1H), 7.70-7.65 (m, 1H), 6.96-6.92 (m, 1H), 4.86-4.75 (m, 1H), 4.23-4.19 (m, 1H), 3.82 (s, 3H), 3.22-3.12 (m, 2H), 2.74-2.62 (m, 5H), 2.14-2.04 (m, 2H), 1.63-1.00 (m, 14H).

Examples 33-43, 109 & 110

The following Examples 33-43, 109 and 110 were prepared analogous to Example 32 employing the appropriate carboxylic acid or carboxylic acid chloride coupling reagents in Steps 9 and 11.

| Ex. | Structure | Name/Characterization |
|---|---|---|
| 33 | 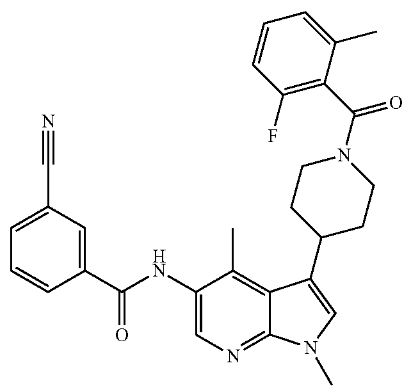 [SMILES: Cc1cccc(F)c1C(=O)N1CCC(c2cn(C)c3ncc(NC(=O)c4cccc(C#N)c4)c(C)c23)CC1] | 3-cyano-N-(3-(1-(2-fluoro-6-methylbenzoyl)piperidin-4-yl)-1,4-dimethyl-1H-pyrrolo[2,3-b]pyridin-5-yl)benzamide. LC/MS [M + H] = 510; $^1$H NMR (400 MHz, DMSO-d$_6$) δ 8.26 (s, 1H), 8.21-8.19 (m, 2H), 8.04-7.99 (m, 1H), 7.84-7.82 (m, 1H), 7.64-7.60 (m, 1H), 7.23-7.21 (m, 1H), 7.08-6.90 (m, 3H), 4.98-4.94 (m, 1H), 3.82 (s, 3H), 3.60-3.57 (m, 1H), 3.27-3.24 (m, 2H), 3.18-3.12 (m, 2H), 2.96-2.92 (m, 1H), 2.57 (s, 3H), 2.28 (s, 3H), 2.20-2.14 (m, 1H), 2.04-1.96 (m, 1H), 1.69-1.43 (m, 3H). |
| 34 | 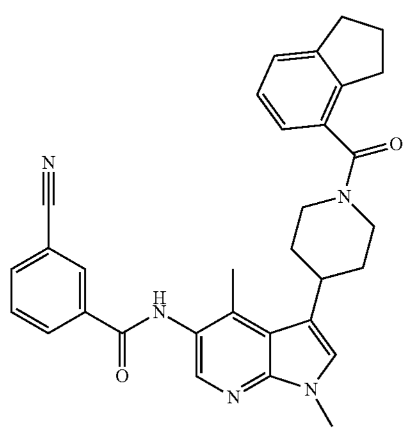 [SMILES: Cc1c(NC(=O)c2cccc(C#N)c2)cnc2c1c(C1CCN(C(=O)c3cccc4c3CCC4)CC1)cn2C] | 3-cyano-N-(3-(1-(2,3-dihydro-1H-indene-4-carbonyl)piperidin-4-yl)-1,4-dimethyl-1H-pyrrolo[2,3-b]pyridin-5-yl)benzamide. LC/MS [M + H] = 518.; ; $^1$H NMR (400 MHz, DMSO-d$_6$) δ 8.27 (s, 1H), 8.21-8.19 (m, 2H), 8.10 (s, 1H), 7.84-7.82 (m, 1H), 7.63-7.61 (m, 1H), 7.23-7.17 (m, 1H), 7.15-7.13 (m, 1H), 7.07-7.05 (m, 1H), 6.96 (s, 1H), 4.98-4.94 (m, 1H), 3.83 (s, 3H), 3.73-3.70 (m, 1H), 3.27-3.14 (m, 2H), 2.96-2.80 (m, 5H), 2.57 (s, 3H), 2.15-1.96 (m, 4H), 1.51-1.48 (m, 2H). |
| 35 | 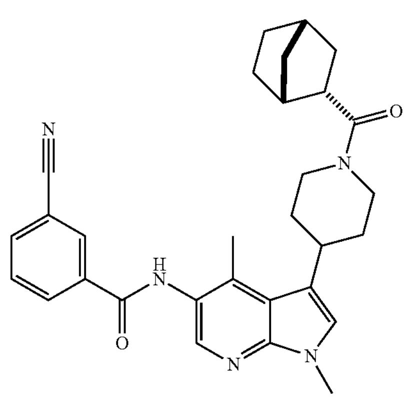 | N-(3-(1-((1R,2S,4S)-bicyclo[2.2.1]heptane-2-carbonyl)piperidin-4-yl)-1,4-dimethyl-1H-pyrrolo[2,3-b]pyridin-5-yl)-3-cyanobenzamide. LC/MS [M + H] = 496.2; Chiral LC: Rt = 2.47 min (Method I); $^1$H NMR (400 MHz, CDCl$_3$) δ 8.32-8.08 (m, 4H), 7.87-7.85 (m, 1H), 7.68-7.64 (m, 1H), 6.93-6.90 (m, 1H), 4.84-4.76 (m, 1H), 4.17-4.14 (m, 1H), 3.83 (s, 3H), 3.21-3.14 (m, 2H), 2.98-2.95 (m, 1H), 2.68-2.60 (m, 4H), 2.43-2.39 (m, 1H), 2.28 (s, 1H), 2.14-1.36 (m, 12H). |

| Ex. | Structure | Name/Characterization |
|---|---|---|
| 36 | 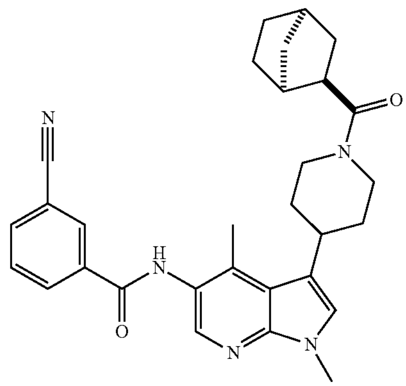 | N-(3-(1-((1S,2R,4R)-bicyclo[2.2.1]heptane-2-carbonyl)piperidin-4-yl)-1,4-dimethyl-1H-pyrrolo[2,3-b]pyridin-5-yl)-3-cyanobenzamide. LC/MS [M + H] = 496.2; Chiral LC: Rt = 1.57 min (Method H); $^1$H NMR (400 MHz, CD$_3$OD) δ 8.38 (s, 1H), 8.32-8.30 (m, 1H), 8.12 (s, 1H), 7.99-7.97 (m, 2H), 7.76-7.73 (m, 1H), 7.23 (s, 1H), 4.74-4.72 (m, 1H), 4.27-4.24 (m, 1H), 3.80 (s, 3H), 3.40-3.27 (m, 2H), 3.24-3.11 (m, 1H), 2.80-2.64 (m, 1H), 2.64-2.49 (m, 1H), 2.26 (s, 3H), 2.26-2.10 (m, 3H), 1.86-1.85 (m, 1H), 1.59-1.32 (m, 9H). |
| 37 | 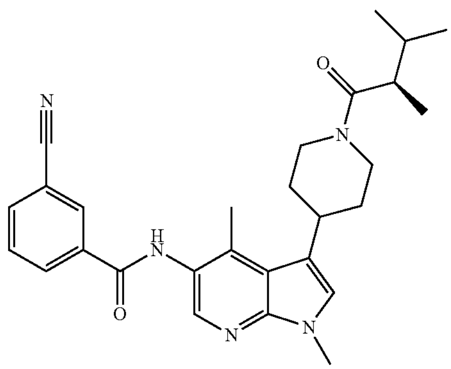 [SMILES: Cc1c(NC(=O)c2cccc(C#N)c2)cnc2c1c(C1CCN(C(=O)[C@H](C)C(C)C)CC1)cn2C] | (R)-3-cyano-N-(3-(1-(2,3-dimethylbutanoyl)piperidin-4-yl)-1,4-dimethyl-1H-pyrrolo[2,3-b]pyridin-5-yl)benzamide. LCMS [M + H] = 472.2. Chiral LC: Rt = 2.4 min (Method A); $^1$H NMR (400 MHz, CD$_3$OD) δ 8.38 (d, J = 1.6 Hz, 1H), 8.26-8.36 (m, 1H), 8.13 (s, 1H), 7.94-8.03 (m, 1H), 7.75 (t, J = 7.8 Hz, 1H), 7.23 (d, J = 2.7 Hz, 1H), 4.75 (d, J = 14.0 Hz, 1H), 4.26 (d, J = 12.9 Hz, 1H), 3.81 (s, 2H), 3.39 (t, J = 12.1 Hz, 1H), 2.72-2.86 (m, 2H), 2.58-2.71 (m, 3H), 2.08-2.24 (m, 2H), 1.87 (d, J = 7.0 Hz, 1H), 1.60 (dd, J = 11.5, 8.8 Hz, 2H), 1.09 (dd, J = 13.9, 6.8 Hz, 3H), 0.83-1.01 (m, 5H). |
| 38 | 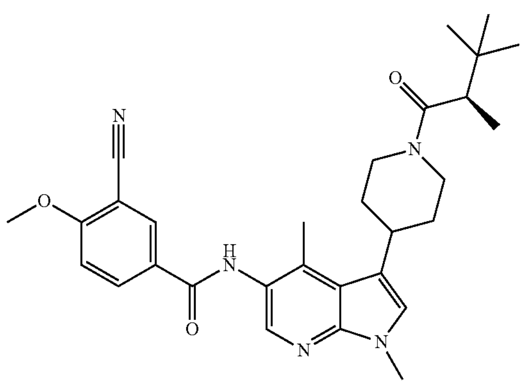 [SMILES: COc1ccc(C(=O)Nc2cnc3c(c(C4CCN(C(=O)[C@H](C)C(C)(C)C)CC4)cn3C)c2C)cc1C#N] | (R)-3-cyano-N-(1,4-dimethyl-3-(1-(2,3,3-trimethylbutanoyl)piperidin-4-yl)-1H-pyrrolo[2,3-b]pyridin-5-yl)-4-methoxybenzamide. LC/MS [M + H] = 516.2; Chiral LC: Rt = 6.69 (Method C); $^1$H NMR (400 MHz, CDCl$_3$) δ 8.06-8.33 (m, 3H), 7.92 (br. s., 1H), 7.09 (d, J = 6.5 Hz, 1H), 6.78-6.96 (m, 1H), 4.71-4.91 (m, 1H), 4.21 (d, J = 13.1 Hz, 1H), 4.03 (s, 3H), 3.82 (s, 3H), 3.19 (d, J = 12.1 Hz, 2H), 2.46-2.79 (m, 5H), 1.88-2.16 (m, 2H), 1.38-1.69 (m, 2H), 1.13 (dd, J = 13.1, 6.5 Hz, 3H), 0.99 (s, 9H). |
| 39 | 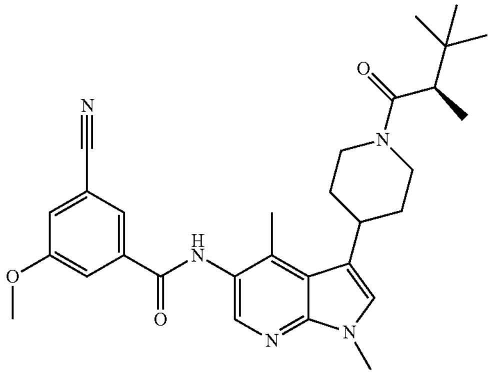 [SMILES: COc1cc(C#N)cc(C(=O)Nc2cnc3c(c(C4CCN(C(=O)[C@H](C)C(C)(C)C)CC4)cn3C)c2C)c1] | (R)-3-cyano-N-(1,4-dimethyl-3-(1-(2,3,3-trimethylbutanoyl)piperidin-4-yl)-1H-pyrrolo[2,3-b]pyridin-5-yl)-5-methoxybenzamide. LC/MS [M + H] = 516.1; Chiral LC: Rt = 6.42 min (Method C); $^1$H NMR (400 MHz, CDCl$_3$) δ 8.20 (d, J = 13.6 Hz, 1H), 7.70-7.92 (m, 2H), 7.33 (br. s., 1H), 6.75-6.94 (m, 1H), 4.67-4.94 (m, 1H), 4.21 (d, J = 13.6 Hz, 1H), 3.92 (s, 3H), 3.82 (s, 3H), 3.18 (d, J = 8.0 Hz, 2H), 2.41-2.77 (m, 5H), 1.85-2.14 (m, 2H), 1.35-1.73 (m, 3H), 1.11-1.20 (m, 3H), 0.99 (s, 9H). |

| Ex. | Structure | Name/Characterization |
|---|---|---|
| 40 | 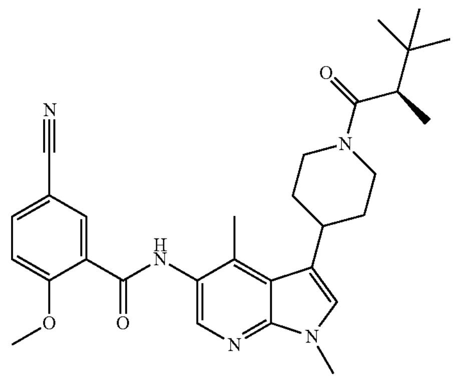 [SMILES: COc1ccc(C#N)cc1C(=O)Nc1cnc2c(c(C3CCN(C(=O)[C@H](C)C(C)(C)C)CC3)cn2C)c1C] | (R)-5-cyano-N-(1,4-dimethyl-3-(1-(2,3,3-trimethylbutanoyl)piperidin-4-yl)-1H-pyrrolo[2,3-b]pyridin-5-yl)-2-methoxybenzamide. LC/MS [M + H] = 516.1; Chiral LC: Rt = 6.42 min (Method C); $^1$H NMR (400 MHz, CDCl$_3$) δ 9.19 (s, 1H), 8.64 (s, 1H), 8.38 (s, 1H), 7.82 (d, J = 8.5 Hz, 1H), 7.18 (d, J = 9.0 Hz, 1H), 6.95 (s, 1H), 4.90 (d, J = 13.1 Hz, 1H), 4.22 (d, J = 13.1 Hz, 4H), 3.84 (s, 3H), 3.05-3.33 (m, 2H), 2.47-2.76 (m, 5H), 2.00-2.20 (m, 2H), 1.45-1.69 (m, 3H), 1.12 (br. s., 3H), 1.01 (d, J = 14.1 Hz, 9H). |
| 41 | 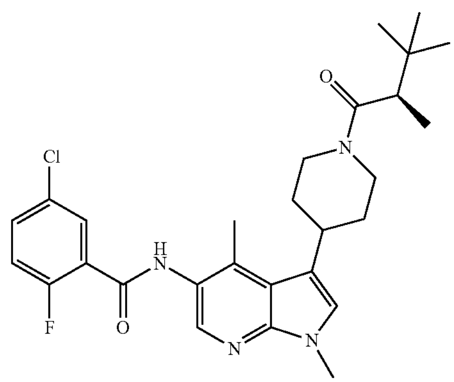 [SMILES: Cc1c(NC(=O)c2cc(Cl)ccc2F)cnc2c1c(C1CCN(C(=O)[C@H](C)C(C)(C)C)CC1)cn2C] | (R)-5-chloro-N-(1,4-dimethyl-3-(1-(2,3,3-trimethylbutanoyl)piperidin-4-yl)-1H-pyrrolo[2,3-b]pyridin-5-yl)-2-fluorobenzamide. LC/MS [M + H] = 513.1. Chiral SFC: Rt = 2.043 min (Method P). $^1$H NMR (400 MHz, CDCl$_3$) δ 8.33 (s, 1H), 8.19-8.17 (m, 2H), 7.53-7.50 (m, 1H), 7.22-7.17 (m, 1H), 6.95 (s, 1H), 4.92-4.88 (m, 1H), 4.24-4.20 (m, 1H), 3.84 (s, 3H), 3.27-3.16 (m, 2H), 2.73-2.62 (m, 5H), 2.10-2.05 (m, 2H), 1.63-1.46 (m, 2H), 1.14-1.09 (m, 3H), 1.02-0.99 (m, 9H). |
| 42 | 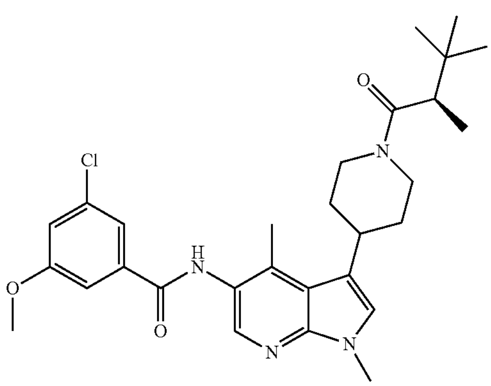 [SMILES: COc1cc(Cl)cc(C(=O)Nc2cnc3c(c(C4CCN(C(=O)[C@H](C)C(C)(C)C)CC4)cn3C)c2C)c1] | (R)-3-chloro-N-(1,4-dimethyl-3-(1-(2,3,3-trimethylbutanoyl)piperidin-4-yl)-1H-pyrrolo[2,3-b]pyridin-5-yl)-5-methoxybenzamide. LC/MS [M + H] = 525.2. Chiral SFC: Rt = 6.072 min (Method Q). $^1$H NMR (400 MHz CDCl$_3$) δ 8.24 (s, 1H), 7.81-7.76 (m, 1H), 7.50 (s, 1H), 7.41 (s, 1H), 7.10 (s, 1H), 6.93 (s, 1H), 4.89-4.84 (m, 1H), 4.24-4.19 (m, 1H), 3.88 (s, 3H), 3.83 (s, 3H), 3.25-3.14 (m, 2H), 3.72-3.59 (m, 5H), 2.12-2.05 (m, 2H), 1.55-1.47 (m, 2H), 1.13-1.11 (m, 3H), 1.09-0.98 (m, 9H). |
| 43 | 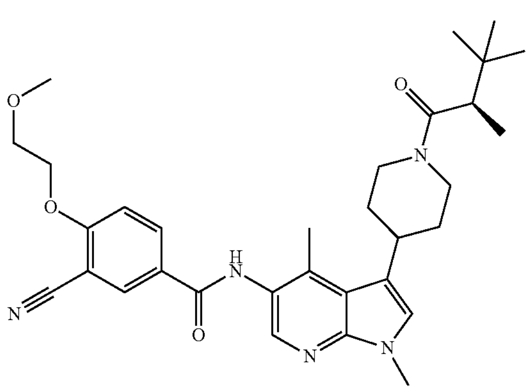 [SMILES: COCCOc1ccc(C(=O)Nc2cnc3c(c(C4CCN(C(=O)[C@H](C)C(C)(C)C)CC4)cn3C)c2C)cc1C#N] | (R)-3-cyano-N-(1,4-dimethyl-3-(1-(2,3,3-trimethylbutanoyl)piperidin-4-yl)-1H-pyrrolo[2,3-b]pyridin-5-yl)-4-(2-methoxyethoxy)benzamide. LC/MS [M + Na] = 582.3; Chiral LC: Rt = 6.34 min (Method V); $^1$H NMR (400 MHz, CDCl$_3$) δ 8.25-8.15 (m, 3H), 7.83-7.73 (m, 1H), 7.15-7.12 (m, 1H), 6.94-6.92 (m, 1H), 4.89-4.84 (m, 1H), 4.40-4.30 (m, 2H), 4.25-4.15 (m, 1H), 3.90-3.85 (m, 2H), 3.82 (s, 3H), 3.50 (s, 3H), 3.25-3.15 (m, 2H), 2.75-2.60 (m, 5H), 2.15-1.95 (m, 2H), 1.55-1.35 (m, 2H), 1.15-1.05 (m, 3H), 1.05-0.95 (m, 9H). |

-continued

| Ex. | Structure | Name/Characterization |
|---|---|---|
| 109 | 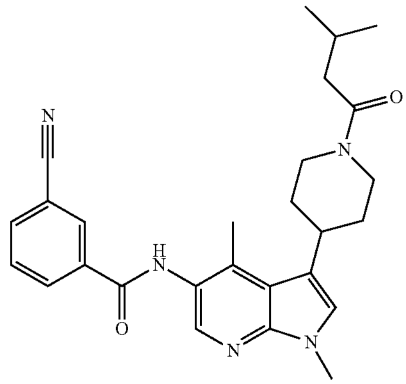 [SMILES: Cc1c(NC(=O)c2cccc(C#N)c2)cnc2c1c(C1CCN(C(=O)CC(C)C)CC1)cn2C] | 3-cyano-N-(1,4-dimethyl-3-(1-(3-methylbutanoyl)piperidin-4-yl)-1H-pyrrolo[2,3-b]pyridin-5-yl)benzamide. LC/MS [M + H] = 458.1; $^1$H NMR (400 MHz, CDCl$_3$) δ 8.80 (s, 1 H), 8.33 (s, 1 H), 8.25 (d, J = 8.0 Hz, 1 H), 8.17 (s, 1 H), 7.79 (d, J = 7.6 Hz, 1 H), 7.57 (t, J = 7.6 Hz, 1 H), 6.87 (s, 1 H), 4.68 (d, J = 13.2 Hz, 1 H), 3.99 (d, J = 13.2 Hz, 1 H), 3.79 (s, 3 H), 3.41-3.27 (m, 2 H), 2.65-2.57 (m, 1 H), 2.55 (s, 3 H), 2.23 (d, J = 7.2 Hz, 2 H), 2.11-2.04 (m, 2 H), 1.91 (d, J = 13.6 Hz, 1 H), 1.55-1.47 (m, 1 H), 1.34-1.21 (m, 1 H), 0.96 (d, J = 6.0 Hz, 6 H). |
| 110 | 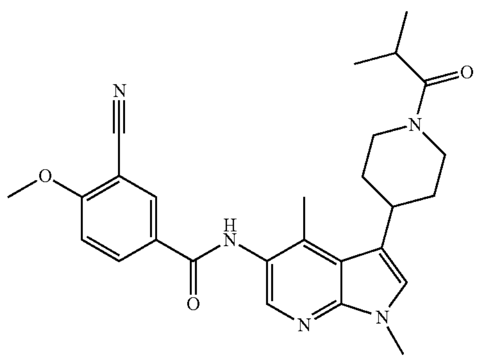 | 3-cyano-N-(3-(1-isobutyrylpiperidin-4-yl)-1,4-dimethyl-1H-pyrrolo[2,3-b]pyridin-5-yl)-4-methoxybenzamide. LC/MS [M + H] = 458.1; $^1$H NMR (400 MHz, CDCl$_3$) δ 8.25-8.15 (m, 3H), 7.83-7.73 (m, 1H), 7.15-7.12 (m, 1H), 6.94-6.92 (m, 1H), 4.89-4.84 (m, 1H), 4.40-4.30 (m, 2H), 4.25-4.15 (m, 1H), 3.90-3.85 (m, 2H), 3.82 (s, 3H), 3.50 (s, 3H), 3.25-3.15 (m, 2H), 2.75-2.60 (m, 5H), 2.15-1.95 (m, 2H), 1.55-1.35 (m, 2H), 1.15-1.05 (m, 3H), 1.05-0.95 (m, 9H). |

Examples 44-45 & 111

The following Examples 44-45 and 111 were prepared analogous to Example 32 employing the appropriate carboxylic acid or carboxylic acid chloride coupling reagents in Steps 9 and rac-3,3,3-trifluoro-2-methylpropanoic acid in Step 11. Although the enantiomers were separated chromatographically, the absolute configuration has been arbitrarily assigned. The enantiomers were obtained through chiral chromatographic separation (Chiralpak AD-3 100×4.6 mm ID, 3 μm, EtOH/CO$_2$, 0.05% DEA, 20 to 80%, 2.5 mL/min).

| Ex. | Structure | Name/Characterization |
|---|---|---|
| 44 | Absolute stereochemistry arbitrary | (R)-3-cyano-N-(1,4-dimethyl-3-(1-(3,3,3-trifluoro-2-methylpropanoyl)piperidin-4-yl)-1H-pyrrolo[2,3-b]pyridin-5-yl)-4-methoxybenzamide. LC/MS [M + H] = 528.5; Chiral LC: Rt = 6.29 min (Method G); $^1$H NMR (400 MHz, CDCl$_3$) δ 8.54 (br. s., 1 H), 8.18 (br. s., 1 H), 8.03 (br. s., 1 H), 7.22 (s, 1 H), 7.11 (d, J = 6.5 Hz, 1 H), 4.90 (br. s., 1 H), 4.20 (d, J = 13.1 Hz, 1 H), 4.04 (s, 3 H), 3.99 (s, 3 H), 3.15 (t, J = 12.3 Hz, 2 H), 2.80-2.46 (m, 3 H), 2.12-1.89 (m, 5 H), 1.75-1.32 (m, 2 H), 1.24-0.72 (m, 3 H). |

-continued

| Ex. | Structure | Name/Characterization |
|---|---|---|
| 45 | *Absolute stereochemistry arbitrary* | (S)-3-cyano-N-(1,4-dimethyl-3-(1-(3,3,3-trifluoro-2-methylpropanoyl)piperidin-4-yl)-1H-pyrrolo[2,3-b]pyridin-5-yl)-4-methoxybenzamide. LC/MS [M + H] = 528.6; Chiral LC: Rt = 7.28 min (Method G); $^1$H NMR (400 MHz, CDCl$_3$) δ 8.54 (br. s., 1 H), 8.18 (br. s., 1 H), 8.03 (br. s., 1 H), 7.22 (s, 1 H), 7.11 (d, J = 6.5 Hz, 1 H), 4.90 (br. s., 1 H), 4.20 (d, J = 13.1 Hz, 1 H), 4.04 (s, 3 H), 3.99 (s, 3 H), 3.15 (t, J = 12.3 Hz, 2 H), 2.80-2.46 (m, 3 H), 2.12-1.89 (m, 5 H), 1.75-1.32 (m, 2 H), 1.24-0.72 (m, 3 H). |
| 111 | 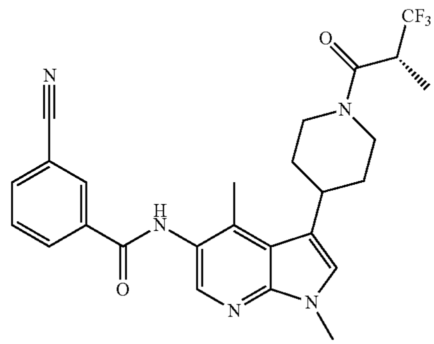 | (R)-3-cyano-(1,4-dimethyl-3-(1-(3,3,3-trifluoro-2-methylpropanoyl)piperidin-4-yl)-1H-pyrrolo[2,3-b]pyridin-5-yl)benzamide. LC/MS [M + 2H+] = 475.6; 1H NMR (400 MHz, CDCl3) δ ppm 8.37 (br. s., 1 H) 8.27 (d, J = 11.3 Hz, 3H) 7.10 (d, J = 9.4 Hz, 1 H) 6.95 (s, 1 H) 4.79 (d, J = 11.7 Hz, 1 H) 4.01 (br. s., 4H) 3.93 (s, 3 H) 3.71 (s, 1 H) 3.07-3.30 (m, 2 H) 2.77-2.95 (m, 1 H) 2.51-2.67 (m, 3 H) 1.93-2.18 (m, 4 H) 1.36-1.63 (m, 2 H) 1.04-1.24 (m, 6 H). |

Examples 46-47

The following Examples 46-47 were prepared analogous to Example 32 employing the 3-cyanobenzoyl chloride in Steps 9 and 2-methylcyclopentane-1-carboxylic acid in Step 11. The resulting trans-isomers were resolved by chiral SFC (ChiralCel IA, 21×250 mm, 5 μM; CO$_2$/MeOH, 60/40; 75 mL/min). Isolation of the first eluting isomer afforded Example 46 and isolation of the second eluting isomer afforded Example 47.

| Ex. | Structure | Name/Characterization |
|---|---|---|
| 46 | *Absolute stereochemistry arbitrary* | 3-cyano-N-(1,4-dimethyl-3-(1-((1S,2S)-2-methylcyclopentane-1-carbonyl)piperidin-4-yl)-1H-pyrrolo[2,3-b]pyridin-5-yl)benzamide. LC/MS [M + H] = 484.4; Chiral LC: Rt = 3.27 min (Method AA); $^1$H NMR (400 MHz, CDCl$_3$) δ 8.61-8.16 (m, 4H), 7.90-7.80 (m, 1H), 7.69-7.58 (m, 1H), 6.95-6.84 (m, 1H), 4.84-4.67 (m, 1H), 4.13-4.06 (m, 1H), 3.81 (s, 3H), 3.25-3.09 (m, 2H), 3.06-2.92 (m, 0.5H), 2.71-2.62 (m, 1H), 2.59 (s, 3H), 2.54-2.45 (m, 0.5H), 2.40-2.26 (m, 1H), 2.23-1.65 (m, 7.5H), 1.59-1.14 (m, 2.5H), 1.04-1.00 (m, 1.75H), 0.94-0.90 (m, 0.75H), 0.86-0.79 (m, 0.75H). |

| Ex. | Structure | Name/Characterization |
|---|---|---|
| 47 | 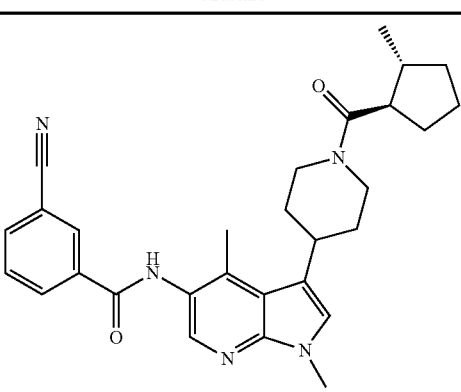 Absolute stereochemistry arbitrary | 3-cyano-N-(1,4-dimethyl-3-(1-((1R,2R)-2-methylcyclopentane-1-carbonyl)piperidin-4-yl)-1H-pyrrolo[2,3-b]pyridin-5-yl)benzamide. LC/MS [M + H]: 484.4; Chiral LC: Rt = 3.81 min (Method AA); $^1$H NMR (400 MHz, CDCl$_3$) δ 8.61-8.16 (m, 4H), 7.90-7.80 (m, 1H), 7.69-7.58 (m, 1H), 6.95-6.84 (m, 1H), 4.84-4.67 (m, 1H), 4.13-4.06 (m, 1H), 3.81 (s, 3H), 3.25-3.09 (m, 2H), 3.06-2.92 (m, 0.5H), 2.71-2.62 (m, 1H), 2.59 (s, 3H), 2.54-2.45 (m, 0.5H), 2.40-2.26 (m, 1H), 2.23-1.65 (m, 7.5H), 1.59-1.14 (m, 2.5H), 1.04-1.00 (m, 1.75H), 0.94-0.90 (m, 0.75H), 0.86-0.79 (m, 0.75H). |

Examples 48-49

The following Examples 48-49 were prepared analogous to Example 32 employing the 3-cyanobenzoyl chloride in Steps 9 and either cis-2-isopropylcyclopentane-1-carboxylic acid (Bigi, M. A. et al, Nature Chemistry 2011, 3, 216-22) or trans-2-isopropylcyclopentane-1-carboxylic acid (Yang, D. et al, Tetrahedron: Asym. 2003, 14, 2927-2937) in Step 11.

| Ex. | Structure | Name/Characterization |
|---|---|---|
| 48 | 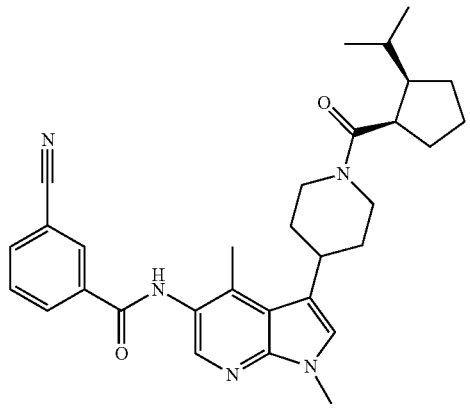 [SMILES: Cc1c(NC(=O)c2cccc(C#N)c2)cnc2c1c(C1CCN(C(=O)[C@@H]3CCC[C@@H]3C(C)C)CC1)cn2C] Absolute stereochemistry arbitrary | 3-cyano-N-(3-(1-((1R,2R)-2-isopropylcyclopentane-1-carbonyl)piperidin-4-yl)-1,4-dimethyl-1H-pyrrolo[2,3-b]pyridin-5-yl)benzamide. LC/MS [M + H] = 512.2; Chiral LC: Rt = 7.66 min (Method X, second eluting enantiomer); $^1$H NMR (400 MHz, CDCl$_3$) δ 8.35-8.17 (m, 3H), 7.88-7.86 (m, 1H), 7.68-7.65 (m, 1H), 6.95-6.89 (m, 1H), 4.83-4.76 (m, 1H), 4.19-4.15 (m, 1H), 3.83 (s, 3H), 3.25-3.15 (m, 2H), 2.68-2.59 (m, 3H), 2.15-1.45 (m, 14H), 1.26 (s, 1H), 0.93-0.83 (m, 5H). |
| 49 | 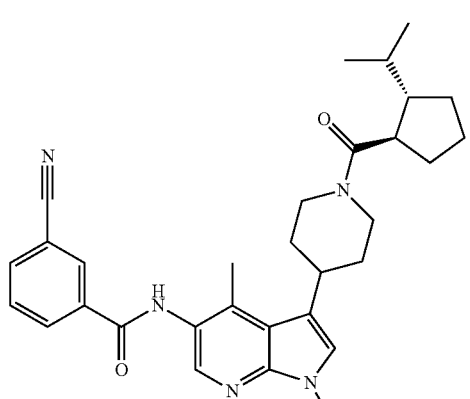 Absolute stereochemistry arbitrary | 3-cyano-N-(3-(1-((1R,2S)-2-isopropylcyclopentane-1-carbonyl)piperidin-4-yl)-1,4-dimethyl-1H-pyrrolo[2,3-b]pyridin-5-yl)benzamide. LC/MS [M + H] = 512.2; Chiral LC: Rt = 7.36 min (Method X, second eluting enantiomer); $^1$H NMR (400 MHz, CDCl$_3$) δ 8.31-8.25 (m, 3H), 8.05 (s, 0.5H), 7.88-7.86 (m, 1H), 7.69-7.64 (m, 1H), 6.96-6.92 (m, 1H), 4.82-4.79 (m, 1H), 4.17-4.14 (m, 1H), 3.82 (s, 3H), 3.24-3.16 (m, 2H), 2.73-2.59 (m, 5H), 2.40-2.30 (m, 1H), 2.10-1.75 (m, 4H), 1.68-1.47 (m, 5H), 1.26-1.15 (m, 2H), 0.91-0.85 (m, 6H). Absolute configuration established by X-ray co-crystallization. |

Example 50

Preparation of (R)—N-(3-(1-(2-(bicyclo[1.1.1]pentan-1-yl)propanoyl)piperidin-4-yl)-1,4-dimethyl-1H-pyrrolo[2,3-b]pyridin-5-yl)-3-cyanobenzamide

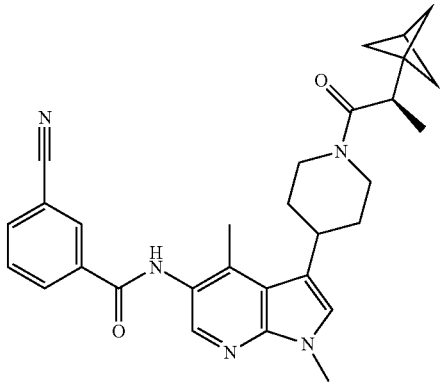 [SMILES: Cc1c(NC(=O)c2cccc(C#N)c2)cnc2c1c(C1CCN(C(=O)[C@H](C)C34CC(C3)C4)CC1)cn2C]

Step 1: 2-(bicyclo[1.1.1]pentan-1-yl)acetic acid. This acid was prepared according to the literature procedure with some modifications (Kaszynski, P.; McMurdie, N. D.; Michl, J. *J. Org. Chem.* 1991, 56, 307). To a stirred suspension of 1,1-dibromo-2,2-bis(chloromethyl)cyclopropane (3.0 g, 9.1 mmol) in pentane (10 mL) at −78° C. was added slowly MeLi (1.6 M in Et$_2$O, 14.2 mL, 22.7 mmol). The resulting yellow mixture was stirred for 15 min at the same temperature, and then the dry ice-acetone bath was replaced with ice-water bath. The reaction was allowed to stir at 0° C. After 1 hr, the cold bath was removed and the pale yellow reaction mixture was heated to 40° C. The volatile material was distilled into a flask cooled in a dry ice-acetone bath with intermittent application of low vacuum. After warming the distillate to 0° C., bromo methylacetate (1.44 g, 0.888 mL, 9.1 mmol) and Et$_2$O (10 mL) were added. The resulting clear solution at 0° C. was passed through a flow reactor irradiated with medium pressure Hanovia lamp. After 3 hr, the solution was collected in a flask and concentrated in vacuo to obtain methyl 2-(3-bromobicyclo[1.1.1]pentan-1-yl)acetate. The crude product was taken up in toluene (5.0 mL). Tributyltin hydride (2.3 mL) and 2,2'-azobisisobutyronitrile (8.0 mg, 0.05 mmol) were added. The resulting clear solution was heated at 80° C. After 2 hr, carbon tetrachloride (0.77 mL) was added and the reaction was stirred for 30 min to destroy the excess tributyltin hydride. Subsequently 10% NaOH in MeOH (8 mL) was added, and the reflux condenser was removed to allow MeOH to evaporate. After another 30 min, the reaction was cooled to ambient temperature and quenched with H$_2$O (15 mL). The reaction mixture was extracted with Et$_2$O (3×5 mL). The remaining yellow aqueous layer was acidified with conc. HCl, and then extracted with EtOAc (3×15 mL). The combined organic extracts were washed with brine, dried over MgSO$_4$, filtered and concentrated in vacuo. The crude product was purified by silica gel column chromatography (MeOH:DCM, 2:98-20:80) to provide the title compound as a colorless oil (364 mg, 35% over 4 steps.). LC/MS [M−H]=125.1, $^1$H NMR (400 MHz, CDCl$_3$) δ 2.52 (s, 2H), 2.50 (s, 1H), 1.83 (s, 7H).

Step 2: (R)-3-(2-(bicyclo[1.1.1]pentan-1-yl)acetyl)-4-isopropyloxazolidin-2-one. To a solution of 2-(bicyclo[1.1.1]pentan-1-yl)acetic acid (160 mg, 1.27 mmol) and DMF (2.8 mg, 0.04 mmol) in DCM (1.3 mL) at 0° C. was added thionyl chloride (0.112 mL, 1.52 mmol). The resulting pale yellow solution was stirred at ambient temperature for 3 hr, and then the reaction mixture was carefully concentrated in vacuo to afford the corresponding acid chloride as a yellow oil. In a separate flask, n-BuLi (2.5 M in hexanes, 0.608 mL, 1.52 mmol) was added dropwise to a solution of (R)-(−)-4-Isopropyl-2-oxazolidinone (196 mg, 1.52 mmol) in THF (5.0 mL) at −78° C. After stirring for 30 min, a solution of the above acid chloride in THF (1.0 mL) was added slowly. The resulting mixture was stirred for 1 hr at the same temperature. The reaction was quenched with saturated aqueous NaHCO$_3$ solution (5.0 mL), extracted with EtOAc (3×5 mL), washed with brine, dried over Na$_2$SO$_4$, filtered and concentrated in vacuo. The crude product was purified using silica gel column chromatography (EtOAc:Heptane, 7:93-40:60) to provide the title compound (93.5 mg, 32%). LC/MS [M+H]=238.1, $^1$H NMR (400 MHz, CDCl$_3$) δ 4.40 (dt, J=8.0, 3.4 Hz, 1H), 4.14-4.26 (m, 2H), 3.21 (d, J=14.8 Hz, 1H), 3.01 (d, J=14.8 Hz, 1H), 2.46 (s, 1H), 2.29-2.39 (m, 1H), 1.79 (s, 6H), 0.88 (dd, J=13.7, 7.0 Hz, 6H).

Step 3: (R)-3-((R)-2-(bicyclo[1.1.1]pentan-1-yl)propanoyl)-4-isopropyloxazolidin-2-one. To a solution of (R)-3-(2-(bicyclo[1.1.1]pentan-1-yl)acetyl)-4-isopropyloxazolidin-2-one (93.5 mg, 0.394 mmol) in THF (2.5 mL) at −78° C. was added dropwise LDA (2.0 M in THF, 0.227 mL, 0.453 mmol). The resulting yellow solution was stirred for 1 hr, and then iodomethane (280 mg, 0.124 mL, 1.97 mmol) was added slowly. The reaction was allowed to stir at −78° C. for 8 hr, and then warm to ambient temperature overnight. The reaction was quenched with saturated aqueous NH$_4$Cl (5.0 mL), extracted with Et$_2$O, washed with brine, dried over MgSO$_4$, filtered and concentrated in vacuo. The crude was purified using silica gel column chromatography (EtOAc: Heptane, 7:93-40:60) to provide the title compound as a colorless oil (78.2 mg, 79%) and the minor diastereomer (17.4 mg, 12%). Major diastereomer: $^1$H NMR (400 MHz, CDCl$_3$) δ 4.40 (dt, J=7.6, 3.6 Hz, 1H), 4.15-4.26 (m, 2H), 4.02 (q, J=7.0 Hz, 1H), 2.47 (s, 1H), 2.36 (dtd, J=14.0, 7.0, 7.0, 4.1 Hz, 1H), 1.63-1.76 (m, 6H), 1.11 (d, J=7.0 Hz, 3H), 0.88 (dd, J=16.6, 6.8 Hz, 6H). Minor diastereomer: $^1$H NMR (400 MHz, CDCl$_3$) δ 4.46 (dt, J=8.2, 3.3 Hz, 1H), 4.16-4.29 (m, 2H), 4.04 (q, J=6.6 Hz, 1H), 2.49 (s, 1H), 2.26-2.38 (m, 1H), 1.74 (s, 6H), 1.09 (d, J=7.0 Hz, 3H), 0.93 (dd, J=7.0, 4.3 Hz, 6H).

Step 4: (R)-2-(bicyclo[1.1.1]pentan-1-yl)propanoic acid. To a solution of (R)-3-((R)-2-(bicyclo[1.1.1]pentan-1-yl)propanoyl)-4-isopropyloxazolidin-2-one (78.2 mg, 0.311 mmol) in THF (1.5 mL) at 0° C. was added H$_2$O$_2$(50 wt %, 0.10 mL, 1.74 mmol) followed by dropwise addition of LiOH.H$_2$O (28.7 mg, 0.684 mmol) in H$_2$O (0.5 mL). The ice-water bath was removed and the reaction was allowed to stir at ambient temperature overnight. The reaction was cooled down to 0° C. and quenched with 1.5 M Na$_2$SO$_3$ (1.0 mL), diluted with H$_2$O (3.0 mL). The reaction mixture was extracted with DCM (2×5 mL). The remaining aqueous layer was acidified with 1.0 N HCl and extracted with EtOAc (3×10 mL). The combined organic extracts were washed with brine, dried over Na$_2$SO$_4$, filtered and concentrated in vacuo to provide the title compound (43.1 mg, 99%). The product was used directly without further purification. [α]$_D^{25}$=−15.9 (c=0.42, EtOH). $^1$H NMR (400 MHz, CDCl$_3$) δ 2.60 (q, J=7.0 Hz, 1H), 2.51 (s, 1H), 1.75 (s, 6H), 1.11 (d, J=7.0 Hz, 3H).

Step 5: (R)—N-(3-(1-(2-(bicyclo[1.1.1]pentan-1-yl)propanoyl)piperidin-4-yl)-1,4-dimethyl-1H-pyrrolo[2,3-b]pyridin-5-yl)-3-cyanobenzamide. 3-Cyano-N-(1,4-dimethyl-3-(piperidin-4-yl)-1H-pyrrolo[2,3-b]pyridin-5-yl)benzamide hydrochloride (60 mg, 0.13 mmol) treated with DMF (0.5 mL), DIPEA (0.24 mL, 1.34 mmol), HATU (62 mg, 0.16 mmol), and (R)-2-(bicyclo[1.1.1]pentan-1-yl)acetic acid (22.6 mg, 0.16 mmol). The mixture was then stirred at room temperature for 1 hr. The mixture was concentrated and the residue was purified by silica gel column chromatography (EtOAc:heptane, 60:40-100:0) to afford the title compound (55.3 mg, 83%) as a white solid: LC/MS [M+H]=496.2; Chiral LC: Rt=8.42 min (Method D). $^1$H NMR (400 MHz, CD$_3$OD) δ 8.41 (s, 1H), 8.30-8.39 (m, 1H), 8.15 (d, J=1.9

Hz, 1H), 8.01 (d, J=7.8 Hz, 1H), 7.78 (t, J=8.0 Hz, 1H), 7.26 (d, J=6.6 Hz, 1H), 4.76 (d, J=14.1 Hz, 1H), 4.25 (d, J=12.9 Hz, 1H), 3.84 (d, J=5.1 Hz, 3H), 3.40-3.25 (m, 2H), 3.14 (dd, J=16.0, 6.6 Hz, 1H), 2.82 (d, J=15.2 Hz, 1H), 2.68 (s, 3H), 2.50 (d, J=10.9 Hz, 1H), 2.07-2.25 (m, 2H), 1.72-1.85 (m, 6H), 1.50-1.72 (m, 2H), 1.09 (dd, J=6.6, 3.9 Hz, 3H).

Example 51

Preparation of (R)-3-cyano-N-(3-(1-(2-cyclopentyl-propanoyl)piperidin-4-yl)-1,4-dimethyl-1H-pyrrolo[2,3-b]pyridin-5-yl)benzamide

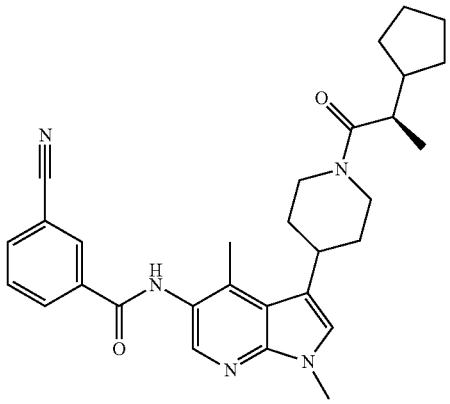 [SMILES: Cc1c(NC(=O)c2cccc(C#N)c2)cnc2c1c(C1CCN(C(=O)[C@H](C)C3CCCC3)CC1)cn2C]

Step 1: (R)-3-(2-cyclopentylacetyl)-4-isopropyloxazolidin-2-one. To a solution of (R)-benzyl oxazolidinone (2.0 g, 10 mmol) in THF (55 mL) at −78° C. was added dropwise n-BuLi (2.5 M in hexanes, 4.92 mL, 12.3 mmol). The resulting solution was allowed to stir at the same temperature for 1 h, then cyclopentyl acetyl chloride (1.86 g, 12.3 mmol) was added. The reaction turned pale yellow rapidly and was allowed to stir at −78° C. for 1 h. The reaction was quenched with sat. NaHCO$_3$ solution, extracted with EtOAc, dried over Na$_2$SO$_4$, filtered and concentrated to afford the title compound (3.20 g, 99%) as a pale yellow oil that solidified on standing. $^1$H NMR (400 MHz, CDCl$_3$) δ 7.40-7.28 (m, 3H), 7.26-7.16 (m, 2H), 4.74-4.64 (m, 1H), 4.24-4.12 (m, 2H), 3.32 (dd, J=13, 3 Hz, 1H), 3.04 (dd, J=17, 7 Hz, 1H), 2.92 (dd, J=17, 7 Hz, 1H), 2.77 (dd, J=14, 10 Hz, 1H), 2.41-2.28 (m, 1H), 1.95-1.84 (m, 2H), 1.72-1.56 (m, 4H), 1.30-1.15 (m, 2H).

Step 2: (R)-3-((R)-2-cyclopentylpropanoyl)-4-isopropyloxazolidin-2-one. To a colorless solution of (R)-3-(2-cyclopentylacetyl)-4-isopropyloxazolidin-2-one (3250 mg, 11.34 mmol) in THF (50 mL) at −78° C. was added dropwise LDA (2.0 M, 6.50 mL, 13.0 mmol). The resulting yellow solution was allowed to stir at the same temperature for 1 h. MeI (3.55 mL, 56.6 mmol) was added and the reaction was allowed to warm to 0° C. over 1 h and allowed to stir at 0° C. for 3 h. The reaction was quenched with sat. NH$_4$Cl and extracted with EtOAc. The combined organic extracts were washed with sat. NaHCO$_3$ and brine, dried over magnesium sulfate, filtered and concentrated in vacuo to afford a white solid. The crude product was purified by silica gel column chromatography twice (EtOAc:Heptane, 5:95-60:40 then 5:95-50:50). The product was recrystallized from n-heptane to provide the title compound (680 mg, 20%) as colorless crystalline needles. $^1$H NMR (400 MHz, CDCl$_3$) δ 7.40-7.17 (m, 5H), 4.69 (ddt, J=10, 7, 3 Hz, 1H), 4.25-4.11 (m, 2H), 3.63 (dg, J=9, 7 Hz, 1H), 3.28 (dd, J=14, 3 Hz, 1H), 2.78 (dd, J=13, 9 Hz, 1H), 2.21-2.08 (m, 1H), 1.90-1.73 (m, 2H), 1.71-1.48 (m, 4H), 1.30-1.17 (m, 4H), 1.11 (ddd, J=12.0, 5.0, 4.0 Hz, 1H).

Step 3: (R)-2-cyclopentylpropanoic acid. To a solution of (R)-3-((R)-2-cyclopentylpropanoyl)-4-isopropyloxazolidin-2-one (680 mg, 2.26 mmol) in THF/H$_2$O (v/v=1/1, 12 mL) at room temperature was added LiOH.H$_2$O (142 mg, 3.38 mmol) followed by H$_2$O$_2$ (237 mL, 4.17 mmol, 50 wt %). The resulting solution was allowed to stir at room temperature overnight. The reaction was quenched with 1.0 M KHSO$_4$ (8 mL) and extracted with EtOAc (3×). The combined organic extracts were washed with brine and dried over Na$_2$SO$_4$, filtered and concentrated. The crude product was purified by silica gel column chromatography (EtOAc:Heptane, 7:93-50:50) to afford the title compound (285 mg, 89%) as a colorless oil. $^1$H NMR (400 MHz, CDCl$_3$) δ 2.29 (dq, J=9, 7 Hz, 1H), 2.07-1.95 (m, 1H), 1.87-1.76 (m, 2H), 1.69-1.51 (m, 4H), 1.31-1.24 (m, 1H), 1.24-1.15 (m, 4H).

Step 4: (R)-3-cyano-N-(3-(1-(2-cyclopentylpropanoyl)piperidin-4-yl)-1,4-dimethyl-1H-pyrrolo[2,3-b]pyridin-5-yl)benzamide. 3-Cyano-N-(1,4-dimethyl-3-(piperidin-4-yl)-1H-pyrrolo[2,3-b]pyridin-5-yl)benzamide hydrochloride (60 mg, 0.13 mmol) was treated with DMF (0.5 mL), DIPEA (0.24 mL, 1.34 mmol), HATU (62 mg, 0.16 mmol), and (R)-2-cyclopentylpropanoic acid (22.9 mg, 0.16 mmol). The reaction mixture was then stirred at room temperature for 48 hr. The mixture was concentrated and purified by silica gel column chromatography (20:1, EtOAc:MeOH) to afford the title compound (65 mg, 97%). LC/MS [M+H]=498.2. Chiral LC: rt=8.74 min (Method C); $^1$H NMR (CDCl$_3$) δ 8.45-8.21 (m, 4H), 7.84 (d, J=7 Hz, 1H), 7.63 (t, J=8 Hz, 1H), 6.90 (d, J=22 Hz, 1H), 4.76 (t, J=12 Hz, 1H), 4.14 (d, J=13 Hz, 1H), 3.76 (s, 3H), 3.22-3.17 (m, 2H), 2.68-2.57 (m, 5H), 2.11-1.02 (m, 16H).

Example 52

Preparation of 3-cyano-N-(3-(1-(cyclopentanecarbonyl)piperidin-4-yl)-1,4-dimethyl-1H-pyrrolo[2,3-b]pyridin-5-yl)-5-methoxybenzamide

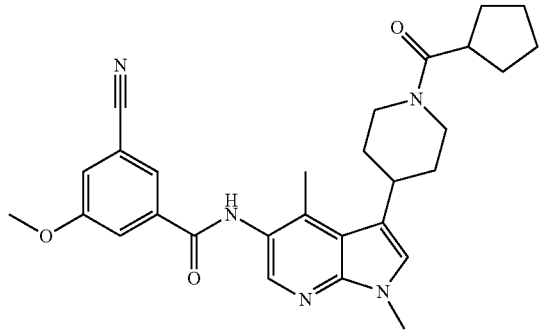 [SMILES: COc1cc(C#N)cc(C(=O)Nc2cnc3c(c(C4CCN(C(=O)C5CCCC5)CC4)cn3C)c2C)c1]

The title compound was prepared by procedures analogous to those described for Example 5 starting from tert-butyl 4-(1,4-dimethyl-5-nitro-1H-pyrrolo[2,3-b]pyridin-3-yl)-3,6-dihydropyridine-1(2H)-carboxylate (prepared as described in Example 32) and utilizing cyclopentanecarbonyl chloride in Step 3. The resulting (4-(5-amino-1,4-dimethyl-1H-pyrrolo[2,3-b]pyridin-3-yl)piperidin-1-yl)(cyclopentyl)methanone intermediate in Step 4 was coupled with 3-cyano-5-methoxybenzoic acid in the presence of 2-chloromethylpyridinium iodide and DIPEA in THF. LC/MS [M+H]=500. 1; $^1$H NMR (500 MHz, CDCl$_3$) δ 8.23 (s, 1H), 7.97 (br s, 1H), 7.82 (s, 1H), 7.77 (br s, 1H), 7.34 (br s, 1H), 6.93 (s, 1H), 4.78 (br d, J=12.9 Hz, 1H), 4.11 (br d, J=13.2 Hz, 1H), 3.92 (s, 3H), 3.82 (s, 3H), 3.26-3.12 (m, 2H), 2.94 (quintet, J=8 Hz, 2H), 2.67 (dt, J=1.8, 13.0 Hz, 1H), 2.59 (s, 3H), 2.12-2.06 (m, 1H), 2.04-1.98 (m, 1H), 1.90-1.37 (m, 10H).

Example 53

Preparation of 3-cyano-N-(3-(1-(cyclopentanecarbonyl)piperidin-4-yl)-1,4-dimethyl-1H-pyrrolo[2,3-b]pyridin-5-yl)-5-hydroxybenzamide

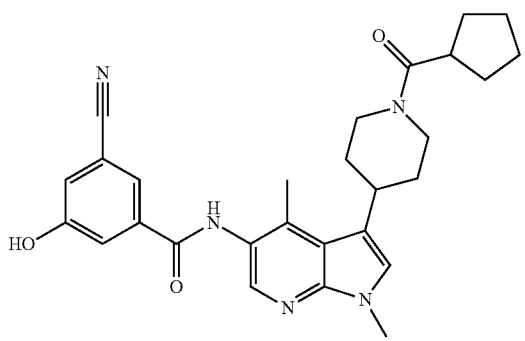 [SMILES: Cc1c(NC(=O)c2cc(O)cc(C#N)c2)cnc2c1c(C1CCN(C(=O)C3CCCC3)CC1)cn2C]

To a solution of 3-cyano-N-(3-(1-(cyclopentanecarbonyl)piperidin-4-yl)-1,4-dimethyl-1H-pyrrolo[2,3-b]pyridin-5-yl)-5-methoxybenzamide (prepared as described in Example 52, 100 mg, 0.200 mmol) in DCM (10 mL) was added boron tribromide (1.5 mL) at −60° C. A precipitate formed from the clear brown solution, and the resulting mixture was stirred at 15° C. for 12 h. The mixture was evaporated and the residue was brought up in $H_2O$ (20 mL) and extracted with EtOAc (15 mL) twice. The combined organic layers were washed with brine, dried over $Na_2SO_4$ and concentrated to afford the title compound (96 mg, 99%) as a solid. LC/MS [M+H]=486.1; $^1$H NMR (400 MHz, CDCl$_3$) δ 10.12 (s, 1H), 8.06 (s, 1H), 7.74 (s, 1H), 7.63 (s, 1H), 7.35 (s, 1H), 7.26 (s, 1H), 4.57-4.54 (m, 1H), 4.11-4.08 (m, 1H), 3.75 (s, 3H), 3.21-2.68 (m, 4H), 2.50 (s, 3H), 2.02-1.99 (m, 2H), 1.77-1.44 (m, 10H).

Examples 54-56

The following Examples 54-56 were prepared analogous to Example 53 employing the corresponding methyl ether.

| Ex. | Structure | Name/Characterization |
|---|---|---|
| 54 | 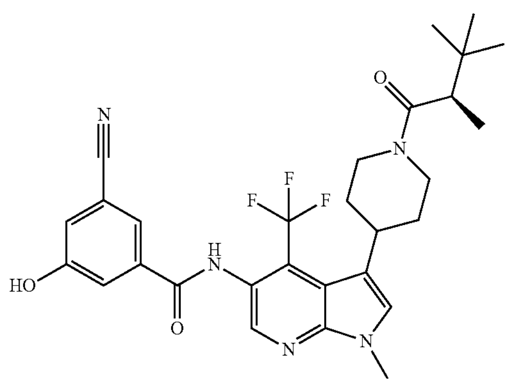 [SMILES: C[C@@H](C(=O)N1CCC(c2cn(C)c3ncc(NC(=O)c4cc(O)cc(C#N)c4)c(C(F)(F)F)c23)CC1)C(C)(C)C] | (R)-3-cyano-5-hydroxy-N-(1-methyl-4-(trifluoromethyl)-3-(1-(2,3,3-trimethylbutanoyl)piperidin-4-yl)-1H-pyrrolo[2,3-b]pyridin-5-yl)benzamide. LC/MS [M + Na] = 578.3. Chiral SFC: Rt = 2.376 min (Method N). $^1$H NMR (400 MHz CDCl$_3$) δ 9.30 (s, 1H), 9.11 (s, 1H), 8.46-8.30 (m, 2H), 7.66-7.62 (m, 2H), 7.22-7.19 (m, 2H), 4.88-4.83 (m, 1H), 4.25-4.22 (m, 1H), 3.85-3.77 (m, 3H), 3.21-3.11 (m, 2H), 2.80-2.65 (m, 2H), 2.04-1.90 (m, 2H), 1.53-0.99 (m, 15H). |
| 55 | 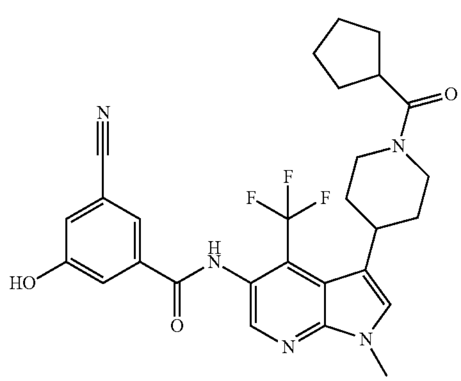 [SMILES: Cn1cc(C2CCN(C(=O)C3CCCC3)CC2)c2c(C(F)(F)F)c(NC(=O)c3cc(O)cc(C#N)c3)cnc21] | 3-cyano-N-(3-(1-(cyclopentanecarbonyl)piperidin-4-yl)-1-methyl-4-(trifluoromethyl)-1H-pyrrolo[2,3-b]pyridin-5-yl)-5-hydroxybenzamide. LC/MS [M + H] = 540.3; $^1$H NMR (400 MHz, DMSO-d$_6$) δ 10.50 (s, 1H), 8.29 (s, 1H), 7.86-7.84 (m, 2H), 7.67-7.66 (m, 1H), 7.89 (s, 1H), 4.57-4.42 (m, 1H), 4.23-4.05 (m, 1H), 3.85 (s, 3H), 3.07-3.01 (m, 3H), 2.57-2.52 (m, 1H), 1.95-1.40 (m, 12H). |

| Ex. | Structure | Name/Characterization |
|---|---|---|
| 56 | 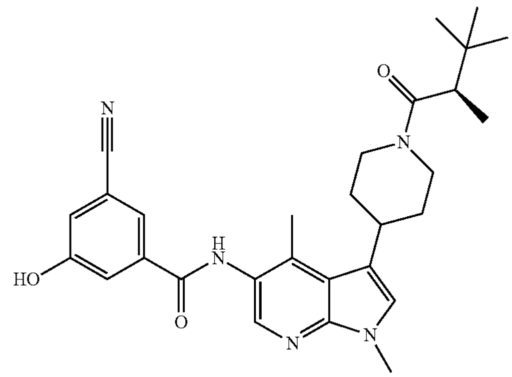 [SMILES: Cc1c(NC(=O)c2cc(O)cc(C#N)c2)cnc2c1c(C1CCN(C(=O)[C@H](C)C(C)(C)C)CC1)cn2C] | (R)-3-cyano-N-(1,4-dimethyl-3-(1-(2,3,3-trimethylbutanoyl)piperidin-4-yl)-1H-pyrrolo[2,3-b]pyridin-5-yl)-5-hydroxybenzamide. LC/MS [M + H] = 502.3; Chiral LC: Rt = 3.23 min (Method U); $^1$H NMR (400 MHz, CDCl$_3$) δ 10.16 (br s, 1H), 8.77 (s, 1H), 8.16-8.06 (m, 1H), 7.61-7.51 (m, 1H), 7.07-7.01 (m, 1H), 6.88-6.85 (m, 1H), 4.83-4.72 (m, 1H), 4.31-4.22 (m, 1H), 3.70-3.60 (m, 3H), 3.23-3.09 (m, 2H), 3.77-3.62 (m, 2H), 2.49 (s, 3H), 2.10-1.20 (m, 5H), 1.14-1.09 (m, 3H), 1.00-0.98 (m, 9H). |

Example 57

Preparation of 3-cyano-N-(3-(1-(cyclopentanecarbonyl)piperidin-4-yl)-1,4-dimethyl-1H-pyrrolo[2,3-b]pyridin-5-yl)-5-(2-methoxyethoxy)benzamide

Example 58

Preparation of (R)-3-cyano-N-(3-(1-(cyclopentanecarbonyl)-2,2-dimethylpiperidin-4-yl)-1,4-dimethyl-1H-pyrrolo[2,3-b]pyridin-5-yl)-5-methoxybenzamide

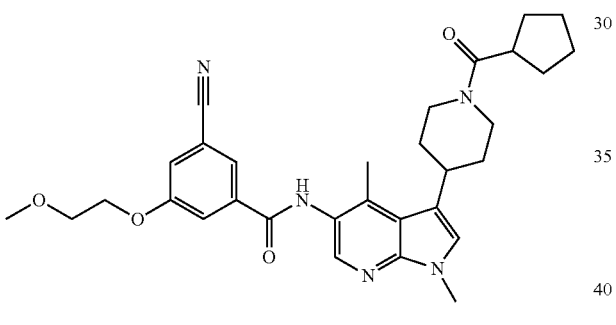

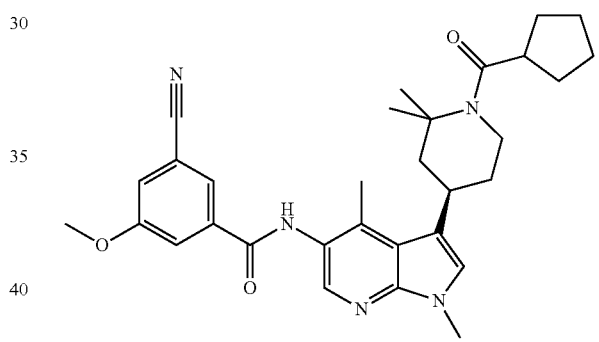

To a mixture of 3-cyano-N-(3-(1-(cyclopentanecarbonyl)piperidin-4-yl)-1,4-dimethyl-1H-pyrrolo[2,3-b]pyridin-5-yl)-5-hydroxybenzamide and K$_2$CO$_3$ (85.4 mg, 0.618 mmol) in DMF (8 mL) was added 1-bromo-2-methoxyethane (57.2 mg, 0.412 mmol). The mixture was stirred at 30° C. for 16 h and then at 50° C. for 12 h. Water (15 mL) was added and the mixture was extracted with EtOAc (15 mL) twice. The combined organic layers were washed with brine, dried over Na$_2$SO$_4$ and concentrated. The crude product was purified by silica gel column chromatography (MeOH:DCM, 0:100-10:90) and then by preparative HPLC (Phenomenex Gemini C18, 250 mm×21.2 mm×8 μm, 27-47% MeCN (0.05% Ammonia) in water (0.05% Ammonia)). Lyophilization provided the title compound (21 mg, 18%) as a white solid. LC/MS [M+H]=544.1; $^1$H NMR (400 MHz, CDCl$_3$) δ 8.44 (s, 1H), 8.17 (s, 1H), 7.88 (s, 1H), 7.80 (s, 1H), 7.33 (s, 1H), 6.80 (s, 1H), 4.72-4.70 (m, 1H), 4.20 (s, 2H), 4.10-4.07 (m, 1H), 3.79-3.77 (m, 5H), 3.17 (s, 3H), 2.95-2.91 (m, 1H), 2.63-2.55 (m, 4H), 2.07-2.04 (m, 1H), 1.94-1.91 (m, 1H), 1.82 (br s, 4H), 1.72-1.24 (m, 10H).

Step 1: 1,4-dimethyl-5-nitro-3-(4,4,5,5-tetramethyl-1,3,2-dioxaborolan-2-yl)-1H-pyrrolo[2,3-b]pyridine. A microwave vial was charged with 3-iodo-1,4-dimethyl-5-nitro-1H-pyrrolo[2,3-b]pyridine (prepared as described in Example 32, 0.5 g, 1.57 mmol) and Xantphos (0.147 g, 0.31 mmol). Toluene (2 mL) was introduced into the vial and the suspension was degassed with argon for 30 min. 4,4,5,5-Tetramethyl-1,3,2-dioxaborolane (0.8 g, 6.31 mmol) and TEA (1.13 mL, 7.9 mmol) was added to the mixture and was further degassed for 2 min. Finally, Pd(OAc)$_2$ (35.8 mg, 0.16 mmol) was added to the suspension and the vial was sealed using a Teflon cap. The reaction was heated to 120° C. under microwave irradiation for 30 min. After cooling, the reaction was filtered through a pad of Celite® and the filtrate was concentrated. The residue was purified by silica gel column chromatography (EtOAc:hexane, 1:4) to provide the title compound (0.4 g, 80%). LC/MS [M+H]=318.05; $^1$H NMR (400 MHz, CDCl$_3$) δ 8.92 (s, 1H), 7.82 (s, 1H), 3.90 (s, 3H), 3.04 (s, 3H), 1.36 (s, 12H).

Step 2a: tert-butyl 2,2-dimethyl-4-((((trifluoromethyl)sulfonyl)oxy)-3,6-dihydropyridine-1(2H)-carboxylate. To a RB flask charged with tert-butyl 2,2-dimethyl-4-oxopiperidine-1-carboxylate (7.76 g, 34.1 mmol) in dry THF (130 mL) was added slowly dropwise at −70° C. a solution of sodium bistrimethyldisilazide (7.51 g 41.0 mmol) in THF (41 mL). Upon complete addition, a solution of N-phenyltriflamide (16.1 g, 41.0 mmol) in THF (10 mL) was added and the mixture was allowed to warm to room temperature over the course of 12 h. The reaction mixture was then concentrated and brought up in EtOAc:heptane (85:15, 100 mL) and washed twice with water. The combined organics were collected and concentrated to give 12.0 g (98%) of the titled compound as a yellow oil. $^1$HNMR (400 MHz, CDCl$_3$) δ 5.78 (t, J=3.5 Hz, 1H), 4.08 (q, J=2.7 Hz, 2H), 2.40 (br s, 2H), 1.37-1.58 (m, 14H).

Step 2b: tert-butyl 4-(1,4-dimethyl-5-nitro-1H-pyrrolo[2,3-b]pyridin-3-yl)-2,2-dimethyl-3,6-dihydropyridine-1(2H)-carboxylate. To a solution of tert-butyl 2,2-dimethyl-4-(((trifluoromethyl)sulfonyl)oxy)-3,6-dihydropyridine-1(2H)-carboxylate (2.9 g, 8.09 mmol) in a mixed solvent of dioxane/H$_2$O (70 mL, 9/1) was added 1,4-dimethyl-5-nitro-3-(4,4,5,5-tetramethyl-1,3,2-dioxaborolan-2-yl)-1H-pyrrolo[2,3-b]pyridine (2.33 g, 7.35 mmol,) and K$_3$PO$_4$ (3.44 g, 16.2 mmol, 2.2 eq). Pd(PPh$_3$)$_4$ (850 mg, 0.736 mmol, 0.1 eq) was added and the reaction was degassed using nitrogen three times. The reaction mixture was heated to 60° C. for 12 hr. The reaction mixture was cooled to room temperature and filtered through a pad of Celite®. The filtrate were concentrated and the residue was purified by silica gel column chromatography (PE:EtOAc, 100:0-89:11) to give the title compound (2.50 g, 77%) as a yellow solid. LCMS [M+H] 401.1; $^1$HNMR (400 MHz, CDCl$_3$) δ 8.91 (s, 1H), 7.12 (s, 1H), 5.97-5.94 (m, 2H), 4.09-4.80 (m, 2H), 3.89 (s, 3H), 2.83 (s, 3H), 2.46 (s, 2H), 1.55-1.49 (m, 15H).

Step 3: 3-(2,2-dimethyl-1,2,3,6-tetrahydropyridin-4-yl)-1,4-dimethyl-5-nitro-1H-pyrrolo[2,3-b]pyridine. An excess of 4N HCl/dioxane (50 mL) was added to a solution of tert-butyl 4-(1,4-dimethyl-5-nitro-1H-pyrrolo[2,3-b]pyridin-3-yl)-2,2-dimethyl-3,6-dihydropyridine-1(2H)-carboxylate (2.50 g, 6.26 mmol) in dioxane (1 mL) and this mixture was allowed to stir at room temperature for 1 hr. The mixture was concentrated under reduced pressure to afford the hydrochloride salt of the title compound (1.87 g, 99.8%) as a yellow solid. LCMS [M+H]=301.2.

Step 4: cyclopentyl(4-(1,4-dimethyl-5-nitro-1H-pyrrolo[2,3-b]pyridin-3-yl)-2,2-dimethyl-3,6-dihydropyridin-1(2H)-yl)methanone. DIPEA (540 mg, 4.18 mmol), HATU (691 mg, 1.67 mmol) and cyclopentane carboxylic acid (286 mg, 2.51 mmol) were added to a mixture of 3-(2,2-dimethyl-1,2,3,6-tetrahydropyridin-4-yl)-1,4-dimethyl-5-nitro-1H-pyrrolo[2,3-b]pyridine hydrochloride (250 mg, 0.83 mmol) in dry DCM (10 mL) and the mixture was allowed to stir at room temperature for 1 hr. The mixture was then poured into water and extracted with ethyl acetate (10 mL). The organic layer was concentrated and the residue was purified by silica gel column chromatography (PE:EtOAc, 100:0-55:45) to afford the title compound (310 mg, 83%) as a yellow solid. LCMS [M+H]=397.1.

Step 5: (4-(5-amino-1,4-dimethyl-1H-pyrrolo[2,3-b]pyridin-3-yl)-2,2-dimethylpiperidin-1-yl)(cyclopentyl)methanone. To a solution of cyclopentyl(4-(1,4-dimethyl-5-nitro-1H-pyrrolo[2,3-b]pyridin-3-yl)-2,2-dimethyl-3,6-dihydropyridin-1(2H)-yl)methanone (1.55 g, 3.92 mmol) in TEA (1.09 mL, 7.84 mmol) was added a mixed solvent of EtOH/DCM (90 mL/30 mL), and the mixture was degassed and purged with hydrogen three times. PtO$_2$ (178 mg, 0.784 mmol) was added and the mixture was stirred under a hydrogen atmosphere (55 psi) for 24 h. The mixture was filtered through a pad of Celite® and washed through with MeOH (3×50 mL). The filtrate was concentrated and the crude product was purified by silica gel column chromatography (DCM:MeOH, 100:0-99:1) to give the title compound (1.45 g, 99.7%) as a red solid. LCMS [M+H]=369.0; $^1$H NMR (400 MHz, CDCl$_3$) δ 7.90 (s, 1H), 6.88 (s, 1H), 4.15-4.09 (m, 1H), 3.84-3.75 (m, 4H), 3.39-3.32 (m, 2H), 2.51 (s, 3H), 2.07-2.09 (m, 1H), 1.84 (s, 1H), 1.81-1.73 (m, 8H), 1.62-1.51 (m, 6H).

Step 6: rac-3-cyano-N-(3-(1-(cyclopentanecarbonyl)-2,2-dimethylpiperidin-4-yl)-1,4-dimethyl-1H-pyrrolo[2,3-b]pyridin-5-yl)-5-methoxybenzamide. TEA (0.170 mL, 1.22 mmol) was added to a solution of (4-(5-amino-1,4-dimethyl-1H-pyrrolo[2,3-b]pyridin-3-yl)-2,2-dimethylpiperidin-1-yl)(cyclopentyl)methanone (150 mg, 0.41 mmol) in dry DCM (25 mL). A solution of 3-cyano-5-methoxybenzoyl chloride (79.6 mg, 0.407 mmol) in dry DCM (5 mL) was then slowly added at 0° C. The mixture was allowed to stir at ambient temperature for 3 hr. The reaction mixture was quenched with water (10 mL) and the organic layer was separated, dried over Na$_2$SO$_4$, and concentrated. The residue was purified by silica gel column chromatography (DCM: MeOH, 100:0-96:4) to afford the title compound (165 mg, 76.8%).

Step 7: (R)-3-cyano-N-(3-(1-(cyclopentanecarbonyl)-2,2-dimethylpiperidin-4-yl)-1,4-dimethyl-1H-pyrrolo[2,3-b]pyridin-5-yl)-5-methoxybenzamide. rac-3-Cyano-N-(3-(1-(cyclopentanecarbonyl)-2,2-dimethyl piperidin-4-yl)-1,4-dimethyl-1H-pyrrolo[2,3-b]pyridin-5-yl)-5-methoxybenzamide was resolved by preparative chiral HPLC (Chiralpak AD, 250×30 mm, 5 μm; 30% IPA+NH$_3$.H$_2$O; 60 mL/min) by collecting the first eluting isomer to afford the title compound. LC/MS [M+Na]=550.0; Chiral LC: Rt=1.96 min (Method E); [α]$^D_{20}$=+28.31 (c=0.0034 g/mL, DCM); $^1$H NMR (400 MHz, CDCl$_3$) δ 8.32-8.08 (m, 2H), 7.64 (br. s., 1H), 7.16-6.89 (m, 2H), 4.04 (s, 3H), 3.92-3.72 (m, 4H), 3.50-3.21 (m, 2H), 2.91 (t, J=7.8 Hz, 1H), 2.62 (s, 2H), 2.17 (br. s., 1H), 1.95-1.68 (m, 8H), 1.37-1.63 (m, 10H). Absolute stereochemistry has been assigned based on potency comparison of enantiomers and the corresponding configuration of Example 60 determined through a co-crystal X-ray structure.

Examples 59-63

The following Examples 59-63 were prepared analogous to Example 58 employing the appropriate carboxylic acid or carboxylic acid chloride coupling partners in Steps 4 and 6.

Absolute stereochemistry has been assigned based on potency comparison of enantiomers and the corresponding configuration of Example 60 determined through a co-crystal X-ray structure.

| Ex. | Structure | Name/Characterization |
|---|---|---|
| 59 | 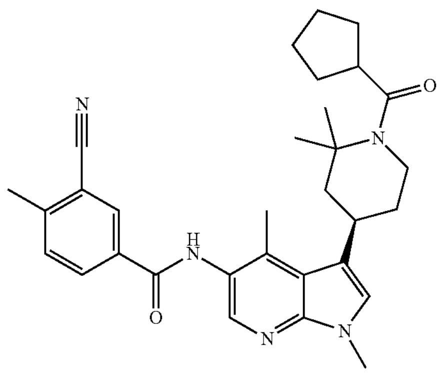 [SMILES: Cc1ccc(C(=O)Nc2cnc3c(c([C@@H]4CCN(C(=O)C5CCCC5)C(C)(C)C4)cn3C)c2C)cc1C#N] | (R)-3-cyano-N-(3-(1-(cyclopentanecarbonyl)-2,2-dimethylpiperidin-4-yl)-1,4-dimethyl-1H-pyrrolo[2,3-b]pyridin-5-yl)-4-methylbenzamide. LC/MS [M + Na] = 534.1; Chiral LC: Rt = 2.79 min (Method E); $[\alpha]^D_{20}$ = +18.6 (c = 0.0023 g/mL, DCM); $^1$H NMR (400 MHz, CDCl$_3$) δ 8.50 (J = 17.6 Hz, 2H), 8.08 (d, J = 7.5 Hz, 1H), 7.65 (s, 1H), 7.50 (d, J = 8.0 Hz, 1H), 7.01 (s, 1H), 3.85 (s, 4H), 3.20-3.49 (m, 1H), 2.91 (t, J = 7.5 Hz, 1H), 2.66 (s, 6H), 1.69-1.93 (m, 7H), 1.32-1.64 (m, 12H). |
| 60 | 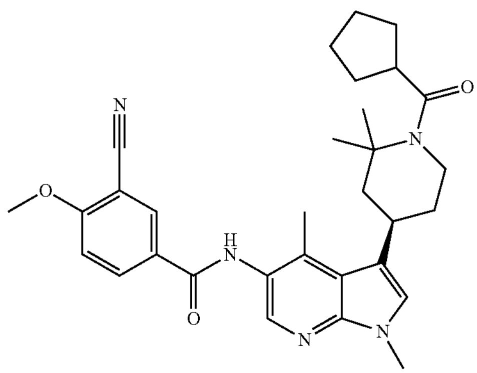 [SMILES: COc1ccc(C(=O)Nc2cnc3c(c([C@@H]4CCN(C(=O)C5CCCC5)C(C)(C)C4)cn3C)c2C)cc1C#N] | (R)-3-cyano-N-(3-(1-(cyclopentanecarbonyl)-2,2-dimethylpiperidin-4-yl)-1,4-dimethyl-1H-pyrrolo[2,3-b]pyridin-5-yl)-4-methoxybenzamide. LC/MS [M + Na] = 550.0; Chiral LC: Rt = 6.72 min (Method E); $[\alpha]^D_{20}$ = +22.4 (c = 0.0039 g/mL, DCM); $^1$H NMR (400 MHz, CDCl$_3$) δ 8.08-8.32, (m, 2 H), 7.64 (br. s., 1 H), 6.89-7.16 (m, 2 H), 4.04 (s, 3 H), 3.72-3.92 (m, 4 H), 3.21-3.50 (m, 2 H), 2.91 (t, J = 7.78 Hz, 1 H) 2.62 (s, 2 H) 2.17 (br. s., 1 H) 1.68-1.95 (m, 8 H), 1.37-1.63 (m, 10 H) |
| 61 | 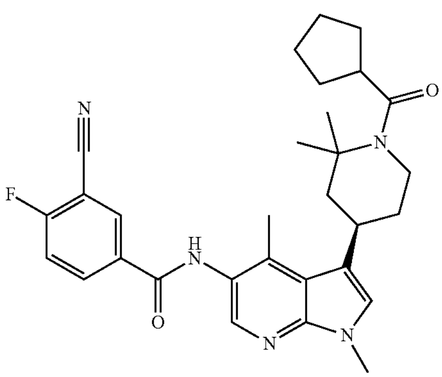 [SMILES: Cc1c(NC(=O)c2ccc(F)c(C#N)c2)cnc2c1c([C@@H]1CCN(C(=O)C3CCCC3)C(C)(C)C1)cn2C] | (R)-3-cyano-N-(3-(1-(cyclopentanecarbonyl)-2,2-dimethylpiperidin-4-yl)-1,4-dimethyl-1H-pyrrolo[2,3-b]pyridin-5-yl)-4-fluorobenzamide. LC/MS [M + Na] = 538.1; Chiral LC: Rt = 5.97 min (Method F); $[\alpha]^D_{20}$ = −41.6 (c = 0.0036 g/mL, DCM); $^1$H NMR (400 MHz, CDCl$_3$) δ 8.34-8.07 (m, 3H), 7.71 (br. s., 1H), 7.39 (t, J = 8.5 Hz, 1H), 7.01 (s, 1H), 3.85 (s, 4H), 3.52-3.25 (m, 2H), 2.82-3.17 (m, 2H), 2.62 (s, 3H), 2.17 (br. s., 1H), 1.93-1.70 (m, 6H), 1.39-1.65 (m, 10H). |
| 62 | 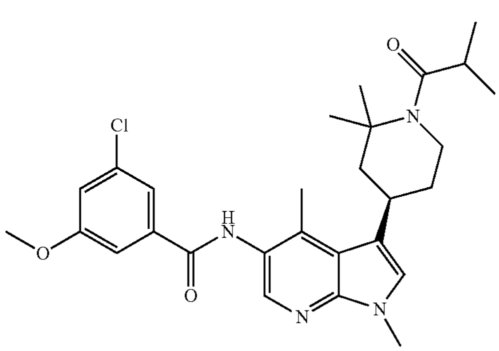 [SMILES: COc1cc(Cl)cc(C(=O)Nc2cnc3c(c([C@@H]4CCN(C(=O)C(C)C)C(C)(C)C4)cn3C)c2C)c1] | (R)-3-chloro-N-(3-(1-isobutyryl-2,2-dimethylpiperidin-4-yl)-1,4-dimethyl-1H-pyrrolo[2,3-b]pyridin-5-yl)-5-methoxybenzamide. LC/MS [M + H] = 511.3; Chiral LC: Rt = 1.55 min (Method Y); $^1$H NMR (400 MHz, CDCl$_3$) δ 8.21 (s, 1H), 7.98 (s, 1H), 7.48 (s, 1H), 7.39 (s, 1H), 7.07 (s, 1H), 6.98 (s, 1H), 3.86-3.77 (m, 7H), 3.45-3.30 (m, 2H), 2.85-2.78 (m, 1H), 2.59 (s, 3H), 2.20-2.15 (m, 1H), 1.90-1.65 (m, 3H), 1.60 (s, 3H), 1.50 (s, 3H), 1.15-1.07 (m, 6H). |

| Ex. | Structure | Name/Characterization |
|---|---|---|
| 63 | 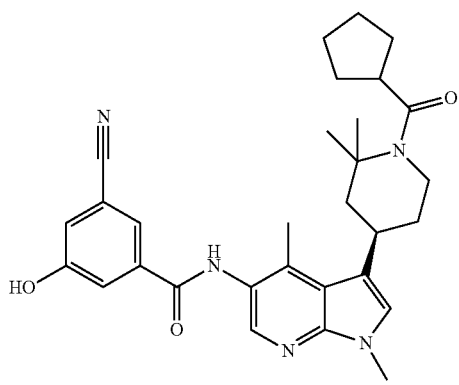 | (R)-3-chloro-N-(3-(1-(cyclopentane-carbonyl)-2(2-dimethylpiperidin-4-yl)-1,4-dimethyl-1H-pyrrolo[2,3-b]pyridin-5-yl)-5-methoxybenzamide. LC/MS [M + Na] = 537.3; Chiral LC: Rt = 1.43 min (Method B); $^1$H NMR (400 MHz, CDCl$_3$) δ 8.23 (s, 1H), 7.84 (s, 1H), 7.48 (s, 1H), 7.39 (s, 1H), 7.08 (s, 1H), 6.99 (s, 1H), 3.87-3.83 (m, 7H), 3.42-3.25 (m, 2H), 2.92-2.85 (m, 1H), 2.61 (s, 3H), 2.25-2.15 (m, 1H), 1.90-1.45 (m, 17H). |

Example 64

Preparation of (R)-3-cyano-N-(3-(1-(cyclopentanecarbonyl)-2,2-dimethylpiperidin-4-yl)-1,4-dimethyl-1H-pyrrolo[2,3-b]pyridin-5-yl)-5-hydroxybenzamide

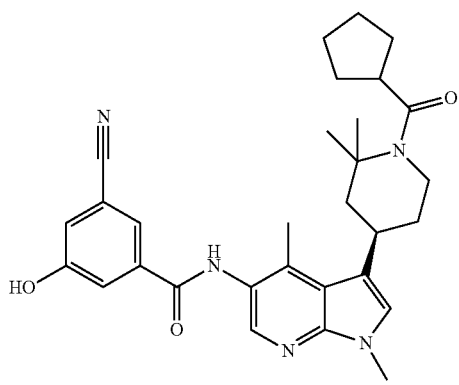 [SMILES: Cc1c(NC(=O)c2cc(O)cc(C#N)c2)cnc2c1c([C@@H]1CCN(C(=O)C3CCCC3)C(C)(C)C1)cn2C]

BBr$_3$ (800 mg, 3.0 mmol, 0.3 mL) was added to a solution of (R)-3-cyano-N-(3-(1-(cyclopentanecarbonyl)-2,2-dimethylpiperidin-4-yl)-1,4-dimethyl-1H-pyrrolo[2,3-b]pyridin-5-yl)-5-methoxybenzamide (prepared in Example 58, 70 mg, 0.133 mmol) in DCM (5.0 mL) at −60° C.

The resulting mixture was stirred at −65° C. for 2 h. Additional BBr$_3$ (2700 mg, 11.0 mmol, 1.0 mL) was added at −60° C. After 20 min, the resulting mixture was stirred at 18° C. for 30 min. The mixture was cooled to −60° C. and then water (12 mL) was added. The mixture was concentrated and the crude product was purified by silica gel column chromatography (DCM/MeOH, 100/0-87/13). The product was dissolved in MeOH (8 mL) and water (25 mL).

The resulting precipitate was collected by filtration and again purified by silica gel column chromatography (DCM/MeOH, 100/0-82/18) to afford the title compound (65 mg, 73%). LC/MS [M+H]=514.2. Chiral SFC: Rt=1.422 min (Method M). $^1$H NMR (400 MHz CD$_3$OD) δ 8.11 (s, 1H), 7.81 (s, 1H), 7.69 (s, 1H), 7.31 (s, 1H), 7.27 (s, 1H), 3.94-3.82 (m, 4H), 3.53-3.47 (m, 2H), 3.07-3.03 (m, 1H), 2.64 (s, 3H), 2.26-2.21 (m, 1H), 1.91-1.54 (m, 19H).

Example 65

Preparation of (R)-3-cyano-N-(3-(1-(cyclopentanecarbonyl)-2,2-dimethylpiperidin-4-yl)-1-methyl-4-(trifluoromethyl)-1H-pyrrolo[2,3-b]pyridin-5-yl)benzamide

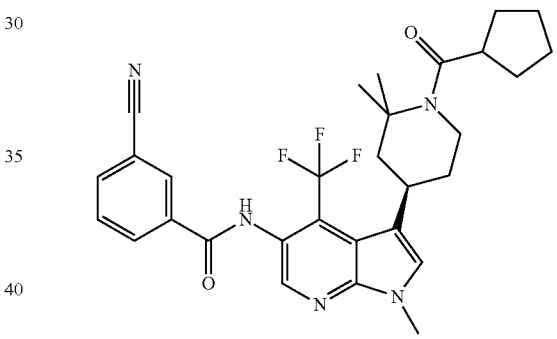

Step 1: 1-methyl-5-nitro-3-(4,4,5,5-tetramethyl-1,3,2-dioxaborolan-2-yl)-4-(trifluoromethyl)-1H-pyrrolo[2,3-b]pyridine. 4,4,5,5-Tetramethyl-1,3,2-dioxaborolane (2760 mg, 21.6 mmol), Pd(OAc)$_2$ (120 mg, 0.54 mmol), X-PHOS (514 mg, 1.08 mmol), and TEA (2760 mg) was added to a solution of 3-iodo-1-methyl-5-nitro-4-(trifluoromethyl)-1H-pyrrolo[2,3-b]pyridine (prepared as described in Example 1, 2000 mg, 5.4 mmol) in toluene (40 mL). The mixture was heated to 120° C. for 0.5 h under N$_2$. The reaction mixture was filtered and concentrated in vacuo. The residue was purified by silica gel column chromatography (PE:EtOAc, 3:1) to afford the title compound (1350 mg, 67.5%) as a pale yellow solid. LC/MS [M+H]=372.0; $^1$H NMR (400 MHz, CDCl$_3$) δ 8.77 (s, 1H), 7.88 (s, 1H), 3.95 (s, 3H), 1.37 (s, 12H).

Step 2: tert-butyl 6,6-dimethyl-4-(1-methyl-5-nitro-4-(trifluoromethyl)-1H-pyrrolo[2,3-b]pyridin-3-yl)-5,6-dihydropyridine-1(2H)-carboxylate: Under N$_2$, a solution of 1-methyl-5-nitro-3-(4,4,5,5-tetramethyl-1,3,2-dioxaborolan-2-yl)-4-(trifluoromethyl)-1H-pyrrolo[2,3-b]pyridine (2500 mg, 6.74 mmol), tert-butyl 6,6-dimethyl-4-(trifluoromethylsulfonyloxy)-5,6-dihydropyridine-1(2H)-carboxylate (2410 mg, 6.74 mmol), Pd(PPh$_3$)$_4$ (778 mg, 0.674 mmol) and K$_2$CO$_3$ (3720 mg, 26.9 mmol) in dioxane/H$_2$O (100 mL/10 mL) was heated to 70° C. and stirred for 15 hr. The reaction mixture was extracted with DCM (500 mL). The organic layer washed with brine (200 mL), dried over Na$_2$SO$_4$, and concentrated. The residue was purified by silica gel column chromatography (DCM:MeOH, 100:1-30:1) to afford the title compound (1700 mg, 55.5%) as a yellow solid. LC/MS [M–Boc]=354.8.

Step 3: (R)-tert-butyl 4-(5-amino-1-methyl-4-(trifluoromethyl)-1H-pyrrolo[2,3-b]pyridin-3-yl)-2,2-dimethylpiperidine-1-carboxylate: A solution of tert-butyl 6,6-dimethyl-4-(1-methyl-5-nitro-4-(trifluoromethyl)-1H-pyrrolo[2,3-b]pyridin-3-yl)-5,6-dihydropyridine-1(2H)-carboxylate (4500 mg, 9.9 mmol) in EtOH (300 mL) and DCM (30 mL) was degassed and purged with hydrogen three times. Pd(OH)$_2$ (200 mg) was added and the mixture was stirred under hydrogen (55 psi) at 50° C. for 45 h. The reaction was then filtered through a pad of Celite® and washed with MeOH (3×30 mL). The filtrate was then concentrated and purified by silica gel column chromatography (PE:EtOAc, 3:1). The resulting solid was resolved by chiral preparatory LC (Chiralcel OJ-R 150×4.6 mm I.D., 5 μm, Water (0.069% TFA):Acetonitrile, 10% to 80%, Flow rate: 0.8 mL/min). Isolation of the first eluting peak afforded (S)-tert-butyl 4-(5-amino-1-methyl-4-(trifluoromethyl)-1H-pyrrolo[2,3-b]pyridin-3-yl)-2,2-dimethylpiperidine-1-carboxylate. Isolation of the second eluting peak afforded the title compound (540 mg) as a pink solid. LC/MS [M+H]=427.0; $^1$H NMR (CDCl$_3$) δ 7.91 (1H, s), 7.09 (1H, s), 4.13 (2H, s, br), 4.08-4.05 (1H, m), 3.81 (3H, s), 3.25-3.17 (1H, m), 3.17-3.08 (1H, m), 1.98 (1H, d, br, J=4.0 Hz), 1.77-1.71 (1H, m), 1.65-1.45 (8H, m), 1.36 (9H, s). Absolute stereochemistry of the products have been assigned based on potency comparison of the enantiomers obtained in step 6 and the corresponding configuration of Example 60 determined through a co-crystal X-ray structure.

Step 4: (R)-tert-butyl 4-(5-(3-cyanobenzamido)-1-methyl-4-(trifluoromethyl)-1H-pyrrolo[2,3-b]pyridin-3-yl)-2,2-dimethylpiperidine-1-carboxylate: To a stirred solution of (R)-tert-butyl 4-(5-amino-1-methyl-4-(trifluoromethyl)-1H-pyrrolo[2,3-b]pyridin-3-yl)-2,2-dimethylpiperidine-1-carboxylate (100 mg, 0.234 mmol) in THF (10 mL) was added 3-cyanobenzoic acid (42 mg, 0.281 mmol), 2-chloromethylpyridinium iodide (120 mg, 0.469 mmol) and DIPEA (0.1 mL) at 55° C. The reaction mixture was allowed to stir for 15 hr. Water was added, and then the mixture was extracted with DCM. The organic layer was separated, dried over Na$_2$SO$_4$, and concentrated. The crude product was purified by silica gel column chromatography (PE:EA, 2:1) to give the title compound (100 mg, 76.8%) as a white solid. LC/MS [M+H]=556.0.

Step 5: (R)-3-cyano-N-(3-(2,2-dimethylpiperidin-4-yl)-1-methyl-4-(trifluoromethyl)-1H-pyrrolo[2,3-b]pyridin-5-yl)benzamide: (R)-tert-butyl 4-(5-(3-cyanobenzamido)-1-methyl-4-(trifluoromethyl)-1H-pyrrolo[2,3-b]pyridin-3-yl)-2,2-dimethylpiperidine-1-carboxylate (100 mg, 0.18 mmol) was added to a solution of HCl in dioxane (4 M, 5 mL) at room temperature. The mixture was stirred for 15 hr and then concentrated to give the hydrochloride salt for the title compound (80 mg, 90%) as a yellow solid. LC/MS [M+H]=456.0.

Step 6: (R)-3-cyano-N-(3-(1-(cyclopentanecarbonyl)-2,2-dimethylpiperidin-4-yl)-1-methyl-4-(trifluoromethyl)-1H-pyrrolo[2,3-b]pyridin-5-yl)benzamide: To a solution of (R)-3-cyano-N-(3-(2,2-dimethylpiperidin-4-yl)-1-methyl-4-(trifluoromethyl)-1H-pyrrolo[2,3-b]pyridin-5-yl)benzamide (80 mg, 0.16 mmol) and TEA (0.1 mL) in DCM (10 mL), was added cyclopentanecarbonyl chloride (22 mg, 0.16 mmol) at room temperature. The resulting mixture was then allowed to stir for 15 hr. The reaction mixture was concentrated and then purified by preparative HPLC (Agela Durashell C18, 250×21.2 mm×5 μm, 45% MeCN/water (0.225% FA) to 65% MeCN in water (0.225% FA)). The resulting product was further purified by chiral preparative LC (Chiralcel OJ-R 150×4.6 mm I.D., 5 um, water (0.069% TFA):Acetonitrile, 10% to 80%, Flow rate: 0.8 mL/min, rt=4.46 min) to afford the title compound (32.7 mg, 36%) as a white solid. LC/MS [M+H]=552.1; $^1$H NMR (CDCl$_3$) δ 8.56 (1H, s), 8.25 (1H, s), 8.17 (1H, d, J=8.0 Hz), 8.10 (1H, s), 7.88 (1H, d, J=7.6 Hz), 7.67 (1H, t, J=8.0 Hz), 7.30 (1H, s), 3.93 (3H, s), 3.88-3.82 (1H, m), 3.34-3.28 (2H, m), 2.93-2.89 (1H, m), 2.14-2.10 (1H, m), 1.87-1.57 (17H, m). Absolute stereochemistry has been assigned based on potency comparison of enantiomers and the corresponding configuration of Example 60 determined through a co-crystal X-ray structure.

Examples 66-67

The following Examples 66-67 were prepared analogous to Example 64 employing the appropriate carboxylic acid or carboxylic acid chloride coupling reagents in Steps 4 and 6. Absolute stereochemistry has been assigned based on potency comparison of enantiomers and the corresponding configuration of Example 44 was determined through a co-crystal X-ray structure.

| Ex. | Structure | Name/Characterization |
| --- | --- | --- |
| 66 | 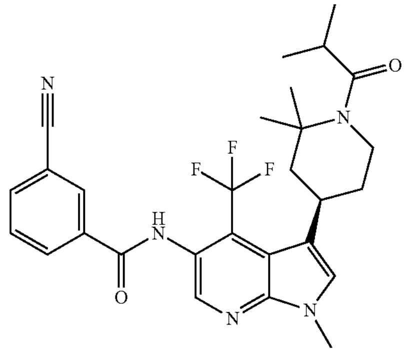 [SMILES: CC(C)C(=O)N1CC[C@@H](c2cn(C)c3ncc(NC(=O)c4cccc(C#N)c4)c(C(F)(F)F)c23)CC1(C)C] | (R)-3-cyano-N-(3-(1-isobutyryl-2,2-dimethylpiperidin-4-yl)-1-methyl-4-(trifluoromethyl)-1H-pyrrolo[2,3-b]pyridin-5-yl)benzamide. LC/MS [M + H] = 526.1; $^1$H NMR (400 MHz, CDCl$_3$) δ 8.55 (s, 1H), 8.25 (s, 1H), 8.18-8.16 (m, 2H), 7.88-7.86 (m, 1H), 7.68-7.64 (m, 1H), 7.30-7.27 (m, 1H), 3.92 (s, 3H), 3.84-3.80 (m, 1H), 3.34-3.28 (m, 2H), 2.82-2.79 (m, 1H), 2.13-2.11 (m, 1H), 1.75-1.08 (m, 13H). |

| Ex. | Structure | Name/Characterization |
|---|---|---|
| 67 | 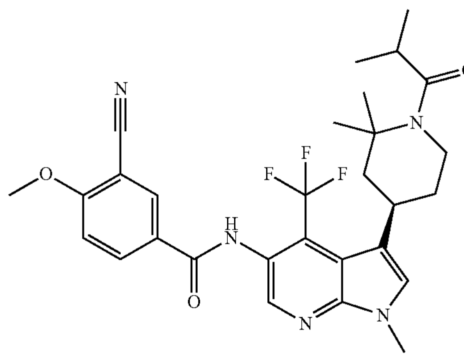 | (R)-3-cyano-N-(3-(1-isobutyryl-2,2-dimethylpiperidin-4-yl)-1-methyl-4-(trifluoromethyl)-1H-pyrrolo[2,3-b]pyridin-5-yl)-4-methoxybenzamide. LC/MS [M + H] = 556.1; ¹H NMR (400 MHz, CDCl₃) δ 8.49 (s, 1H), 8.19-8.14 (m, 3H), 7.27-7.25 (m, 1H), 7.08-7.06 (m, 1H), 4.01 (s, 3H), 3.89 (s, 3H), 3.81-3.80 (m, 1H), 3.31-3.22 (m, 2H), 2.80-2.77 (m, 1H), 2.10-2.08 (m, 1H), 1.72-1.05 (m, 15H), |

Example 68

Preparation of 3-cyano-N-(3-((R)-2,2-dimethyl-1-((R)-2,3,3-trimethylbutanoyl)piperidin-4-yl)-1,4-dimethyl-1H-pyrrolo[2,3-b]pyridin-5-yl)benzamide

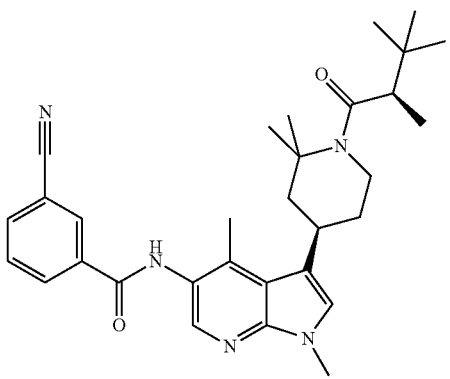 [SMILES: Cc1c(NC(=O)c2cccc(C#N)c2)cnc2c1c([C@@H]1CCN(C(=O)[C@H](C)C(C)(C)C)C(C)(C)C1)cn2C]

Step 1: tert-butyl 4-(5-amino-1,4-dimethyl-1H-pyrrolo[2,3-b]pyridin-3-yl)-2,2-dimethylpiperidine-1-carboxylate.
This reaction was run in six parallel batches. To a Parr hydrogenation vessel charged with tert-butyl 4-(1,4-dimethyl-5-nitro-1H-pyrrolo[2,3-b]pyridin-3-yl)-2,2-dimethyl-3,6-dihydropyridine-1(2H)-carboxylate (prepared as described in Example 58, 850 mg, 2.12 mmol) was added Pd(OH)₂ (29.8 mg, 0.21 mmol), DCM (30 mL), and methanol (100 mL), sequentially. The vessel was sealed and its atmosphere was replaced with hydrogen gas (50 psi H₂) and agitated at room temperature for 24 hours. The vessel's atmosphere was then reequilibrated with atmospheric conditions. The reaction mixture was filtered through a pad of Celite® and rinsed with methanol (10 mL). The filtrates were then concentrated under reduced pressure and each crude residue was combined with all previous batches totaling (3.6 g, 70% for the combined 6 batches). The crude residue was then purified by SFC chiral separation (Chiralcel OJ, 300×50 mm, 10 μm, 35% MeOH+NH₄OH, 200 mL/min). Peak 1 (1.1 g recovered after concentration) corresponded to the (R)-enantiomer which using Method K eluted at 8.15 min. Peak 2 (1.2 g recovered after concentration) corresponded to the (S)-enantiomer which using Method K eluted at 8.35 mins. The absolute configuration of the second eluting enantiomer was established by X-ray crystallography methods as described in Example 108.

LC/MS [M+H]=373.1; ¹H NMR (400 MHz, CDCl₃) δ 7.89 (br s, 1H), 6.86 (s, 1H), 4.04-4.01 (m, 1H); 3.77 (s, 3H), 3.37-3.17 (m, 4H), 2.50 (s, 3H), 2.11-2.08 (m, 1H), 1.86-1.83 (m, 1H), 1.70-1.42 (m, 17H).

Step 2: tert-butyl (R)-4-(5-(3-cyanobenzamido)-1,4-dimethyl-1H-pyrrolo[2,3-b]pyridin-3-yl)-2,2-dimethylpiperidine-1-carboxylate. To a vessel charged with tert-butyl-(R)-4-(5-amino-1,4-dimethyl-1H-pyrrolo[2,3-b]pyridin-3-yl)-2,2-dimethylpiperidine-1-carboxylate (500 mg, 1.45 mmol), was sequentially added at room temperature 3-cyanobenzoic acid (214 mg, 1.45 mmol), 2-chloro-1-methylpyridinium iodide (370 mg, 1.45 mmol), DIPEA (750 mg, 5.81 mmol), and THF (15 mL). The mixture was warmed to 70° C. and allowed to stir for 3 hours. The mixture was then concentrated under reduced pressure to give a crude residue which was dissolved in ethyl acetate (30 mL), then washed with water (30 mL), brine (30 mL). The organic layer was dried over Na₂SO₄, and concentrated to give the title compound (640 mg, 93.1%) as a light yellow solid.

Step 3: (R)-3-cyano-N-(3-(2,2-dimethylpiperidin-4-yl)-1,4-dimethyl-1H-pyrrolo[2,3-b]pyridin-5-yl)benzamide hydrochloride. To a vessel charged with crude tert-butyl (R)-4-(5-(3-cyanobenzamido)-1,4-dimethyl-1H-pyrrolo[2,3-b]pyridin-3-yl)-2,2-dimethylpiperidine-1-carboxylate (80 mg, 0.16 mmol) was added EtOAc (2 mL) and HCl in EtOAc (4 M, 2 mL) dropwise at room temperature. The mixture was stirred at room temperature for an additional 2 hours. The reaction mixture was then concentrated to give the hydrochloride salt of the title compound (80 mg, 120% crude yield) as a light yellow solid. LC/MS [M+H]=373.1.

Step 4: 3-cyano-N-(3-((R)-2,2-dimethyl-1-((R)-2,3,3-trimethylbutanoyl)piperidin-4-yl)-1,4-dimethyl-1H-pyrrolo[2,3-b]pyridin-5-yl)benzamide. To a stirred solution of (R)-3-cyano-N-(3-(2,2-dimethylpiperidin-4-yl)-1,4-dimethyl-1H-pyrrolo[2,3-b]pyridin-5-yl)benzamide hydrochloride (100 mg, 0.232 mmol) in DCM (4 mL) was added triethylamine (0.5 mL, 0.9 mmol) and (-)-(R)-2,3,3-trimethylbutanoic acid (Kido, M.; Sugiyama, S.; Satoh, T. Tetrahedron: Assym 2007, 18, 1934-47.) (100 mg, 0.67 mmol) at room temperature. The mixture was then stirred for 1 hour, then the solvent was removed under reduced pressure, and the residue was purified by HPLC. After lyophilization, the title compound (20 mg, 16%) was obtained as a white solid. LC/MS [M+H]=514.1; ¹H NMR (400 MHz, CDCl₃) δ 8.38-8.10 (m, 3H), 7.87 (d, J=7.0 Hz, 1H), 7.80-7.55 (m, 2H), 7.01 (br. s., 1H), 3.84 (br. s., 4H), 3.42 (br. s., 2H), 2.62 (br. s., 4H), 2.23 (br. s., 1H), 1.94-1.74 (m, 2H), 1.56 (m, 6H), 1.17-0.78 (m, 13H); Chiral SFC: Rt=5.28 min (Method L).

Examples 69-76

The following Examples 69-76 were prepared analogous to Example 68, employing the appropriate carboxylic acid or carboxylic acid chloride coupling reagents in Steps 2 and 4.

Absolute configuration is based on a single crystal X-ray structure of tert-butyl (S)-4-(5-amino-1,4-dimethyl-1H-pyrrolo[2,3-b]pyridin-3-yl)-2,2-dimethylpiperidine-1-carboxylate intermediate in Step 3 of Example 77 (see Example 108).

| Ex. | Structure | Name/Characterization |
|---|---|---|
| 69 | 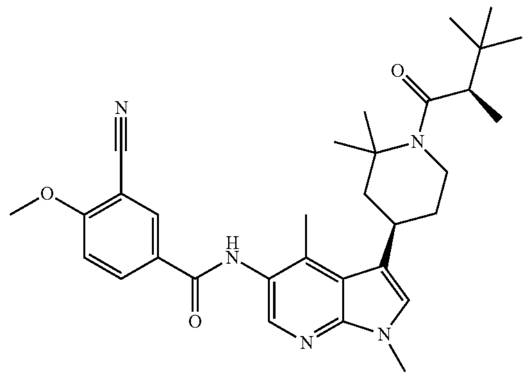 [SMILES: COc1ccc(C(=O)Nc2cnc3c(c([C@@H]4CCN(C(=O)[C@H](C)C(C)(C)C)C(C)(C)C4)cn3C)c2C)cc1C#N] | S-cyano-N-(3-((R)-2,2-dimethyl-1-((R)-2,2,3-trimethylbutanoyl)piperidin-4-yl)-1,4-dimethyl-1H-pyrrolo[2,3-b]pyridin-5-yl)-4-methoxybenzamide. LC/MS [M + H] = 544.2; $^1$H NMR (400 MHz, CDCl$_3$) δ 8.30-8.12 (m, 3H), 7.76 (br. s., 1H), 7.10 (d, J = 9.1 Hz, 1H), 6.99 (s, 1H), 4.03 (s, 3H), 3.88-3.69 (m, 4H), 3.48-3.36 (m, 2H), 2.61 (s, 4H), 2.31-2.12 (m, 1H), 1.89-1.78 (m, 2H), 1.41-1.72 (m, 7H), 1.09 (d, J = 6.5 Hz, 3H), 1.00 (s, 9H). |
| 70 | 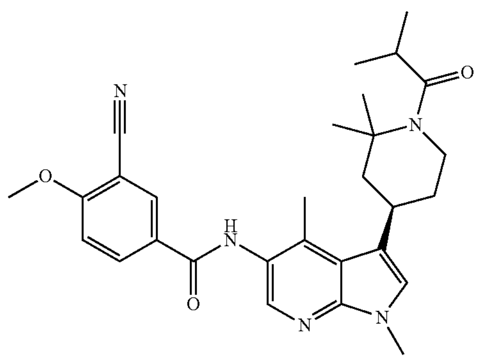 [SMILES: COc1ccc(C(=O)Nc2cnc3c(c([C@@H]4CCN(C(=O)C(C)C)C(C)(C)C4)cn3C)c2C)cc1C#N] | (R)-3-cyano-N-(3-(1-isobutyryl-2,2-dimethylpiperidin-4-yl)-1,4-dimethyl-1H-pyrrolo[2,3-b]pyridin-5-yl)-4-methoxybenzamide. LC/MS [M + H] = 502.1; $^1$H NMR (400 MHz, CDCl$_3$) δ 8.22 (br. s., 3H), 7.95 (br. s., 1H), 7.08 (d, J = 9.0 Hz, 1H), 6.99 (s, 1H), 4.02 (s, 3H), 3.89-3.69 (m, 4H), 3.51-3.21 (m, 2H), 2.84-2.77 (m, 1H), 2.60 (s, 3H), 2.24-2.12 (m, 1H), 1.90-1.68 (m, 3H), 1.60 (s, 3H), 1.48 (s, 3H), 1.14-1.08 (m, 6H). |
| 71 | 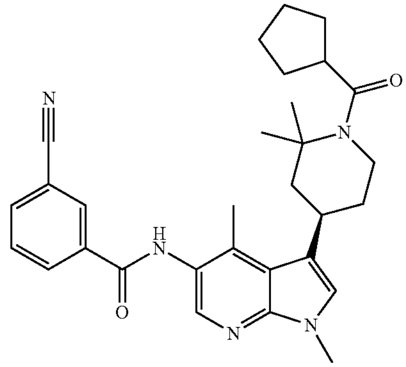 [SMILES: Cc1c(NC(=O)c2cccc(C#N)c2)cnc2c1c([C@@H]1CCN(C(=O)C3CCCC3)C(C)(C)C1)cn2C] | (R)-3-cyano-N-(3-(1-(cyclopentanecarbonyl)-2,2-dimethylpiperidin-4-yl)-1,4-dimethyl-1H-pyrrolo[2,3-b]pyridin-5-yl)benzamide. LC/MS [M + H] = 498.4; Chiral LC: Rt = 2.58 min (Method J); $^1$H NMR (CDCl$_3$) δ 10.05 (1 H, s), 8.65-8.37 (3 H, m), 7.84 (1 H, d, J = 7 Hz), 7.66 (s, 1H), 7.08 (s, 1H), 4.07 (s, 3H), 3.85-3.82 (m, 1H), 3.49-3.20 (m, 2H), 2.91-2.87 (m, 1H), 2.75 (s, 3H), 2.25-2.19 (m, 1H), 1.81-1.38 (m, 17H). |
| 72 | 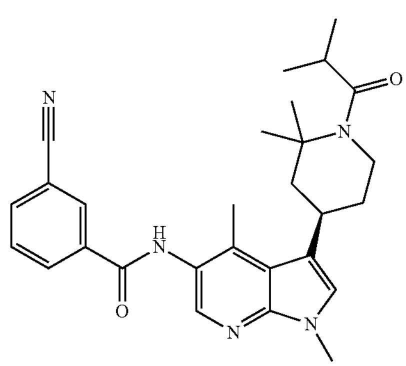 [SMILES: Cc1c(NC(=O)c2cccc(C#N)c2)cnc2c1c([C@@H]1CCN(C(=O)C(C)C)C(C)(C)C1)cn2C] | (R)-3-cyano-N-(3-(1-isobutyryl-2,2-dimethylpiperidin-4-yl)-1,4-dimethyl-1H-pyrrolo[2,3-b]pyridin-5-yl)benzamide. LC/MS [M + H] = 472.2; $^1$H NMR (CDCl$_3$) δ 8.28-8.15 (4 H, m), 7.81 (1 H, d, J = 8 Hz), 7.61 (1 H, t, J = 8 Hz), 6.98 (1 H, s), 3.82-3.74 (4 H, m), 3.45-3.36 (1 H, m), 3.29 (1 H, ddd, J = 14, 10, 3 Hz), 2.83-2.70 (m, 1H), 2.59 (s, 3H), 2.22-2.11 (m, 1H), 1.84-1.61 (m, 3H), 1.57 (s, 3H), 1.46 (s, 3H), 1.08 (dd, J = 16, 7 Hz, 6H). |

| Ex. | Structure | Name/Characterization |
|---|---|---|
| 73 | 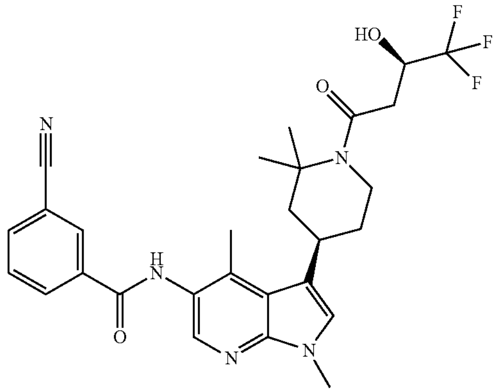 [SMILES: Cc1c(NC(=O)c2cccc(C#N)c2)cnc2c1c([C@@H]1CCN(C(=O)C[C@@H](O)C(F)(F)F)C(C)(C)C1)cn2C] | 3-cyano-N-(3-((R)-2,2-dimethyl-1-((R)-4,4,4-trifluoro-3-hydroxybutanoyl)piperidin-4-yl)-1,4-dimethyl-1H-pyrrolo[2,3-b]pyridin-5-yl)benzamide. LC/MS [M + H] = 542.2; LC: Rt = 4.08 min (Method AB); $^1$H NMR (CDCl$_3$) δ 8.35-8.15 (4 H, m), 7.87-7.73 (1 H, m), 7.66-7.54 (1 H, m), 6.92 (1 H, s). 4.70 (1 H, s), 4.41-4.28 (1 H, s), 3.82 (3 H, s), 3.74-3.59 (2 H, m), 3.45-3.17 (2 H, m), 2.54 (3 H, s), 2.22-2.08 (1 H, m), 1.82-0.69 (10 H, m). |
| 74 | 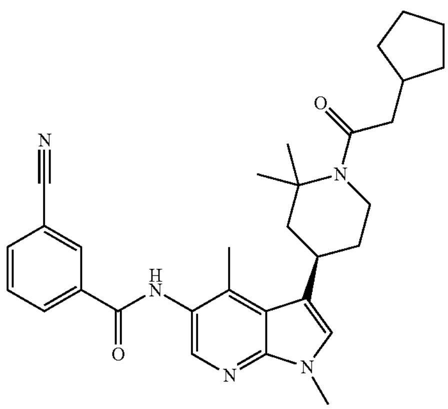 [SMILES: Cc1c(NC(=O)c2cccc(C#N)c2)cnc2c1c([C@@H]1CCN(C(=O)CC3CCCC3)C(C)(C)C1)cn2C] | (R)-3-cyano-N-(3-(1-(2-cyclopentylacetyl)-2,2-dimethylpiperidin-4-yl)-1,4-dimethyl-1H-pyrrolo[2,3-b]pyridin-5-yl)benzamide. LC/MS [M + H] = 512.3; $^1$H NMR (CDCl$_3$) δ 8.26-8.12 (m, 4H), 7.85-7.83 (m, 1H), 7.65-7.61 (m, 1H), 6.99 (s, 1H), 3.78 (s, 3H), 3.77-3.74 (m, 1H), 3.38-3.27 (m, 2H), 2.61 (s, 3H), 2.36-2.18 (m, 4H), 1.81-1.47 (m, 13H), 1.15-1.14 (m, 2H). |
| 75 | 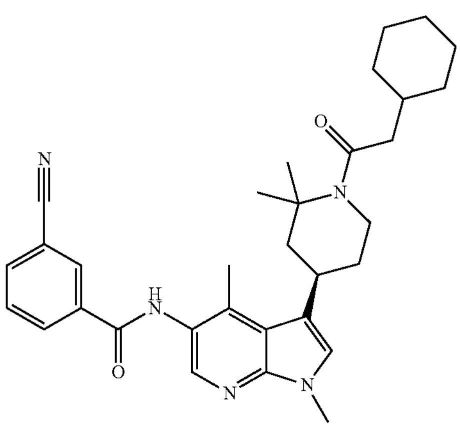 [SMILES: Cc1c(NC(=O)c2cccc(C#N)c2)cnc2c1c([C@@H]1CCN(C(=O)CC3CCCCC3)C(C)(C)C1)cn2C] | (R)-3-cyano-N-(3-(1-(2-cyclohexylacetyl)-2,2-dimethylpiperidin-4-yl)-1,4-dimethyl-1H-pyrrolo[2,3-b]pyridin-5-yl)benzamide. LC/MS [M + H] = 526.4; $^1$H NMR (400 MHz, CDCl$_3$) δ 8.30-8.15 (m, 4 H), 7.86-7.84 (m, 1H), 7.67-7.63 (m, 1H), 7.00 (s, 1 H), 3.84 (s, 3H)( 3.81-3.71 (m, 1H) 3.43-3.36 (m, 1H), 3.32-3.23 (m, 1H), 2.62 (s, 3H), 2.44-2.11 (m, 4H), 1.89-1.78 (m, 4H), 1.78-1.66 (m, 4H), 1.63 (s, 3H), 1.58-1.55 (m, 2H), 1.49 (s, 3H), 1.47-1.42 (m, 1H), 1.21-1.09 (m, 2H). |
| 76 | 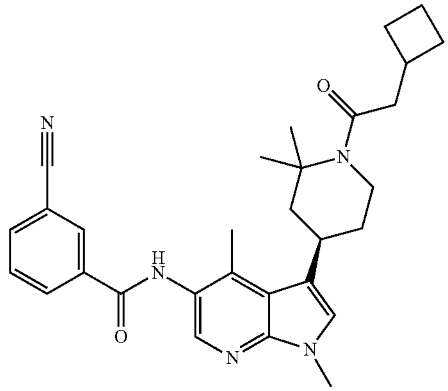 [SMILES: Cc1c(NC(=O)c2cccc(C#N)c2)cnc2c1c([C@@H]1CCN(C(=O)CC3CCC3)C(C)(C)C1)cn2C] | (R)-3-cyano-N-(3-(1-(2-cyclobutylacetyl)-2,2-dimethylpiperidin-4-yl)-1,4-dimethyl-1H-pyrrolo[2,3-b]pyridin-5-yl)benzamide. LC/MS [M + H] = 498.3. $^1$H NMR (400 MHz, CDCl$_3$) δ 8.33-8.18 (m, 3H), 8.03 (s, 1H), 7.86 (d, J = 7.8 Hz, 1H), 7.66 (t, J = 7.8 Hz, 1H), 7.00 (s, 1H), 3.85 (s, 3H), 3.75 (dt, J = 13.6, 5.1 Hz, 1H), 3.40 (t, J = 11.12 Hz, 1H), 3.26 (ddd, J = 13.7, 9.9, 3.7 Hz, 1H), 2.75-2.62 (m, 1H), 2.63 (s, 3H), 2.56-2.38 (m, 2H), 2.16 (td, J = 7.5, 3.3 Hz, 3H), 1.94-1.73 (m, 3H), 1.75-1.65 (m, 2H), 1.62 (s, 3H), 1.52-1.49 (m, 1H), 1.47 (s, 3H), 1.56-1.37 (m, 1H). |

Example 77

Preparation of 3-cyano-N-(3-((1R,5S,8r)-3-isobutyryl-3-azabicyclo[3.2.1]octan-8-yl)-1-methyl-4-(trifluoromethyl)-1H-pyrrolo[2,3-b]pyridin-5-yl)benzamide

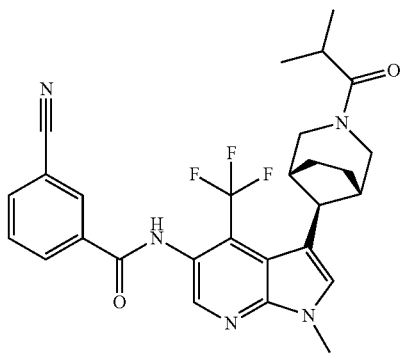 [SMILES: CC(C)C(=O)N1C[C@H]2CC[C@@H](C1)[C@@H]2c1cn(C)c2ncc(NC(=O)c3cccc(C#N)c3)c(C(F)(F)F)c12]

Step 1: tert-butyl 8-oxo-3-azabicyclo[3.2.1]octane-3-carboxylate. BOC anhydride (5.81 g, 26.6 mmol) and Pearlman's catalyst (1.55 g, 23.2 mmol) were successively added to a solution of 3-benzyl-3-azabicyclo[3.2.1]octan-8-one obtained from commercial sources (CAS 83507-33-9) (5.0 g, 22.0 mmol) in EtOAc (74 mL) at room temperature. The reaction vessel was alternately filled with nitrogen and evacuated (3×) and then filled and evacuated with hydrogen (2×). The mixture was stirred overnight under 100 psi of $H_2$. The mixture was filtered through a pad of Celite® which was washed with ethyl acetate. The filtrate was concentrated and the crude product was purified by silica gel chromatography (heptane:EtOAc, 0:100-100:0) to provide the title compound (4.49 g, 90%) as a solid. LC/MS [M−Me]=211.1. $^1$H NMR (400 MHz, CDCl$_3$) δ 4.38 (d, J=14.0 Hz, 1H), 4.20 (d, J=14.0 Hz, 1H), 3.27 (d, J=13.3 Hz, 1H), 3.17 (d, J=13.3 Hz, 1H), 2.24 (d, J=15.6 Hz, 2H), 1.76-1.99 (m, 4H), 1.49 (s, 9H).

Step 2: tert-butyl 8-(methoxymethylidene)-3-azabicyclo[3.2.1]octane-3-carboxylate. Potassium tert-butoxide (4.47 g, 39.8 mmol) was added portionwise to a suspension of (methoxymethyl)triphenylphosphonium chloride (12.4 g, 36.1 mmol) and tert-butyl 8-oxo-3-azabicyclo[3.2.1]octane-3-carboxylate (4.49 g, 19.9 mmol) in THF (100 mL) at 0° C. After 45 min, the cold bath was removed and the reaction was stirred overnight at room temperature. The reaction was recooled at 0° C. and a saturated solution of NH$_4$Cl was added until pH=6. After warming to room temperature, the mixture was diluted with water and extracted with DCM. The combined organic layers were washed with brine, dried with Na$_2$SO$_4$, filtered and concentrated. The resulting oil was diluted with a small amount of ether and a large volume of heptane. After vigorous stirring for 1 h, the resulting solid was filtered off and washed with additional heptane. The filtrate was concentrated and the resulting oil was purified by silica gel chromatography (heptane:EtOAc, 100/0-70/30) to provide the title compound (4.73 g, 94%). LC/MS [M−Me]=239.1. $^1$H NMR (400 MHz, CDCl$_3$) δ 5.86 (s, 1H), 4.02 (t, J=12.1 Hz, 1H), 3.79-3.94 (m, 1H), 3.57 (s, 3H), 2.76-3.05 (m, 3H), 2.41 (m, 1H), 1.58-1.65 (m, 4H), 1.47 (br. s., 9H).

Step 3: tert-butyl (8-anti)-formyl-3-azabicyclo[3.2.1]octane-3-carboxylate. Water (0.473 mL) followed by para-toluenesulfonic acid monohydrate (2.71 g, 13.8 mmol) was added to a solution of tert-butyl 8-(methoxymethylidene)-3-azabicyclo[3.2.1]octane-3-carboxylate (3.33 g, 13.14 mmol) in acetone (87.6 mL) at 0° C. The mixture was stirred at 0° C. for 2 h and was quenched at the same temperature with a saturated solution of NaHCO$_3$ until pH=8. Acetone was carefully removed under vacuum (bath at 10° C.) and the aqueous layer was extracted with DCM. The combined organic layers were washed with brine, dried with Na$_2$SO$_4$, filtered and concentrated to afford a mixture of predominantly undesired diastereomer (10.09 ppm) versus desired aldehyde (9.62 ppm) in a 3:1 ratio. Complete epimerization was obtained after stirring the crude mixture at room temperature in a mixture of DCM (13.1 mL) and DBU (26.3 mmol, 3.93 mL). EtOAc (100 mL) was added and DCM was carefully evaporated (150 mbar, bath 35° C.) leaving most of the EtOAc in the flask. The reaction was then quenched with a saturated solution of NH$_4$Cl. The phases were separated and the organic phase was washed with a saturated solution of NH$_4$Cl followed by brine, dried with Na$_2$SO$_4$, filtered and concentrated. The resulting oil was purified by silica gel chromatography (heptane/EtOAc, 100:0-0:100) to afford the title compound (2.41 g, 77%) as a solid. LC/MS [M−Me]=225.0. $^1$H NMR (400 MHz, CDCl$_3$) δ ppm 9.63 (s, 1H), 4.03 (d, J=13.3 Hz, 1H), 3.88 (d, J=13.3 Hz, 1H), 2.87 (m, 2H), 2.50-2.66 (m, 3H), 1.52-1.67 (m, 4H), 1.47 (s, 9H).

Step 4: tert-butyl 8-(1-hydroxy-2-nitroethyl)-3-azabicyclo[3.2.1]octane-3-carboxylate. Nitromethane (815 μL, 15.0 mmol) and potassium tert-butoxide (1 M in THF, 2.0 mL, 2.0 mmol) were successively added to a solution of tert-butyl (8-anti)-formyl-3-azabicyclo[3.2.1]octane-3-carboxylate (2.40 g, 10.0 mmol) in a mixture of THF:t-BuOH (1:1, 10 mL). The mixture was stirred at 0° C. for 1 h, warmed to room temperature and stirred overnight. The reaction was quenched with a saturated solution of NH$_4$Cl. The phases were separated and the aqueous phase was extracted with DCM. The combined organic phases were dried over Na$_2$SO$_4$, filtered and concentrated under vacuum. After drying the crude residue for 1 h under high vacuum, the title compound (3.10 g, 100%) was obtained as a white solid and was used for the next step without purification. LC/MS [M−Me]=286.1. $^1$H NMR (500 MHz, CDCl$_3$) δ ppm 4.55 (d, J=13.7 Hz, 1H), 4.36-4.45 (m, 1H), 3.77-4.04 (m, 3H), 3.33-3.41 (m, 1H), 2.72-2.91 (m, 2H), 2.58-2.68 (m, 1H), 2.46-2.58 (m, 1H), 1.88-2.01 (m, 1H), 1.53-1.82 (m, 4H), 1.47 (br. s, 9H).

Step 5: tert-butyl (E)-8-(2-nitrovinyl)-3-azabicyclo[3.2.1]octane-3-carboxylate. TEA (8.56 mmol, 1.19 mL) was added to a solution of tert-butyl (8-anti)-(1-hydroxy-2-nitroethyl)-3-azabicyclo[3.2.1]octane-3-carboxylate (1.28 g, 4.28 mmol) in DCM (5.48 mL) at 0° C. Methanesulfonyl chloride (4.71 mmol, 0.367 mL) was then slowly added. After stirring for 10 min at 0° C., the mixture was quenched with water. The layers were separated and the organic phase was washed with a saturated aqueous of NH$_4$Cl and then filtered through a plug of fluorisil eluting with additional DCM. The filtrate was dried with Na$_2$SO$_4$, filtered and concentrated to afford the title compound (1.11 g, 92%) as a colorless oil. LC/MS [M−Me]=268.1. $^1$H NMR (500 MHz, CDCl$_3$) δ 7.14 (dd, J=13.4, 7.8 Hz, 1H), 7.02 (dd, J=13.4, 1.2 Hz, 1H), 4.01 (d, J=13.0 Hz, 1H), 3.87 (d, J=12.5 Hz, 1H), 2.95 (d, J=13.2 Hz, 1H), 2.86 (d, J=12.5 Hz, 1H), 2.53 (d, J=7.8 Hz, 1H), 2.23-2.28 (m, 1H), 2.17-2.22 (m, 1H), 1.75-1.82 (m, 2H), 1.55-1.72 (m, 2H), 1.47 (s, 9H).

Step 6: tert-butyl (8-anti)-{1-[2-chloro-4-(trifluoromethyl)pyridin-3-yl]-2-nitroethyl}-3-azabicyclo[3.2.1]octane-3-carboxylate. A solution of LiCl-iPrMgCl (1.3 M in THF, 3.50 mL, 4.55 mmol) was slowly added to a solution of 2-chloro-3-iodo-4-(trifluoromethyl)pyridine (1.40 g, 4.55 mmol) in THF (4.55 mL) at −40° C. The mixture was stirred 1 h at −40° C. and a pre-cooled solution of tert-butyl (8-anti)-8-[(E)-2-nitroethenyl]-3-azabicyclo[3.2.1]octane-3- carboxylate (1.10 g, 3.90 mmol) in THF (4.55 mL) was slowly added. The reaction was stirred 10 min at −40° C., then the cold bath was removed and the reaction was stirred until it reached room temperature. The resulting mixture was quenched with a saturated solution of $NH_4Cl$. The aqueous phase was extracted with DCM and the combined organic phases were washed with brine, dried over $Na_2SO_4$, filtered and concentrated. The crude product was purified by silica gel column chromatography (heptane:EtOAc, 100/0-55/45) to afford the title compound (1.26 g, 69%) as a yellow powder. LC/MS [M+H-tBu]=408.2; $^1$HNMR (400 MHz, $CDCl_3$) δ 8.57 (d, J=5.1 Hz, 1H), 7.59 (d, J=5.1 Hz, 1H), 4.84-5.02 (m, 2H), 3.80-4.08 (m, 2H), 3.67-3.77 (m, 2H), 2.71-3.01 (m, 4H), 2.09-2.24 (m, 1H), 1.83-1.95 (m, 1H), 1.62-1.76 (m, 2H), 1.41-1.47 (m, 9H).

Step 7: 1-[(8-anti)-{1-[2-chloro-4-(trifluoromethyl)pyridin-3-yl]-2-nitroethyl}-3-azabicyclo[3.2.1]oct-3-yl]-2-methylpropan-1-one. To a solution of tert-butyl (8-anti)-{1-[2-chloro-4-(trifluoromethyl)pyridin-3-yl]-2-nitroethyl}-3-azabicyclo[3.2.1]octane-3-carboxylate (1.26 g, 2.72 mmol) in DCM (9 mL) was slowly added HCl (4M in dioxane, 6.79 mL, 27.2 mmol) at room temperature. The mixture was stirred for 4 hr at 50° C. The solvent was removed under reduced pressure. The residue was suspended in DCM (9 mL) and was added to a saturated solution of $NaHCO_3$ (25 mL). The mixture was stirred vigorously and isobutyryl chloride (314 µL, 3.00 mmol) was slowly added. The reaction was transferred to a separating funnel and the phases were separated. The aqueous layer was extracted twice with DCM and the combined organic phases were dried with $Na_2SO_4$, filtered and concentrated to provide the title compound (1.17 g, 98% yield) which required no further purification. LC/MS [M+H]=434.0; $^1$HNMR (400 MHz, $CDCl_3$) δ ppm 8.58 (d, J=5.1 Hz, 1H), 7.60 (d, J=5.1 Hz, 1H), 5.02-4.86 (m, 2H), 4.51-4.28 (m, 2H), 3.84-3.68 (m, 2H), 3.28-3.14 (m, 1H), 2.89-2.66 (m, 3H), 2.35-2.18 (m, 1H), 1.99-1.84 (m, 1H), 1.69-1.46 (m, 4H), 1.44-1.34 (m, 1H), 1.20-1.05 (m, 6H).

Step 8: 2-methyl-1-{(8-anti)-[4-(trifluoromethyl)-2,3-dihydro-1H-pyrrolo[2,3-b]pyridin-3-yl]-3-azabicyclo[3.2.1]oct-3-yl}propan-1-one. Acetic acid (1.54 mL, 26.9 mmol) and zinc powder (1.23 g, 18.9 mmol) were successively added to a solution of 1-[(8-anti)-{1-[2-chloro-4-(trifluoromethyl)pyridin-3-yl]-2-nitroethyl}-3-azabicyclo[3.2.1]oct-3-yl]-2-methylpropan-1-one (1.17 g, 2.69 mmol) in THF (5.39 mL) were successively added at room temperature. The solution was stirred overnight at room temperature and then refluxed at 90° C. for 6 h. The mixture was cooled to room temperature and then was filtered through a plug of Celite® eluting with DCM. The organic layer was concentrated. The crude product was purified by silica gel column chromatography (DCM:MeOH, 100:0-90:10) to afford the title compound (342 mg, 35%) as a white powder. LC/MS [M+H]=368.1; $^1$H NMR (400 MHz, $CDCl_3$) δ 8.05 (d, J=5.5 Hz, 1H), 6.58-6.64 (m, 1H), 4.43 (dd, J=12.9, 2.7 Hz, 0.6H), 4.31 (dd, J=12.9, 3.3 Hz, 0.4H), 3.80-3.62 (m, 1H), 3.56-3.40 (m, 2H), 3.32 (dd, J=9.4, 7.0 Hz, 0.4H), 3.19-3.01 (m, 1H), 2.97-2.6 (m, 4H), 2.47-2.22 (m, 2H), 2.07-1.99 (m, 1H), 1.97-1.68 (m, 3H), 1.61-1.43 (m, 2H), 1.19-1.00 (m, 6H).

Step 9: 2-methyl-1-{(8-anti)-[1-methyl-4-(trifluoromethyl)-2,3-dihydro-1H-pyrrolo[2,3-b]pyridin-3-yl]-3-azabicyclo[3.2.1]oct-3-yl}propan-1-one. At room temperature, to a solution of 2-methyl-1-{(8-anti)-[4-(trifluoromethyl)-2,3-dihydro-1H-pyrrolo[2,3-b]pyridin-3-yl]-3-azabicyclo[3.2.1]oct-3-yl}propan-1-one (342 mg, 0.93 mmol) in THF (3.1 mL) was added in one portion of NaH (60% in oil, 47 mg, 1.16 mmol) followed by methyl iodide (64 µL, 1.02 mmol).

The mixture was stirred for 2 h and then was quenched with a saturated solution of $NH_4Cl$ and diluted with DCM. The phases were separated and the aqueous layer was extracted twice with DCM. The combined organic layers were dried over $Na_2SO_4$, filtered and concentrated. The crude product was purified by silica gel column chromatography (heptane:EtOAc, 100/0-0/100) to afford the title compound (197 mg, 56%) as a colorless oil. LC/MS [M+H]=382.1; $^1$H NMR (400 MHz, $CDCl_3$) δ 8.05 (d, J=5.5 Hz, 1H), 6.64 (t, J=5.9 Hz, 1H), 4.45 (dd, J=12.5, 3.1 Hz, 0.6H), 4.33 (dd, J=12.9, 3.9 Hz, 0.4H), 3.78 (dd, J=12.1, 3.5 Hz, 0.4H), 3.67 (dd, J=11.7, 2.7 Hz, 0.6H), 3.49 (t, J=9.8 Hz, 1H), 3.36 (t, J=8.6 Hz, 1H), 3.16 (d, J=11.7 Hz, 0.6H), 3.12-3.04 (m, 1H), 3.01 (br. s., 3H), 2.98-2.92 (m, 1H), 2.83-2.72 (m, 1.4H), 2.68 (d, J=13.3 Hz, 0.6H), 2.48 (d, J=12.5 Hz, 0.4H), 2.29 (br. s., 0.6H), 2.25 (br. s., 0.4H), 2.05-2.00 (m, 1H), 1.99-1.69 (m, 3H), 1.62-1.46 (m, 2H), 1.19-1.14 (m, 3H), 1.10-1.03 (m, 3H).

Step 10: 2-methyl-1-{(8-anti)-8-[1-methyl-5-nitro-4-(trifluoromethyl)-1H-pyrrolo[2,3-b]pyridin-3-yl]-3-azabicyclo[3.2.1]oct-3-yl}propan-1-one. Trifluoroacetic acid (118 µL, 1.55 mmol), followed by a premixed solution of tetrabutylammonium nitrate (471 mg, 1.55 mmol) and trifluoroacetic anhydride (215 µL, 1.55 mmol) in DCM (720 µL) were added to a solution of 2-methyl-1-{(8-anti)-[1-methyl-4-(trifluoromethyl)-2,3-dihydro-1H-pyrrolo[2,3-b]pyridin-3-yl]-3-azabicyclo[3.2.1]oct-3-yl}propan-1-one (197 mg, 0.516 mmol) in DCM (1.0 mL) at 0° C. The mixture was stirred 1 h at 0° C. and 2 h at room temperature. The mixture was quenched with a saturated solution of $NaHCO_3$ until pH=8. The phases were separated and the aqueous layer was extracted three times with DCM. The combined organic layers were dried with $Na_2SO_4$, filtered, and concentrated under reduced pressure. The crude product was purified by silica gel column chromatography (heptane:EtOAc, 40:60-0:100) to afforded the title compound (138 mg, 63%) as a yellow powder. LC/MS [M+H]=425.1; $^1$H NMR (400 MHz, $CDCl_3$) δ 8.69 (s, 1H), 7.34 (s, 1H), 4.53 (d, J=14.4 Hz, 1H), 3.95 (s, 3H), 3.85 (d, J=12.5 Hz, 1H), 3.43 (d, J=12.5 Hz, 1H), 3.31 (s, 1H), 2.92 (d, J=12.5 Hz, 1H), 2.86 (quin, J=6.6 Hz, 1H), 2.55-2.43 (m, 2H), 1.90-1.58 (m, 4H), 1.24-1.08 (m, 6H).

Step 11: 1-{(8-anti)-[5-amino-1-methyl-4-(trifluoromethyl)-1H-pyrrolo[2,3-b]pyridin-3-yl]-3-azabicyclo[3.2.1]oct-3-yl}-2-methylpropan-1-one. A saturated solution of $NH_4Cl$ (0.442 mL) followed by zinc dust (55 mg, 0.84 mmol) was added to a solution of 2-methyl-1-{(8-anti)-[1-methyl-5-nitro-4-(trifluoromethyl)-1H-pyrrolo[2,3-b]pyridin-3-yl]-3-azabicyclo[3.2.1]oct-3-yl}propan-1-one (76 mg, 0.17 mmol) in a mixture of MeOH/THF (1:1, 2.7 mL) at room temperature. The mixture was stirred at room temperature for 10 min and was filtered through a fritted plastic funnel eluting with DCM and water. The phases were separated and the aqueous layer was extracted three times with DCM. The combined organic layers were dried over $Na_2SO_4$, filtered and concentrated under reduced pressure to provide the title compound which was immediately carried forward in the synthetic sequence and required no further purification. LC/MS [M+H]=395.1; $^1$HNMR (400 MHz, $CDCl_3$) δ 8.02 (s, 1H), 7.03 (s, 1H), 4.48 (dd, J=12.9, 2.7 Hz, 1H), 3.86 (s, 3H), 3.83 (dd, J=12.1, 2.7 Hz, 1H), 3.41 (d, J=11.3 Hz, 1H), 3.28 (br. s, 1H), 3.16 (s, 1H), 2.92 (d, J=12.5 Hz, 1H), 2.86 (quin, J=7.0 Hz, 1H), 1.14 (d, J=6.6 Hz, 3H), 2.44 (br. s., 1H), 2.38 (br. s., 1H), 1.89-1.77 (m, 2H), 1.66-1.49 (m, 2H), 1.20 (d, J=7.0 Hz, 3H). The structure of 1-{(8-anti)-[5-amino-1-methyl-4-(trifluoromethyl)-1H-pyrrolo[2,3-b]pyridin-3-yl]-3-azabicyclo[3.2.1]oct-3-yl}-2-methylpropan-1-one was established by single crystal X-ray analysis (Example 107).

Step 12: 3-cyano-N-(3-((1R,5S,8r)-3-isobutyryl-3-azabicyclo[3.2.1]octan-8-yl)-1-methyl-4-(trifluoromethyl)-1H-pyrrolo[2,3-b]pyridin-5-yl)benzamide. TEA (0.14 mL, 1.05 mmol) and 3-cyanobenzoyl chloride (75 mg, 0.46 mmol) were added sequentially at room temperature to a solution of 1-{(8-anti)-[5-amino-1-methyl-4-(trifluoromethyl)-1H-pyrrolo[2,3-b]pyridin-3-yl]-3-azabicyclo[3.2.1]oct-3-yl}-2-methylpropan-1-one (138 mg, 0.35 mmol) in DCM (4.3 mL). The reaction was stirred overnight at room temperature and monitored by LCMS. Upon completion, the mixture was poured into saturated sodium bicarbonate and extracted three times with DCM. The combined organic layers were dried with sodium sulfate and filtered. The filtrate was concentrated and the residue was purified using silica gel column chromatography (heptane/ethyl acetate, 50/50-0/100) to give the title compound (31 mg, 22%) as a white powder: LC/MS [M−H]=522.5; $^1$H NMR (400 MHz, CDCl$_3$) δ 8.64 (s, 1H), 8.25 (s, 1H), 8.17 (d, J=9.0 Hz, 1H), 7.94 (br. s., 1H), 7.89 (d, J=7.8 Hz, 1H), 7.69 (t, J=7.4 Hz, 1H), 7.21 (s, 1H), 4.49 (d, J=13.7 Hz, 1H), 3.93 (s, 3H), 3.88-3.80 (m, 1H), 3.42 (d, J=11.7 Hz, 1H), 3.31 (br. s., 1H), 2.93 (d, J=12.5 Hz, 1H), 2.86 (quin, J=6.6 Hz, 1H), 2.47 (br. s., 1H), 2.43 (br. s., 1H), 1.88-1.74 (m, 2H), 1.72-1.48 (m, 2H), 1.21-1.19 (m., 3H), 1.15-1.13 (m, 3H).

Example 78-79

The following Examples 78-79 were prepared analogous to Example 77 however employing the appropriate benzoic acid in Step 11 and the appropriate carboxylic acid in step 8.

Example 80

Preparation of 3-cyano-N-(3-((3R,4R)-1-isobutyryl-3-methylpiperidin-4-yl)-1-methyl-4-(trifluoromethyl)-1H-pyrrolo[2,3-b]pyridin-5-yl)benzamide

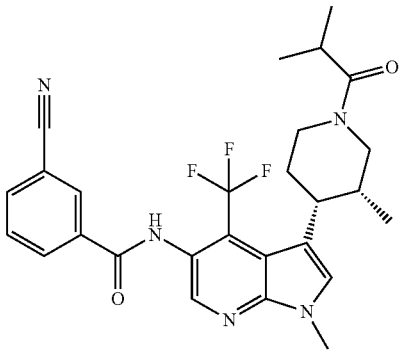 [SMILES: CC(C)C(=O)N1CC[C@@H](c2cn(C)c3ncc(NC(=O)c4cccc(C#N)c4)c(C(F)(F)F)c23)[C@@H](C)C1]

Step 1: tert-butyl 3-methyl-4-(1-methyl-5-nitro-4-(trifluoromethyl)-1H-pyrrolo[2,3-b]pyridin-3-yl)-3,6-dihydropyridine-1(2H)-carboxylate. A solution of 1-methyl-5-nitro-3-(4,4,5,5-tetramethyl-1,3,2-dioxaborolan-2-yl)-4-(trifluoromethyl)-1H-pyrrolo[2,3-b]pyridine (prepared as described in Example 65, 1 g, 2.7 mmol), tert-butyl 3-methyl-4-(((trifluoromethyl)sulfonyl)oxy)-3,6-dihydropyridine-1(2H)-carboxylate (Janssen, R. D. et al. WO2014/23815) (743 mg, 2.2 mmol) and K$_2$CO$_3$ (1.12 g, 8.1 mmol) in 1,4-dioxane (20 mL) was degassed using Argon for 1 h.

To the above reaction mixture was introduced Pd(PPh$_3$)$_4$ (156 mg, 0.14 mmol) and the mixture was heated at 80° C.

| Ex. | Structure | Name/Characterization |
|---|---|---|
| 78 | 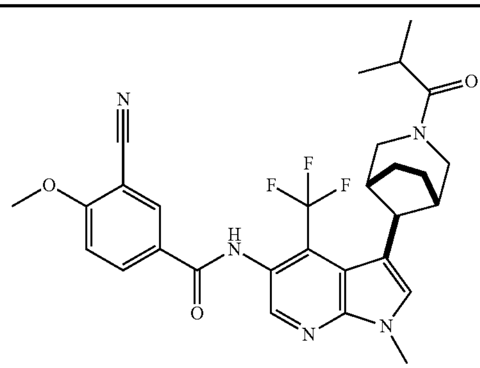 | 3-cyano-N-(3-((1R,5S,8r)-3-isobutyryl-3-azabicyclo[3.2.1]octan-8-yl)-1-methyl-4-(trifluoromethyl)-1H-pyrrolo[2,3-b]pyridin-5-yl)-4-methoxybenzamide. LC/MS [M + H] = 554.3; $^1$H NMR (400 MHz, CDCl$_3$) δ 8.61 (s, 1H), 8.13-8.19 (m, 2H), 7.85 (s, 1H), 7.19 (s, 1H), 7.12 (m, 1H), 4.49 (m, 1H), 4.05 (s, 3H), 3.92 (s, 3H), 3.84 (m, 1H), 3.42 (m, 1 H), 3.31 (br. s, 1H), 2.93 (m, 1H), 2.86 (m, 1H), 2.45-2.50 (m, 1H), 2.38-2.45 (m, 1H), 1.70-1.89 (m, 2H), 1.58 (m, 2H), 1.20 (m, 3H), 1.13 (m, 3H). |
| 79 | | 3-cyano-N-{3-((1R,5S,8r)-3-(cyclopentanecarbonyl)-3-azabicyclo[3.2.1]octan-8-yl]-1-methyl-4-(trifluoromethyl)-1H-pyrrolo[2,3-b]pyridin-5-yl}benzamide. LC/MS [M + H] = 550.3; $^1$H NMR (400 MHz, CDCl$_3$) δ 8.61 (s, 1H), 8.26 (s, 1H), 8.21-8.14 (m, 1H), 8.08-8.01 (m, 1H), 7.92-7.85 (m, 1H), 7.72-7.64 (m, 1H), 7.20 (s, 1 H), 4.54-4.42 (m, 1H), 3.92 (s, 3H), 3.90-3.83 (m, 1H), 3.44-3.35 (m, 1H), 3.31 (br. s., 1H), 3.00-2.86 (m, 2H), 2.50-2.37 (m, 2H), 1.94-1.50 (m, 12H). | for 1 h under microwave irradiation. The reaction mixture was filtered through a pad of Celite® and the filtrate was extracted using EtOAc. The combined organic layers were washed with brine, dried over anhydrous Na$_2$SO$_4$, filtered and concentrated. The crude product was purified by silica gel column chromatography (EtOAc:hexane, 10:90-15:85) to afford the title compound (620 mg, 52%). $^1$H NMR (400 MHz, CDCl$_3$) δ 8.74 (s, 1H), 7.32 (s, 1H), 5.45-5.62 (m, 1H), 4.36-4.12 (m, 1H), 3.96 (s, 3H), 3.87-3.72 (m, 2H), 3.42-3.38 (m, 1H), 2.60-2.45 (m, 1H), 1.50 (s, 9H), 0.95 (d, J=7.0 Hz, 3H).

Step 2: tert-butyl 4-(5-amino-1-methyl-4-(trifluoromethyl)-1H-pyrrolo[2,3-b]pyridin-3-yl)-3-methylpiperidine-1-carboxylate. A solution of tert-butyl 3-methyl-4-(1-methyl-5-nitro-4-(trifluoromethyl)-1H-pyrrolo[2,3-b]pyridin-3-yl)-3,6-dihydropyridine-1(2H)-carboxylate (600 mg, 0.14 mmol), Pd(OH)$_2$/C (1.2 mg, 20% w/w) and ammonium formate (8.59 g, 136 mmol) in 50 mL of EtOH/H$_2$O (1:1) was heated at 80° C. for 48 h. The reaction mixture was cooled to room temperature, filtered through a pad of Celite® and washed with MeOH and DCM. The filtrate was concentrated to dryness and the crude residue obtained was diluted with water and extracted with DCM. The combined organic layers were washed with brine, dried over anhydrous Na$_2$SO$_4$, filtered and concentrated to afford the title compound (450 mg, 80%), which was used without further purification in the subsequent step. LC/MS [M+H]=413.4

Step 3: tert-butyl 4-(5-(3-cyanobenzamido)-1-methyl-4-(trifluoromethyl)-1H-pyrrolo[2,3-b]pyridin-3-yl)-3-methylpiperidine-1-carboxylate. To a stirred solution of tert-butyl 4-(5-amino-1-methyl-4-(trifluoromethyl)-1H-pyrrolo[2,3-b]pyridin-3-yl)-3-methylpiperidine-1-carboxylate (450 mg, 0.11 mmol) and TEA (0.45 mL, 0.33 mmol) in DCM (25 mL) at 0° C. was added 3-cyanobenzoyl chloride (218 mg, 0.13 mmol), followed by catalytic DMAP. The cooling bath was removed, and the reaction mixture was stirred at room temperature for 16 h. The reaction mixture was quenched with 10% NaHCO$_3$ solution and extracted with DCM. The combined organic layers were dried over anhydrous Na$_2$SO$_4$, filtered and concentrated. The crude product was purified by silica gel column chromatography (MeOH:DCM, 2:98-4:96) to provide the title compound (190 mg, 32%). $^1$H NMR (400 MHz, CDCl$_3$) δ 8.57 (d, J=7.0 Hz, 1H), 8.23 (s, 1H), 8.16 (d, J=7.7 Hz, 1H), 7.97 (d, J=16.7 Hz, 1H), 7.88 (d, J=7.7 Hz, 1H), 7.67 (t, J=7.7 Hz, 1H), 7.15 (s, 1H), 4.37-4.20 (m, 1H), 3.92 (s, 3H), 3.34 (d, J=12.8 Hz, 1H), 3.04-2.86 (m, 2H), 2.79-2.70 (m, 1H), 2.55 (d, J=12.4 Hz, 1H), 2.01 (d, J=7.7 Hz, 1H), 1.91 (d, J=12.8 Hz, 1H), 1.48 (d, J=7.4 Hz, 9H), 0.71 (d, J=7.0 Hz, 3H); LC/MS [M+H]=542.3.

Step 4: 3-cyano-N-(1-methyl-3-(3-methylpiperidin-4-yl)-4-(trifluoromethyl)-1H-pyrrolo[2,3-b]pyridin-5-yl)benzamide. To a stirred solution of tert-butyl 4-(5-(3-cyanobenzamido)-1-methyl-4-(trifluoromethyl)-1H-pyrrolo[2,3-b]pyridin-3-yl)-3-methylpiperidine-1-carboxylate (190 mg, 0.35 mmol) in MeOH (10 mL) at 0° C. was added 4M HCl in dioxane (2 mL) and the reaction mixture was warmed to room temperature and stirred for 4 h. The reaction mixture was concentrated and the residue obtained was dissolved in MeOH and basified using carbonate resin. The resulting solution was filtered and washed with MeOH. The filtrate was concentrated to afford the title compound (150 mg, 96%). LC/MS [M+H]=442; $^1$H NMR (400 MHz, DMSO-d$_6$) δ 10.59 (s, 1H), 8.44-8.39 (m, 1H), 8.32-8.27 (m, 2H), 8.13-8.09 (m, 1H), 7.83-7.76 (m, 1H), 7.68-7.64 (m, 1H), 3.89 (s, 3H), 3.54-3.42 (m, 2H), 3.16-3.12 (m, 1H), 3.07-3.02 (m, 1H), 2.81-2.77 (m, 1H), 1.96 (s, 1H), 1.86-1.77 (m, 2H), 1.46-1.41 (m, 1H), 0.79 (s, 3H).

Step 5: 3-cyano-N-(3-(1-isobutyryl-3-methylpiperidin-4-yl)-1-methyl-4-(trifluoromethyl)-1H-pyrrolo[2,3-b]pyridin-5-yl)benzamide. To a solution of 3-cyano-N-(1-methyl-3-(3-methylpiperidin-4-yl)-4-(trifluoromethyl)-1H-pyrrolo[2,3-b]pyridin-5-yl)benzamide (150 mg, 0.34 mmol) and TEA (131 μL, 1.02 mmol) in DCM (10 mL) at 0° C. was added isobutyryl chloride (43 μL, 0.41 mmol). The cooling bath was removed, and the reaction mixture was stirred at room temperature for 1 h. The reaction mixture was basified using 10% NaHCO$_3$ and extracted with DCM. The organic layer was washed with brine, dried over anhydrous Na$_2$SO$_4$, filtered and concentrated. The crude product was purified by preparative HPLC to provide the title compound (69 mg, 40%) as an off-white solid. LC/MS [M+H]=512.1; $^1$H NMR (400 MHz, CDCl$_3$) δ 8.58 (d, J=6.9 Hz, 1H), 8.24 (s, 1H), 8.17 (d, J=7.7 Hz, 1H), 8.05-7.92 (m, 1H), 7.88 (d, J=7.7 Hz, 1H), 7.68 (t, J=7.9 Hz, 1H), 7.17 (s, 1H), 3.93 (s, 3H), 3.51-3.34 (m, 1H), 3.24-3.09 (m, 1H), 2.92-2.81 (m, 2H), 2.72-2.56 (m, 1H), 2.30 (t, J=11.8 Hz, 1H), 2.16-2.01 (m, 1H), 1.23-1.11 (m, 8H), 0.80 (d, J=6.0 Hz, 3H).

Step 6: 3-cyano-N-(3-((3R,4R)-1-isobutyryl-3-methylpiperidin-4-yl)-1-methyl-4-(trifluoromethyl)-1H-pyrrolo[2,3-b]pyridin-5-yl)benzamide. Racemic 3-cyano-N-(3-(1-isobutyryl-3-methylpiperidin-4-yl)-1-methyl-4-(trifluoromethyl)-1H-pyrrolo[2, 3-b]pyridin-5-yl)benzamide (125 mg) was resolved by chiral supercritical fluid chromatography (Lux Cellulose-4, 250 mm×21.2 mm, 5 μm, MeOH/CO$_2$, 40%, 80 mL/min). Isolation of the first eluting cis-isomer (rt=8.793) afforded the title compound (34 mg). LC/MS [M+H]=512.2; $^1$H NMR (400 MHz, CDCl$_3$) δ 8.85 (br s, 1H), 8.51-8.17 (m, 3H), 7.84 (s, 1H), 7.65-7.60 (m, 1H), 7.12-7.09 (m, 1H), 4.85-4.53 (m, 1H), 3.91-3.84 (m, 5H), 3.43-3.34 (m, 2H), 2.89-2.65 (m, 2H), 2.11-1.97 (m, 2H), 1.72-1.69 (m, 2H), 1.25-1.07 (m, 6H), 0.72-0.70 (M, 2H), 0.40-0.38 (m, 1H). Absolute stereochemistry has been assigned based on potency comparison of enantiomers and the corresponding configuration of Example 84 determined through a co-crystal X-ray structure.

Example 81-82

Examples 81 and 81 was prepared analogous to Example 80 employing the appropriate acid chloride in step 4 and 6. Absolute stereochemistry has been assigned based on potency comparison of enantiomers and the corresponding configuration of Example 84 determined through a co-crystal X-ray structure.

| Ex. | Structure | Name/Characterization |
|---|---|---|
| 81 | 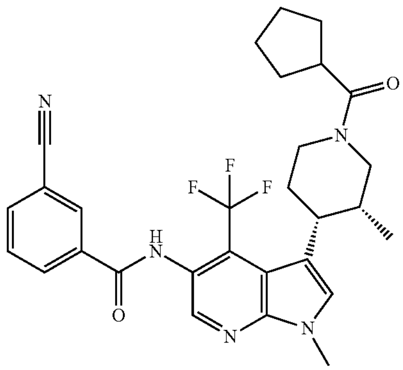 [SMILES: C[C@H]1CN(C(=O)C2CCCC2)CC[C@H]1c1cn(C)c2ncc(NC(=O)c3cccc(C#N)c3)c(C(F)(F)F)c12] | 3-cyano-N-(3-((3R,4R)-1-(cyclopentane-carbonyl)-3-methylpiperidin-4-yl)-1-methyl-4-(trifluoro-methyl)-1H-pyrrolo[2,3-b]pyridin-5-yl)benzamide. LC/MS [M + H] = 538.5; Chiral LC: Rt = 1.60 min (Method E); $^1$H NMR (400 MHz, CD$_3$OD) δ 8.40-8.20 (m, 3H), 8.01-7.95 (m, 1H), 7.80-7.70 (m, 1H), 7.55-7.50 (m, 1H) 4.80-4.70 (m, 1H), 4.58-4.50 (m, 1H), 4.30-4.20 (m, 1H), 4.10-4.05 (m, 1H), 3.93 (s, 3H), 3.58-3.45 (m, 2H), 3.30-3.05 (m, 2H), 2.95-2.85 (m, 1H), 2.80-2.70 (m, 1H), 2.20-2.05 (m, 2H), 2.05-1.55 (m, 5H), 0.80-0.65 (m, 3H). |
| 82 | 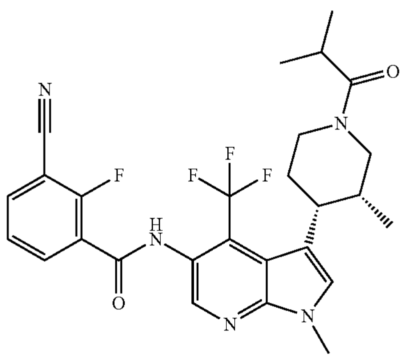 [SMILES: CC(C)C(=O)N1CC[C@@H](c2cn(C)c3ncc(NC(=O)c4cccc(C#N)c4F)c(C(F)(F)F)c23)[C@@H](C)C1] | 3-cyano-2-fluoro-N-(3-((3R,4R)-1-isobutyryl-3-methylpiperidin-4-yl)-1-methyl-4-(trifluoromethyl)-1H-pyrrolo[2,3-b]pyridin-5-yl)benzamide. LC/MS [M + H] = 530.5; $^1$H NMR (400 MHz, CD$_3$OD) δ 8.35 (s, 1H), 8.11 (t, J = 7.0 Hz, 1H), 7.98 (t, J = 6.8 Hz, 1H), 7.47-7.58 (m, 2H), 4.76 (d, J = 14.4 Hz, 1H), 4.57 (d, J = 12.1 Hz, 1H), 4.24 (d, J = 11.3 Hz, 1H), 4.04 (d, J = 14.4 Hz, 1H), 3.93 (s, 3H), 3.37-3.59 (m, 2H), 3.20-3.28 (m, 1H), 2.95-3.17 (m, 2 H), 2.91 (d, J = 13.3 Hz, 1 H), 2.76 (t, J = 13.1 Hz, 1H), 1.99-2.26 (m, 3H), 1.62-1.84 (m, 2H), 1.20 (d, J = 6.6 Hz, 2H), 1.02-1.15 (m, 5H), 0.65-0.80 (m, 4H). |

Example 83

Preparation of 3-cyano-N-(34(3R,4R)-1-(2-cyclopropylacetyl)-3-methylpiperidin-4-yl)-1,4-dimethyl-1H-pyrrolo[2,3-b]pyridin-5-yl)benzamide

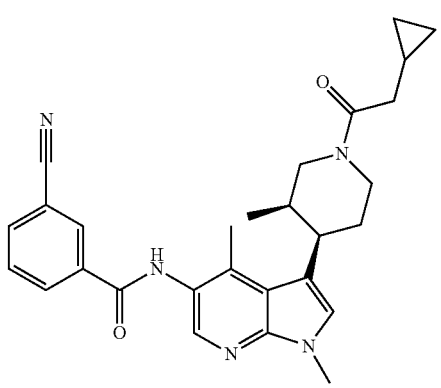 [SMILES: Cc1c(NC(=O)c2cccc(C#N)c2)cnc2c1c([C@@H]1CCN(C(=O)CC3CC3)C[C@@H]1C)cn2C]

Step 1. tert-butyl 3-methyl-4-oxopiperidine-1-carboxylate. To a Parr vessel charged with 1-benzyl-3-methylpiperidone (25.0 g, 120 mmol) in ethyl acetate (122 mL) was added di-tert-butyl dicarbonate (27.4 g, 122 mmol), and Pd(OH)$_2$/C (20%) (8.55 g). The vessel was sealed and its atmosphere replaced with hydrogen four times. On the fifth recharge, the hydrogen gas pressure was set to 100 psi. The vessel was shook for 4 h at room temperature and then the atmosphere was brought to ambient conditions. The mixture was filtered through a pad of Celite® and the filter cake was washed with ethyl acetate. The filtrates were then concentrated and residue was purified by silica gel column chromatography (DCM:EtOAc, 100:0-70:30) to afford the title compound (20.6 g, 79%) as an off-white solid. $^1$H NMR (400 MHz, CDCl$_3$) δ 4.14-4.23 (m, 2H), 3.20-3.32 (m, 1H), 2.86 (br. s., 1H), 2.34-2.60 (m, 3H), 1.50 (s, 9H), 1.05 (d, J=6.6 Hz, 3H).

Step 2. tert-butyl 3-methyl-4-(((trifluoromethyl)sulfonyl)oxy)-3,6-dihydropyridine-1(2H)-carboxylate. To a solution of LDA (28 mL of 2.0 M in THF, 56.0 mmol) in THF (68 mL) at −78° C. was added tert-butyl 3-methyl-4-oxopiperidine-1-carboxylate (11.9 g, 56.0 mmol), and N-phenyl triflimide (22.0 g, 56.0 mmol), sequentially. The mixture was allowed to warm to room temperature and was then quenched with saturated aqueous ammonium chloride (50 mL). The phases were separated. The organic layer was filtered and concentrated. The crude residue was purified by silica gel column chromatography (Heptane:EtOAc, 75:25-0:100) to give the title compound (14.9 g, 77%) as a colorless oil. $^1$H NMR (400 MHz, CDCl$_3$) δ 5.65-5.82 (m, 1H), 3.88-4.26 (m, 2H), 3.52-3.76 (m, 1H), 3.30-3.51 (m, 1H), 2.55-2.71 (m, 1H), 1.48 (s, 9H), 1.16 (d, J=7.0 Hz, 3H).

Step 3. tert-butyl 4-(1,4-dimethyl-5-nitro-1H-pyrrolo[2,3-b]pyridin-3-yl)-3-methyl-3,6-dihydropyridine-1(2H)-carboxylate. To a RB flask equipped with a condenser was sequentially added tert-butyl 3-methyl-4-(((trifluoromethyl)sulfonyl)oxy)-3,6-dihydropyridine-1(2H)-carboxylate (14.2 g, 40.8 mmol), 1,4-dimethyl-5-nitro-3-(4,4,5,5-tetramethyl-1,3,2-dioxaborolan-2-yl)-1H-pyrrolo[2,3-b]pyridine (prepared as described in Example 58) (14.1 g, 40.8 mmol), potassium phosphate tribasic (19.1 g, 89.9 mmol), and palladium (tetrakis)triphenylphosphine (4.7 g, 4.08 mmol). The mixture was suspended in water:dioxane (1:1, 430 mL), and was heated to 90° C. for 18 hours. After cooling, the mixture was filtered through a pad of silica gel. The filtrate was absorbed onto silica and purified twice by silica gel column chromatography (DCM:EtOAc, 50:50-0:100) to give the title compound (13.2 g, 84%) as an off-white solid. $^1$H NMR (400 MHz, CDCl$_3$) δ 8.98 (s, 1H), 7.06 (s, 1H), 5.61-5.76 (m, 1H), 4.05-4.43 (m, 2H), 3.90 (s, 3H), 3.69-3.85 (m, 1H), 3.36-3.54 (m, 1H), 2.81 (s, 3H), 2.44-2.62 (m, 1H), 1.52 (s, 9H), 0.98 (d, J=6.63 Hz, 3H).

Step 4. (R,R)-tert-butyl 4-(5-amino-1,4-dimethyl-1H-pyrrolo[2,3-b]pyridin-3-yl)-3-methylpiperidine-1-carboxylate. To a pressure vessel charged with tert-butyl 4-(1,4-dimethyl-5-nitro-1H-pyrrolo[2,3-b]pyridin-3-yl)-3-methyl-3,6-dihydropyridine-1(2H)-carboxylate (13.24 g, 34.26 mmol) in MeOH (69 mL) was added triethylamine (7.14 mL, 51.4 mmol) and palladium hydroxide (4.81 g, 3.43 mmol). The vessel was sealed and its atmosphere was replaced with hydrogen gas at 100 psi. The vessel was then agitated for 24 h at room temperature. The mixture filtered through a pad of celite. The filtrate was concentrated to afford the crude product as a mixture of cis:trans isomers (ca 13:1). The mixture was purified by chromatography through a pad of silica gel (DCM:EtOAc, 100:0-0:100) to remove the minor diastereomer. The major isomer was resolved by chiral chromatography (Chiral Tech OJ-H, 21.2×500 mm, 5 µm, 0-10% MeOH in CO$_2$, 80.0 mL/min) to afford two peaks which were distinguishable by the following method: ChiralTech OJ-H 250, 4.6×250 mm, 5 µm, 0-10% MeOH (0.2% NH$_4$+) in CO$_2$, 3 mL/min, 10 min. The first peak eluted at 4.46 min, and the second peak eluted at 5.13 min. The second peak corresponded to the (R,R) stereochemistry as established by X-ray co-crystal analysis of Example 84. The second peak was collected to give the title compound (5.9 g, 48%) as a white solid $^1$H NMR (400 MHz, CDCl$_3$) δ 7.89 (s, 1H), 6.78 (s, 1H), 4.19-4.46 (m, 1.5 H), 3.98-4.18 (m, 1.5 H), 3.80 (s, 3H), 3.39 (dt, J=12.5, 3.1 Hz, 1H), 2.97-3.16 (m, 1.5 H), 2.74-2.94 (m, 1.5 H), 2.49 (s, 3H), 2.07-2.18 (m, 1H), 1.93-2.07 (m, 1H), 1.66 (d, J=14.0 Hz, 1H), 1.49 (s, 9H), 0.70 (d, J=7.0 Hz, 3H).

Step 5. tert-butyl (3R,4R)-4-(5-(3-cyanobenzamido)-1,4-dimethyl-1H-pyrrolo[2,3-b]pyridin-3-yl)-3-methylpiperidine-1-carboxylate. To a round-bottomed flask charged with (R,R)-tert-butyl 4-(5-amino-1,4-dimethyl-1H-pyrrolo[2,3-b]pyridin-3-yl)-3-methylpiperidine-1-carboxylate (5.71 g, 15.9 mmol), DCM (106 mL), and triethylamine (4.44 mL, 31.9 mmol) was added 3-cyanobenzoyl chloride (2.9 g, 17.5 mmol) and a catalytic amount of DMAP. The mixture was stirred at room temperature for 15 h and then was poured into saturated sodium bicarbonate (100 mL). The organic layer was concentrated and the residue was purified by silica gel column chromatography (DCM:EtOAc, 70:30-100:0) to give the title compound (7.2 g, 93%) as an off-white solid. LCMS [M+H]=488.2.

Step 6. 3-cyano-N-(3-((3R,4R)-1-(2-cyclopropylacetyl)-3-methylpiperidin-4-yl)-1,4-dimethyl-1H-pyrrolo[2,3-b]pyridin-5-yl)benzamide. Trifluoroacetic acid (5 mL) was added to a suspension of tert-butyl (3R,4R)-4-(5-(3-cyanobenzamido)-1,4-dimethyl-1H-pyrrolo[2,3-b]pyridin-3-yl)-3-methylpiperidine-1-carboxylate (80 mg, 0.17 mmol) in DCM (10 mL). The mixture was stirred for 2 h at room temperature and then concentrated. The residue was suspended in TEA (52.7 mg, 0.521 mmol), DCM (10 mL), and 2-cyclopropylacetyl chloride (30.9 mg, 0.261 mmol) at 20° C. The resulting solution was stirred for 4 h and then was poured into aqueous sodium bicarbonate. The organic layer was concentrated and the crude product was purified by silica gel column chromatography to give the title compound (30 mg, 43%) as an off-white solid. LC/MS [M+H]=470.1; Chiral SFC: Rt=1.738 min (Method M); $^1$H NMR (400 MHz, CDCl$_3$) δ 8.32-8.31 (m, 3H), 8.04 (s, 0.5H), 7.78 (s, 1H), 7.80 (s, 0.5H), 7.68-7.66 (m, 1H), 6.89 (s, 1H), 4.91-4.87 (m, 0.5H), 4.64-4.60 (m, 0.5H), 4.03-4.00 (m, 0.5H), 3.85-3.77 (m, 4H), 3.51-3.48 (m, 1H), 3.39-3.36 (m, 0.5), 3.23-3.19 (m, 0.5H), 2.78-2.74 (m, 0.5H), 2.70-2.62 (m, 3.5H), 2.41-1.99 (m, 3.5H), 1.76-1.73 (m, 1H), 1.13-1.08 (m, 1H), 0.62-0.61 (m, 1.5H), 0.59-0.57 (m, 3.5H), 0.23-0.17 (m, 2H).

Examples 84-87 & 112

The following Examples 84-87 and 112 were prepared analogous to Example 83 employing the appropriate carboxylic acid or carboxylic acid chloride coupling partners in Steps 5 and 6. Absolute stereochemistry has been assigned based on potency comparison of enantiomers and the corresponding configuration of Example 84 determined through a co-crystal X-ray structure.

| Ex. | Structure | Name/Characterization |
|---|---|---|
| 84 | 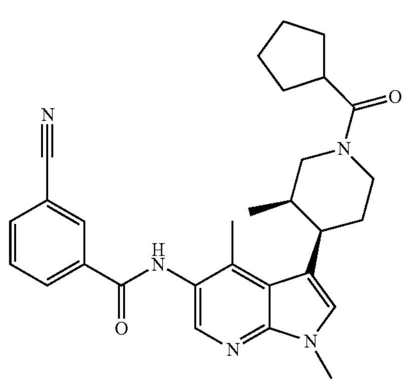 [SMILES: Cc1c(NC(=O)c2cccc(C#N)c2)cnc2c1c([C@@H]1CCN(C(=O)C3CCCC3)C[C@@H]1C)cn2C] | 3-cyano-N-(3-((3R,4R)-1-(cyclopentanecarbonyl)-3-methylpiperidin-4-yl)-1,4-dimethyl-1H-pyrrolo[2,3-b]pyridin-5-yl)benzamide. LC/MS [M + H] = 484.2; $^1$H NMR (400 MHz, CD$_3$OD) δ 8.37 (s, 1 H), 8.34-8.26 (m, 1 H), 8.12 (s, 1 H), 7.96 (d, J = 7.8 Hz, 1 H), 7.73 (t, J = 8.0 Hz, 1 H), 7.16 (d, J = 6.2 Hz, 1 H), 4.74 (d, J = 13.3 Hz, 1H), 4.26 (d, J = 14.1 Hz, 1H), 4.07 (s, 3H), 3.82 (s, 3 H), 3.62 (dd, J = 7.8, 4.3 Hz, 1 H), 3.48 (dd, J = 13.5, 2.2 Hz, 1 H), 3.28-3.04 (m, 2 H), 2.72-2.64 (s, 3 H), 2.31-2.16 (m, 1 H), 2.09-1.93 (m, 1 H), 1.88-1.60 (m, 9 H), 0.73 (d, J = 7.0 Hz, 1.5 H), 0.66 (d, J = 6.6 Hz, 2 H). |

| Ex. | Structure | Name/Characterization |
|---|---|---|
| 85 | 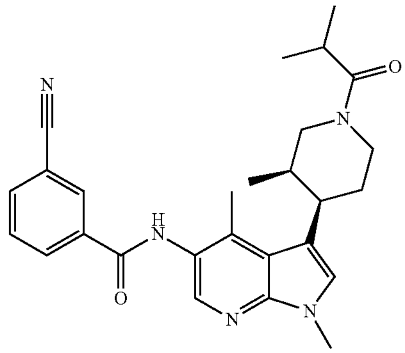 [SMILES: Cc1c(NC(=O)c2cccc(C#N)c2)cnc2c1c([C@@H]1CCN(C(=O)C(C)C)C[C@@H]1C)cn2C] | 3-cyano-N-(3-((3R,4R)-1-isobutyryl-3-methylpiperidin-4-yl)-1,4-dimethyl-1H-pyrrolo[2,3-b]pyridin-5-yl)benzamide. LC/MS [M + H] = 458.2; ¹H NMR (400 MHz, CD₃OD) δ 8.46-8.29 (m, 2 H), 8.13 (s, 1 H), 7.98 (d, J = 7.8 Hz, 1 H), 7.75 (t, J = 7.6 Hz, 1 H), 7.17 (d, J = 5.1 Hz, 1 H), 4.58 (d, J = 12.9 Hz, 1 H), 4.24 (d, J = 10.9 Hz, 1 H), 3.83 (s, 3 H), 3.64 (d, J = 8.6 Hz, 1 H), 3.50 (d, J = 17.2 Hz, 1 H), 3.16-2.89 (m, 2 H), 2.35-1.99 (m, 3 H), 1.88-1.62 (m, 1 H), 1.15-1.04 (m, 6 H). |
| 112 | 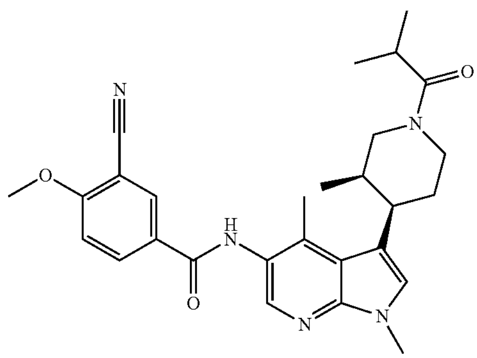 [SMILES: COc1ccc(C(=O)Nc2cnc3c(c([C@@H]4CCN(C(=O)C(C)C)C[C@@H]4C)cn3C)c2C)cc1C#N] | 3-cyano-N-(3-((3R,4R)-1-isobutyryl-3-methylpiperidin-4-yl)-1,4-dimethyl-1H-pyrrolo[2,3-b]pyridin-5-yl)-4-methoxybenzamide. LC/MS [M + H] = 488.2; ¹H NMR (400 MHz, CDCl₃) δ 8.64 (br s, 0.5 H), 8.31-8.19 (m, 3 H), 8.06 (br s, 0.5 H), 7.07 (t, J = 6.4 Hz, 1 H), 6.83 (d, J = 14.0 Hz, 1 H), 4.85 (d, J = 13.2 Hz, 0.5 H), 4.56 (d, J = 13.2 Hz, 0.5 H), 4.13 (d, J = 13.2 Hz, 0.5 H), 4.02 (s, 3 H), 3.89 (d, J = 13.2 Hz, 0.5 H), 3.82 (d, J = 13.6 Hz, 3 H), 3.48-3.46 (m, 1 H), 3.42-3.38 (m, 0.5 H), 3.21-3.17 (m, 0.5 H), 2.91-2.82 (m, 1.5 H), 2.75-2.66 (m, 0.5 H), 2.56 (s, 3 H), 2.40 (br s, 0.5 H), 2.05-1.97 (m, 1.5 H), 1.77-1.72 (m, 1 H), 1.26-1.12 (m, 6 H), 0.72 (d, J = 6.8 Hz, 1.5 H), 0.36 (d, J = 6.8 Hz, 1.5 H). |
| 86 | 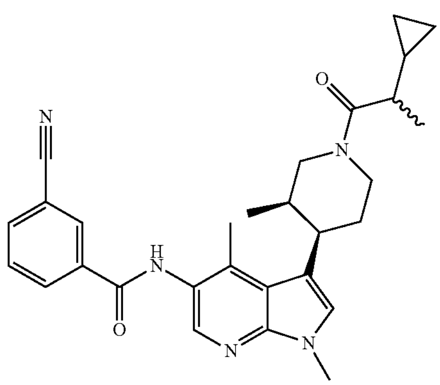 [SMILES: Cc1c(NC(=O)c2cccc(C#N)c2)cnc2c1c([C@@H]1CCN(C(=O)C(C)C3CC3)C[C@@H]1C)cn2C] | 3-cyano-N-(3-((3R,4R)-1-(2-cyclopropylpropanoyl)-3-methylpiperidin-4-yl)-1,4-dimethyl-1H-pyrrolo[2,3-b]pyridin-5-yl)benzamide. LC/MS [M + H] = 484.2. Chiral SFC: Rt = 1.844 min (Method M). ¹HNMR (400 MHz, CDCl₃) δ 8.38-8.21 (m, 3.5H), 7.86 (s, br, 1.5H), 7.68-7.65 (m, 1H), 6.88-6.85 (m, 1H), 4.93-4.89 (m, 0.5H), 4.66-4.63 (m, 0.5H), 4.05-4.02 (m, 0.5H), 3.85-3.76 (m, 3.5H), 3.51-3.48 (m, 1H), 3.41-3.37 (m, 0.5H), 3.18-3.16 (m, 0.5H), 2.89-2.61 (m, 4H), 2.18-1.29 (m, 4H), 1.62-1.14 (m, 4H), 0.71-0.68 (m, 1.5H), 0.55-0.48 (m, 3.5H), 0.18-0.09 (m, 2H). |
| 87 | 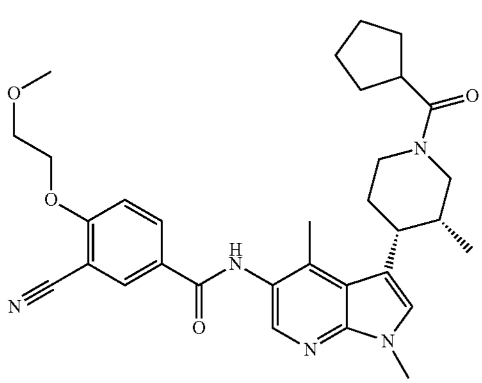 [SMILES: COCCOc1ccc(C(=O)Nc2cnc3c(c([C@@H]4CCN(C(=O)C5CCCC5)C[C@@H]4C)cn3C)c2C)cc1C#N] | 3-cyano-N-(3-((3R,4R)-1-(cyclopentanecarbonyl)-3-methylpiperidin-4-yl)-1,4-dimethyl-1H-pyrrolo[2,3-b]pyridin-5-yl)-4-(2-methoxyethoxy)benzamide. LC/MS [M + H] = 558.3; ¹H NMR (400 MHz, DMSO-d₆) δ ¹H NMR (400 MHz, CDCl₃) δ 8.57 (s, 1H), 8.34-8.26 (m, 3H), 8.02 (s, 1H), 7.06 (d, J = 6.2 Hz, 1H), 6.80-6.81 (m, 1H), 4.84 (d, J = 13.3 Hz, 1H), 4.56 (d, J = 14.1 Hz, 1H), 4.37 (s, 3H), 4.15-4.10 (m, 1H), 3.97-3.65 (m, 5 H), 3.50-3.35 (m, 3 H), 3.28-3.04 (m, 2 H), 2.72-2.64 (s, 3 H), 2.20-2.05 (m, 2 H), 2.04-1.50 (m, 13 H), 0.73 (d, J = 7.0 Hz, 2 H), 0.66 (d, J = 6.6 Hz, 2 H). |

Examples 88-89

The following Examples 88-89 were prepared analogous to Example 83 employing rac-3,3,3-trifluoro-2-methylpropanoic acid in Step 6. The product was resolved by chiral SFC (Lux cellulose-1, 250×21.2 mm, 5 μm, CO$_2$/MeOH-0.2% NH$_3$, 70/30, 80 mL/min). The absolute configuration was determined by independent synthesis from the enantiopure 2-trifluoromethylpropionic acid obtained by the method described by O'Hagan, et al, Tetrahedron: Asym., 2004, 15(16), 2447-2449.

| Ex. | Structure | Name/Characterization |
|---|---|---|
| 88 | 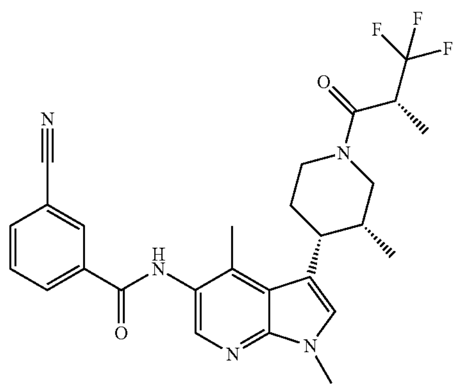 [SMILES: Cc1c(NC(=O)c2cccc(C#N)c2)cnc2c1c([C@@H]1CCN(C(=O)[C@@H](C)C(F)(F)F)C[C@@H]1C)cn2C] | 3-cyano-N-(1,4-dimethyl-3-((3R,4R)-3-methyl-1-((R)-3,3,3-trifluoro-2-methylpropanoyl)piperidin-4-yl)-1H-pyrrolo[2,3-b]pyridin-5-yl)benzamide. LC/MS [M + H] = 512.2; Chiral SFC: Rt = 6.747 min (Method D); $^1$H NMR (400 MHz, DMSO-d$_6$) δ 10.21 (s, 1H), 8.44 (s, 1H), 8.30 (d, J = 7.8 Hz, 1H), 7.97-8.12 (m, 2H), 7.76 (t, J = 8.0 Hz, 1H), 7.27 (d, J = 2.7 Hz, 1 H), 4.33-4.62 (m, 1H), 4.00-4.24 (m, 1H), 3.93 (d, J = 9.8 Hz, 1H), 3.69-3.77 (m, 3H), 3.54 (t, J = 12.1 Hz, 1H), 3.43 (d, J = 12.5 Hz, 1H), 3.12-3.26 (m, 1H), 2.95 (d, J = 12.1 Hz, 1H), 2.75 (t, J = 12.1 Hz, 1H), 1.82-2.19 (m, 5H), 1.67 (br. s., 3H), 1.09-1.35 (m, 11H), 0.45-0.71 (m, 7H). |
| 89 | 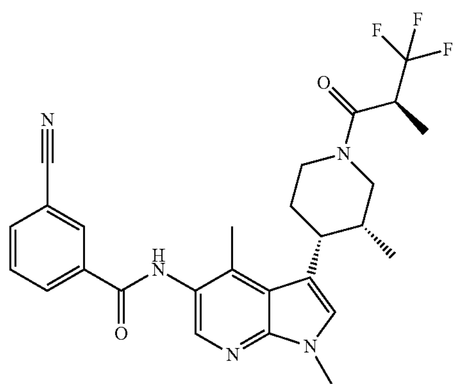 [SMILES: Cc1c(NC(=O)c2cccc(C#N)c2)cnc2c1c([C@@H]1CCN(C(=O)[C@H](C)C(F)(F)F)C[C@@H]1C)cn2C] | 3-cyano-N-(1,4-dimethyl-3-((3R,4R)-3-methyl-1-((S)-3,3,3-trifluoro-2-methylpropanoyl)piperidin-4-yl)-1H-pyrrolo[2,3-b]pyridin-5-yl)benzamide. LC/MS [M + H] = 512.2; Chiral SFC: Rt = 7.084 min min (Method D); $^1$H NMR (400 MHz, DMSO-d$_6$) δ 10.23 (s, 1H), 8.46 (s, 1H), 8.35-8.26 (m, 1H), 8.12-8.02 (m, 2H), 7.83-7.73 (m, 1H), 7.27 (s, 1H), 4.63-4.53 (m, 0.5H), 4.48-4.39 (m, 0.5H), 4.25-4.00 (m, 2H), 3.77 (s, 3H), 3.61-3.52 (m, 1H), 3.51-3.44 (m, 0.5H), 3.29-3.20 (m, 0.5H), 2.99-2.91 (m, 0.5H), 2.86-2.76 (m, 0.5H), 2.52 (s, 3H), 2.18-1.87 (m, 2H), 1.73-1.61 (m, 1H), 1.29-1.21 (m, 3H), 0.66-0.60 (m, 1.5H), 0.59-0.52 (m, 1.5H). |

Example 90

Preparation of 3-cyano-N-(34(2S,4R)-1-(cyclopentanecarbonyl)-2-methylpiperidin-4-yl)-1,4-dimethyl-1H-pyrrolo[2,3-b]pyridin-5-yl)-5-methoxybenzamide

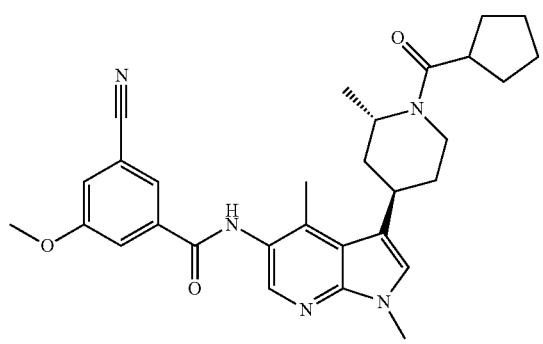 [SMILES: COc1cc(C#N)cc(C(=O)Nc2cnc3c(c([C@@H]4CCN(C(=O)C5CCCC5)[C@@H](C)C4)cn3C)c2C)c1]

Step 1: (S)-1-(cyclopentanecarbonyl)-2-methylpiperidin-4-one. A flask with a mixture of benzyl (S)-2-methyl-4-oxopiperidine-1-carboxylate (500 mg, 2.02 mmol) and Pd/C (5% by weight, 215 mg) in EtOH (10 mL) was evacuated and then put under hydrogen gas. The mixture was stirred under 1.1 bar hydrogen over pressure for 1 h. The mixture was filtered through a Celite® plug, and the filtrate was concentrated in vacuo. To the residue was added DCM (10 ml) followed by TEA (1.41 mL, 10.1 mmol) and then cyclopentanecarbonyl chloride (492 μL, 4.04 mmol) was added dropwise. The reaction mixture was stirred at room temperature for 1 h, whereupon the reaction was quenched with 40 mL water followed by extraction with DCM (4×). The combined organic extracts were evaporated and the residue was purified by silica gel column chromatography (EtOAc/heptane; 1:1) to provide the title compound (301 mg, 71%) as a colorless oil. $^1$H NMR (500 MHz, CDCl$_3$) δ 5.24-4.84 (2 br s, 1H), 4.64-4.10 (2 br s, 1H), 3.55-3.11 (2 br s, 1H), 2.95 (m, 1H), 2.65 (dd, J=6.7, 14.4 Hz, 1H), 2.50-2.30 (m, 3H), 1.93-1.77 (m, 6H), 1.64-1.56 (m, 2H), 1.29-1.16 (m, 3H).

Step 2: (S)-1-(cyclopentanecarbonyl)-2-methyl-1,2,3,6-tetrahydropyridin-4-yl trifluoromethanesulfonate. n-BuLi (2.5M solution in hexanes, 1.15 mL, 2.87 mmol) was added dropwise to diisopropylamine (402 μL, 2.87 mmol) in dry THF (5 mL) under nitrogen at −78° C.

The mixture was stirred at −78° C. for 30 min, whereupon (S)-1-(cyclopentanecarbonyl)-2-methylpiperidin-4-one (300 mg, 1.43 mmol) in dry THF (4 mL) was added. After 30 min, N-phenyl-bis(trifluoromethanesulfonimide) (1.02 g, 2.86 mmol) was added. The temperature was allowed to warm to room temperature. After stirring for 30 min, the reaction mixture was cooled to 0° C. and the reaction was quenched with NaHCO$_3$ (50% sat.) and extracted with diethyl ether. The organic phase was washed with citric acid (10%), NaOH (1M), water and brine. The organic phase was dried (Na₂SO₄) and evaporated. The residue was purified by silica gel column chromatography (EtOAc/heptane, 15:85-2:8) to provide the title compound (329 mg, 67%) as an orange oil. ¹H NMR (500 MHz, CDCl₃) δ 5.81-5.74 (m, 1H), 5.29-3.26 (m, 3H), 2.90-2.52 (m, 2H), 1.98-1.53 (m, 8H), 1.35-1.15 (m, 3H).

Step 3: (S)-cyclopentyl(4-(1,4-dimethyl-5-nitro-1H-pyrrolo[2,3-b]pyridin-3-yl)-2-methyl-3,6-dihydropyridin-1 (2H)-yl)methanone. (S)-1-(cyclopentanecarbonyl)-2-methyl-1,2,3,6-tetrahydropyridin-4-yl trifluoromethanesulfonate (182 mg, 0.95 mmol), 1,4-dimethyl-5-nitro-3-(4,4,5,5-tetramethyl-1,3,2-dioxaborolan-2-yl)-1H-pyrrolo[2,3-b]pyridine (prepared as described in Example 58, 300 mg, 0.95 mmol), tetrakis triphenylphosphine Pd(0) (109 mg, 0.09 mmol) and K₃PO₄ (442 mg, 2.08 mmol) were stirred in dioxane/water 9:1 at 60° C. under an atmosphere of nitrogen overnight. The mixture was concentrated to dryness, whereupon water and DCM were added. The phases were separated and the organic layer was evaporated. The residue was purified by silica gel column chromatography (EtOAc/heptane; 3:7-6:4) to provide the title compound (221 mg, 61%) as a yellow solid foam. LC/MS [M+H]=383.

Step 4: 3-cyano-N-(3-((2S,4S)-1-(cyclopentanecarbonyl)-2-methylpiperidin-4-yl)-1,4-dimethyl-1H-pyrrolo[2,3-b]pyridin-5-yl)-5-methoxybenzamide. A mixture of (S)-cyclopentyl(4-(1,4-dimethyl-5-nitro-1H-pyrrolo[2,3-b]pyridin-3-yl)-2-methyl-3,6-dihydropyridin-1(2H)-yl)methanone (59 mg, 0.15 mmol), Pd/C (5% by weight, 24 mg), TEA (24 μL, 0.17 mmol) in EtOH (96%, 5 mL) was stirred under 5 bar of hydrogen for 6 h. The mixture was filtered through Celite® and the filtrate was concentrated. The residue was dissolved in DMF (1 mL) and a solution of 3-cyano-5-methoxybenzoic acid (30 mg, 0.17 mmol), HATU (54 mg, 0.17 mmol) and DIEA (56 μL, 0.34 mmol) in DMF (1 mL) was added. The mixture was stirred at room temperature overnight. The reaction mixture was purified by preparatory HPLC to provide the title compound (22 mg, 27%) as a white powder. LCMS [M+H]=514; ¹H NMR (500 MHz, CDCl₃) δ 8.31 (s, 1H), 8.00 (s, 1H), 7.90 (s, 1H), 7.30 (s, 1H), 6.95 (s, 1H), 4.27 (br s, 1H), 3.92 (s, 3H), 3.91 (s, 3H), 3.90 (m, 1H), 3.21 (br s, 1H), 3.07 (m, 1H), 2.87 (m, 1H), 2.58 (s, 3H), 2.26 (br s, 1H), 2.02 (br s, 1H), 1.88-1.66 (m, 6H), 1.61-1.52 (m, 4H), 1.17 (d, J=6.0 Hz, 3H).

Example 91

Preparation of 3-cyano-N-(1,4-dimethyl-3-((2S,4R)-2-methyl-1-((S)-3,3,3-trifluoro-2-methylpropanoyl)-piperidin-4-yl)-1H-pyrrolo[2,3-b]pyridin-5-yl)benzamide

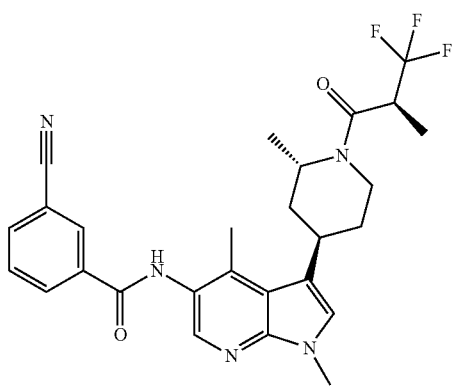 [SMILES: Cc1c(NC(=O)c2cccc(C#N)c2)cnc2c1c([C@@H]1CCN(C(=O)[C@H](C)C(F)(F)F)[C@@H](C)C1)cn2C]

Step 1. tert-butyl (S)-2-methyl-4-oxopiperidine-1-carboxylate. A suspension of benzyl (S)-2-methyl-4-oxopiperidine-1-carboxylate (600 mg, 2.43 mmol), palladium on carbon (100 mg, wet), ethanol (5 mL) and THF (5 mL) was treated with Boc₂O (582 mg, 2.67 mmol) and subjected to Parr hydrogenation at 15 psi for 18 hours at room temperature. The reaction was filtered through Celite® and washed with ethanol (3×15 mL). The combined filtrates were concentrated in vacuum. The crude product was purified by silica gel column chromatography (PE:EtOAc, 100:0-90:10) to afford the title compound (500 mg, 96.6%) as a white solid. ¹H NMR (400 MHz, CDCl₃) δ 4.70 (s, 1H), 4.24-4.19 (m, 1H), 3.32-3.27 (m, 1H), 2.68-2.45 (m, 4H), 1.47 (s, 9H), 1.17-1.15 (m, 3H).

Step 2. tert-butyl (S)-2-methyl-4-(((trifluoromethyl)sulfonyl)oxy)-3,6-dihydropyridine-1(2H)-carboxylate. To a solution of (S)-2-methyl-4-oxopiperidine-1-carboxylate (213 mg, 0.99 mmol) in THF (20 ml) was slowly added a solution of NaHMDS (2 mL, 2 mmol) at −78° C. under nitrogen (in oven-dried glassware). After 30 minutes, a solution of N-phenyl bis(trifluoromethanesulfonimide (714 mg, 2.0 mmol) in THF (8 ml) was slowly added. The reaction mixture was left stirring overnight, by which time it was slowly warmed to room temperature. The solvent was removed at 35° C. and the resulting residue was purified by column chromatography on neutral Al₂O₃ (PE:EtOAc, 30:1) to afford the title compound (317 mg, 91.9%) as colorless oil. ¹H NMR (400 MHz, CDCl₃) δ 5.74-5.70 (m, 1H), 4.66 (br s, 1H), 4.44-4.39 (m, 1H), 3.65-3.61 (m, 1H), 2.98-2.75 (m, 1H), 2.57-2.04 (m, 1H), 1.67-1.16 (m, 11H).

Step 3. tert-butyl (S)-4-(1,4-dimethyl-5-nitro-1H-pyrrolo[2,3-b]pyridin-3-yl)-2-methyl-3,6-dihydropyridine-1(2H)-carboxylate. A solution of tert-butyl (S)-2-methyl-4-(((trifluoromethyl)-sulfonyl)oxy)-3,6-dihydropyridine-1(2H)-carboxylate (424 mg, 1.23 mmol), 1,4-dimethyl-5-nitro-3-(4,4,5,5-tetramethyl-1,3,2-dioxaborolan-2-yl)-1H-pyrrolo[2,3-b]pyridine (prepared as in Example 58) (389 mg, 1.23 mmol), and K₃PO₄ (521 mg, 2.46 mmol) in a mixed solvent of dioxane/H₂O (9 mL, 8/1) was degassed using N₂ for 10 min. Pd(PPh3)4 (142 mg, 0.123 mmol) wad added, again degassed for 10 min and then heated at 100° C. for 4 h. The mixture was concentrated and the resulting residue was partitioned between H₂O (20 mL) and DCM (20 mL). The organic layer was dried, concentrated, and purified by silica gel column chromatography (DCM followed by PE:EtOAc, 85:15-80:20) to afford the title compound as a yellow solid. LCMS [M+H]=387.1.

Step 4. tert-butyl (2S,4R)-4-(5-amino-1,4-dimethyl-1H-pyrrolo[2,3-b]pyridin-3-yl)-2-methylpiperidine-1-carboxylate. A solution of tert-butyl (S)-4-(1,4-dimethyl-5-nitro-1H-pyrrolo[2,3-b]pyridin-3-yl)-2-methyl-3,6-dihydropyridine-1 (2H)-carboxylate (76 mg, 0.2 mmol) and ammonium formate (13.5 mg, 0.214 mmol) in EtOH (10 mL) was heated to reflux in presence of Pd/C (76 mg, 20% by wt) for 14 h. The reaction mixture was filtered through a pad of Celite® and the filtrate was concentrated. The residue was purified by silica gel column chromatography (PE:EtOAc, 50:50-100:0). The racemic product was resolved by chiral SFC (ChiralCel OJ, 300×50 mm, 10 μm, CO₂/EtOH—NH₃H₂O, 80:20, 180 mL/min). Two peaks were recovered, and analyzed using the following method: Ultimate XB-C18, 3 μm, 3.0×50 mm, 1-100% MeCN in water (0.1% TFA), 15 min. The first peak eluted at 5.61 min. The second eluting peak eluted at 6.34 min. The second eluting peak was collected and concentrated to afford the title compound. LCMS [M+H]=359.1.

Step 5. tert-butyl (2S,4R)-4-(5-(3-cyanobenzamido)-1,4-dimethyl-1H-pyrrolo[2,3-b]pyridin-3-yl)-2-methylpiperidine-1-carboxylate. tert-Butyl (2S,4R)-4-(5-amino-1,4-dimethyl-1H-pyrrolo[2,3-b]pyridin-3-yl)-2-methylpiperidine-1-carboxylate (500 mg, 1.39 mmol) was dissolved in DCM (20 mL), and TEA (212 mg, 2.09 mmol) was added. The solution was cooled to 0° C. Then 3-cyanobenzoyl chloride (254 mg, 1.53 mmol) in DCM (10 mL) was added over a period of 10 min. After addition, the solution was stirred at 0° C. for 1 h. The reaction was quenched by water (20 mL), and extracted with DCM (20 mL×2). The combined organic layers were dried over $Na_2SO_4$, filtered, and concentrated. The crude product was purified via silica gel column chromatography (PE/EtOAc, 70:30-47:63) to give the title compound as yellow solid. LCMS [M+H]=359.1.

Step 6. 3-cyano-N-(1,4-dimethyl-3-((2S,4R)-2-methylpiperidin-4-yl)-1H-pyrrolo[2,3-b]pyridin-5-yl)benzamide hydrochloride. tert-Butyl (2S,4R)-4-(5-(3-cyanobenzamido)-1,4-dimethyl-1H-pyrrolo[2,3-b]pyridin-3-yl)-2-methylpiperidine-1-carboxylate (590 mg, 1.2 mmol) was dissolved in dixoane (15 mL), and 4M HCl/Dioxane (15 mL) was added drop wise at an ice-water bath. The mixture was stirred at 20° C. for 16 h. The mixture was concentrated to afford the title compound (600 mg). LCMS [M+H]=488.1.

Step 7. 3-cyano-N-(1,4-dimethyl-3-((2S,4R)-2-methyl-1-((S)-3,3,3-trifluoro-2-methylpropanoyl)-piperidin-4-yl)-1H-pyrrolo[2, 3-b]pyridin-5-yl)benzamide. 3-Cyano-N-(1,4-dimethyl-3-((2S,4R)-2-methylpiperidin-4-yl)-1H-pyrrolo[2,3-b]pyridin-5-yl)benzamide hydrochloride (600 mg, 1.3 mmol) was dissolved in DMF (20 mL) and DIPEA (505 mg, 3.91 mmol) was added, followed by rac-3,3,3-trifluoro-2-methylpropanoic acid (185 mg, 1.3 mmol) and HATU (743 mg, 1.95 mmol). The reaction solution was stirred at 25° C. for 1 h. The reaction was quenched by brine (20 mL), and extracted with EtOAc (20 mL×3). The combined organic layers were dried over $Na_2SO_4$, filtered, and concentrate. The crude product was purified by silica gel column chromatography (EtOAc:PE, 50:50-80:20). The mixture of diastereomers was separated by chiral SFC (ChiralCel OJ, 250×30 mm, 5 μm, $CO_2$/EtOH—$NH_3H_2O$, 80/20, 60 mL/min) and the first eluting isomer was isolated to afford the title compound (170 mg). LC/MS [M+H]=512.1. Chiral SFC: Rt=4.202 min (Method N). $^1$H NMR (400 MHz, $CD_3OD$) δ 8.40 (s, 1H), 8.34-8.31 (m, 1H), 8.15 (s, 1H), 8.01-7.98 (m, 1H), 7.79-7.75 (m, 1H), 7.25 (s, 1H), 5.06-5.03 (m, 0.5H), 4.85-4.83 (m, 1H), 4.66-4.62 (m, 0.5H), 4.51-4.47 (m, 0.5H), 4.06-4.03 (m, 0.5H), 3.95-3.92 (m, 1H), 3.82 (s, 3H), 3.69-3.64 (m, 1H), 3.63-3.51 (m, 0.5H), 3.08-3.04 (m, 0.5H), 2.17-2.06 (m, 2H), 1.79-1.55 (m, 2H), 1.50-1.30 (m, 6H).

Example 92

Preparation of 3-cyano-N-(1,4-dimethyl-3-((2S,4R)-2-methyl-1-((R)-3,3,3-trifluoro-2-methylpropanoyl)piperidin-4-yl)-1H-pyrrolo[2,3-b]pyridin-5-yl)benzamide

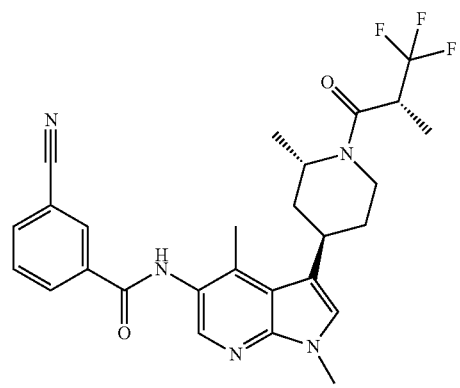 [SMILES: Cc1c(NC(=O)c2cccc(C#N)c2)cnc2c1c([C@@H]1CCN(C(=O)[C@@H](C)C(F)(F)F)[C@@H](C)C1)cn2C]

Isolation of the second eluting peak from chiral SFC separation of the diastereomeric mixture described in Example 91, step 7 afforded the title compound (185 mg). LC/MS [M+H]=512.1. Chiral SFC: Rt=4.649 min (Method N). $^1$H NMR (400 MHz, $CD_3OD$) δ 8.40 (s, 1H), 8.34-8.31 (m, 1H), 8.15 (s, 1H), 8.01-7.98 (m, 1H), 7.79-7.75 (m, 1H), 7.25 (s, 1H), 5.06-5.03 (m, 0.5H), 4.85-4.83 (m, 1H), 4.66-4.62 (m, 0.5H), 4.51-4.47 (m, 0.5H), 4.06-4.03 (m, 0.5H), 3.95-3.92 (m, 1H), 3.82 (s, 3H), 3.69-3.64 (m, 1H), 3.63-3.51 (m, 0.5H), 3.08-3.04 (m, 0.5H), 2.17-2.06 (m, 2H), 1.79-1.55 (m, 2H), 1.50-1.30 (m, 6H).

Examples 93-94 & 113

The following Examples 93-94 and 113 were prepared analogous to Example 91 employing 3-cyano-4-methoxybenzoic acid in Step 5. Chiral SFC separation (ChiralCel AS, 250×30 mm, 5 μm, $CO_2$/IPA-$NH_3H_2O$, 60/40, 50 mL/min) of the resulting diastereomers afforded Example 93 as the first eluting isomer and Example 94 as the second eluting isomer.

| Ex. | Structure | Name/Characterization |
|---|---|---|
| 93 | 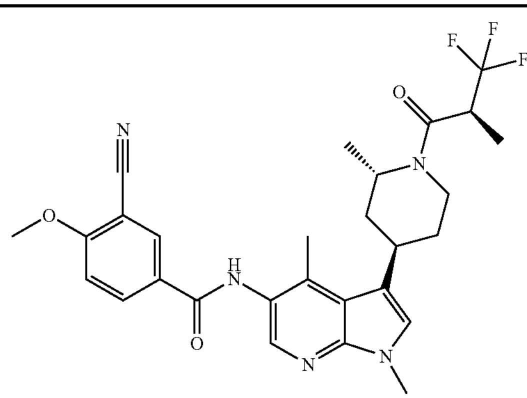 | 3-cyano-N-(1,4-dimethyl-3-((2S,4R)-2-methyl-1-((S)-3,3,3-trifluoro-2-methylpropanoyl)piperidin-4-yl)-1H-pyrrolo[2,3-b]pyridin-5-yl)-4-methoxybenzamide. LC/MS [M + H] = 542.2. Chiral SFC: Rt = 9.21 min (Method O). $^1$H NMR (400 MHz, $CD_3OD$) δ 8.34-8.31 (m, 2H), 8.12 (s, 1H), 7.38-7.35 (m, 1H), 7.23 (s, 1H), 5.04-5.02 (m, 0.5H), 4.73-4.50 (m, 2H), 4.09 (s, 3H), 4.01-3.97 (m, 1H), 3.82 (s, 3H), 3.73-3.46 (m, 2H), 3.17-3.13 (m, 0.5H), 2.66 (s, 3H), 2.17-2.06 (m, 2H), 1.75-1.02 (m, 8H). |

| Ex. | Structure | Name/Characterization |
|---|---|---|
| 94 | 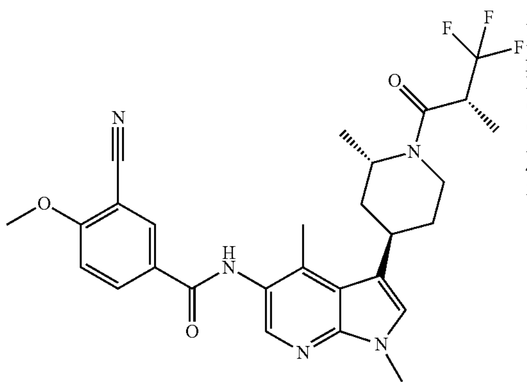 [SMILES: COc1ccc(C(=O)Nc2cnc3c(c([C@@H]4CCN(C(=O)[C@@H](C)C(F)(F)F)[C@@H](C)C4)cn3C)c2C)cc1C#N] | 3-cyano-N-(1,4-dimethyl-3-((2S,4R)-2-methyl-1-((R)-3,3,3-trifluoro-2-methylpropanoyl)piperidin-4-yl)-1H-pyrrolo[2,3-b]pyridin-5-yl)-4-methoxybenzamide. LC/MS [M + H] = 542.2. Chiral SFC: Rt = 9.65 min (Method O). ¹H NMR (400 MHz, CD₃OD) δ 8.34-8.31 (m, 2H), 8.12 (s, 1H), 7.38-7.35 (m, 1H), 7.23 (s, 1H), 5.04-5.02 (m, 0.5H), 4.73-4.50 (m, 2H), 4.09 (s, 3H), 4.01-3.97 (m, 1H), 3.82 (s, 3H), 3.73-3.46 (m, 2H), 3.17-3.13 (m, 0.5H), 2.66 (s, 3H), 2.17-2.06 (m, 2H), 1.75-1.02 (m, 8H). |
| 113 | 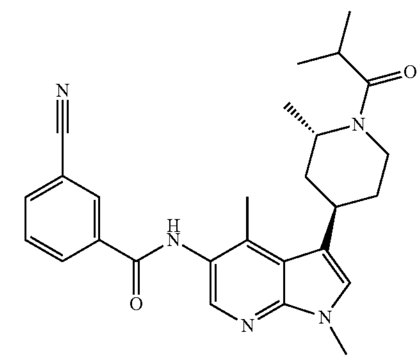 [SMILES: Cc1c(NC(=O)c2cccc(C#N)c2)cnc2c1c([C@@H]1CCN(C(=O)C(C)C)[C@@H](C)C1)cn2C] | 3-cyano-N-(3-((2S,4R)-1-isobutyryl-2-methylpiperidin-4-yl)-1,4-dimethyl-1H-pyrrolo[2,3-b]pyridin-5-yl)benzamide. 1H NMR (400 MHz, CDCl3) δ 8.34 (s, 1 H), 8.27-8.26 (m, 2 H), 8.20 (s, 1H), 7.85 (d, J = 7.7 Hz, 1 H), 7.65 (t, J = 7.8 Hz, 1 H), 6.92 (s, 1 H), 4.22 (br s, 1 H), 3.94 (br s, 1 H), 3.83 (s, 3 H), 3.30-2.96 (m, 2 H), 2.80 (p, J = 6.7 Hz, 1 H), 2.54 (s, 3H), 2.26 (d, J = 11.8 Hz, 1 H), 1.99 (s, 1 H), 1.62-1.53 (m, 2 H), 1.20-1.06 (m, 9H). |

Example 95

Example 95 was prepared analogous to Example 90 employing 1-methyl-5-nitro-3-(4,4,5,5-tetramethyl-1,3,2-dioxaborolan-2-yl)-4-(trifluoromethyl)-1H-pyrrolo[2,3-b]pyridine (prepared as described in Example 65, step 1) in Step 3 and isobutyryl chloride in step 7.

| Ex. | Structure | Name/Characterization |
|---|---|---|
| 95 | 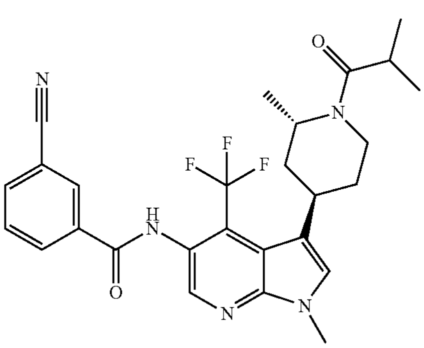 [SMILES: CC(C)C(=O)N1CC[C@@H](c2cn(C)c3ncc(NC(=O)c4cccc(C#N)c4)c(C(F)(F)F)c23)C[C@@H]1C] | 3-cyano-N-(3-((2S,4R)-1-isobutyryl-2-methylpiperidin-4-yl)-1-methyl-4-(trifluoromethyl)-1H-pyrrolo[2,3-b]pyridin-5-yl)ben2amide. LC/MS [M + H] = 512.1; ¹H NMR (400 MHz, CD₃OD) δ 8.36-8.29 (m, 3H), 8.01-7.99 (m, 1H), 7.79-7.75 (m, 1H), 7.68-7.65 (m, 1H), 5.02-4.99 (m, 0.5H), 4.65-4.62 (m, 0.5H), 4.45-4.50 (m, 0.5H), 4.07-4.03 (m, 0.5H), 3.92 (s, 3H), 3.57-3.52 (m, 1H), 3.40-3.39 (m, 0.5H), 3.03-2.98 (m, 1.5H), 2.03-1.92 (m, 2H). 1.73-1.55 (m, 2H), 1.43-1.23 (m, 3H), 1.18-0.95 (m, 6H). |

Example 96

Preparation of 3-cyano-N-(3-(4-isobutyryl-4-azaspiro[2.5]octan-7-yl)-1,4-dimethyl-1H-pyrrolo[2,3-b]pyridin-5-yl)benzamide

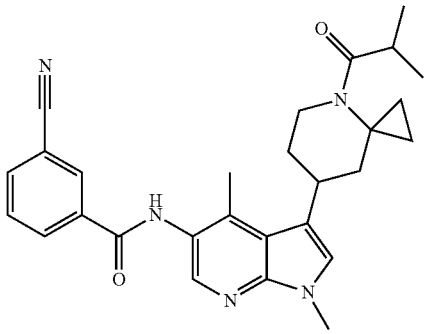 [SMILES: Cc1c(NC(=O)c2cccc(C#N)c2)cnc2c1c(C1CCN(C(=O)C(C)C)C3(CC3)C1)cn2C]

Step 1: ethyl 3-((1-(2-ethoxy-2-oxoethyl)cyclopropyl)amino)propanoate. Cyclopropylidene ethyl ester (500 mg, 3.96 mmol), ethyl 3-aminopropanoate hydrochloride salt (1.22 g, 7.93 mmol) and DIPEA (2.76 mL, 15.9 mmol) were loaded into a microwave vial and dissolved in THF (8 mL). The mixture was heated to 100° C. for 60 min. An NH$_4$Cl solution and DCM were added and the phases were separated. The organic layer was concentrated and the residue was purified by silica gel column chromatography (heptane/EtOAc, 1:1) to provide the title compound (770 mg, 80%) as a yellow oil. $^1$H NMR (500 MHz, CDCl$_3$) δ 4.16 (q, J=7.3 Hz, 2H), 4.12 (q, J=7.3 Hz, 2H), 2.93 (t, J=6.6 Hz, 2H), 2.44 (m, 4H), 1.27 (t, J=7.3 Hz, 3H), 1.25 (t, J=7.3 Hz, 3H), 0.69 (m, 2H), 0.48 (m, 2H).

Step 2: ethyl 7-oxo-4-azaspiro[2.5]octane-6-carboxylate. To a solution of ethyl 3-((1-(2-ethoxy-2-oxoethyl)cyclopropyl)amino)propanoate (310 mg, 1.27 mmol) in THF (8 mL) was added KOtBu (572 mg, 5.10 mmol) at 0° C. The mixture was stirred for 60 min at 0° C. and then at room temperature for 30 min, whereupon dilute NH$_4$Cl solution and DCM were added. The organic layer was separated and concentrated in vacuo to provide the title compound (150 mg, 60%) as a light yellow oil. The crude product was used in the subsequent step without further purification. $^1$H NMR (500 MHz, CDCl$_3$) δ 4.21 (m, 2H), 3.75-1.84 (m, 5H), 1.29 (m, 3H), 0.90-0.47 (m, 2H), 0.75-0.67 (m, 2H)

Step 3: 4-azaspiro[2.5]octan-7-one. A solution of ethyl 7-oxo-4-azaspiro[2.5]octane-6-carboxylate (250 mg, 1.27 mmol) in acetonitrile/water (9:1, 4 mL) was heated to 140° C. under microwave irradiation for 3 h. Evaporation of the volatiles in vacuo provided the title compound (105 mg, 66%) as an orange oil. The crude product was used in the subsequent step without further purification. $^1$H NMR (500 MHz, CDCl$_3$) δ 3.19 (m, 2H), 2.39 (m, 2H), 2.30 (s, 2H), 0.67 (m, 2H), 0.47 (m, 2H).

Step 4: tert-butyl 7-oxo-4-azaspiro[2.5]octane-4-carboxylate. 4-azaspiro[2.5]octan-7-one (105 mg, 0.839 mmol) was dissolved in DCM (5 mL). TEA (234 µL, 1.68 mmol), DMAP (10 mg, 0.084 mmol) and Boc$_2$O (366 mg, 1.68 mmol) were added and the mixture was stirred for 18 h at room temperature. A NaHCO$_3$ solution and DCM were added and the phases were separated. The organic layer was concentrated and the residue was purified by silica gel column chromatography (heptane/EtOAc, 90:10-80:20) to provide the title compound (50 mg, 26%) as a colorless oil. $^1$H NMR (500 MHz, CDCl$_3$) δ 3.70 (t, J=6.0 Hz, 2H), 2.43 (t, J=6.0 Hz, 2H), 2.32 (s, 2H), 1.49 (s, 9H), 0.95 (m, 2H), 0.70 (m, 2H).

Step 5: tert-butyl 7-(((trifluoromethyl)sulfonyl)oxy)-4-azaspiro[2.5]oct-6-ene-4-carboxylate. To a solution of tert-butyl 7-oxo-4-azaspiro[2.5]octane-4-carboxylate (50 mg, 0.222 mmol) in THF (2 mL) at −78° C. was added KHMDS (0.53 mL, 0.266 mmol, 0.5 M solution in toluene). After 30 min at −78° C., triflic anhydride (56 µL, 0.333 mmol) was added. The mixture was stirred for 30 min at −78° C. and 1 h at 0° C. A NaHCO$_3$ solution and DCM were added, and the phases were separated. The organic layer was concentrated in vacuo. The residue was purified by silica gel column chromatography (heptane/EtOAc, 9:1) to provide the title compound (59 mg, 73%) as a colorless oil. $^1$H NMR (500 MHz, CDCl$_3$) δ 5.87 (m, 1H), 4.07 (br s, 2H), 2.35 (br s, 2H), 1.45 (s, 9H), 0.97 (br s, 2H), 0.76 (br s, 2H).

Step 6: tert-butyl 7-(1,4-dimethyl-5-nitro-1H-pyrrolo[2,3-b]pyridin-3-yl)-4-azaspiro[2.5]oct-6-ene-4-carboxylate. A solution of 1,4-dimethyl-5-nitro-3-(4,4,5,5-tetramethyl-1,3,2-dioxaborolan-2-yl)-1H-pyrrolo[2,3-b]pyridine (prepared as described in Example 58, 52 mg, 0.162 mmol), tert-butyl 7-(((trifluoromethyl)sulfonyl)oxy)-4-azaspiro[2.5]oct-6-ene-4-carboxylate (29 mg, 0.081 mmol), Pd(PPh$_3$)$_4$ (9.4 mg, 0.008 mmol) and a 2M solution of K$_3$PO$_4$ in water (0.1 mL, 0.203 mmol) in dioxane (0.5 ml) was heated under microwave irradiation at 120° C. for 30 min. A NaHCO$_3$ solution and DCM were added. The organic layer was concentrated. The residue was purified by silica gel column chromatography (heptane/EtOAc, 4:1) to provide the title compound (22 mg, 79%) as a solid. LC/MS [M+H]=399.

Step 7: tert-butyl 7-(5-amino-1,4-dimethyl-1H-pyrrolo[2,3-b]pyridin-3-yl)-4-azaspiro[2.5]octane-4-carboxylate. TEA (14 µL, 0.100 mmol) and Pd/C (10.2 mg, 0.005 mmol, 5% w/w) were added to a solution of tert-butyl 7-(1,4-dimethyl-5-nitro-1H-pyrrolo[2,3-b]pyridin-3-yl)-4-azaspiro[2.5]oct-6-ene-4-carboxylate (20 mg, 0.050 mmol) in a mixture of MeOH:EtOAc (3 mL, 2:1). The mixture was stirred under an atmosphere of hydrogen (1 bar) for 5 h. The reaction mixture was filtered through a pad of Celite® eluting with EtOAc. The filtrate was concentrated in vacuo to afford the title compound. The crude product was used in the subsequent step without further purification. LC/MS [M+H]=371.

Step 8: tert-butyl 7-(5-(3-cyanobenzamido)-1,4-dimethyl-1H-pyrrolo[2,3-b]pyridin-3-yl)-4-azaspiro[2.5]octane-4-carboxylate. 3-Cyanobenzoyl chloride (23 mg, 0.138 mmol) was added to a solution of tert-butyl 7-(5-amino-1,4-dimethyl-1H-pyrrolo[2,3-b]pyridin-3-yl)-4-azaspiro[2.5]octane-4-carboxylate (17 mg, 0.046 mmol) in pyridine (2 mL). The mixture was stirred at room temperature overnight and then concentrated in vacuo. The residue was purified by silica gel column chromatography (heptane/EtOAc, 1:1-1:3) to provide the title compound (12 mg, 52%) as a colorless oil. LC/MS [M+H]=500.

Step 9: 3-cyano-N-(1,4-dimethyl-3-(4-azaspiro[2.5]octan-7-yl)-1H-pyrrolo[2,3-b]pyridin-5-yl)benzamide. To a stirred solution of tert-butyl 7-(5-(3-cyanobenzamido)-1,4-dimethyl-1H-pyrrolo[2,3-b]pyridin-3-yl)-4-azaspiro[2.5]octane-4-carboxylate (12 mg, 0.024 mmol) in DCM (2 mL) was added TFA (89 µL, 1.20 mmol). The mixture was stirred at room temperature for 18 h. Saturated NaHCO$_3$ solution was added and the mixture was extracted with DCM and EtOAc. The combined organic layers were washed with water and then concentrated in vacuo to provide the title compound as a colorless oil, which was used in the subsequent step without further purification.

Step 10: 3-cyano-N-(3-(4-isobutyryl-4-azaspiro[2.5]octan-7-yl)-1,4-dimethyl-1H-pyrrolo[2,3-b]pyridin-5-yl)benzamide. 3-Cyano-N-(1,4-dimethyl-3-(4-azaspiro[2.5]octan-7-yl)-1H-pyrrolo[2,3-b]pyridin-5-yl)benzamide was dissolved in DCM (1 mL) and cooled to 0° C. TEA (7 μL, 0.048 mmol) and isobutyryl chloride (4 μL, 0.036 mmol) were added. The cooling bath was removed and the mixture was stirred for 90 min at room temperature. A 1M HCl solution and DCM were added. The organic phase was separated and concentrated in vacuo to provide the title compound (7 mg, 62% over two steps) as a white solid. LC/MS [M+H] 470; $^1$H NMR (500 MHz, CDCl$_3$) δ 8.34 (s, 1H), 8.25 (m, 1H), 8.19 (s, 1H), 7.84 (m, 1H), 7.64 (t, J=7.6 Hz, 1H), 6.87 (s, 1H), 4.59-3.97 (m, 1H), 3.79 (s, 3H), 3.49 (m, 1H), 3.30 (m, 1H), 2.87-2.74 (m, 1H), 2.56 (s, 3H), 2.10-1.91 (m, 2H), 1.54-0.82 (m, 11H), 0.71-0.49 (m, 2H).

Example 97

Preparation of rel-3-cyano-N-(3-((2S,4S,5S)-1-(cyclopentanecarbonyl)-2,5-dimethylpiperidin-4-yl)-1,4-dimethyl-1H-pyrrolo[2,3-b]pyridin-5-yl)benzamide

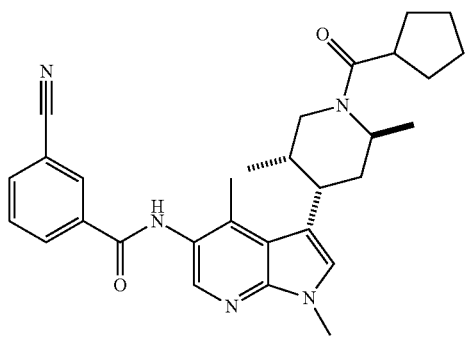

Step 1: tert-butyl (3,6-trans)-3,6-dimethyl-4-(((trifluoromethyl)sulfonyl)oxy)-3,6-dihydropyridine-1(2H)-carboxylate. To a solution of tert-butyl trans-2,5-dimethyl-4-oxopiperidine-1-carboxylate (J. B. Thomas et al. J. Med. Chem. 2001, 44, 972-987) (1.05 g, 4.62 mmol) in THF (30 mL) at −78° C. was added 1M solution of NaHMDS in THF (9.7 mL, 9.7 mmol). The mixture was stirred for 30 min., whereupon 1,1,1-trifluoro-N-phenyl-N-((trifluoromethyl)sulfonyl)methanesulfonamide (3.5 g, 9.7 mmol) was added, and the reaction mixture was stirred at −78° C. for 30 min. The mixture was allowed to warm to room temperature. After 16 hr, the reaction mixture was concentrated in vacuo. The residue was diluted with saturated ammonium chloride solution and extracted twice with DCM. The combined organic layers were dried over anhydrous Na$_2$SO$_4$, filtered and concentrated. The residue was purified by silica gel column chromatography (EtOAc:hexane, 2:98-4:96) to provide the title compound (1.2 g, 72%). $^1$H NMR (400 MHz, CDCl$_3$) δ 5.70-5.65 (m, 1H), 4.75-4.66 (m, 0.5H), 4.10-3.80 (m, 0.5H), 3.12-3.10 (m, 1H), 2.45-2.44 (m, 1H), 1.78-1.63 (m, 1H), 1.47 (s, 2H), 1.47 (s, 9H), 1.21 (d, J=6.8 Hz, 3H), 1.15 (d, J=6.8 Hz, 3H).

Step 2: tert-butyl 4-(1,4-dimethyl-5-nitro-1H-pyrrolo[2,3-b]pyridin-3-yl)-(3,6-trans)-3,6-dimethyl-3,6-dihydropyridine-1(2H)-carboxylate. To a solution of 1,4-dimethyl-5-nitro-3-(4,4,5,5-tetramethyl-1,3,2-dioxaborolan-2-yl)-1H-pyrrolo[2,3-b]pyridine (prepared as described in Example 58, 800 mg, 2.52 mmol) in dioxane/water (18 mL:2 mL) was degassed with nitrogen for 30 min at room temperature in a seal tube. tert-butyl (3,6-trans)-3,6-dimethyl-4-(((trifluoromethyl)sulfonyl)oxy)-3,6-dihydropyridine-1(2H)-carboxylate (996 mg, 2.78 mmol), K$_3$PO$_4$ (1.17 g, 5.54 mmol) and tetrakis(triphenyl phosphine)palladium(0) (32 mg, 0.02 mmol) were added and the resulting solution was degassed for 15 min. The reaction mixture was sealed and heated at 105° C. for 2 h. The reaction mixture was cooled to room temperature and concentrated in vacuo. The residue was triturated with EtOAc and the solid obtained was filtered off. The filtrate was washed with water. The organic layer was dried over anhydrous Na$_2$SO$_4$ and concentrated. The crude product was purified by silica gel column chromatography (EtOAc:hexane, 10:90) to afford the title compound (820 mg, 82%). $^1$H NMR (400 MHz, CDCl$_3$) δ 8.98 (s, 1H), 7.05 (s, 1H), 5.60-5.58 (m, 1H), 4.72-4.51 (m, 1H), 4.20-3.92 (m, 1H), 3.89 (s, 3H), 3.24-3.16 (m, 1H), 2.81 (s, 3H), 2.38-2.37 (m, 1H), 1.51 (s, 9H), 1.24 (d, J=6.4 Hz, 3H), 0.99 (d, J=6.4 Hz, 3H); LC/MS [M+CH$_3$CN]=442.

Step 3: tert-butyl 4-(5-amino-1,4-dimethyl-1H-pyrrolo[2,3-b]pyridin-3-yl)-(2,5-trans)-2,5-dimethylpiperidine-1-carboxylate. A solution of tert-butyl 4-(1,4-dimethyl-5-nitro-1H-pyrrolo[2,3-b]pyridin-3-yl)-(3,6-trans)-3,6-dimethyl-3,6-dihydropyridine-1(2H)-carboxylate (800 mg, 1.9 mmol), 10% Pd/C (800 mg) and ammonium formate (1.3 g, 19.9 mmol) in MeOH (50 mL) was heated at 80° C. for 24 h. The reaction mixture was cooled to room temperature, filtered through a pad of Celite® and washed with EtOH. The filtrate was concentrated to provide the title compound (720 mg, 89%), which was used in the subsequent step without further purification. LC/MS [M+H]=373; $^1$H NMR (400 MHz, CDCl$_3$) δ 7.98-7.86 (m, 1H), 6.74-6.73 (m, 1H), 4.68-4.43 (m, 1H), 4.20-3.92 (m, 1H), 4.12-3.90 (m, 1H), 3.89 (s, 3H), 3.62-3.12 (m, 3H), 2.49 (s, 3H), 2.25-1.98 (m, 2H), 1.48-1.45 (m, 9H), 1.40-1.02 (m, 3H), 0.65 (d, J=6.4 Hz, 3H).

Step 4: tert-butyl 4-(5-(3-cyanobenzamido)-1,4-dimethyl-1H-pyrrolo[2,3-b]pyridin-3-yl)-(2,5-trans)-2,5-dimethylpiperidine-1-carboxylate. To a solution of tert-butyl 4-(5-amino-1,4-dimethyl-1H-pyrrolo[2,3-b]pyridin-3-yl)-(2,5-trans)-2,5-dimethylpiperidine-1-carboxylate (700 mg, 1.74 mmol) and TEA (0.7 mL, 5.22 mmol) in DCM (20 mL) at 0° C. was added 3-cyanobenzoyl chloride (347 mg, 2.1 mmol) in DCM (10 mL). The reaction mixture was warmed to room temperature and stirred for 3 h. The reaction mixture was diluted with DCM and extracted with 10% aqueous NaHCO$_3$ solution. The organic layer was dried over anhydrous Na$_2$SO$_4$ and concentrated to provide the title compound (700 mg, 80%), which was used in the next step without further purification. LC/MS [M+H]=502; $^1$H NMR (400 MHz, CDCl$_3$): δ 8.27-8.19 (m, 3H), 7.86-7.84 (m, 2H), 7.64 (t, J=7.6 Hz, 1H), 6.99-6.98 (m, 0.25H), 6.86-6.85 (m, 0.75H), 4.70-4.43 (m, 1H), 3.99-3.85 (m, 1H), 3.82 (s, 3H), 3.70-3.15 (m, 2H), 2.62 (s, 3H), 2.25-1.98 (m, 3H), 1.48-1.47 (m, 9H), 1.39-1.02 (m, 3H), 0.67-0.66 (m, 3H).

Step 5: 3-cyano-N-(3-(2,5-trans)-(2,5-dimethylpiperidin-4-yl)-1,4-dimethyl-1H-pyrrolo[2,3-b]pyridin-5-yl)benzamide. To a solution of tert-butyl 4-(5-(3-cyanobenzamido)-1,4-dimethyl-1H-pyrrolo[2,3-b]pyridin-3-yl)-(2,5-trans)-2,5-dimethylpiperidine-1-carboxylate (700 mg, 1.39 mmol) in MeOH (5 mL) at 0° C. was added 4M HCl in dioxane (15 mL). The reaction mixture was allowed to warm to room temperature and stir for 6 h. The mixture was concentrated in vacuo, and the residue was washed with pentane to afford the title compound (600 mg, 99%). LC/MS [M+H]=402.

Step 6: rel-3-cyano-N-(3-((2S,4S,5S)-1-(cyclopentanecarbonyl)-2,5-dimethylpiperidin-4-yl)-1,4-dimethyl-1H-pyrrolo[2,3-b]pyridin-5-yl)benzamide. To a solution of 3-cyano-N-(3-(2,5-trans)-(2,5-dimethylpiperidin-4-yl)-1,4-dimethyl-1H-pyrrolo[2,3-b]pyridin-5-yl)benzamide (150 mg, 0.37 mmol) in DCM (5 mL) at 0° C. was added TEA (259 μL, 1.87 mmol) and the mixture was stirred for 10 min. Cyclopentanecarbonyl chloride (59 mg, 0.45 mmol) in DCM (1 mL) was added, and the mixture was stirred for 3 h at room temperature. The reaction mixture was diluted with DCM and washed with 10% aqueous NaHCO$_3$ solution. The organic layer was dried over anhydrous Na$_2$SO$_4$, filtered and concentrated. The residue was purified by preparative HPLC to provide the title compound (85 mg, 46%) as a white solid. LC/MS [M+H]=498.55; $^1$H NMR (400 MHz, CD$_3$OD) δ 8.40-8.38 (m, 1H), 8.30 (d, J=8.0 Hz, 1H), 8.12 (s, 1H), 7.97 (t, J=8.0 Hz, 1H), 7.75 (t, J=7.6 Hz, 1H), 7.33-7.32 (m, 0.25H), 7.17-7.16 (m, 0.75H), 5.14-5.07 (m, 0.5H), 4.63-4.22 (m, 1.5H), 3.91-2.61 (m, 7H), 3.16-3.06 (m, 2H), 2.63 (s, 3H), 2.30-2.23 (m, 2H), 1.92-1.62 (m, 6H), 1.43-1.08 (m, 3H), 0.73 (d, J=6.8 Hz, 2H), 0.64 (d, J=6.8, 1H).

Example 98

Preparation of 3-cyano-N-(3-((1R,5S,8r)-3-isobutyryl-3-azabicyclo[3.2.1]octan-8-yl)-1,4-dimethyl-1H-pyrrolo[2,3-b]pyridin-5-yl)benzamide

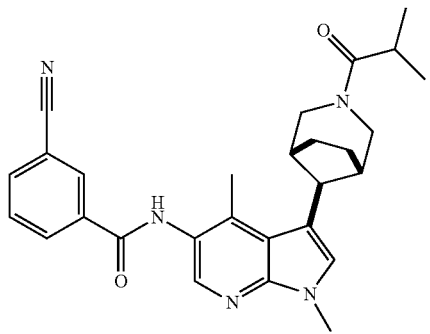

Step 1. tert-butyl (8-anti)-[1-(4-bromo-2-fluoropyridin-3-yl)-2-nitroethyl]-3-azabicyclo[3.2.1]octane-3-carboxylate. At −78° C., 4-bromo-2-fluoropyridine (4.29 mmol, 0.455 mL) was slowly added to a solution of lithium diisopropylamide (2 M in THF/heptane/ethylbenzyne, 4.29 mmol, 2.14 mL) in THF (4.29 mL). The mixture was stirred 1 h at −78° C. and tert-butyl (8-anti)-8-[(E)-2-nitroethenyl]-3-azabicyclo[3.2.1]octane-3-carboxylate (prepared as described in Example 77, step 5) (1.09 g, 3.86 mmol) in THF (4.29 mL) was slowly added. The mixture was stirred 30 min at −78° C. and then the cold bath was removed. The mixture was stirred until it reached room temperature and was then quenched with a saturated solution of NH$_4$Cl (5 mL). The aqueous phase was extracted several times with DCM (5 mL). The combined organic layers were washed with brine, dried over sodium sulfate, filtered, and evaporated. The crude product was purification by flash chromatography (heptane:AcOEt, 100/0-40/60) to provide the title compound (912 mg, 52%) as a yellow solid. LC/MS [M−Me+H]=445.0; $^1$H NMR (400 MHz, CDCl$_3$) δ 7.98 (d, J=5.3 Hz, 1H), 7.45 (d, J=5.1 Hz, 1H), 4.67-4.85 (m, 2H), 4.04 (d, J=14.0 Hz, 0.5 H), 3.81-3.95 (m, 3H), 3.72 (d, J=12.9 Hz, 0.5 H), 2.66-2.96 (m, 2H), 2.11-2.28 (m, 2H), 1.80-2.02 (m, 2H), 1.71 (m, 2H), 1.45 (br. s., 9H).

Step 2. (8-anti)-[1-(4-bromo-2-fluoropyridin-3-yl)-2-nitroethyl]-3-azabicyclo[3.2.1]octane-3-carboxylate. At 25° C., a solution of HCl (4M in dioxane, 4.97 mL, 19.9 mmol) was slowly added to a solution of tert-butyl (8-anti)-[1-(4-bromo-2-fluoropyridin-3-yl)-2-nitroethyl]-3-azabicyclo[3.2.1]octane-3-carboxylate (912.0 mg, 1.99 mmol) in DCM (6.63 mL). The reaction mixture was stirred for 1 h at 50° C. The solvent was directly removed under reduced pressure, providing the hydrochloride salt of the title compound (785 mg, 100%) which was dried over 1 h under high vacuum. LC/MS [M+H]=358.0; $^1$H NMR (400 MHz, CD$_3$OD) δ 8.03 (d, J=5.5 Hz, 1H), 7.62 (d, J=5.5 Hz, 1H), 5.01 (dd, J=12.9, 4.7 Hz, 1H), 4.85-4.95 (m, 2H), 3.98 (td, J=10.1, 4.7 Hz, 1H), 3.20-3.29 (m, 2H), 3.03-3.16 (m, 2H), 2.54-2.59 (m, 1H), 2.45-2.51 (m, 1H), 2.12-2.33 (m, 2H), 1.82-1.92 (m, 1H), 1.70-1.82 (m, 2H).

Step 3. 1-{(8-anti)-[1-(4-bromo-2-fluoropyridin-3-yl)-2-nitroethyl]-3-azabicyclo[3.2.1]oct-3-yl}-2-methylpropan-1-one. At room temperature, a saturated solution of NaHCO$_3$ (18.0 mL) was added to a solution of tert-butyl (8-anti)-[1-(4-bromo-2-fluoropyridin-3-yl)-2-nitroethyl]-3-azabicyclo[3.2.1]octane-3-carboxylate hydrochloride (785 mg, 1.99 mmol) in DCM (6.63 mL). The mixture was stirred vigorously and isobutyryl chloride (230 μL, 2.19 mmol) was slowly added. After 10 min, the mixture was transferred to a separating funnel and the phases were separated. The aqueous layer was extracted twice with DCM (5 mL) and the combined organic layers were dried with sodium sulfate, filtered, and evaporated to provide the title compound (819 mg, 97% yield). LC/MS [M+H]=428.0; (Note: $^1$H NMR complex due to the presence of rotamers and diastereomers). $^1$H NMR (400 MHz, CDCl$_3$) δ 7.99 (d, J=5.1 Hz, 1H), 7.46 (d, J=5.1 Hz, 1H), 4.69-4.86 (m, 2H), 4.49 (d, J=13.7 Hz, 0.5 H), 4.32 (d, J=13.7 Hz, 0.5 H), 3.93 (t, J=11.1 Hz, 1H), 3.81 (d, J=12.9 Hz, 0.5 H), 3.64 (d, J=11.7 Hz, 0.5 H), 3.21 (d, J=11.9 Hz, 0.5 H), 3.08 (d, J=12.9 Hz, 0.5 H), 2.66-2.84 (m, 1.5 H), 2.57 (d, J=13.3 Hz, 0.5 H), 2.32-2.21 (m, 2H), 2.03-1.78 (m, 2H), 1.75-1.43 (m, 4H), 1.20-1.02 (m, 6H).

Step 4. 1-[(8-anti)-(4-bromo-2,3-dihydro-1H-pyrrolo[2,3-b]pyridin-3-yl)-3-azabicyclo[3.2.1]oct-3-yl]-2-methylpropan-1-one. At room temperature, AcOH (1.11 mL, 19.4 mmol) and zinc powder (1.27 g, 19.4 mmol) were successively added to a solution of 1-{(8-anti)-[1-(4-bromo-2-fluoropyridin-3-yl)-2-nitroethyl]-3-azabicyclo[3.2.1]oct-3-yl}-2-methylpropan-1-one (819 mg, 1.94 mmol) in THF (3.87 mL). The mixture was stirred overnight at room temperature. The mixture was filtered through a plug of Celite® and rinsed with DCM. The filtrate was concentrated and the residue was purification by silica gel column chromatography (DCM:MeOH, 100/0-85/15) to afford the title compound (268 mg, 37% yield) as a white powder which was immediately used in the next step.

Step 5. 1-[(8-anti)-(4-bromo-1-methyl-2,3-dihydro-1H-pyrrolo[2,3-b]pyridin-3-yl)-3-azabicyclo[3.2.1]oct-3-yl]-2-methylpropan-1-one. At room temperature, to a solution of 1-[(8-anti)-(4-bromo-2,3-dihydro-1H-pyrrolo[2,3-b]pyridin-3-yl)-3-azabicyclo[3.2.1]oct-3-yl]-2-methylpropan-1-one (268 mg, 0.708 mmol) in THF (2.36 mL) was added in one portion NaH (60% in oil, 57 mg, 1.42 mmol) followed by methyl iodide (49 uL, 0.78 mmol). The reaction was stirred for 2 h and was then quenched with a saturated solution of NH$_4$Cl (5 mL) and diluted with DCM (5 mL). The phases were separated and the aqueous layer was extracted twice with DCM (5 mL). The combined organic layers were dried over Na$_2$SO$_4$, filtered and evaporated. The crude product was purification by silica gel column chromatography (heptane:EtOAc, 100/0-0/100) to afford the title compound (123 mg, 44% yield) as a colorless oil. LC/MS [M+H]=392.1; ¹H NMR (400 MHz, CDCl₃) δ 7.73 (d, J=5.9 Hz, 1H), 6.68-6.60 (m, 1H), 4.49-4.41 (m, 0.6 H), 4.39-4.31 (m, 0.4 H), 3.82-3.74 (m, 0.4 H), 3.73-3.65 (m, 0.6 H), 3.47-3.30 (m, 2H), 3.18 (d, J=12.1 Hz, 0.6 H), 3.03-2.74 (m, 5.4 H), 2.69 (d, J=12.5 Hz, 0.6 H), 2.52 (d, J=13.3 Hz, 0.4 H), 2.38-2.11 (m, 3H), 1.97-1.74 (m, 2H), 1.71-1.41 (m, 2H), 1.21-1.02 (m, 6H).

Step 6. 1-[(8-anti)-8-(4-bromo-1-methyl-5-nitro-1H-pyrrolo[2,3-b]pyridin-3-yl)-3-azabicyclo[3.2.1]oct-3-yl]-2-methylpropan-1-one. At 0° C., to a solution of 1-[(8-anti)-(4-bromo-1-methyl-2,3-dihydro-1H-pyrrolo[2,3-b]pyridin-3-yl)-3-azabicyclo[3.2.1]oct-3-yl]-2-methylpropan-1-one (123 mg, 0.313 mmol) in DCM (2.08 mL) were successively added trifluoroacetic acid (72 µL, 0.94 mmol), followed by tetramethylammonium nitrate (128 mg, 0.94 mmol) and trifluoroacetic anhydride (131 µL, 0.94 mmol). The mixture was stirred 1 h at 0° C. and 3 h at room temperature. The mixture was neutralized with a saturated solution of NaHCO₃ until pH=8. The phases were separated and the aqueous layer was extracted three times with DCM (5 mL). The combined organic layers were dried with Na₂SO₄, filtered, and concentrated to afford the title compound (135 mg, 99% yield) as a yellow powder which was used immediately for the next step.

Step 7. 1-[(8-anti)-8-(4-methyl-1-methyl-5-nitro-1H-pyrrolo[2,3-b]pyridin-3-yl)-3-azabicyclo[3.2.1]oct-3-yl]-2-methylpropan-1-one. At room temperature, dimethylzinc (17.0 mg, 0.178 mmol) was added to a solution of 1-[(8-anti)-8-(4-bromo-1-methyl-5-nitro-1H-pyrrolo[2,3-b]pyridin-3-yl)-3-azabicyclo[3.2.1]oct-3-yl]-2-methylpropan-1-one (31.0 mg, 0.071 mmol) in dioxane (0.475 mL). The reaction was then heated to 80° C. in a microwave vessel for 90 minutes and then cooled to room temperature. The mixture was then treated with a saturated solution of NH₄Cl until pH=6. The phases were separated and the aqueous layer was extracted three times with DCM (5 mL). The combined organic phases were dried over Na₂SO₄, filtered, and evaporated. The crude product was purified by flash chromatography (DCM:EtOAc, 100/0-0/100) to provide the titled compound (10 mg, 38% yield) as a white powder. LC/MS [M+H]=372.0; ¹H NMR (400 MHz, CDCl₃) δ 1.14 (d, J=7.0 Hz, 3H), 1.21 (d, J=7.0 Hz, 3H), 1.21-1.30 (m, 2H), 1.79 (m, 2H), 2.57 (br. s., 2H), 2.87 (spt, J=7.0 Hz, 1H), 2.88 (s, 3H), 2.92 (d, J=14.0 Hz, 1H), 3.32 (s, 1H), 3.41 (d, J=11.7 Hz, 1H), 3.86 (m, 1H), 4.11 (s, 3H), 4.53 (d, J=12.9 Hz, 1H), 6.92 (s, 1H), 8.91 (s, 1H).

Step 8. 1-[(8-anti)-8-(5-amino-4-methyl-1-methyl-1H-pyrrolo[2,3-b]pyridin-3-yl)-3-azabicyclo[3.2.1]oct-3-yl]-2-methylpropan-1-one. At room temperature, to a solution of 1-[(8-anti)-8-(4-methyl-1-methyl-5-nitro-1H-pyrrolo[2,3-b]pyridin-3-yl)-3-azabicyclo[3.2.1]oct-3-yl]-2-methylpropan-1-one (20 mg, 0.052 mmol) in mixture of methanol/THF (1:1, 1.73 mL) was added a saturated solution of NH₄Cl (0.450 mL) followed by zinc dust (17 mg, 0.259 mmol). The resulting gray mixture was stirred at room temperature for 10 min and was filtered through a fritted plastic funnel and the filter cake was rinsed with DCM and water. The phases were separated and the aqueous layer was extracted three times with DCM (5 mL). The combined organic layers were dried over sodium sulfate, filtered, and concentrated to provide the title compound (18 mg, 90%) which was used immediately in the next step. LC/MS [M+H]=341.2.

Step 9. 3-cyano-N-(3-(3-isobutyryl-3-azabicyclo[3.2.1]octan-8-yl)-4-methyl-1-methyl-1H-pyrrolo[2,3-b]pyridin-5-yl)benzamide. At room temperature, to a solution of 1-[(8-anti)-8-(5-amino-4-methyl-1-methyl-1H-pyrrolo[2,3-b]pyridin-3-yl)-3-azabicyclo[3.2.1]oct-3-yl]-2-methylpropan-1-one (18 mg, 0.050 mmol) in DCM (0.505 mL) were successively added diisopropylethylamine (DIEA, 0.076 mmol, 13.3 µL) and 3-cyanobenzoyl chloride (10.9 mg, 0.066 mmol). The mixture was stirred for 30 min and then was quenched with a saturated solution of NaHCO₃ (5 mL). The phases were separated and the aqueous layer was extracted three times with DCM (5 mL). The combined organic phases were dried with sodium sulfate, filtered, and concentrated. The crude product was purification by silica gel column chromatography (DCM:EtOAc, 0/100-0/100) to give the title compound (16.5 mg) as a white powder. LC/MS [M+H]=470.2; ¹H NMR (400 MHz, CDCl₃) δ 8.58 (br. s., 1H), 8.52-8.50 (m, 2H), 7.87-7.86 (m, 1H), 7.64-7.73 (m, 1H), 7.02 (br. s., 1H), 4.53-4.51 (m, 1H), 4.09 (br. s., 3H), 3.89-3.88 (m, 1H), 3.42-3.41 (m, 1H), 3.39 (b. s., 1H), 2.92-2.90 (m, 1H), 2.85-2.80 (m, 1H), 2.78 (s, 3H), 2.47-2.57 (m, 2H), 1.80-1.89 (m, 2H), 1.64-1.63 (m, 2H), 1.21-1.20 (m, 3H), 1.13-1.10 (m, 3H).

Example 99

The following Example 99 was prepared analogous to Example 98 however employing the appropriate benzoic acid in Step 11 and the appropriate carboxylic acid in step 8.

| Ex. | Structure | Name/Characterization |
|---|---|---|
| 99 | 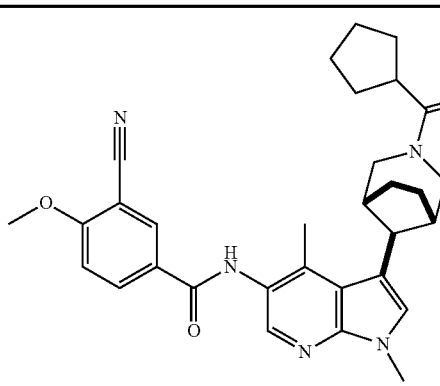 | 3-cyano-N-(3-((1R,5S,8r)-3-(cyclopentanecarbonyl)-3-azabicyclo[3.2.1]octan-8-yl)-1,4-dimethyl-1H-pyrrolo[2,3-b]pyridin-5-yl)-4-methoxybenzamide. LC/MS [M + H] = 526.5; ¹H NMR (400 MHz, CDCl₃) δ 8.21 (s, 1H), 8.25 (s, 1H), 7.73 (br. s., 1H), 7.11 (m, 1H), 6.93 (s, 1 H), 4.49 (m, 1H), 4.04 (s, 3 H), 3.91 (m, 1H), 3.83 (s, 3 H), 3.34-3.43 (m, 2 H), 2.87-2.99 (m, 2 H), 2.65 (s, 3 H), 2.50 (br. s., 2 H), 1.75-1.94 (m, 12 H). |

Example 100

Preparation of 3-cyano-N-(3-((1R*,4S*,5R*)-2-(cyclopentanecarbonyl)-2-azabicyclo[2.2.2]octan-5-yl)-1,4-dimethyl-1H-pyrrolo[2,3-b]pyridin-5-yl)benzamide

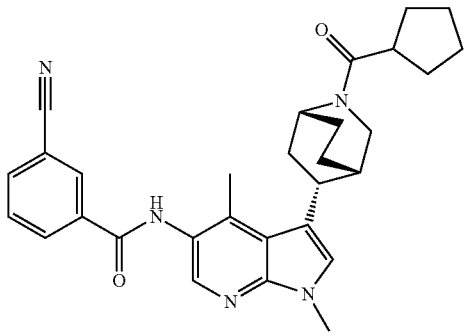 [SMILES: Cc1c(NC(=O)c2cccc(C#N)c2)cnc2c1c([C@@H]1C[C@H]3CC[C@@H]1CN3C(=O)C1CCCC1)cn2C]

Step 1. tert-butyl 5-(((trifluoromethyl)sulfonyl)oxy)-2-azabicyclo[2.2.2]oct-5-ene-2-carboxylate. A solution of 1,1,1-trifluoro-N-phenyl-N-((trifluoromethyl)sulfonyl)methanesulfonamide (1.44 g, 4.05 mmol) in THF (5 mL) was added to a solution of tert-butyl 5-oxo-2-azabicyclo[2.2.2]octane-2-carboxylate (760 mg, 3.37 mmol) in THF (15 mL) chilled to −78 C. The resulting mixture was warmed to room temperature and stirred over the course of 2 h. The mixture was then concentrated, brought up in DCM, and to this mixture was added aq NaHCO$_3$. The layers were separated and the aqueous layer was then washed three times with DCM. The combined organic layers were concentrated under reduced pressure and purified by silica gel column chromatography (heptane:EtOAc, 100:0-90:10) to give 1.07 g (89%) of the title compound as a colorless oil. $^1$H NMR (400 MHz, CDCl$_3$) δ 6.60-6.25 (m, 1H), 5.00-4.50 (m, 1H), 3.40-3.25 (m, 2H), 3.00-2.75 (m, 1H), 2.10-2.00 (m, 1H), 1.75-1.65 (m, 2H), 1.55-1.45 (m, 11H).

Step 2: tert-butyl 5-(1,4-dimethyl-5-nitro-1H-pyrrolo[2,3-b]pyridin-3-yl)-2-azabicyclo[2.2.2]oct-5-ene-2-carboxylate. To a microwave vessel charged with tert-butyl 5-(((trifluoromethyl)sulfonyl)oxy)-2-azabicyclo[2.2.2]oct-5-ene-2-carboxylate (500 mg, 1.40 mmol) was added sequentially 1,4-dimethyl-5-nitro-3-(4,4,5,5-tetramethyl-1,3,2-dioxaborolan-2-yl)-1H-pyrrolo[2,3-b]pyridine (prepared as in Example 58, step 1) (665 mg, 2.10 mmol), palladium tetrakis(triphenylphosphine) (161 mg, 0.14 mmol), potassium phosphate (891 mg, 4.20 mmol), and p-dioxane (10 mL). The mixture was then bubbled with argon and the vessel was then equipped with a stirbar and sealed and heated to 120° C. in a microwave for 30 minutes. After allowing to cool, the mixture was filtered through a pad of Celite® and the pad was washed with DCM. The organic filtrates were then washed with 1N HCl followed by water and then concentrated under reduced pressure. The crude residue was then purified by silica gel column chromatography (heptane:EtOAc, 80:20-50:50) to give 398 mg (87%) of the title compound as a brown solid. $^1$H NMR (400 MHz, CDCl$_3$) δ 8.95 (s, 1H), 7.30-7.10 (m, 1H), 6.55-6.45 (m, 1H), 4.95-4.60 (m, 1H), 3.97 (s, 3H), 3.47-3.40 (m, 1H), 3.39-3.20 (m, 1H), 2.99-2.90 (m, 1H), 2.85 (s, 3H), 2.20-2.10 (m, 1H), 1.80-1.30 (m, 12H).

Step 3: tert-butyl 5-(5-amino-1,4-dimethyl-1H-pyrrolo[2,3-b]pyridin-3-yl)-2-azabicyclo[2.2.2]octane-2-carboxylate. To a microwave vessel charged with tert-butyl 5-(1,4-dimethyl-5-nitro-1H-pyrrolo[2,3-b]pyridin-3-yl)-2-azabicyclo[2.2.2]oct-5-ene-2-carboxylate was added ammonium formate (917 mg, 14.5 mmol) and 20% palladium hydroxide on carbon (240 mg). The mixture was suspended in ethanol:water (3:1, 15 mL) and heated to 90° C. for 1 h. The mixture was then filtered through a pad of Celite® and the filtrate was concentrated to give 449 mg (90%) of the title compound.

Step 4: N-(3-(2-azabicyclo[2.2.2]octan-5-yl)-1,4-dimethyl-1H-pyrrolo[2,3-b]pyridin-5-yl)-3-cyanobenzamide. 3-Cyanobenzoyl chloride (344 mg, 2.08 mmol) and pyridine (10 mL) were added to a round-bottomed flask charged with tert-butyl 5-(5-amino-1,4-dimethyl-1H-pyrrolo[2,3-b]pyridin-3-yl)-2-azabicyclo[2.2.2]octane-2-carboxylate (514 mg, 1.39 mmol). The mixture was allowed to stir at 0° C. for 24 h and then was concentrated under reduced pressure. The crude residue was brought up in 1N HCl and extracted with DCM. The organic layer was concentrated and the crude residue was purified by silica gel column chromatography (heptane:EtOAc, 50:50). The concentrated major fraction was treated with DCM:TFA (9:1, 10 mL) and allowed to stir for 1 h. The mixture was concentrated under reduced pressure and treated with 1N NaOH and MeOH until the pH~8. The mixture was extracted with DCM and concentrated to give 399 mg (44%) of the title compound.

Step 5: 3-cyano-N-(3-(2-(cyclopentanecarbonyl)-2-azabicyclo[2.2.2]octan-5-yl)-1,4-dimethyl-1H-pyrrolo[2,3-b]pyridin-5-yl)benzamide. Cyclopentanoyl chloride (66.8 mg, 0.5 mmol) and pyridine (3 mL) were added to a round-bottomed flask charged with N-(3-(2-azabicyclo[2.2.2]octan-5-yl)-1,4-dimethyl-1H-pyrrolo[2,3-b]pyridin-5-yl)-3-cyanobenzamide (100 mg, 0.25 mmol). The mixture was stirred at 0° C. for 1 h, and then was concentrated under reduced pressure. The crude residue was then brought up in 1N HCl and extracted with DCM. The organic layer was concentrated and the crude product was purified by HPLC to provide 50 mg (40%) of the title compound as a mixture of diastereomers. LCMS m/z [M+H]=496.3. $^1$H NMR (400 MHz, CDCl$_3$) δ 8.40-8.35 (m, 1H), 8.34-8.28 (m, 1H), 8.12 (s, 1H), 8.00-7.95 (m, 1H), 7.80-7.70 (m, 1H), 7.50-7.40 (m, 1H), 4.60-4.15 (m, 1H), 3.95-3.65 (m, 5H),

Example 101

Assay of Co-Activator Recruitment by TR-FRET

The activity of compound of the invention can be determined by a co-activator recruitment by TR-FRET (time-resolved fluorescence resonance energy transfer) assay. In general, the assay is based on the interaction between N-terminally Six-Histidine-tagged-RORC2 ligand binding domain (6-His-RORC2 LBD), expressed in *E. coli* and purified by affinity chromatography, and biotin-coactivator peptide SRC1-2 (biotin-aminohexanoic acid-CPSSHSS-LTERHKILHRLLQEGSPS-NH$_2$; SEQ ID NO: 1) containing the LXXLL (SEQ ID NO: 2) consensus domain which is responsible for receptor binding. This interaction is detected by addition of Europium labeled-anti-His antibody (Ex. 337 nm, Em. 620 nm, which binds to 6His) and Streptavidin-APC (Ex. 620 nm, Em. 665 nm, which binds to biotin). When receptor and coactivator are bound to each other, upon shining light at 337 nm on the sample, the Europium emits fluorescence that excites APC due to close proximity (FRET) and this signal is measured at 665 nm. Due to the long lasting fluorescence emission of Europium, the non-specific, short-lived fluorescence is time-resolved (TR) from the fluorescence of interest. Inhibitors of the interaction of receptor and coactivator peptide are detected by a decrease in TR-FRET signal.

Specifically, in one embodiment the aforementioned assay was performed as outlined below. The assay was carried out in black polystyrene, 384-well plates in a total assay volume of 50.5 µL. The assay buffer contained 50 mM TRIS-HCL pH 7.5, 1 mM NaCl, 2 mM $MgCl_2$, 0.5 mg/mL bovine serum albumin, and 5 mM dithiothreitol. The final concentration of reagents was 6.3 nM RORC2 LBD, 200 nM SRC1-2, 50 nM streptavidin APC, 1 nM Europium-labeled anti-His antibody, and varying concentrations of compounds such that final concentration of DMSO is 1% (v/v). The assay steps were: (1) dispensing 500 µL compound at 100× final concentration in DMSO (test wells) or DMSO only (control wells for no inhibition); and (2) dispensing 50 µL mixture of the other assay components including receptor (test wells) or excluding receptor (control wells for maximal inhibition).

Assay mixtures were incubated are room temperature for 3 hr and read in EnVision 2100 Multilabel Reader (PerkinElmer Life Sciences) at Excitation Filter 320, Emission Europium Filter 615, Emission APC Filter 665, Dichroic Mirror D400/D630.

TR-FRET signal was determined by calculating the ratio of 665 nm by 615 nm and $IC_{50}$ values of compounds of the invention (Table 1) were determined by the non-linear regression analysis of dose response curves.

References which relate to the above-referenced assay include: Kallen et al. Structure, 2002, 10, 1697-1707; Stehlin et al. EMBO J 2001, 20, 5822-5831; and Zhou et al. Mol Endocrinol 1998, 12, 1594-1604.

TABLE 1

| Example | $IC_{50}$ (nM) |
|---|---|
| 1 | 7.1 |
| 2 | 4.0 |
| 3 | 3.2 |
| 4 | 8.5 |
| 5 | 16.6 |
| 6 | 5.7 |
| 7 | 4.9 |
| 8 | 5.4 |
| 9 | 5.4 |
| 10 | 3.5 |
| 11 | 1.5 |
| 12 | 11.8 |
| 13 | 5.0 |
| 14 | 5.6 |
| 15 | 3.9 |
| 16 | 10.2 |
| 17 | 5.3 |
| 18 | 3.8 |
| 19 | 8.8 |
| 20 | 5.2 |
| 21 | 5.0 |
| 22 | 2.7 |
| 23 | 4.7 |
| 24 | 5.8 |
| 25 | 5.8 |
| 26 | 6.6 |
| 27 | 6.4 |
| 28 | 7.1 |
| 29 | 0.9 |
| 30 | 2.8 |
| 31 | 5.6 |
| 32 | 19.4 |
| 33 | 18.0 |
| 34 | 5.7 |
| 35 | 7.2 |
| 36 | 4.5 |
| 37 | 11.6 |
| 38 | 7.7 |
| 39 | 9.3 |
| 40 | 7.6 |
| 41 | 4.5 |
| 42 | 7.6 |
| 43 | 13.5 |
| 44 | 40.7 |
| 45 | 13.5 |
| 46 | 16.4 |
| 47 | 10.1 |
| 48 | ND |
| 49 | 6.2 |
| 50 | 7.5 |
| 51 | 6.9 |
| 52 | 13.7 |
| 53 | 8.5 |
| 54 | 4.7 |
| 55 | 10.6 |
| 56 | 5.6 |
| 57 | 11.7 |
| 58 | 15.0 |
| 59 | 11.8 |
| 60 | 15.4 |
| 61 | 15.2 |
| 62 | 9.7 |
| 63 | 12.9 |
| 64 | 41.8 |
| 65 | 5.7 |
| 66 | 7.4 |
| 67 | 8.7 |
| 68 | 9.7 |
| 69 | 10.2 |
| 70 | 5.6 |
| 71 | 9.8 |
| 72 | 15.3 |
| 73 | 22.6 |
| 74 | 6.2 |
| 75 | 7.3 |
| 76 | 7.5 |
| 77 | 5.2 |
| 78 | 2.1 |
| 79 | 39.1 |
| 80 | 4.3 |
| 81 | 1.2 |
| 82 | 5.1 |
| 83 | 28.8 |
| 84 | 14.4 |
| 85 | 40.9 |
| 86 | 16.0 |
| 87 | 15.0 |
| 88 | 26.0 |
| 89 | 31.0 |
| 90 | 21.2 |
| 91 | 26.9 |
| 92 | 16.5 |
| 93 | 32.9 |
| 94 | 39.4 |
| 95 | 2.7 |
| 96 | 24.3 |
| 97 | 18.6 |
| 98 | 102 |
| 99 | 21.1 |
| 100 | 23.0 |
| 109 | 26.8 |
| 110 | 9.5 |
| 111 | 18.4 |
| 112 | 25.1 |
| 113 | 20.2 |

ND = not determined

Example 102

Assay of Gal4-RORC2 Activity by Luciferase Reporter

The activity of compound of the invention can be also be determined by a luciferase reporter Gal4-RORC2 activity assay. In general, Neuro2A cells (murine neuroblastoma cell line obtained from HPACC, cat #89121404) are transiently transfected with a mammalian expression vector (pM) containing Gal4-RORC2 LBD and a Gal4-responsive reporter gene containing firefly luciferase (5×GAL4UAS-Luc3). Gal4-RORC2 LBD is constitutively active in the transfected Neuro2a cells, resulting in a robust luciferase response in the absence of stimulation. Upon treatment with an RORC2 inhibitor the transcriptional response is decreased and the magnitude of the decrease in response is dose-dependently related to the intrinsic efficacy of the inhibitor.

Specifically, the growth medium was composed by MEM EBS w/o L-glutamine, 10% (v/v) FBS, 2 mM L-glutamine and 1× non-essential aminoacid (NEAA); the seeding medium was composed by MEM EBS w/o L-glutamine, w/o phenol red, 4% (v/v) FBS, 2 mM L-glutamine, 1×NEAA, 1% Penicillin (10,000 U/mL)/Streptomycin (10,000 µg/mL); and the assay medium was composed by MEM EBS w/o L-glutamine, w/o phenol red, 4% (v/v) FBS, 2 mM L-glutamine, 1×NEAA, 1% Penicillin (10,000 U/mL)/Streptomycin (10,000 µg/mL). In addition, Neuro2A cells were cultured in growth medium in humidified chambers at 37° C. and 5% $CO_2$ using standard tissue culture procedures.

On day one of the assay, cells were seeded and transfected. Specifically, Neuro2A cells were suspended in seeding medium and mixed with plasmids and transfection reagent which was dissolved in OptiMEM I reduced serum medium (InVitrogen), and then seeded to 384-well plates (Corning, Black, Clear bottom) in 40 µL/well containing 12,500 cells, 17.25 ng Gal4-Luc3, 5.75 ng either empty pM vector (no receptor control' wells) or pM-Gal4RORgamma-LBD, and 0.11 µL Lipofectamine2000.

On day two of the assay, the cells were treated with compounds of the invention. Specifically, the treatment was started 20-24 hr after seeding and transfection of the cells. Compounds of the invention were serially diluted in a 384-well polypropylene plate with assay medium containing 0.5% (v/v) DMSO at 5× final assay concentration. 10 µL of the compounds (or 0.5% DMSO in assay medium for 'no compound control' wells) were transferred from the dilution plate to the 384-format cell plate such that final assay volume was 50 µL and final DMSO concentration was 0.1% (v/v), followed by incubation for 20-24 hr in humidified chambers at 37° C. and 5% $CO_2$.

On day three of the assay, luminescence was measured and the results analyzed. Specifically, 10 µL of SteadyLite Plus reagent (Perkin Elmer) was added to each well. The cell plates were incubated at room temperature for 15 min in the dark before reading of luminescence on the MicroBeta Trilux (Wallac). $IC_{50}$ values of the compounds tested were determined by the non-linear regression analysis of dose response curves.

References which relate to the above-referenced assay include: Stehlin-Gaon et al. Nature Structural Biology 2003, 10, 820-825; Wang et al. J Biol Chem. 2010, 285(7), 5013-5025; Kumar et al. Mol Pharmacol. 2010, 77(2), 228-36.

Example 103

Assay of IL-17 Production from Human Th17 Cells

The activity of compound of the invention can be also be determined by an IL-17 production from human Th17 cells assay. In general, this assay measures blockade of IL-17 production, the signature cytokine of T helper 17 (Th17) cells, by compounds. Purified human CD4+ T cells are stimulated with anti-CD3+ anti-CD28 and incubated with a cytokine cocktail that induce their differentiation into Th17 in the absence or presence of various concentrations of compound. After 6 days, IL-17A concentration is measured in the cell culture supernatant with an ELISA kit (MSD).

Preparation of human CD4+ T cells. CD4+ T cells were purified from buffy coats from healthy donors (obtained from Massachusetts General Hospital) by negative selection the following procedure: Mixing 25 mL of blood with 1 mL of Rosette Sep CD4+ T cell enrichment cocktail (StemCell Technologies) followed by application of a layer of 14 mL Ficoll Paque Plus (Amersham GE Healthcare) and subsequent centrifugation at 1200 g for 20 min at room temperature. The Ficoll layer was then harvested and washed with phosphate saline buffer containing 2% (v/v) fetal bovine serum and cells were resuspended with RPMI medium containing 10% (v/v) fetal bovine serum and 10% (v/v) DMSO, frozen and kept in LN2 until used.

On the first day of the assay, a vial containing $10^7$ CD4+ T cells is thawed rapidly in 37° C. water bath, immediately transferred into 20 mL X-Vivo 15 medium (Lonza), is spun for 6 min at 300×g, the supernatant is discarded, and the resulting pellet is re-suspended at $10^6$ cells/mL in 50 mL fresh X-Vivo 15 medium, followed by storage overnight in a tissue culture vessel in a humidified chamber at 37° C. and 5% $CO_2$. Serial dilutions of compounds of the invention are prepared at 10× final concentration in X-Vivo15 medium containing 3% (v/v) DMSO.

On the second day of the assay, a 384-well tissue culture plate was coated with 10 µg/mL anti-hCD3 (eBioscience) at 50 µL/well. After 2 hr at 37° C., the supernatant is discarded and the coated plates are kept in a sterile tissue culture hood.

Cytokine plus anti-CD28 cocktail is prepared by mixing 25 ng/mL hI L-6 (Peprotech), 5 ng/mL hTGFbeta1 (Peprotech), 12.5 ng/mL IL-1beta (Peprotech), 25 ng/mL hI L-21, 25 ng/mL hIL-23 (R&D Systems), and 1 ug/mL anti-hCD28 (eBioscience) in X-Vivo 15 medium. The cytokine plus anti-CD28 cocktail with CD4+ cells is prepared such that the cocktail is diluted 10-fold and cell density is $0.22 \times 10^6$/mL. The mixture is incubated 1 hr at 37° C.

90 µL (20,000 cells) dispensed per well in the anti-hCD3 coated plate prepared as noted above.

10 µL 10× compound is added per well (final DMSO=0.3%) from the compound plate that was previously prepared, followed by 6 days of incubation in a tissue culture vessel in a humidified chamber at 37° C. and 5% $CO_2$.

On day six of the assay, production of IL-17A in 10 µL of the supernatant is determined by sandwich ELISA using 384 w hIL17 MSD plates following the manufacturer's protocol. Measurement is carried out in a Sector Imager 6000 by the same manufacturer. Signal units from the instrument are converted to pg/mL using a calibration curve with known amounts of IL-17A. $IC_{50}$ values of test compounds (Table 2) are determined by the non-linear regression analysis of dose response curves.

A reference which relates to the above-referenced assay is: Yang et al. Nature 2008, 454, 350-352.

TABLE 2

| Example | $IC_{50}$ (nM) |
| --- | --- |
| 1 | 11.8 |
| 2 | 15.2 |
| 3 | 39.2 |
| 4 | 3.5 |
| 5 | 9.5 |

TABLE 2-continued

| Example | IC$_{50}$ (nM) |
|---|---|
| 6 | 5.0 |
| 7 | 6.2 |
| 8 | 14.4 |
| 9 | 27.5 |
| 10 | 51.3 |
| 11 | 7.8 |
| 12 | 57.9 |
| 13 | 48.7 |
| 14 | 8.7 |
| 15 | 9.9 |
| 16 | 10.7 |
| 17 | 10.7 |
| 18 | 10.8 |
| 19 | 12.6 |
| 20 | 18.5 |
| 21 | 3.4 |
| 22 | 5.9 |
| 23 | 9.4 |
| 24 | 17.4 |
| 25 | 14.1 |
| 26 | 7.7 |
| 27 | 8.4 |
| 28 | 118 |
| 29 | 8.5 |
| 30 | 3.9 |
| 31 | 4.7 |
| 32 | 3.4 |
| 33 | 13.7 |
| 34 | 9.5 |
| 35 | 14.3 |
| 36 | 6.6 |
| 37 | 9.2 |
| 38 | 11.0 |
| 39 | 11.2 |
| 40 | 7.9 |
| 41 | 18.9 |
| 42 | 31.3 |
| 43 | 6.4 |
| 44 | 17.1 |
| 45 | 16.0 |
| 46 | 57.4 |
| 47 | 8.4 |
| 48 | 13.4 |
| 49 | 8.0 |
| 50 | 3.4 |
| 51 | 6.4 |
| 52 | 12.0 |
| 53 | 121.4 |
| 54 | 5.0 |
| 55 | 6.0 |
| 56 | 4.9 |
| 57 | 36.4 |
| 58 | 9.3 |
| 59 | 9.9 |
| 60 | 15.0 |
| 61 | 25.6 |
| 62 | 15.8 |
| 63 | 12.0 |
| 64 | 10.2 |
| 65 | 10.7 |
| 66 | 13.4 |
| 67 | 4.2 |
| 68 | 5.3 |
| 69 | 11.4 |
| 70 | 3.5 |
| 71 | 4.8 |
| 72 | 4.8 |
| 73 | 25.3 |
| 74 | 3.6 |
| 75 | 6.8 |
| 76 | 5.0 |
| 77 | 8.9 |
| 78 | 4.0 |
| 79 | 4.1 |
| 80 | 9.3 |
| 81 | 3.3 |
| 82 | 5.7 |
| 83 | 70.5 |
| 84 | 6.0 |
| 85 | 15.5 |
| 86 | 34.9 |
| 87 | 12.6 |
| 88 | 19.0 |
| 89 | 16.6 |
| 90 | 12.2 |
| 91 | 16.2 |
| 92 | 22.3 |
| 93 | 13.4 |
| 94 | 22.8 |
| 95 | 5.7 |
| 96 | 46.0 |
| 97 | 123.8 |
| 98 | 276 |
| 99 | 14.7 |
| 100 | 10.4 |
| 109 | 32.1 |
| 110 | 24.7 |
| 111 | 24.2 |
| 112 | 36.0 |
| 113 | 29.8 |

Example 104

Inhibition of Superantigen-Induced Th17 Cytokine Production

Exotoxins called "superantigens" are among the most powerful T cell activators. Superantigens bind to the cell surface of major histocompatibilty complex (MHC) molecules, without intracellular processing. They stimulate T cells via the T cell receptor, irrespective of the antigen specificities. Therefore, bacterial superantigens are able to activate a large pool of CD4+ as well as CD8+ T cells in contrast to the low T cell frequency for conventional antigens. CD4+ T cells can be classified into various subsets (Th0, Th1, Th2, Th17) based on their respective cytokine secretion profiles. Th0 cells are uncommitted naïve precursor cells that primarily produce IL-2 upon stimulation. Th0 cells upon activation can differentiate into Th1, Th2, or the Th17 subset depending on the local cytokine milieu. Th1 cells mainly produce Inf-γ; Th2 cells, IL-4, IL-5, and IL-13, and Th17 cells, IL-17, and IL-22. During a classical immune response, the differentiation of T helper subset occurs over days, or longer. In the superantigen in-vivo model in mice injection of superantigen triggers a rapid transcription and translation of the various cytokines (i.e. IL-2, IL-4, Inf-γ, IL-17) of the different Th subsets after only 6 hr. A RORγt inhibitor given to animals prior to the superantigen stimulus would impair the Th17 cytokine profile without affecting the cytokine profile of the other Th subsets (Th0, Th1, Th2). The model uses approximately 8 week old C57BL/6, Balb/c, or C3H/HeJ mice which are dosed orally with compound 1 to 2 hr prior to superantigen injection on the day of the experiment (Day 0) based on the pharmacokinetic (PK) profile of the compound. An optional dose may be given the day before superantigen injection (Day −1) to further inhibit the response if necessary. C57BL/6 and Balb/c mice will be sensitized 1 hr prior to supernatigen injection with approximately 25 mg/mouse D-Galactosamine intraperitoneally (C3H/HeJ mice do not need to be sensitized). Based on the literature superantigen is typically given at 10 μg/mouse intraperitoneally. Mice will be sacrificed at 3 hr for RNA analysis or up to 6 hr for cytokine analysis.

A reference which relates to the above-referenced assay is: Rajagopalan, G. et. al. Physiol Genomics 2009, 37, 279.

Example 105

Imiquimod Assay

Commercially available 5% imiquimod (IMQ) cream (3M Pharmaceuticals) is applied to the back and right ear of each experimental mouse for two consecutive days. Control mice are treated similarly with a commercially available vehicle cream. The experimental mice are then administered with RORγt inhibitors, and the control mice with vehicle, for 4 days. The ear thickness is measured on all days by digital micrometer (Mitutoyo). Tissues, such as ears and speens, are harvested on Day 5 for RNA analysis. Ear swelling and serum measurements are also made.

References describing aspects of this assay include: Van der Fits, L. et al. J. Immunol. 2009, 182(9), 5836-45; Van Belle, A. B. et al. J Immunol. 2012, 188(1), 462-9; Cai, Y. et al. Immunity 2011, 35(4), 596-610; Fanti, P. A. et al. Int. J. Dermatol. 2006, 45(12), 1464-5; Swindell, W. R. et al. PLoS One 2011, 6(4), e18266; and Roller, A. et al. J. Immunol. 2012, 189(9), 4612-20.

Example 106

IL-23 Injection Model of Mouse Skin Inflammation

Ears from BALB/c mice were each injected intra-dermally every other day with 150 ng of mouse recombinant IL-23 (eBiosciences) or PBS in a total volume of 25 μl. Ear swelling was measured in triplicate using a micrometer (Mitutoyo) right before each IL-23 challenge. On Day 14, mice were euthanized and ears were collected for measurement of cytokine levels, gene expression levels and hystopathological evaluation. Mice were administered 3-100 mg/kg of an RORC2 modulator or vehicle once daily orally for the duration of the study. Alternatively, the RORC2 modulator was applied topically once or twice daily using a standard formulation (EtOH:propylene glycol:dimethyl isosorbide: DMSO, 38:30:15:15) at a concentration of 0.1% to 5.0%.

References describing aspects of this assay include: Muramoto, K. et al. J. Pharmacol. Exp. Ther. 2010, 335(1), 23-31; Fridman, J. S. et al. J. Invest. Dermatol. 2011, 131(9), 1838-1844.

Example 107

Single Crystal X-Ray Analysis of 1-{(8-anti)-[5-amino-1-methyl-4-(trifluoromethyl)-1H-pyrrolo[2,3-b]pyridin-3-yl]-3-azabicyclo[3.2.1]oct-3-yl}-2-methylpropan-1-one 1-{(8-anti)-[5-amino-1-methyl-4-(trifluoromethyl)-1H-pyrrolo[2, 3-b]pyridin-3-yl]-3-azabicyclo[3.2.1]oct-3-yl}-2-methylpropan-1-one is the product of step 11 of Example 56. A crystal suitable for X-ray analysis was prepared by recrystallization from ethyl acetate.

Data collection was performed on a Bruker APEX diffractometer at room temperature. Data collection consisted of omega and psi scans.

The structure was solved by direct methods using SHELX software suite in the space group $P2_{1/n}$. The structure was subsequently refined by the full-matrix least squares method. All non-hydrogen atoms were found and refined using anisotropic displacement parameters.

The hydrogen atoms located on nitrogen was found from the Fourier difference map and refined with distances restrained. The remaining hydrogen atoms were placed in calculated positions and were allowed to ride on their carrier atoms. The final refinement included isotropic displacement parameters for all hydrogen atoms.

The final R-index was 6.6%. A final difference Fourier revealed no missing or misplaced electron density.

FIG. 1 is an ORTEP Drawing of 1-{(8-anti)-[5-amino-1-methyl-4-(trifluoromethyl)-1H-pyrrolo[2,3-b]pyridin-3-yl]-3-azabicyclo[3.2.1]oct-3-yl}-2-methylpropan-1-one. Pertinent crystal, data collection and refinement are summarized in Table 3. Atomic coordinates, bond lengths, bond angles, torsion angles and displacement parameters are listed in Tables 4-7.

TABLE 3

Crystal data and structure refinement for 1-{(8-anti)-[5-amino-1-methyl-4-(trifluoromethyl)-1H-pyrrolo[2,3-b]pyridin-3-yl]-3-azabicyclo[3.2.1]oct-3-yl}-2-methylpropan-1-one.

| | |
|---|---|
| Crystallization | EtOAc |
| Empirical Formula | C20 H25 F3 N4 O |
| Formula weight | 394.44 |
| Temperature | 296(2) K |
| Wavelength | 1.54178 Å |
| Crystal system | Monoclinic |
| Space group | P2(1)/n |
| Unit cell dimensions | a = 12.2804(3) Å; α = 900. |
| | b = 10.7277(3) Å; β = 101.714(2)°. |
| | c = 14.7594(4) Å; γ = 90°. |
| Volume | 1903.91(9) Å$^3$ |
| Z | 4 |
| Density (calculated) | 1.376 Mg/m$^3$ |
| Absorption coefficient | 0.904 mm$^{-1}$ |
| F(000) | 832 |
| Crystal size | 0.18 × 0.16 × 0.04 mm$^3$ |
| Theta range for data collection | 4.28 to 54.22°. |
| Index ranges | −11 <= h <= 12, −10 <= k <= 11, −14 <= l <= 11 |
| Reflections collected | 6183 |
| Independent reflections | 1992 [R(int) = 0.0573] |
| Completeness to theta = 54.22° | 86.1% |
| Absorption correction | Empirical |
| Max. and min. transmission | 0.9647 and 0.8542 |
| Refinement method | Full-matrix least-squares on F$^2$ |
| Data/restraints/parameters | 1992/2/265 |
| Goodness-of-fit on F$^2$ | 1.185 |
| Final R indices [I > 2sigma(I)] | R1 = 0.0661, wR2 = 0.1767 |
| R indices (all data) | R1 = 0.0912, wR2 = 0.2093 |
| Extinction coefficient | 0.0038(7) |
| Largest diff. peak and hole | 0.266 and −0.310 e · Å$^{-3}$ |

TABLE 4

Atomic coordinates (×10$^4$) and equivalent isotropic displacement parameters (Å$^2$ × 10$^3$) for 1-{(8-anti)-[5-amino-1-methyl-4-(trifluoromethyl)-1H-pyrrolo[2,3-b]pyridin-3-yl]-3-azabicyclo[3.2.1]oct-3-yl}-2-methylpropan-1-one. U(eq) is defined as one third of the trace of the orthogonalized U$^{ij}$ tensor.

| | x | y | z | U(eq) |
|---|---|---|---|---|
| C(1) | 2026(4) | −1414(6) | 114(3) | 62(2) |
| C(2) | 2266(4) | −2663(6) | 418(3) | 67(2) |
| C(3) | 1526(5) | −3574(7) | 26(4) | 75(2) |
| C(4) | 544(5) | −3232(8) | −596(4) | 83(2) |
| C(5) | 1026(4) | −1236(6) | −544(3) | 64(2) |
| C(6) | 3309(5) | −2950(7) | 1082(4) | 77(2) |
| C(7) | 1809(4) | 614(6) | −293(3) | 62(2) |
| C(8) | 2525(4) | −182(5) | 264(3) | 58(2) |
| C(9) | −20(4) | 541(6) | −1438(3) | 79(2) |

TABLE 4-continued

Atomic coordinates (×10⁴) and equivalent isotropic displacement parameters (Å² × 10³) for 1-{(8-anti)-[5-amino-1-methyl-4-(trifluoromethyl)-1H-pyrrolo[2,3-b]pyridin-3-yl]-3-azabicyclo[3.2.1]oct-3-yl}-2-methylpropan-1-one. U(eq) is defined as one third of the trace of the orthogonalized $U^{ij}$ tensor.

| | x | y | z | U(eq) |
|---|---|---|---|---|
| C(10) | 3606(4) | 206(5) | 904(3) | 60(2) |
| C(11) | 3489(4) | 677(6) | 1859(3) | 65(2) |
| C(12) | 4629(4) | 672(6) | 2500(3) | 67(2) |
| C(13) | 5410(4) | 1297(6) | 1122(3) | 63(2) |
| C(14) | 4210(4) | 1324(6) | 591(3) | 60(2) |
| C(15) | 3617(5) | 2463(7) | 877(4) | 81(2) |
| C(16) | 3072(5) | 2007(7) | 1658(4) | 85(2) |
| C(17) | 6402(4) | 1731(5) | 2726(4) | 63(2) |
| C(18) | 7343(4) | 2286(6) | 2340(3) | 70(2) |
| C(19) | 8456(4) | 2140(7) | 3013(4) | 97(2) |
| C(20) | 7118(5) | 3659(7) | 2119(4) | 94(2) |
| F(1) | 4207(3) | −2855(4) | 709(2) | 105(1) |
| F(2) | 3498(3) | −2182(3) | 1811(2) | 91(1) |
| F(3) | 3344(3) | −4078(4) | 1467(3) | 116(2) |
| N(1) | 1645(5) | −4865(6) | 225(4) | 100(1) |
| N(2) | 281(4) | −2101(6) | −900(3) | 78(2) |
| N(3) | 907(3) | −3(5) | −782(3) | 67(1) |
| N(4) | 5468(3) | 1358(4) | 2124(2) | 60(1) |
| O(1) | 6462(3) | 1642(4) | 3571(2) | 76(1) |

TABLE 5

Bond lengths [Å] and angles [°] for 1-{(8-anti)-[5-amino-1-methyl-4-(trifluoromethyl)-1H-pyrrolo[2,3-b]pyridin-3-yl]-3-azabicyclo[3.2.1]oct-3-yl}-2-methylpropan-1-one.

| | |
|---|---|
| C(1)—C(5) | 1.415(6) |
| C(1)—C(2) | 1.425(8) |
| C(1)—C(8) | 1.455(8) |
| C(2)—C(3) | 1.379(8) |
| C(2)—C(6) | 1.479(7) |
| C(3)—C(4) | 1.408(8) |
| C(3)—N(1) | 1.417(8) |
| C(4)—N(2) | 1.311(8) |
| C(5)—N(2) | 1.335(7) |
| C(5)—N(3) | 1.368(7) |
| C(6)—F(1) | 1.332(7) |
| C(6)—F(3) | 1.334(7) |
| C(6)—F(2) | 1.338(7) |
| N(2)—C(4)—C(3) | 125.7(6) |
| N(2)—C(5)—N(3) | 122.8(5) |
| N(2)—C(5)—C(1) | 127.3(6) |
| N(3)—C(5)—C(1) | 109.9(5) |
| F(1)—C(6)—F(3) | 106.8(6) |
| F(1)—C(6)—F(2) | 105.2(5) |
| F(3)—C(6)—F(2) | 103.3(5) |
| F(1)—C(6)—C(2) | 112.9(5) |
| F(3)—C(6)—C(2) | 114.8(5) |
| F(2)—C(6)—C(2) | 113.0(5) |
| N(3)—C(7)—C(8) | 111.5(5) |
| C(7)—C(8)—C(1) | 106.0(4) |
| C(7)—C(8)—C(10) | 125.0(5) |
| C(7)—N(3) | 1.365(6) |
| C(7)—C(8) | 1.373(7) |
| C(8)—C(10) | 1.522(6) |
| C(9)—N(3) | 1.458(6) |
| C(10)—C(14) | 1.531(7) |
| C(10)—C(11) | 1.531(7) |
| C(11)—C(12) | 1.522(6) |
| C(11)—C(16) | 1.524(8) |
| C(12)—N(4) | 1.465(6) |
| C(13)—N(4) | 1.468(6) |
| C(13)—C(14) | 1.522(6) |
| C(14)—C(15) | 1.525(7) |
| C(15)—C(16) | 1.528(8) |
| C(17)—O(1) | 1.237(6) |
| C(17)—N(4) | 1.360(6) |
| C(17)—C(18) | 1.512(8) |
| C(18)—C(20) | 1.522(9) |

TABLE 5-continued

Bond lengths [Å] and angles [°] for 1-{(8-anti)-[5-amino-1-methyl-4-(trifluoromethyl)-1H-pyrrolo[2,3-b]pyridin-3-yl]-3-azabicyclo[3.2.1]oct-3-yl}-2-methylpropan-1-one.

| | |
|---|---|
| C(18)—C(19) | 1.526(6) |
| C(5)—C(1)—C(2) | 116.0(5) |
| C(5)—C(1)—C(8) | 105.1(5) |
| C(2)—C(1)—C(8) | 138.8(4) |
| C(3)—C(2)—C(1) | 117.3(5) |
| C(3)—C(2)—C(6) | 122.6(6) |
| C(1)—C(2)—C(6) | 120.0(5) |
| C(1)—C(8)—C(10) | 129.0(5) |
| C(8)—C(10)—C(14) | 116.2(4) |
| C(8)—C(10)—C(11) | 115.4(4) |
| C(14)—C(10)—C(11) | 99.2(4) |
| C(12)—C(11)—C(16) | 110.8(5) |
| C(12)—C(11)—C(10) | 109.0(4) |
| C(16)—C(11)—C(10) | 102.8(4) |
| N(4)—C(12)—C(11) | 113.0(4) |
| N(4)—C(13)—C(14) | 111.2(4) |
| C(13)—C(14)—C(15) | 109.9(4) |
| C(13)—C(14)—C(10) | 107.9(4) |
| C(15)—C(14)—C(10) | 104.9(5) |
| C(14)—C(15)—C(16) | 105.0(5) |
| C(11)—C(16)—C(15) | 105.3(5) |
| C(1)—C(17)—N(4) | 120.4(5) |
| C(1)—C(17)—C(18) | 121.1(4) |
| N(4)—C(17)—C(18) | 118.5(4) |
| C(17)—C(18)—C(20) | 110.0(5) |
| C(17)—C(18)—C(19) | 111.4(5) |
| C(20)—C(18)—C(19) | 109.8(5) |
| C(4)—N(2)—C(5) | 114.0(5) |
| C(7)—N(3)—C(5) | 107.4(4) |
| C(7)—N(3)—C(9) | 126.6(5) |
| C(5)—N(3)—C(9) | 125.9(4) |
| C(2)—C(3)—C(4) | 119.5(7) |
| C(2)—C(3)—N(1) | 125.0(5) |
| C(4)—C(3)—N(1) | 115.4(6) |
| C(17)—N(4)—C(12) | 117.7(4) |
| C(17)—N(4)—C(13) | 122.3(4) |
| C(12)—N(4)—C(13) | 117.7(4) |

TABLE 6

Anisotropic displacement parameters (Å² × 10³) for 1-{(8-anti)-[5-amino-1-methyl-4-(trifluoromethyl)-1H-pyrrolo[2,3-b]pyridin-3-yl]-3-azabicyclo[3.2.1]oct-3-yl}-2-methylpropan-1-one. The anisotropic displacement factor exponent takes the form: $-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| C(1) | 27(3) | 122(5) | 35(3) | −7(3) | −4(2) | −6(3) |
| C(2) | 37(3) | 112(5) | 46(3) | −3(3) | −5(3) | −6(3) |
| C(3) | 55(4) | 112(5) | 56(3) | −8(3) | 6(3) | −3(4) |
| C(4) | 56(4) | 125(6) | 62(4) | −16(4) | 0(3) | −24(4) |
| C(5) | 33(3) | 111(5) | 43(3) | −5(3) | −2(2) | −3(3) |
| C(6) | 59(4) | 113(6) | 52(4) | 14(4) | −6(3) | −3(4) |
| C(7) | 34(3) | 100(4) | 48(3) | −4(3) | −6(3) | −7(3) |
| C(8) | 28(3) | 102(4) | 39(3) | −8(3) | −6(2) | −5(3) |
| C(9) | 38(3) | 132(5) | 56(3) | 5(3) | −14(3) | 4(3) |
| C(10) | 29(3) | 108(4) | 36(3) | 0(3) | −6(2) | −3(3) |
| C(11) | 36(3) | 111(5) | 44(3) | −4(3) | −2(2) | −14(3) |
| C(12) | 46(3) | 113(5) | 38(3) | −5(3) | −4(3) | −15(3) |
| C(13) | 36(3) | 114(5) | 35(3) | −5(3) | −6(2) | −13(3) |
| C(14) | 30(3) | 108(5) | 38(3) | −1(3) | −1(2) | −2(3) |
| C(15) | 47(3) | 125(6) | 62(4) | −7(4) | −11(3) | −5(4) |
| C(16) | 43(3) | 143(6) | 65(4) | −31(4) | −3(3) | −2(4) |
| C(17) | 32(3) | 103(4) | 47(3) | −9(3) | −10(3) | 1(3) |
| C(18) | 36(3) | 116(5) | 51(3) | −12(3) | −6(3) | −6(3) |
| C(19) | 44(3) | 154(6) | 79(4) | −11(4) | −16(3) | −17(4) |
| C(20) | 69(4) | 131(7) | 80(4) | 1(4) | 10(3) | −16(4) |
| F(1) | 44(2) | 186(4) | 82(2) | 17(2) | 1(2) | 15(2) |
| F(2) | 87(2) | 121(3) | 53(2) | 2(2) | −17(2) | −10(2) |
| F(3) | 112(3) | 116(3) | 99(3) | 29(2) | −30(2) | −12(2) |
| N(1) | 90(4) | 107(5) | 91(4) | −12(4) | −6(3) | −13(4) |
| N(2) | 40(3) | 135(5) | 51(3) | −13(3) | −9(2) | −21(3) |

TABLE 6-continued

Anisotropic displacement parameters ($Å^2 \times 10^3$) for
1-{(8-anti)-[5-amino-1-methyl-4-(trifluoromethyl)-1H-pyrrolo[2,3-
b]pyridin-3-yl]-3-azabicyclo[3.2.1]oct-3-yl}-2-methylpropan-1-one.
The anisotropic displacement factor exponent takes the form:
$-2\pi^2[h^2 a^{*2}U^{11} + \ldots + 2 h k a^* b^* U^{12}]$.

|      | $U^{11}$ | $U^{22}$ | $U^{33}$ | $U^{23}$ | $U^{13}$ | $U^{12}$ |
|------|----------|----------|----------|----------|----------|----------|
| N(3) | 31(2)    | 113(4)   | 48(3)    | 1(2)     | −15(2)   | 0(2)     |
| N(4) | 33(2)    | 107(4)   | 36(2)    | −4(2)    | −3(2)    | −11(2)   |
| O(1) | 57(2)    | 122(3)   | 39(2)    | −3(2)    | −15(2)   | −13(2)   |

TABLE 7

Hydrogen coordinates ($\times 10^4$) and isotropic displacement
parameters ($Å^2 \times 10^3$) for 1-{(8-anti)-[5-amino-
1-methyl-4-(trifluoromethyl)-1H-pyrrolo[2,3-b]pyridin-3-
yl]-3-azabicyclo[3.2.1]oct-3-yl}-2-methylpropan-1-one.

|        | x        | y        | z       | U(eq)   |
|--------|----------|----------|---------|---------|
| H(4)   | 39       | −3864    | −811    | 99      |
| H(7)   | 1925     | 1468     | −333    | 75      |
| H(9A)  | 84       | 402      | −2058   | 118     |
| H(9B)  | −51      | 1421     | −1328   | 118     |
| H(9C)  | −702     | 160      | −1362   | 118     |
| H(10)  | 4113     | −509     | 989     | 71      |
| H(11)  | 2955     | 175      | 2112    | 78      |
| H(12A) | 4566     | 1039     | 3088    | 81      |
| H(12B) | 4873     | −183     | 2616    | 81      |
| H(13A) | 5764     | 536      | 974     | 76      |
| H(13B) | 5811     | 1997     | 933     | 76      |
| H(14)  | 4170     | 1309     | −79     | 72      |
| H(15A) | 3061     | 2769     | 361     | 97      |
| H(15B) | 4143     | 3127     | 1091    | 97      |
| H(16A) | 3288     | 2527     | 2203    | 102     |
| H(16B) | 2268     | 2021     | 1468    | 102     |
| H(18)  | 7386     | 1849     | 1765    | 84      |
| H(19A) | 8447     | 2618     | 3562    | 145     |
| H(19B) | 9043     | 2433     | 2727    | 145     |
| H(19C) | 8576     | 1277     | 3175    | 145     |
| H(20A) | 6423     | 3745     | 1687    | 141     |
| H(20B) | 7706     | 3997     | 1854    | 141     |
| H(20C) | 7081     | 4102     | 2677    | 141     |
| H(99A) | 2370(40) | −5160(70)| 590(50) | 160(30) |
| H(99B) | 1280(50) | −5340(50)| −320(30)| 100(20) |

Software and References. SHELXTL, Version 5.1, Bruker AXS, 1997; PLATON, A. L. Spek, J. Appl. Cryst. 2003, 36, 7-13; MERCURY, C. F. Macrae, P. R. Edington, P. McCabe, E. Pidcock, G. P. Shields, R. Taylor, M. Towler and J. van de Streek, J. Appl. Cryst. 39, 453-457, 2006; OLEX2, Dolomanov, O. V.; Bourhis, L. J.; Gildea, R. J.; Howard, J. A. K.; Puschmann, H., (2009). J. Appl. Cryst., 42, 339-341; R. W. W. Hooft et al. J. Appl. Cryst. (2008). 41. 96-103; and H. D. Flack, Acta Cryst. 1983, A39, 867-881.

Example 108

Single Crystal X-Ray Analysis of (S)-tert-butyl 4-(5-amino-1-methyl-4-(trifluoromethyl)-1H-pyrrolo[2,3-b]pyridin-3-yl)-2,2-dimethylpiperidine-1-carboxylate (S)-tert-butyl 4-(5-amino-1-methyl-4-(trifluoromethyl)-1H-pyrrolo[2,3-b]pyridin-3-yl)-2,2-dimethylpiperidine-1-carboxylate is the undesired chiral product of step 1 of Example 49. A crystal suitable for X-ray analysis (a plate with the dimensions 0.4×0.36×0.48 mm$^{-1}$) was selected from the bulk material by the use of a polarizing microscope.

The crystal was mounted on a MiTeGen™ mount with mineral oil and diffraction data (psi- and omega-scans) were collected at 100 K on a Bruker-AXS X8 Kappa diffractometer coupled to an APEX2 CCD detector with CuK$_\alpha$ radiation ($\lambda$=1.54178 Å) form an 1 μS microsource. Data reduction was carried out with the program SAINT (Bruker (2011). SAINT, Bruker-AXS Inc., Madison, Wis., USA) and semi-imperical absorption correction based on equivalents was performed with the program SADABS (Sheldrick, G. M., (2009). SADABS, University of Göttingen, Germany).

The structure was solved by direct methods using SHELXT software suite (Sheldrick, G. M., (2014). SHELXT, University of Göttingen, Germany) in the space group P2$_1$, with one target molecule per asymmetric unit. The structure was subsequently refined against F$^2$ on data with SHELXL (Sheldrick, G. M., *Acta Cryst.* 2008, A64, 112-122) using established refined techniques (Müller, P., *Crystallography Reviews* 2009, 15, 57-83). All non-hydrogen atoms were found and refined using anisotropic displacement parameters.

All carbon-bound hydrogen atoms were placed in geometrically calculated positions and refined using a riding model while constraining their U$_{iso}$ to 1.2 times the U$_{eq}$ of the atoms to which they bind (1.5 times for methyl groups). Coordinates for the hydrogen atoms on nitrogen were taken from the difference Fourier synthesis. Those hydrogen atoms were subsequently refined semi-freely with the help of N—H distance restraints (target value 0.91(2) Å) while constraining their U$_{iso}$ to 1.2 times the U$_{eq}$ of the corresponding nitrogen atom.

Figure 2:
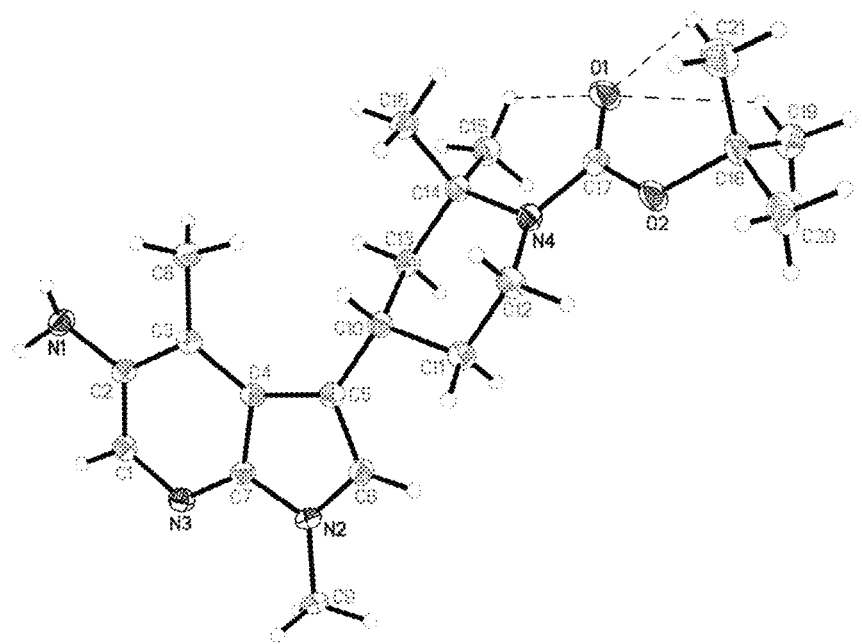
FIG. 2 is an X-ray crystal structure (ORTEP drawing) of (S)-tert-butyl 4-(5-amino-1-methyl-4-(methyl)-1H-pyrrolo[2,3-b]pyridin-3-yl)-2,2-dimethylpiperidine-1-carboxylate. The three intramolecular C—H . . . O hydrogen bonds are drawn as thin dashed lines.

FIG. 2 is an ORTEP Drawing of (S)-tert-butyl 4-(5-amino-1-methyl-4-(trifluoromethyl)-1H-pyrrolo[2,3-b]pyridin-3-yl)-2,2-dimethylpiperidine-1-carboxylate. Pertinent crystal, data collection and refinement are summarized in Table 8. Hydrogen bond parameters [Å and °] are shown in Table 9. Atomic coordinates, bond lengths, bond angles, torsion angles and displacement parameters are listed in Tables 10-13. The diffraction data, show significant anomalous signal and the absolute structure could be established with confidence. The configurations of the chiral carbon atom C10 is S.

TABLE 8

Crystal data and structure refinement for 4-(5-amino-1-methyl-4-(methyl)-1H-pyrrolo[2,3-b]pyridin-3-yl)-2,2-dimethylpiperidine-1-carboxylate.

| | |
|---|---|
| Empirical Formula | C21 H32 N4 O2 |
| Formula weight | 372.50 |
| Temperature | 1002) K |
| Wavelength | 1.54178 Å |
| Crystal system | Monoclinic |
| Space group | P2(1) |
| Unit cell dimensions | a = 6.1660(2) Å; α = 90°. |
| | b = 7.1039(2) Å ; β = 91.1941(12)°. |
| | c = 23.3830(7) Å; γ = 90°. |
| Volume | 1024.01(5) Å$^3$ |
| Z | 2 |
| Density (calculated) | 1.208 Mg/m$^3$ |
| Absorption coefficient | 0.627 mm$^{-1}$ |
| F(000) | 202 |
| Crystal size | 0.480 × 0.360 × 0.040 mm$^3$ |
| Theta range for data collection | 1.890 to 68.225°. |
| Index ranges | −7 <= h <= 7, −8 <= k <= 8, −28 <= l <= 28 |
| Reflections collected | 37009 |
| Independent reflections | 3690 [R(int) = 0.0292] |
| Completeness to theta = 67.679° | 100% |
| Absorption correction | Semi-empirical form equivalents |
| Max. and min. transmission | 0.7531 and 0.6451 |
| Refinement method | Full-matrix least-squares on F$^2$ |
| Data/restraints/parameters | 3690/3/257 |
| Goodness-of-fit on F$^2$ | 1.059 |

TABLE 8-continued

Crystal data and structure refinement for 4-(5-amino-1-methyl-4-(methyl)-1H-pyrrolo[2,3-b]pyridin-3-yl)-2,2-dimethylpiperidine-1-carboxylate.

| | |
|---|---|
| Final R indices [I > 2sigma(I)] | R1 = 0.0260, wR2 = 0.0672 |
| R indices (all data) | R1 = 0.0261, wR2 = 0.0673 |
| Absolute structure parameter | 0.12(4) |
| Largest diff. peak and hole | 0.157 and −0.133 e · Å$^{-3}$ |

TABLE 9

Hydrogen bond parameters for 4-(5-amino-1-methyl-4-(methyl)-1H-pyrrolo[2,3-b]pyridin-3-yl)-2,2-dimethylpiperidine-1-carboxylate [Å and °].

| D-H . . . A | d(D-H) | d(H . . . A) | d(D . . . A) | <(DHA) |
|---|---|---|---|---|
| N(1)—H(1B) . . . N(3)#1 | 0.906(18) | 2.391(19) | 3.194(2) | 147.7(17) |
| C(9)—H(9A) . . . N(1)#2 | 0.98 | 2.58 | 3.487(2) | 153.6 |
| C(1)—H(1) . . . N(3)#1 | 0.95 | 2.69 | 3.511(2) | 144.6 |
| C(15)—H(15A) . . . O(1) | 0.98 | 2.262 | .789(2) | 112.7 |
| C(19)—H(19C) . . . O(1) | 0.98 | 2.47 | 3.028(2) | 115.7 |
| C(21)—H(21A) . . . O(1) | 0.98 | 2.43 | 2.984(3) | 115.0 |

Symmetry transformations used to generate equivalent atoms: #1 −x+3,y−1/2,−z+1  #2 x,y+1,z

TABLE 10

Atomic coordinates (×10$^4$) and equivalent isotropic displacement parameters (Å$^2$ × 10$^3$) for 4-(5-amino-1-methyl-4-(methyl)-1H-pyrrolo[2,3-b]pyridin-3-yl)-2,2-dimethylpiperidine-1-carboxylate. U(eq) is defined as one third of the trace of the orthogonalized U$^{ij}$ tensor.

| | x | y | z | U(eq) |
|---|---|---|---|---|
| O(1) | 3870(2) | 3578(2) | 1091(1) | 31(1) |
| O(2) | 3623(2) | 6733(2) | 1211(1) | 27(1) |
| N(1) | 11515(2) | 803(2) | 4835(1) | 23(1) |
| N(2) | 13049(2) | 7254(2) | 3654(1) | 19(1) |
| N(3) | 14213(2) | 5159(2) | 4394(1) | 19(1) |
| N(4) | 5739(2) | 5104(2) | 1818(1) | 19(1) |
| C(1) | 13674(3) | 3572(3) | 4662(1) | 19(1) |
| C(2) | 11838(3) | 2478(3) | 4528(1) | 17(1) |
| C(3) | 10434(3) | 3006(2) | 4075(1) | 17(1) |
| C(4) | 10957(3) | 4663(2) | 3780(1) | 16(1) |
| C(5) | 10030(3) | 5779(2) | 3315(1) | 18(1) |
| C(6) | 11348(3) | 7318(3) | 3269(1) | 20(1) |
| C(7) | 12835(3) | 5654(2) | 3971(1) | 17(1) |
| C(8) | 8474(3) | 1816(2) | 3945(1) | 21(1) |
| C(9) | 14616(3) | 8735(3) | 3774(1) | 23(1) |
| C(10) | 8079(3) | 5407(2) | 2928(1) | 18(1) |
| C(11) | 7544(3) | 7110(2) | 2554(1) | 22(1) |
| C(12) | 5531(3) | 6761(3) | 2191(1) | 23(1) |
| C(13) | 8417(3) | 3773(2) | 2511(1) | 19(1) |
| C(14) | 6485(3) | 3313(2) | 2101(1) | 19(1) |
| C(15) | 7380(3) | 1905(3) | 1665(1) | 24(1) |
| C(16) | 4603(3) | 2414(3) | 2422(1) | 24(1) |
| C(17) | 4350(3) | 4998(2) | 1349(1) | 21(1) |
| C(18) | 2161(3) | 7059(3) | 714(1) | 23(1) |
| C(19) | 3297(3) | 6539(3) | 168(1) | 29(1) |
| C(20) | 1801(4) | 9167(3) | 751(1) | 35(1) |
| C(21) | 60(3) | 5992(4) | 785(1) | 36(1) |

TABLE 11

Bond lengths [Å] and angles [°] for 4-(5-amino-1-methyl-4-(methyl)-1H-pyrrolo[2,3-b]pyridin-3-yl)-2,2-dimethylpiperidine-1-carboxylate.

| | |
|---|---|
| O(1)—C(17) | 1.210(2) |
| O(2)—C(17) | 1.349(2) |
| O(2)—C(18) | 1.4739(19) |
| N(1)—C(2) | 1.405(2) |
| N(1)—H(1A) | 0.881(18) |
| N(1)—H(1B) | 0.906(18) |
| N(2)—C(7) | 1.366(2) |
| N(2)—C(6) | 1.369(2) |
| N(2)—C(9) | 1.452(2) |
| N(3)—C(1) | 1.336(2) |
| N(3)—C(7) | 1.337(2) |
| N(4)—C(17) | 1.379(2) |
| N(4)—C(12) | 1.472(2) |
| N(4)—C(14) | 1.501(2) |
| C(1)—C(2) | 1.403(2) |
| C(1)—H(1) | 0.95 |
| C(2)—C(3) | 1.405(2) |
| C(3)—C(4) | 1.406(2) |
| C(3)—C(8) | 1.501(2) |
| C(4)—C(7) | 1.420(2) |
| C(4)—C(5) | 1.453(2) |
| C(5)—C(6) | 1.368(2) |
| C(5)—C(10) | 1.513(2) |
| C(6)—H(6) | 0.95 |
| C(8)—H(8A) | 0.98 |
| C(8)—H(8B) | 0.98 |
| C(8)—H(8C) | 0.98 |
| C(9)—H(9A) | 0.98 |
| C(9)—H(9B) | 0.98 |
| C(9)—H(9C) | 0.98 |
| C(10)—C(11) | 1.525(2) |
| C(10)—C(13) | 1.533(2) |
| C(10)—H(10) | 1 |
| C(11)—C(12) | 1.509(2) |
| C(11)—H(11A) | 0.99 |
| C(11)—H(11B) | 0.99 |
| C(12)—H(12A) | 0.99 |
| C(12)—H(12B) | 0.99 |
| C(13)—C(14) | 1.550(2) |
| C(13)—H(13A) | 0.99 |
| C(13)—H(13B) | 0.99 |
| C(14)—C(16) | 1.534(2) |
| C(14)—C(15) | 1.537(2) |
| C(15)—H(15A) | 0.98 |
| C(15)—H(15B) | 0.98 |
| C(15)—H(15C) | 0.98 |
| C(16)—H(16A) | 0.98 |
| C(16)—H(16B) | 0.98 |
| C(16)—H(16C) | 0.98 |
| C(18)—C(21) | 1.513(3) |
| C(18)—C(19) | 1.515(3) |
| C(18)—C(20) | 1.517(3) |
| C(19)—H(19A) | 0.98 |
| C(19)—H(19B) | 0.98 |
| C(19)—H(19C) | 0.98 |
| C(20)—H(20A) | 0.98 |
| C(20)—H(20B) | 0.98 |
| C(20)—H(20C) | 0.98 |
| C(21)—H(21A) | 0.98 |
| C(21)—H(21B) | 0.98 |
| C(21)—H(21C) | 0.98 |
| C(17)—O(2)—C(18) | 121.80(13) |
| C(2)—N(1)—H(1A) | 115.4(15) |
| C(2)—N(1)—H(1B) | 112.0(15) |
| H(1A)—N(1)—H(1B) | 112.5(19) |
| C(7)—N(2)—C(6) | 107.69(14) |
| C(7)—N(2)—C(9) | 124.68(14) |
| C(6)—N(2)—C(9) | 126.96(15) |
| C(1)—N(3)—C(7) | 114.08(14) |
| C(17)—N(4)—C(12) | 117.01(14) |
| C(17)—N(4)—C(14) | 118.86(13) |
| C(12)—N(4)—C(14) | 116.56(13) |
| N(3)—C(1)—C(2) | 124.80(15) |
| N(3)—C(1)—H(1) | 117.6 |
| C(2)—C(1)—H(1) | 117.6 |
| C(1)—C(2)—C(3) | 120.12(15) |
| C(1)—C(2)—N(1) | 118.54(15) |

TABLE 11-continued

Bond lengths [Å] and angles [°] for 4-(5-amino-1-methyl-4-(methyl)-1H-pyrrolo[2,3-b]pyridin-3-yl)-2,2-dimethylpiperidine-1-carboxylate.

| | |
|---|---|
| C(3)—C(2)—N(1) | 121.25(15) |
| C(2)—C(3)—C(4) | 116.74(15) |
| C(2)—C(3)—C(8) | 118.91(15) |
| C(4)—C(3)—C(8) | 124.34(15) |
| C(3)—C(4)—C(7) | 117.00(15) |
| C(3)—C(4)—C(5) | 137.21(15) |
| C(7)—C(4)—C(5) | 105.75(14) |
| C(6)—C(5)—C(4) | 105.65(14) |
| C(6)—C(5)—C(10) | 123.99(15) |
| C(4)—C(5)—C(10) | 130.33(15) |
| C(5)—C(6)—N(2) | 111.73(15) |
| C(5)—C(6)—H(6) | 124.1 |
| N(2)—C(6)—H(6) | 124.1 |
| N(3)—C(7)—N(2) | 123.61(15) |
| N(3)—C(7)—C(4) | 127.23(15) |
| N(2)—C(7)—C(4) | 109.17(14) |
| C(3)—C(8)—H(8A) | 109.5 |
| C(3)—C(8)—H(8B) | 109.5 |
| H(8A)—C(8)—H(8B) | 109.5 |
| C(3)—C(8)—H(8C) | 109.5 |
| H(8A)—C(8)—H(8C) | 109.5 |
| H(8B)—C(8)—H(8C) | 109.5 |
| N(2)—C(9)—H(9A) | 109.5 |
| N(2)—C(9)—H(9B) | 109.5 |
| H(9A)—C(9)—H(9B) | 109.5 |
| N(2)—C(9)—H(9C) | 109.5 |
| H(9A)—C(9)—H(9C) | 109.5 |
| H(96)—C(9)—H(9C) | 109.5 |
| C(5)—C(10)—C(11) | 111.33(14) |
| C(5)—C(10)—C(13) | 113.26(13) |
| C(11)—C(10)—C(13) | 105.46(12) |
| C(5)—C(10)—H(10) | 108.9 |
| C(11)—C(10)—H(10) | 108.9 |
| C(13)—C(10)—H(10) | 108.9 |
| C(12)—C(11)—C(10) | 110.94(14) |
| C(12)—C(11)—H(11A) | 109.5 |
| C(10)—C(11)—H(11A) | 109.5 |
| C(12)—C(11)—H(11B) | 109.5 |
| C(10)—C(11)—H(11B) | 109.5 |
| H(11A)—C(11)—H(11B) | 108 |
| N(4)—C(12)—C(11) | 112.53(14) |
| N(4)—C(12)—H(12A) | 109.1 |
| C(11)—C(12)—H(12A) | 109.1 |
| N(4)—C(12)—H(12B) | 109.1 |
| C(11)—C(12)—H(12B) | 109.1 |
| H(12A)—C(12)—H(12B) | 107.8 |
| C(10)—C(13)—C(14) | 116.15(13) |
| C(10)—C(13)—H(13A) | 108.2 |
| C(14)—C(13)—H(13A) | 108.2 |
| C(10)—C(13)—H(13B) | 108.2 |
| C(14)—C(13)—H(13B) | 108.2 |
| H(13A)—C(13)—H(13B) | 107.4 |
| N(4)—C(14)—C(16) | 109.86(13) |
| N(4)—C(14)—C(15) | 111.79(13) |
| C(16)—C(14)—C(15) | 109.79(14) |
| N(4)—C(14)—C(13) | 108.56(13) |
| C(16)—C(14)—C(13) | 111.37(13) |
| C(15)—C(14)—C(13) | 105.41(13) |
| C(14)—C(15)—H(15A) | 109.5 |
| C(14)—C(15)—H(15B) | 109.5 |
| H(15A)—C(15)—H(15B) | 109.5 |
| C(14)—C(15)—H(15C) | 109.5 |
| H(15A)—C(15)—H(15C) | 109.5 |
| H(15B)—C(15)—H(15C) | 109.5 |
| C(14)—C(16)—H(16A) | 109.5 |
| C(14)—C(16)—H(16B) | 109.5 |
| H(16A)—C(16)—H(16B) | 109.5 |
| C(14)—C(16)—H(16C) | 109.5 |
| H(16A)—C(16)—H(16C) | 109.5 |
| H(16B)—C(16)—H(16C) | 109.5 |
| O(1)—C(17)—O(2) | 124.46(15) |
| O(1)—C(17)—N(4) | 125.75(16) |
| O(2)—C(17)—N(4) | 109.78(14) |
| O(2)—C(18)—C(21) | 110.27(14) |
| O(2)—C(18)—C(19) | 109.91(14) |
| C(21)—C(18)—C(19) | 112.43(16) |
| O(2)—C(18)—C(20) | 101.41(14) |
| C(21)—C(18)—C(20) | 111.21(17) |
| C(19)—C(18)—C(20) | 111.07(16) |
| C(18)—C(19)—H(19A) | 109.5 |
| C(18)—C(19)—H(19B) | 109.5 |
| H(19A)—C(19)—H(19B) | 109.5 |
| C(18)—C(19)—H(19C) | 109.5 |
| H(19A)—C(19)—H(19C) | 109.5 |
| H(19B)—C(19)—H(19C) | 109.5 |
| C(18)—C(20)—H(20A) | 109.5 |
| C(18)—C(20)—H(20B) | 109.5 |
| H(20A)—C(20)—H(20B) | 109.5 |
| C(18)—C(20)—H(20C) | 109.5 |
| H(20A)—C(20)—H(20C) | 109.5 |
| H(20B)—C(20)—H(20C) | 109.5 |
| C(18)—C(21)—H(21A) | 109.5 |
| C(18)—C(21)—H(21B) | 109.5 |
| H(21A)—C(21)—H(21B) | 109.5 |
| C(18)—C(21)—H(21C) | 109.5 |
| H(21A)—C(21)—H(21C) | 109.5 |
| H(21B)—C(21)—H(21C) | 109.5 |

TABLE 12

Anisotropic displacement parameters (Å$^2$ × 10$^3$) for 4-(5-amino-1-methyl-4-(methyl)-1H-pyrrolo[2,3-b]pyridin-3-yl)-2,2-dimethylpiperidine-1-carboxylate. The anisotropic displacement factor exponent takes the form: $-2\pi^2[h^2 a^{*2}U^{11} + \ldots + 2 h k a^* b^* U^{12}]$.

| | U$^{11}$ | U$^{22}$ | U$^{33}$ | U$^{23}$ | U$^{13}$ | U$^{12}$ |
|---|---|---|---|---|---|---|
| O(1) | 44(1) | 17(1) | 31(1) | −1(1) | −16(1) | −2(1) |
| O(2) | 36(1) | 17(1) | 27(1) | 0(1) | −15(1) | 2(1) |
| N(1) | 23(1) | 20(1) | 25(1) | 6(1) | −2(1) | −2(1) |
| N(2) | 21(1) | 16(1) | 21(1) | 1(1) | −1(1) | −5(1) |
| N(3) | 18(1) | 18(1) | 21(1) | −1(1) | −2(1) | −1(1) |
| N(4) | 24(1) | 14(1) | 19(1) | 1(1) | −3(1) | 2(1) |
| C(1) | 19(1) | 19(1) | 18(1) | 1(1) | −2(1) | 3(1) |
| C(2) | 18(1) | 14(1) | 19(1) | −1(1) | 2(1) | 1(1) |
| C(3) | 16(1) | 17(1) | 18(1) | −1(1) | 2(1) | 1(1) |
| C(4) | 16(1) | 16(1) | 17(1) | −2(1) | 1(1) | 0(1) |
| C(5) | 19(1) | 17(1) | 18(1) | 0(1) | 1(1) | 1(1) |
| C(6) | 23(1) | 18(1) | 19(1) | 2(1) | 0(1) | 1(1) |
| C(7) | 18(1) | 16(1) | 18(1) | −1(1) | 2(1) | −1(1) |
| C(8) | 21(1) | 18(1) | 24(1) | 2(1) | −1(1) | −3(1) |
| C(9) | 27(1) | 17(1) | 24(1) | 0(1) | 0(1) | −9(1) |
| C(10) | 18(1) | 17(1) | 18(1) | 1(1) | −1(1) | 1(1) |
| C(11) | 28(1) | 15(1) | 22(1) | −1(1) | −4(1) | 3(1) |
| C(12) | 30(1) | 16(1) | 23(1) | −3(1) | −6(1) | 7(1) |
| C(13) | 19(1) | 17(1) | 21(1) | 3(1) | −1(1) | 3(1) |
| C(14) | 22(1) | 14(1) | 20(1) | 2(1) | −2(1) | 2(1) |
| C(15) | 30(1) | 18(1) | 24(1) | 0(1) | −1(1) | 2(1) |
| C(16) | 22(1) | 22(1) | 26(1) | 5(1) | −2(1) | −1(1) |
| C(17) | 25(1) | 16(1) | 22(1) | 3(1) | −3(1) | −1(1) |
| C(18) | 24(1) | 24(1) | 20(1) | 3(1) | −7(1) | 3(1) |
| C(19) | 32(1) | 27(1) | 26(1) | 4(1) | 1(1) | 1(1) |
| C(20) | 46(1) | 28(1) | 30(1) | −1(1) | −13(1) | 15(1) |
| C(21) | 27(1) | 50(1) | 32(1) | 5(1) | −1(1) | −5(1) |

TABLE 13

Hydrogen coordinates (×10$^4$) and isotropic displacement parameters (Å$^2$ × 10$^3$) for 4-(5-amino-1-methyl-4-(methyl)-1H-pyrrolo[2,3-b]pyridin-3-yl)-2,2-dimethylpiperidine-1-carboxylate.

| | x | y | z | U(eq) |
|---|---|---|---|---|
| H(1A) | 10150(30) | 500(30) | 4890(9) | 27 |
| H(1B) | 12330(30) | 760(30) | 5162(8) | 27 |
| H(1) | 14601 | 3153 | 4965 | 22 |
| H(6) | 11111 | 8311 | 3003 | 24 |
| H(8A) | 7582 | 2425 | 3647 | 31 |
| H(8B) | 7624 | 1673 | 4292 | 31 |

TABLE 13-continued

Hydrogen coordinates (×10⁴) and isotropic displacement parameters ($Å^2 \times 10^3$) for 4-(5-amino-1-methyl-4-(methyl)-1H-pyrrolo[2,3-b]pyridin-3-yl)-2,2-dimethylpiperidine-1-carboxylate.

| | x | y | z | U(eq) |
|---|---|---|---|---|
| H(8C) | 8936 | 574 | 3812 | 31 |
| H(9A) | 14230 | 9386 | 4127 | 34 |
| H(9B) | 14610 | 9635 | 3457 | 34 |
| H(9C) | 16066 | 8183 | 3820 | 34 |
| H(10) | 6802 | 5118 | 3170 | 22 |
| H(11A) | 7318 | 8225 | 2800 | 26 |
| H(11B) | 8780 | 7379 | 2303 | 26 |
| H(12A) | 4281 | 6577 | 2444 | 28 |
| H(12B) | 5231 | 7885 | 1952 | 28 |
| H(13A) | 8766 | 2629 | 2737 | 23 |
| H(13B) | 9696 | 4064 | 2278 | 23 |
| H(15A) | 6177 | 1365 | 1439 | 36 |
| H(15B) | 8158 | 896 | 1869 | 36 |
| H(15C) | 8375 | 2556 | 1411 | 36 |
| H(16A) | 4078 | 3297 | 2709 | 35 |
| H(16B) | 5106 | 1258 | 2610 | 35 |
| H(16C) | 3421 | 2113 | 2150 | 35 |
| H(19A) | 4711 | 7167 | 160 | 43 |
| H(19B) | 2410 | 6941 | −162 | 43 |
| H(19C) | 3504 | 5172 | 154 | 43 |
| H(20A) | 1163 | 9476 | 1120 | 52 |
| H(20B) | 814 | 9567 | 440 | 52 |
| H(20C) | 3192 | 9820 | 717 | 52 |
| H(21A) | 329 | 4639 | 743 | 55 |
| H(21B) | −997 | 6402 | 492 | 55 |
| H(21C) | −513 | 6243 | 1165 | 55 |

Software and References. SHELXTL, Version 5.1, Bruker AXS, 1997; PLATON, A. L. Spek, J. Appl. Cryst. 2003, 36, 7-13; MERCURY, C. F. Macrae, P. R. Edington, P. McCabe, E. Pidcock, G. P. Shields, R. Taylor, M. Towler and J. van de Streek, J. Appl. Cryst. 39, 453-457, 2006; OLEX2, Dolomanov, O. V.; Bourhis, L. J.; Gildea, R. J.; Howard, J. A. K.; Puschmann, H., (2009). J. Appl. Cryst., 42, 339-341; R. W. W. Hooft et al. J. Appl. Cryst. (2008). 41. 96-103; and H. D. Flack, Acta Cryst. 1983, A39, 867-881.

INCORPORATION BY REFERENCE

All publications, patents and patent applications mentioned in this specification are herein incorporated by reference to the same extent as if each individual publication, patent or patent application was specifically and individually indicated to be incorporated by reference.

I claim:
1. (R)-3-Cyano-N-(3-(1-(cyclopentanecarbonyl)-2,2 dimethylpiperidin-4-yl)-1,4-dimethyl-1H-pyrrolo[2,3-b]pyridin-5-yl)benzamide or a pharmaceutically acceptable salt thereof.
2. A compound of structure

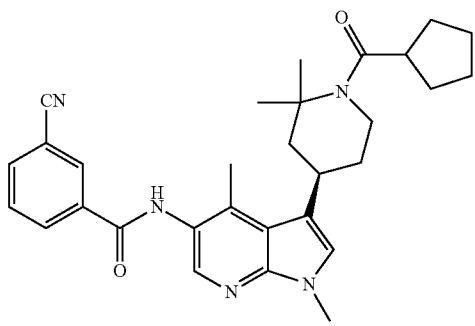

3. A pharmaceutical composition comprising (R)-3-cyano-N-(3-(1-(cyclopentanecarbonyl)-2,2 dimethylpiperidin-4-yl)-1,4-dimethyl-1H-pyrrolo[2,3-b]pyridin-5-yl)benzamide, or a pharmaceutically acceptable salt thereof, and at least one pharmaceutically acceptable carrier, excipient, or diluent.
4. A method of treating psoriasis in a patient comprising administering to the patient in need of such treatment a therapeutically effective amount of (R)-3-cyano-N-(3-(1-(cyclopentanecarbonyl)-2,2 dimethylpiperidin-4-yl)-1,4-dimethyl-1H-pyrrolo[2,3-b]pyridin-5-yl)benzamide, or a pharmaceutically acceptable salt thereof.
5. A method of treating psoriasis in a patient comprising administering to the patient in need of such treatment a pharmaceutical composition comprising a therapeutically effective amount of (R)-3-cyano-N-(3-(1-(cyclopentanecarbonyl)-2,2 dimethylpiperidin-4-yl)-1,4-dimethyl-1H-pyrrolo[2,3-b]pyridin-5-yl)benzamide, or a pharmaceutically acceptable salt thereof, and at least one pharmaceutically acceptable carrier, excipient, or diluent.

* * * * *

SEQUENCE LISTING

```
<160> NUMBER OF SEQ ID NOS: 2

<210> SEQ ID NO 1
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (25)..(25)
<223> OTHER INFORMATION: c-term amidated

<400> SEQUENCE: 1

Cys Pro Ser Ser His Ser Ser Leu Thr Glu Arg His Lys Ile Leu His
1               5                   10                  15

Arg Leu Leu Gln Glu Gly Ser Pro Ser
            20                  25

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 2

Leu Xaa Xaa Leu Leu
1               5
```